(12) United States Patent
Kock et al.

(10) Patent No.: US 7,786,344 B2
(45) Date of Patent: Aug. 31, 2010

(54) SELECTION METHOD

(75) Inventors: Michael Kock, Shifferstadt (DE); Markus Frank, Mannheim (DE); Ralf Badur, Limburgerhof (DE)

(73) Assignee: BASF Plant Science GmbH (DE)

( * ) Notice: Subject to any disclaimer, the term of this patent is extended or adjusted under 35 U.S.C. 154(b) by 420 days.

(21) Appl. No.: 10/522,341

(22) PCT Filed: Jul. 18, 2003

(86) PCT No.: PCT/EP03/07877

§ 371 (c)(1),
(2), (4) Date: Jan. 25, 2005

(87) PCT Pub. No.: WO2004/013333

PCT Pub. Date: Feb. 12, 2004

(65) Prior Publication Data

US 2006/0218658 A1 Sep. 28, 2006

(30) Foreign Application Priority Data

Jul. 26, 2002 (DE) ............................... 102 34 287

(51) Int. Cl.
*C12N 15/82* (2006.01)
*C12N 15/87* (2006.01)
*A01H 1/00* (2006.01)

(52) U.S. Cl. ....................... 800/278; 800/285; 800/286; 800/288; 800/260

(58) Field of Classification Search ....................... None
See application file for complete search history.

(56) References Cited

U.S. PATENT DOCUMENTS

| 5,180,873 A | 1/1993 | Jorgensen |
| 5,254,801 A | 10/1993 | Dotson et al. |
| 5,358,866 A | 10/1994 | Mullen et al. |
| 5,426,041 A | 6/1995 | Fabijanski et al. |

FOREIGN PATENT DOCUMENTS

| EP | 0716147 A2 | 6/1996 |
| EP | 0595873 B1 | 4/2000 |
| WO | WO-93/01281 | 1/1993 |
| WO | WO 01/21768 | * 3/2001 |

OTHER PUBLICATIONS

Gleave et al 1999, Plant Molecular Biolog 40: 223-235.*
Smith et al. 2000, Nature, 407:319-320.*
Wood, D. W. et al., "Agrobacterium tumefaciens str. C58 Ti plasmid, section 2 of 21 of the complete sequence", GenBank Accession No. AE009419.
Calabresi, P., et al., "Antineoplastic Agents", Chapter 51 in Goodman and Gilman: The Pharmacological Basis of Therapeutics, 8th ed., Pergamon Press, New York, 1990, pp. 1209-1263.
Taylor, Milton W., et al., "The APRT System", Chapter 12 in Molecular Cell Genetics, John Wiley and Sons, NY, 1985, pp. 311-332.
Fenwick, Raymond G., "The HGPRT System", Chapter 13 in Molecular Cell Genetics, John Wiley and Sons, NY, 1985, pp. 333-373.
L. Andersen et al. (1989) "Pyrimidine, Purine and Nitrogen Control of Cytosine Deaminase Synthesis in *Escherichia coli* K 12. Involvement of the ginLG and purR Genes in the Regulation of codA Expression," *Arch. Microbiol.* 152, pp. 115-118.
C. Beclin et al. (1993) "Potential Use of the aux2 Gene from Agrobacterium Rhizogenes as a Conditional Negative Marker in Transgenic Cabbage," *Transgenic Research* 2, pp. 48-55.
John E. Bennett. "Antimicrobial Agents" Chapter 50 *In* Goodman and Gilman's The Pharmacological Basis of Therapeutics. Alfred Goodman Gilman, Theodore W. Rall, Alan S. Niles, and Palmer Taylor, Pergamon Press, New York, pp. 1165-11181.
C. Besnard et al. (1987) "Selection Against Expression of the *Escherichia coli* Gene gpt in hprt+ Mouse Teratocarcinoma and Hybrid Cells," *Molecular and Cellular Biology* 7(11), pp. 4139-4141.
V. Blanc et al. (1996) "Control of Gene Expression by Base Deamination: The Case of RNA Editing in Wheat Mitochondria," *Biochemie* 78, pp. 511-517.
J. Canaday et al. (1992) "Organization and Functional Analysis of Three T-DNAs from the Vitopine Ti Plasmid pTiS4," *Mol. Gen. Genet.* 235, pp. 292-303.
E. Cecchini et al. (1998) "Characterization of Gamma Irradiation-Induced Deletion Mutations at a Selectable Locus in Arabidopsis," *Mutation Research* 401, pp. 199-206.
C. Chuang et al. (2000) "Specific and Heritable Genetic Interference by Double-stranded RNA in Arabidopsis thaliana," Proceedings of the National Academy of Sciences of USA, Bd. 97(9), pp. 4985-4990.
S. Corneille et al. (2001) "Efficient Elimination of Selectable Marker Genes from the Plastid Genome by the CRE-lox site-specific Recombination System," *The Plant Journal* 27(2), pp. 171-178.
K. Cornell et al. (1996) "Affinity Purification of 5-Methylthioadenosine Kinase and 5-Methylthioribose/S-Adenosylhomocysteine nucleosidase from Klebsiella pneumoniae," *Biochem J.* 317, pp. 285-290.
M. Czako et al. (1994) "The Herpes Simplex Virus Thymidine Kinase Gene as a Conditional Negative-Selection Marker Gene in Arabidopsis thaliana," *Plant Physiol.* 104, pp. 1067-1071.

(Continued)

*Primary Examiner*—David T Fox
*Assistant Examiner*—Li Zheng
(74) *Attorney, Agent, or Firm*—Connolly Bove Lodge & Hutz LLP

(57) ABSTRACT

The present invention relates to processes for preparing transformed plant cells or organisms by transforming a population of plant cells which comprises at least one marker protein having a direct or indirect toxic effect for said population, with at least one nucleic acid sequence to be inserted in combination with at least one compound, preferably a DNA construct, capable of reducing the expression, amount, activity and/or function of the marker protein, with the transformed plant cells having a growth advantage over nontransformed cells, due to the action of said compound.

18 Claims, 11 Drawing Sheets

OTHER PUBLICATIONS

L. Damon et al. (1989) "Enhancement of 5-Fluoroouracil Antitumor Effects by the Prior Adminstration of Methotrexate," *Pharmac. Ther* 43, pp. 155-185.

A. Depicker et al. (1988) "A Negative Selection Scheme for Tobacco Protoplast-Derived Cells Expressing the T-DNA Gene 2," *Plant Cell Reports* 104, pp. 1067-1071.

R. Donald et al. (1996) "Insertional Tagging, Cloning, and Expression of the Toxoplasma gondii Hypoxanthine-Xanthine-Guanine Phosphoribosyltransferase Gene," *The Journal of Biological Chemistry* 271(24), pp. 14010-14019.

S. Dotson et al. (1996) "Identification, Characterization, and Cloning of a Phosphonate Monoester Hydrolase from Burkholderia caryophilli PG2982," *The Journal of Biological Chemistry* 271(42), pp. 25754-25761.

S. Dotson et al. (1996) "A Phosphonate Monoester Hydrolase from Burkholderia caryophilli PG2982 is Useful as a Conditional Lethal Gene in Plants," *The Plant Journal* 10(2), pp. 383-392.

S. Endo et al. (2002) "A New GST-MAT Vector Containing both ipt and iaaM/H Genes Can Produce Marker-free Transgenic Tobacco Plants with High Frequency," *Plant Cell Rep* 20, pp. 923-928.

N. Fedoroff et al. (1993) "A Versatile System for Detecting Transposition in Arabidopsis," *The Plant Journal* 3(2), pp. 273-289.

M. Gallego et al. (1999) "Positive-negative Selection and T-DNA Stability in Arabidopsis Transformation," *Plant Molecular Biology* 39, pp. 83-93.

V. Gaudin et al. (1995) "Expression of Agrobacterium rhizogenes Auxin Biosynthesis Genes in Trangenic Tobacco Plants," *Plant Molecular Biology* 28, pp. 123-136.

GenBank Acc. No. AB016260.
GenBank Acc. No. AB025110.
GenBank Acc. No. AC079674.
GenBank Acc. No. AF039169.
GenBank Acc. No. AF172282.
GenBank Acc. No. AF253472.
GenBank Acc. No. M12196.
GenBank Acc. No. M13422.
GenBank Acc. No. M61151.
GenBank Acc. No. NC002147.
GenBank Acc. No. V00467.
GenBank Acc. No. V00470.
GenBank Acc. No. X00221.
GenBank Acc. No. X04049.
GenBank Acc. No. X77943.
GenBank Acc. No. M26950.
GenBank Acc. No. U10247.
GenBank Acc. No. NC_003308.
GenBank Acc. No. M60917.
GenBank Acc. No. U44852.
GenBank Acc. No. AF212863.
GenBank Acc. No. J02224.
GenBank Acc. No. M32238.
GenBank Acc. No. S56903.

A. Gleave et al. (1999) "Slectable Marker-Free Transgenic Plants without Sexual Crossing: Transient Expression of cre Recombinase and Use of a Conditional Lethal Dominant Gene," *Plant Molecular Biology* 40, pp. 223-235.

D. Inze et al. (1984)) "Genetic Analysis of the Individual T-DNA Genes of Agrobacterium tumefaciens; Further Evidence that Two Genes are Involved in Indole-3-acetic acid Synthesis," *Mol. Gen. Genet.* 194, pp. 265-274.

M. Jacobs et al. (1988) "Isolation and Biochemical Analysis of Ethyl Methanesulfonate-Induced Alcohol Dehydrogenase Null Mutants of Arabidopsis thaliana (L.) Heynh," *Biochemical Genetic* 26(1/2), pp. 105-122.

D. Janssen et al. (1994) "Genetics and Biochemistry of Dehalogenating Enzymes," *Annu. Rev. Microbiol.* 48, pp. 163-191.

D. Janssen et al. (1989) "Cloning of 1, 2-Dichloroethane Degradation Genes of Xanthobacter autotrophicus GJ10 and Expression and Sequencing of the dhlA Gene," Journal of Bacteriology 171(12), pp. 6791-6799.

D. J. Jolly et al. (1983) "Isolation and Characterization of a Full-Length Expressible cDNA for Human Hypoxanthine Phosphoribosyltransferase," *Proc. Natl. Acad. Sci.* 80, pp. 477-481.

G. Karlin-Neumann et al. (1991) "Phytochrome Control of the tms2 Gene in Trasngenic Arabidopsis: A Strategy for Selecting Mutants in the Signal Transduction Pathway," *The Plant Cell* 3, pp. 573-582.

M. Kitstrup et al. (1989) "Genetic Evidence for a Repressor of Synthesis of Cytosine Deaminase and Purine Biosynthesis Enzymes in *Escherichia coli*," *Journal of Bacteriology* 171(4), pp. 2124-2127.

L. J. Knoll et al. (1998) *Mol. Cell Biol.* 18(2), pp. 807-814.

T. Kobayashi et al. (1995) "A Conditional Negative Selection for Arabidopsis Expressing a Bacterial Cytosine Deaminase Gene," *Jpn. J. Genet.* 70, pp. 409-422.

B. A. Koechlin et al. (1966) "The Metabolism of 5-Fluorocytosine-$2^{14}$C and of Cytosine-$^{14}$C in the Rat and the Disposition of 5-Fluorocytosine-$2^{14}$C in Man," *Biochemical Pharmacology* 15, pp. 435-446.

T. Koprek et al. (1999) "Negative Selection Systems for Trasngenic Barley (Hordeum vulgare L.): Comparison of Bacterial codA- and Cytochrome P450 Gene-Mediated Selection," *The Plant Journal* 19(6), pp. 719-726.

J. Van Herrewege et al. (1980) "Dietary Utilization of Aliphatic Alcohols by Drosphila," *Experientia* 36, pp. 846-847.

S. McCormick et al. (1986) "Leaf Disc Transformation of Cultivated Tomato (L. esculentum) Using Agrobacterium tumefaciens," *Plant Cell Reports* 5, pp. 81-84.

S. McKnight et al. (1980) "Expression of the Herpes Thymidine Kinase Gene in Xenopus laevis oocytes: An Assay for the Study of Deletion Mutants Constructed in Vitro," *Nucleic Acids Research* 8(24), pp. 5931-5948.

S. McKnight et al. (1980) "The Nucleotide Sequence and Transcript Map of the Herpes Simplex Virus Thymidine Kinase Gene," *Nucleic Acids Research* 8(24), pp. 5949-5964.

C. Mullen et al. (1992) "Transfer of the Bacterial Gene for Cytosine Deaminase to Mammalian Cells Confers Lethal Sensitivity to 5-fluorocytosine: A Negative Selection System," *Proc. Natl. Acad. Sci. USA* 89, pp. 33-37.

P. J. Mroz et al. (1993) "Retrovirally Transduced *Escherichia coli* gpt Genes Combine Slectability with Chemosensitivity Capable of Mediating Tumor Eradication," *Human Gene Therapy* 4, pp. 589-595.

H. Naested et al. (1999) "A Bacterial Haloalkane Dehalogenase Gene as a Negative Selectable Marker in Arabidopsis," *The Plant Journal* 18(5), pp. 571-578.

Daniel P. O'Keefe et al. (1994) "Plant Expression of a Bacterial Cytochrome P450 That Catalyzes Activation of a Sulfonylurea Pro-Herbicide," *Plant Physiol.* 105, pp. 473-782.

Daniel P. O'Keefe et al. (1991) "Ferredoxins from Two Sulfonylurea Herbicide Monooxygenase Systems in Streptomyces griseolus," *Biochemistry* 30(2), pp. 447-455.

Yasuhiro Ono et al. (1997) "Regression of Experimental Brain Tumors with 6-Thioxanthine and *Escherichia coli* gpt Gene Therapy," *Human Gene Therapy* 8, pp. 2043-2055.

Lowell D. Owens. (1973) "Herbicidal Potential of Rhizobitoxine," *Weed Science* 21(1), pp. 63-66.

Ranjan J. Perera et al. (1993) "Cytosine Deaminase as a Negative Selective Marker for Arabidopsis," *Plant Molecular Biology* 23, pp. 793-799.

Annemarie Polak et al. (1975) "Mode of Action of 5-Fluorocytosine and Mechanisms of Resistance," *Chemotherapy* 21, pp. 113-130.

Annemarie Polak et al. (1976) "Metabolic Studies with 5-Fluorocytosine-6-$^{14}$C in Mouse, Rat, Rabbit, Dog and Man," *Chemotherapy* 22, pp. 137-153.

Chris M. Preston et al. (1981) "Identification and Mapping of Two Polypeptides Encoded within the Herpes Simplex Virus Type I Thymidine Kinase Gene Sequences," *Journal of Virology* 38(2), pp. 593-605.

Eddy Risseauw et al. (1997) "Gene Targeting and Instability of Agrobacterium T-DNA loci in the Plant Genome," *The Plant Journal* 11(4), pp. 717-728.

Siegfried Salomon et al. (1998) "Capture of Genomic and T-DNA Sequences during Double-Strand Break Repair in Somatic Plant Cells," *The EMBO Journal* 17(20), pp. 6086-6095.

Helmi R. M. Schlaman et al. (1997) "Effectiveness of the Bacterial Gene codA Encoding Cytosine Deaminase as a Negative Selectable Marker in Agrobacterium-mediated Plant Transformation," *The Plant Journal* 11(6), pp. 1377-1385.

Gudrun Schroder et al. (1984) "The T-region of Ti Plasmids Codes for an Enzyme Synthesizing Indole-3-acetic acid," *European Journal of Biochem.* 138, pp. 387-391.

Drew Schwartz. (1981) "Adh Locus in Maize for Detection of Mutagens in the Enviroment," *Environmental Health Perspectives* 37, pp. 75-77.

Agnieszka Sekowska et al. (2001) "MtnK, Methylthioribose Kinase, is a Starvation-induced Protein in *Bacillus subtilis*," *BMC Microbiol.* 1:15.

German Serino et al. (1997) "A Negative Selection Scheme Based on the Expression of Cytosine Deaminase in Plastids," *The Plant Journal* 12(3), pp. 697-701.

Eric J. Sorscher et al. (1994) "Tumor Cell Bystander Killing in Colonic Carcinoma Utilizing the *Escherichia coli* DeoD Gene to Generate Toxic Purines," *Gene Therapy* 1, pp. 223-238.

Marty H. St. Clair et al. (1987) "Inhibition of Ganciclovir of Cell Growth and DNA Synthesis of Cells Biochemically transformed with Herpes virus Genetic Information," *Antimicrobial Agents and Chemotherapy* 31(6), pp. 844-849.

Jens Stougaard. (1993) "Substrate-dependent Negative Selection in Plants Using a Bacterial Cytosine Deaminase Gene," *The Plant Journal* 3(5), pp. 755-761.

Venkatesan Sundaresan et al. (1995) "Patterns of Gene Action in Plant Development Revealed by Enhancer Trap and Gene Trap Transposable Elements," *Genes & Development* 9, pp. 1797-1810.

Thomas Thykjaer et al. (1997) "Gene Targeting Approaches Using Positive-negative Slection and Large Flanking Regions," *Plant Molecular Biology* 35, pp. 523-530.

A. F. Tissier et al. (1999) "Plant Molecular Genetics-Presentation," *Plant Cell* 11, pp. 1841-1852.

Linda Thomashow et al. (1984) "Crown Gall Oncogenesis: Evidence that a T-DNA Gene from the Agrobacterium Ti Plasmid pTiAB Encodes and Enzyme that Catalyzes Synthesis of Indoleacetic Acid," *Proc. Natl. Acad. Sci. USA* 81, pp. 5071-5075.

Narayana M. Upadhyaya et al. (2000) "The tms2 Gene as a Negative Selection Marker in Rice," *Plant Molecular Biology Reporter* 18, pp. 227-233.

H. Van Onckelen et al. (1986) "Agrobacterium T-DNA Gene 1 codes for Tryptophan 2-Monooxygenase Activity in Tobacco Crown Gall Cells," *FEBS Lett.* 198, pp. 357-360.

Michael J. Wagner et al. (1981) "Nucleotide Sequence of the Thymidine Kinase Gene of Herpes Simplex virus type 1," *Proc. Natl. Acad. Scie. USA.* 78(3), pp. 1441-1445.

Michael Wigler et al. (1977) "Transfer of Purified Herpes Virus Thymidine Kinase Gene to Cultured Mouse Cells," *Cell* 11, pp. 223-232.

Michael Wigler et al. (1979) "DNA-Mediated Transfer of the Adenine Phosphoribosyltransferase Locus into Mammalian Cells," *Proc. Natl. Acad. Sci. USA*, 76(3), pp. 1373-1376.

E. Wisman et al. (1991) "Genetic and Molecular Characterization of an Adh-1 null Mutant in Tomato," *Mol. Gen. Genet.* 226, pp. 120-128.

Helen Xiaohui Wang et al. (2001) "Positive-Negative Selection for Homologous Recombination in arabidopsis," *Gene* 272, pp. 249-255.

Tetsuji Yamada et al. (1985) "Nucleotide Sequences of the Pseudomonas Savastanoi Indoleacetic Acid Genes Show Homology with Agrobacterium Tumefaciens T-DNA," *Proc. Natl. Acad. Sci. USA* 82, pp. 6522-6526.

Elena Zubko et al. (2000) "Intrachromosomal Recombination Between attP Regions as a Tool to Remove Selectable Marker Genes from Tobacco Transgenes," *Nat. Biotechnol.* 18, pp. 442-445.

\* cited by examiner

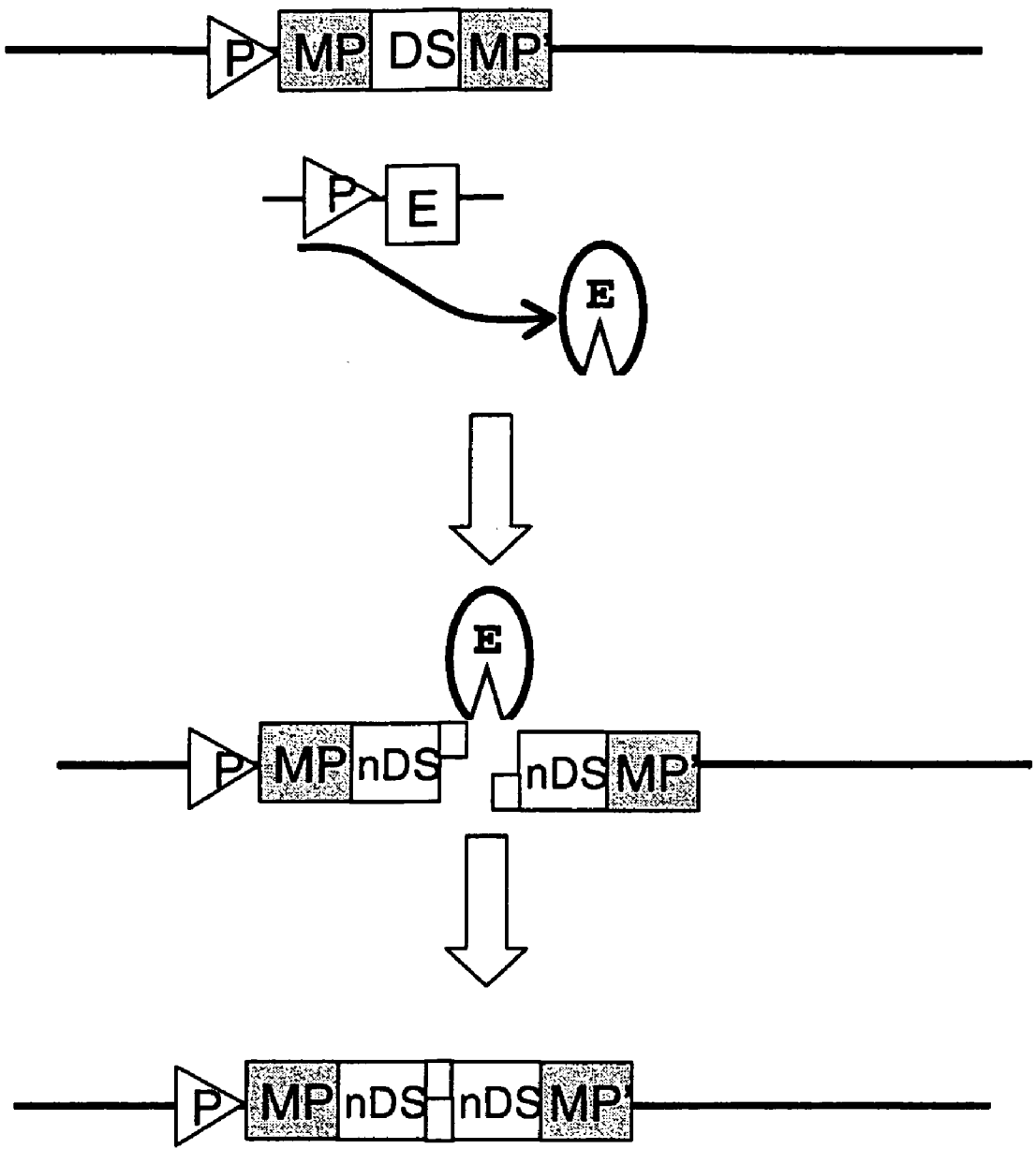
Fig. 2-A

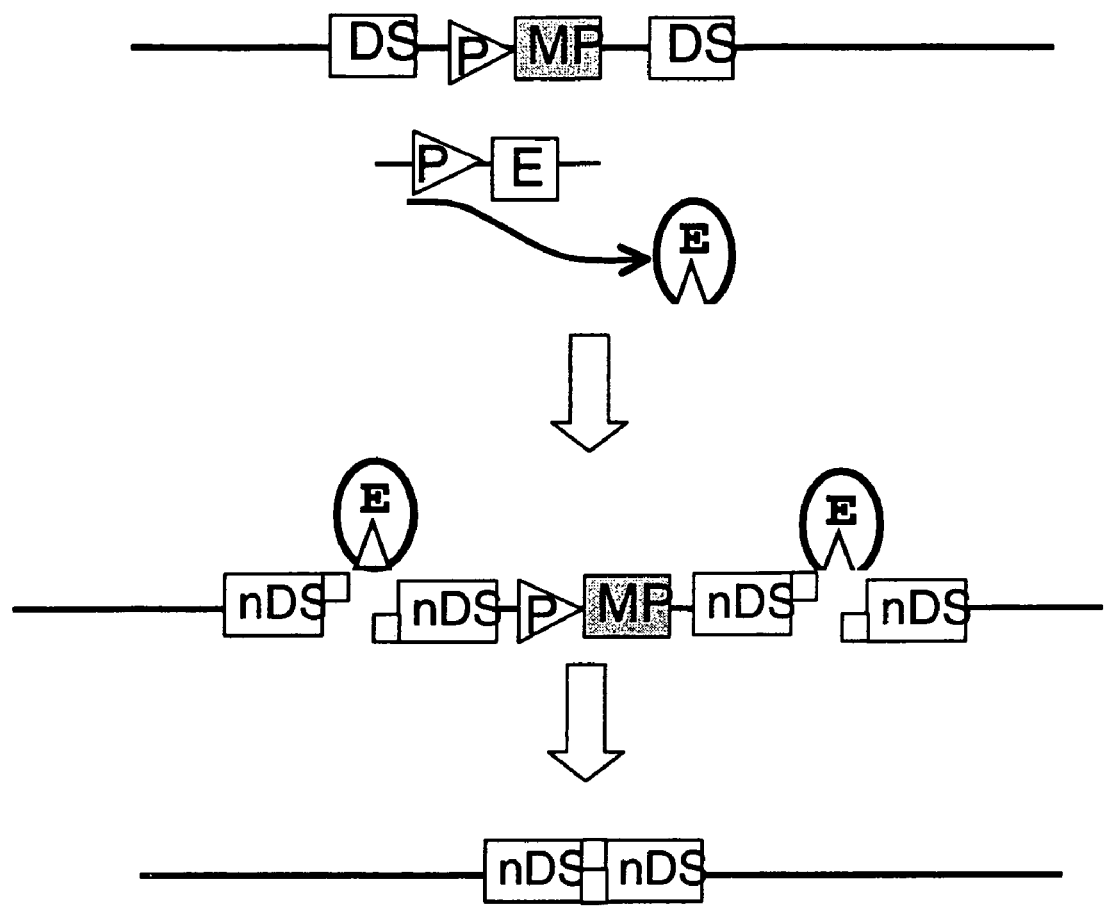
Fig. 2-B

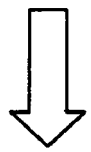
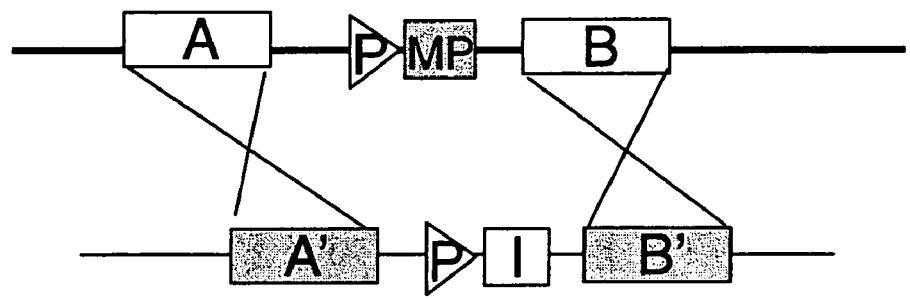
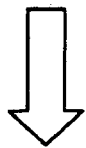
Fig. 4 pSUN1-codA-RNAi-*At.Act.*-2-*At.Als*-*R*-ocsT

```
                              1                                                 50
Klebsiella pneumoniae    (1)  -----------------------------MSQYHTFTAHDAVAYAQQ
Clostridium tetani.      (1)  ---------------------------MSRFDSHFRMETEDAILYAKE
Zea mays                 (1)  ARALLSSPLAGASPDCQSASAMAAEEEQGFRPLDESSLLAYIKATPALAS
A.thaliana               (1)  ----------------------MSFEEFTPLNEKSLVDYIKSTPALSS
Brassica napus-2         (1)  --------------VDDFVLRAKEMSFDEFKPLNEKSLVEYIKATPALSS
Soy-1                    (1)  --------------------------------------------------
Oryza sativa-1           (1)  --------------------------------------------------
Consensus                (1)                                    L       V     A 51                                                100
Klebsiella pneumoniae   (19)  FAGIDNPSELVSAQEVGDGNLNLVFKVFDRQGVSRAIVKQALPYVRCVGE
Clostridium tetani.     (22)  KLGIFDEHAKLQAEEIGDGNINYVFKVWDVNTKKSVIIKHADIFLRSSGR
Zea mays                (51)  RLGGGGSLDSIEIKEVGDGNLNFVYIVQSEAGA--IVVKQALPYVRCVGD
A.thaliana              (27)  KIGADKSDDDLVIKEVGDGNLNFVFIVVGSSGS--LVIKQALPYIRCIGE
Brassica napus -2       (37)  RLGDKY--DDLVIKEVGDGNLNFVFIVVGSTGS--LVIKQALPYIRCIGE
Soy -1                   (1)  --------------------------------------------------
Oryza sativa -1          (1)  --------------------------------------------------
Consensus               (51)  KLG      D L   EVGDGNLNFVF V   G   LVIKQALPYIRCIGE 101                                               150
Klebsiella pneumoniae   (69)  SWPLTLDRARLEAQTLVAHYQHSPQHTVKIHHFDPELAVMVMEDLS-DHR
Clostridium tetani.     (72)  --ELDVDRNRIEAEVLMLQGILAPGLVPKVYKYDSVMCNLSMEDIS-DHR
Zea mays                (99)  SWPMTRERAYFEASTLREHGRLCPEHTPEVYHFDRTLSLMGMRYIEPPHI
A.thaliana              (75)  SWPMTKERAYFEATTLRKHGNLSPDHVPEVYHFDRTMALIGMRYLEPPHI
Brassica napus -2       (83)  SWPMTKERAYFEATTLRKHGGLSPDHVPEVYHFDRTMALIGMRYLEPPHI
Soy -1                   (1)  --------------------IPEHVPEVYHFDRTMSLIGMRYLEPPHI
sativa -1                (1)  --------------------------------------------------
Consensus              (101)  SWPMT ERA  EA TL  HG LSPDHVPEVYHFDRTMALIGMRYLEPPHI 151                                               200
Klebsiella pneumoniae  (118)  IWRGELIANVYYPQAARQLGDYLAQVLFHTSDFYLHPHEKKAQVAQFIN-
Clostridium tetani.    (119)  NLRKELLKRNTFPSFAEHITTFIVDTLLPTTDLVMDSGEKKDNVKKYIN-
Zea mays               (149)  ILRKGLVAGVEYPLLADHMSDYMAKTLFFTSLLYNNTTDHKNGVAKYSAN
A.thaliana             (125)  ILRKGLIAGIEYPFLADHMSDYMAKTLFFTSLLYHDTTEHRRAVTEFCGN
Brassica napus -2      (133)  ILRKG---------------------------------------------
Soy -1                  (29)  ILIKGLIAGIEYPFLAEHMADFMAKTLFFTSLLFRSTADHKRDVAEFCGN
Oryza sativa -1          (1)  ----------------------LLYNSTTDHKKGVAQYCDN
Consensus              (151)  ILRKGLIA I YP  ADHM DYMA TLF TSLLY  T DHK  VA F N 201                                               250
Klebsiella pneumoniae  (167)  PAMCEITEDLFFNDPYQIHERN--NYPAELEADVAALRDDAQLKLAVAAL
Clostridium tetani.    (168)  KDLCKISEDLVFTEPFIDYKSRNTVLEENIEFVKRQLYEDKELILEAGKL
Zea mays               (199)  VEMCRLTEQVVFSDPYRVSKFNR-WTSPYLDKDAEAVREDDELKLEVAGL
A.thaliana             (175)  VELCRLTEQVVFSDPYRVSTFNR-WTSPYLDDDAKAVREDSALKLEIAEL
Brassica napus -2      (138)  --------------------------------------------------
Soy -1                  (79)  VELCRLTEQVVFSDPYKVSQYNR-WTSPYLDRDAEAVREDNLLKLEVAEL
Oryza sativa -1         (20)  VEMCRLTEQVVFSDPYMLAKYNR-CTSPFLDNDAAAVREDAELKLEIAEL
Consensus              (201)  VELCRLTEQVVFSDPY VS FNR  TSPYLD DA AVRED  LKLEVA L
```

Fig. 9a

```
                                251                                          300
Klebsiella pneumoniae   (215) KHRFFAHAEALLHGDIHSGSIFVAEGSLKAIDAEFGYFGPIGFDIGTAIG
Clostridium tetani.     (218) KNNFMNNSQALIHGDLHSGSIFVNEESTKILDPEFAFYGPIGYDLGNVIG
Zea mays                (248) KSMFIERAQALIHGDLHTGSIMVTEVQLKSLIQNLGSMGPMGFDIGSLPW
A.thaliana              (224) KSMFCERAQALIHGDLHTGSVMVTQDSTQVIDPEFSFYGPMGFDIGAYLG
Brassica napus -2       (138) --------------------------------------------------
Soy -1                  (128) KSKFIES-------------------------------------------
Oryza sativa -1          (69) KSMFIERAQALLHGDLHTGSIMVTPDSTQVIDPEFAFYGPMGYDIGAFLG
Consensus               (251) KS FIE AQALIHGDLHTGSI V   S   ID EFAFYGPMGFDIG  IG 301                                          350
Klebsiella pneumoniae   (265) NLLLNYCGLPGQLGIRDAAAAREQRLNDIHQLWTTFAERFQALAAEKTRD
Clostridium tetani.     (268) NLFFAWANAYVTEDGKEVEEFTIWIEKTIENILELFKEKFIKKYKEIVTD
Zea mays                (298) KPDFGHTMHRMGMLIKRMIVRLTRMDLEDN--------------------
A.thaliana              (274) NLILAFFAQDGHATQENDRKEYKQWILRTIEQTWNLFNKRFIALWDQNKD
Brassica napus -2       (138) --------------------------------------------------
Soy -1                  (135) --------------------------------------------------
Oryza sativa -1         (119) NLILAYFSQDGHADQANDRKAY----------------------------
Consensus               (301) NL  AY 351                                          400
Klebsiella pneumoniae   (315) AALAYPGYASAFLKKVWADAVGFCGSELIRRSVGLSHVADIDTIQDDAMR
Clostridium tetani.     (318) VMAKEEYYMNWYLHSILSDTAGQVGLEIIRRVVGDSKVLDITSITDINKR
Zea mays                (328) --------------------------------------------------
A.thaliana              (324) GPGEAYLADIYNNTEVLKFVQENYMRNLLHDSLGFGAAKMIRRIVGVAHV
Brassica napus -2       (138) --------------------------------------------------
Soy -1                  (135) --------------------------------------------------
Oryza sativa -1         (141) --------------------------------------------------
Consensus               (351)

401                              447
Klebsiella pneumoniae   (365) HECLRHAITLGRALIVLAERIDSVDELLARVRQYS-----------
Clostridium tetani.     (368) VKAERILILSAKTFIKNRHKIKTGKRYVEIFNSNMY----------
Zea mays                (328) ----------------------------------------------
A.thaliana              (374) EDFESIEEDKRRAICERSALEFAKMLLKERRKFKSIGEVVSAIQQQS
Brassica napus -2       (138) ----------------------------------------------
Soy -1                  (135) ----------------------------------------------
Oryza sativa -1         (141) ----------------------------------------------
Consensus               (401)
```

Fig. 9b

SELECTION METHOD

RELATED APPLICATIONS

This application is a national stage application (under 35 U.S.C. 371) of PCT/EP2003/007877 filed Jul. 18, 2003, which claims benefit of German application 102 34 287.3 filed Jul. 26, 2002.

INCORPORATION OF SEQUENCE LISTING

The contents of the following submission on compact discs are incorporated herein by reference in its entirety: two copies of the Sequence Listing (COPY 1 and COPY 2 REPLACEMENT Mar. 3, 2006) and a computer-readable form of the Sequence Listing (CRF COPY REPLACEMENT Mar. 3, 2006), all on CD-Rs, each containing: file name: Final Sequence list-12810-00057-US, date recorded: Mar. 3, 2006, size: 307 KB.

FIELD OF THE INVENTION

The present invention relates to processes for preparing transformed plant cells or organisms by transforming a population of plant cells which comprises at least one marker protein having a direct or indirect toxic effect for said population, with at least one nucleic acid sequence to be inserted in combination with at least one compound, preferably a DNA construct, capable of reducing the expression, amount, activity and/or function of the marker protein, with the transformed plant cells having a growth advantage over nontransformed cells, due to the action of said compound.

BACKGROUND OF THE INVENTION

Genetic material is successfully introduced usually only into a very limited number of target cells of a population. This necessitates the distinction and isolation of successfully transformed from nontransformed cells, a process which is referred to as selection. Traditionally, the selection is carried out by way of a "positive" selection, wherein the transformed cell is enabled to grow and to survive, whereas the untransformed cell is inhibited in its growth or destroyed (McCormick et al. (1986) Plant Cell Reports 5:81-84). A positive selection of this kind is usually implemented by genes which code for a resistance to a biocide (e.g. a herbicide such as phosphinothricin, glyphosate or bromoxynil, a metabolism inhibitor such as 2-deoxyglucose 6-phosphate (WO 98/45456) or an antibiotic such as tetracycline, ampicillin, kanamycin, G 418, neomycin, bleomycin or hygromycin). Such genes are also referred to as positive selection markers. The positive selection marker is coupled (physically or by means of cotransformation) to the nucleic acid sequence to be introduced into the cell genome and is then introduced into the cell. Subsequently, the cells are cultured on a medium under the appropriate selection pressure (for example in the presence of an appropriate antibiotic or herbicide), whereby the transformed cells, owing to the required resistance to said selection pressure, have a growth/survival advantage and can thus be selected. Positive selection markers which may be mentioned by way of example are:

phosphinothricin acetyltransferases (PAT) (also: Bialophos® resistance; bar) acetylate the free amino group of the glutamine synthase inhibitor phosphinothricin (PPT) and thus achieve a detoxification (de Block et al. (1987) EMBO J. 6:2513-2518; Vickers J E et al. (1996) Plant Mol Biol Reporter 14:363-368; Thompson C J et al. (1987) EMBO J 6:2519-2523).

5-enolpyruvylshikimate 3-phosphate synthases (EPSPS) impart a resistance to the unselective herbicide Glyphosat® (N-(phosphonomethyl)glycine; Steinrucken H C et al. (1980) Biochem Biophys Res Commun 94:1207-1212; Levin J G and Sprinson D B (1964) J Biol Chem 239:1142-1150; Cole D J (1985) Mode of action of glyphosate; A literature analysis, p. 48-74. In: Grossbard E and Atkinson D (eds.) The herbicide glyphosate. Buttersworths, Boston.). Glyphosate-tolerant EPSPS variants for use as selection markers have been described (Padgette S R et al. (1996). New weed control opportunities: development of soybeans with a Roundup Ready™ gene. In: Herbicide Resistant Crops (Duke S O, ed.), pp. 53-84. CRC Press, Boca Raton, Fla.; Saroha M K and Malik V S (1998) J Plant Biochemistry and Biotechnology 7:65-72; Padgette S R et al. (1995) Crop Science 35(5):1451-1461; U.S. Pat. No. 5,510,471; U.S. Pat. No. 5,776,760; U.S. Pat. No. 5,864,425; U.S. Pat. No. 5,633,435; U.S. Pat. No. 5,627,061; U.S. Pat. No. 5,463,175; EP-A 0 218 571).

neomycin phosphotransferases constantly impart a resistance to aminoglycoside antibiotics such as neomycin, G418, hygromycin, paromomycin or kanamycin by reducing the inhibiting action thereof by means of a phosphorylation reaction (Beck et al. (1982) Gene 19:327-336).

2-deoxyglucose 6-phosphate phosphatases impart a resistance to 2-deoxyglucose (EP-A 0 807 836; Randez-Gil et al. (1995) Yeast 11:1233-1240; Sanz et al. (1994) Yeast 10:1195-1202).

acetolactate synthases impart a resistance to imidazolinone/sulfonylurea herbicides (e.g. imazzamox, imazapyr, imazaquin, imazethapyr, amidosulforon, azimsulfuron, chlorimuron ethyl, chlorsulfuron; Sathasivan K et al. (1990) Nucleic Acids Res 18(8):2188).

In addition, resistance genes to the antibiotics hygromycin (hygromycin phosphotransferases), chloramphenicol (chloramphenicol acetyltransferase), tetracycline, streptomycin, zeocine and ampicillin (β-lactamase gene; Datta N, Richmond M H. (1966) Biochem J 98(1):204-9) have been described.

Genes such as isopentenyl transferase (ipt) from Agrobacterium tumefaciens (strain:PO22) (GenBank Acc. No.: AB025109) may likewise be used as selection markers. The ipt gene is a key enzyme of cytokine biosynthesis. Its overexpression facilitates the regeneration of plants (e.g. selection on cytokine-free medium) (Ebinuma H et al. (2000) Proc Natl Acad Sci USA 94:2117-2121; Ebinuma H et al. (2000) Selection of Marker-free transgenic plants using the oncogenes (ipt, rol A, B, C) of Agrobacterium as selectable markers, In Molecular Biology of Woody Plants. Kluwer Academic Publishers). The disadvantages here are, firstly, the fact that the selection disadvantage is based on usually subtle differences in cell proliferation and, secondly, the fact that the plant acquires unwanted properties (gall tumor formation) due to transformation with an oncogene.

EP-A 0 601 092 describes various other positive selection markers. Examples which may be mentioned are: β-glucuronidase (in connection with, for example, cytokinine glucuronide), mannose 6-phosphate isomerase (in connection with mannose), UDP-galactose 4-epimerase (in connection with galactose, for example).

Negative selection markers are used for selecting organisms in which marker sequences have been successfully deleted (Koprek T et al. (1999) Plant J 19(6):719-726). In the presence of a negative selection marker, the corresponding cell is destroyed or experiences a growth disadvantage. Negative selection involves, for example, the negative selection marker introduced into the plant converting a compound which otherwise has no action disadvantageous to the plant into a compound with a disadvantageous (i.e. toxic) action. Examples of negative selection markers include: thymidine kinase (TK), for example of Herpes simplex virus (Wigler et al. (1977) Cell 11:223), cellular adenine phosphoribosyl transferase (APRT) (Wigler et al. (1979) Proc Natl Acad Sci USA 76:1373), hypoxanthine phosphoribosyl transferase (HPRT) (Jolly et al. (1983) Proc Natl Acad Sci USA 80:477), diphtheria toxin A fragment (DT-A), the bacterial xanthine-guanine phosphoribosyl transferase (gpt; Besnard et al. (1987) Mol. Cell. Biol. 7:4139; Mzoz and Moolten (1993) Human Gene Therapy 4:589-595), the codA gene product coding for a cytosine deaminase (Gleave A P et al. (1999) Plant Mol. Biol. 40(2):223-35; Perera R J et al. (1993) Plant Mol Biol 23(4): 793-799; Stougaard J; (1993) Plant J 3:755-761; EP-A1 595 873), the cytochrome P450 gene (Koprek et al. (1999) Plant J 16:719-726), genes coding for a haloalkane dehalogenase (Naested H (1999) Plant J 18:571-576), the iaaH gene (Sundaresan V et al. (1995) Genes & Development 9:1797-1810) or the tms2 gene (Fedoroff N V & Smith D L (1993) Plant J 3: 273-289). The negative selection markers are usually employed in combination with "prodrugs" or "pro-toxins", compounds which are converted into toxins by the activity of the selection marker.

5-Methylthioribose (MTR) kinase is an enzyme whose enzymic activity in plants, bacteria and protozoa, but not in mammals, has been described. The enzyme may convert an MTR analog (5-(triromethyl)thioribose) as a "subversive substrate" of the methionine salvage pathway via an unstable intermediate to give the toxic compound carbothionyl difluoride.

Said selection systems have various disadvantages. The introduced selection marker (e.g. resistance to antibiotics) is justified only during transformation and selection but is later a usually unnecessary and often also undesired protein product. This may be disadvantageous for reasons of consumer acceptance and/or approval as a food and/or feed product. Another disadvantage in this connection is the fact that the selection marker used for selection is usually genetically coupled to the nucleic acid sequence to be inserted into the genome and cannot be decoupled by segregation during propagation or crossing. Usually, deletion of the marker sequence is required, making additional steps necessary. In addition, biotechnological studies require in numerous cases multiple transformation with various gene constructs. Here, each transformation step requires a new selection marker unless the previously used marker is to be laboriously deleted first. This, however, necessitates a broad palette of well-functioning selection markers which are not available for most plant organisms.

SUMMARY OF THE INVENTION

Consequently, it was the object of the invention to provide novel selection processes for selecting transformed plant cells and organisms, which, if possible, no longer have the disadvantages of the available systems. This object is achieved by the present invention.

The invention firstly relates to a process for preparing transformed plant cells or organisms, which process comprises the following steps:
 a) transforming a population of plant cells, with the cells of said population containing at least one marker protein capable of causing directly or indirectly a toxic effect for said population, with at least one nucleic acid sequence to be inserted in combination with at least one compound capable of reducing the expression, amount, activity and/or function of at least one marker protein, and
 b) selecting transformed plant cells whose genome contains said nucleic acid sequence and which have a growth advantage over nontransformed cells, due to the action of said compound, from said population of plant cells, the selection being carried out under conditions under which the marker protein can exert its toxic effect on the non-transformed cells.

In a preferred embodiment, the marker protein is a protein capable of converting directly or indirectly a substance X which is nontoxic for said population of plant cells into a substance Y which is toxic for said population. In this case, the process of the invention preferably comprises the following steps:
 a) transforming the population of plant cells with at least one nucleic acid sequence to be inserted in combination with at least one compound capable of reducing the expression, amount, activity and/or function of at least one marker protein, and
 b) treating said population of plant cells with the substance X at a concentration which causes a toxic effect for nontransformed cells, due to the conversion by the marker protein, and
 c) selecting transformed plant cells whose genome contains said inserted nucleic acid sequence and which have a growth advantage over nontransformed cells, due to the action of said compound, from said population of plant cells, the selection being carried out under conditions under which the marker protein can exert its toxic effect on the nontransformed cells.

The nontoxic substance X is preferably a substance which does not naturally occur in plant cells or organisms or occurs naturally therein only at a concentration which can essentially not cause any toxic effect. In the scope of the process of the invention, preference is given to applying the nontoxic substance X exogenously, for example via the medium or the growth substrate.

The term "compound capable of reducing the expression, amount, activity and/or function of at least one marker protein" is to be understood broadly and generally means any compounds which cause, directly or indirectly, alone or in cooperation with other factors, a reduction in the amount of protein, amount of RNA, gene activity, protein activity or protein function of at least one marker protein. Said compounds are also referred to under the generic term "anti-marker protein" compounds. The term "anti-marker protein" compound includes in particular, but is not limited to, the nucleic acid sequences, ribonucleic acid sequences, double-stranded ribonucleic acid sequences, antisense ribonucleic acid sequences, expression cassettes, peptides, proteins or other factors used in the preferred embodiments within the scope of the process of the invention.

In a preferred embodiment, "anti-marker protein" compound means a DNA construct comprising
 a) at least one expression cassette suitable for expressing a ribonucleic acid sequence and/or, if appropriate, a protein, said nucleic acid sequence and/or protein being capable of reducing the expression, amount, activity and/or function of the marker protein, or
 b) at least one sequence which causes a partial or complete deletion or inversion of the sequence coding for said marker protein and thus enables the expression, amount, activity and/or function of the marker protein to be reduced, and also, if appropriate, further functional elements which facilitate and/or promote said deletion or inversion, or c) at least one sequence which causes an insertion into the sequence coding for said marker protein and thus enables the expression, amount, activity and/or function of the marker protein to be reduced, and also, if appropriate, further functional elements which facilitate and/or promote said insertion.

The process of the invention stops the negative-selective action of the marker protein. To this extent, an "anti-marker protein" compound acts directly (e.g. via inactivation by means of insertion into the gene coding for the marker protein) or indirectly (e.g. by means of the ribonucleic acid sequence expressed via the expression cassette and/or, where appropriate, of the protein translated therefrom) as a positive selection marker. Hence, the selection system of the invention is to be referred to as a "reverse selection system", since it "reverts" the negative-selective action of the marker protein.

The process of the invention means a drastic broadening of the repertoire of positive selection processes for selecting transformed plant cells.

Another advantage is the fact that in a particular, preferred embodiment (e.g. via the action of a double-stranded or anti-sense RNA), it is possible to implement the selection effect without expressing a foreign protein (see below).

It is also advantageous that the marker protein used indirectly for selection (e.g. the negative selection marker) is not coupled genetically to the nucleic acid sequence to be inserted into the genome. In contrast to the otherwise customary selection processes, the marker protein, if it is a transgene, may be removed by simple segregation in the course of subsequent propagation or crossing.

"Plant cell" means within the scope of the present invention any type of cell which has been derived from a plant organism or is present therein. In this context, the term includes by way of example protoplasts, callus or cell cultures, microspores, pollen, cells in the form of tissues such as leaves, meristem, flowers, embryos, roots, etc. Included are, in particular, all of those cells and cell populations which are suitable as target tissues for a transformation.

In this context, "plant organism" comprises any organism capable of photosynthesis and also the cells, tissues, parts or propagation material (such as seeds or fruits) derived therefrom. Included within the scope of the invention are all genera and species of higher and lower plants of the plant kingdom. Preference is given to annual, perennial, monocotyledonous and dicotyledonous plants and also gymnosperms.

"Plant" means within the scope of the invention all genera and species of higher and lower plants of the plant kingdom. The term includes the mature plants, seed, shoots and seedlings, and also parts, propagation material (for example tubers, seeds or fruits), plant organs, tissues, protoplasts, callus and other cultures, for example cell cultures, derived therefrom, and also any other types of groupings of plant cells to give functional or structural units. Mature plants means plants at any developmental stage beyond that of the seedling. Seedling means a young immature plant at an early developmental stage. "Plant" comprises all annual and perennial monocotyledonous and dicotyledonous plants and includes by way of example but not by limitation those of the genera *Cucurbita, Rosa, Vitis, Juglans, Fragaria, Lotus, Medicago, Onobrychis, Trifolium, Trigonella, Vigna, Citrus, Linum, Geranium, Manihot, Daucus, Arabidopsis, Brassica, Raphanus, Sinapis, Atropa, Capsicum, Datura, Hyoscyamus, Lycopersicon, Nicotiana, Solarium, Petunia, Digitalis, Majorana, Cichorium, Helianthus, Lactuca, Bromus, Asparagus, Antirrhinum, Heterocallis, Nemesis, Pelargonium, Panieum, Pennisetum, Ranunculus, Senecio, Salpiglossis, Cucumis, Browaalia, Glycine, Pisum, Phaseolus, Lolium, Oryza, Zea, Avena, Hordeum, Secale, Triticum, Sorghum, Picea* and *Populus.*

Preference is given to plants of the following plant families: Amaranthaceae, Asteraceae, Brassicaceae, Carophyllaceae, Chenopodiaceae, Compositae, Cruciferae, Cucurbitaceae, Labiatae, Leguminosae, Papilionoideae, Liliaceae, Linaceae, Malvaceae, Rosaceae, Rubiaceae, Saxifragaceae, Scrophulariaceae, Solanacea, Sterculiaceae, Tetragoniacea, Theaceae, Umbelliferae.

Preferred monocotyledonous plants are selected in particular from the monocotyledonous crop plants such as, for example, those in the family of Gramineae such as alfalfa, rice, corn, wheat or other cereal species such as barley, millet, rye, triticale or oats and also from sugar cane and all grass species.

Preferred dicotyledonous plants are selected in particular from the dicotyledonous crop plants such as, for example, Asteraceae, such as sunflower, tagetes or *calendula* and others, Compositae, in particular the genus *Lactuca*, very especially the species sativa (lettuce) and others, Cruciferae, especially the genus *Brassica*, very especially the species *napus* (oilseed rape), *campestris* (beet), *oleracea* cv Tastie (cabbage), *oleracea* cv Snowball Y (cauliflower) and *oleracea* cv Emperor (broccoli) and other cabbage species; and the genus *Arabidopsis*, very especially the species *thaliana*, and cress or canola and others, Cucurbitaceae, such as melon, pumpkin/squash or zucchini and others, Leguminosae, especially the genus *Glycine*, very especially the species *max* (soybean) and alfalfa, pea, bean plant or peanut, and others Rubiaceae, preferably the subclass Lamiidae, such as, for example, *Coffea arabica* or *Coffea liberica* (coffee bush) and others, Solanaceae, in particular the genus *Lycopersicon*, very especially the species *esculentum* (tomato), the genus *Solanum*, very especially the species *tuberosum* (potato) and *melongena* (eggplant), and the genus *Capsicum*, very especially the species *annuum* (pepper) and tobacco and others, Sterculiaceae, preferably the subclass Dilleniidae, such as, for example, *Theobroma cacao* (cacao tree) and others, Theaceae, preferably the subclass Dilleniidae, such as, for example, *Camellia sinensis* or *Thea sinensis* (tea shrub) and others, Umbelliferae, especially the genus *Daucus* (very especially the species *carota* (carrot)) and *Apium* (very especially the species *graveolens dulce* (celery)) and others, and linseed, cotton, hemp, flax, cucumber, spinach, carrot, sugar beet and the various tree, nut and grapevine species, in particular banana and kiwi.

Plant organisms for the purposes of the invention are furthermore other photosynthetically active capable organisms such as, for example, algae, cyanobacteria and mosses. Preferred algae are green algae such as, for example, algae of the genus *Haematococcus, Phaedactylum tricornatum, Volvox* or *Dunaliella*. Particular preference is given to *Synechocystis*.

Particular preference is given to the group of plants, consisting of wheat, oats, millet, barley, rye, corn, rice, buckwheat, sorghum, triticale, spelt, linseed, sugar cane, oilseed rape, cress, *Arabidopsis*, cabbage species, soybean, alfalfa, pea, bean plants, peanut, potato, tobacco, tomato, eggplant, paprika, sunflower, tagetes, lettuce, *calendula*, melon, pumpkin and zucchini.

Most preference is given to
a) plants suitable for producing oil, such as, for example, oilseed rape, sunflower, sesame, safflower (*Carthamus tinctorius*), olive tree, soybean, corn, peanut, *ricinus*, oil palm, wheat, cacao tree or various nut species such as, for example, walnut, coconut or almond. Among these, particular preference is in turn given to dicotyledonous plants, in particular oilseed rape, soybean and sunflower.
b) plants suitable for producing starch, such as corn, wheat or potato, for example.
c) plants which are utilized as food and/or feedstuff and/or as useful plants and in which a resistance to pathogens would be advantageous, such as barley, rye, rice, potato, cotton, flax or linseed, for example.
d) plants which may be suitable for producing fine chemicals such as, for example, vitamins and/or carotenoids, such as oilseed rape, for example.

"Population of plant cells" means any group of plant cells, which may be subjected within the scope of the present invention to a transformation and from which transgenic plant cells transformed by the process of the invention may be obtained and isolated. In this context, said population may also be, for example, a plant tissue, organ or a cell culture, etc. Said population may comprise by way of example but not by limitation an isolated zygote, an isolated immature embryo, embryogenic callus, plant or else various flower tissues (both in vitro and in vivo).

"Genome" means the entirety of genetic information of a plant cell and comprises both genetic information of the nucleus and that of the plastids (e.g. chloroplasts) and mitochondria. However, genome preferably means the genetic information of the nucleus (for example of the nuclear chromosomes).

"Selection" means identifying and/or isolating successfully transformed plant cells from a population of nontransformed cells by using the process of the invention. This does not necessarily require that the selection be carried out directly with the transformed cells immediately after transformation. It is also possible to carry out the selection only at a later time, even with a later generation of the plant organisms (or cells, tissues, organs or propagation material derived therefrom) resulting from the transformation. Thus it is possible, for example, to transform *Arabidopsis* plants directly using, for example, the vacuum infiltration method (Clough S & Bent A (1998) Plant J 16(6):735-43; Bechtold N et al. (1993) CR Acad Sci Paris 1144(2):204-212), which subsequently produce transgenic seeds which may then be subjected to selection.

The fact that the nucleic acid sequence to be inserted is transformed "in combination with" the "anti-marker protein" compound (e.g. a DNA construct) is to be understood broadly and means that at least one nucleic acid, sequence to be inserted and at least one "anti-marker protein" compound are functionally coupled to one another so that the presence of the "anti-marker protein" compound in the plant cell, and of the selection advantage related thereto, indicates the parallel presence of the inserted nucleic acid sequence as likely. The nucleic acid sequence to be inserted and the "anti-marker protein" compound (e.g. a DNA construct) here may be, preferably but not necessarily, part of a single nucleic acid construct (e.g. a transformation construct or transformation vector), i.e. be present physicochemically coupled via a covalent bond. However, they may also be jointly introduced separately, for example in the course of a cotransformation, and exert their function within the scope of the process of the invention also in this way. In the case of the "anti-marker protein compound" acting via expressing an RNA (e.g. an antisense RNA or double-stranded RNA) or being such an RNA, "in combination" may also include those embodiments in which said RNA and the RNA expressed by the nucleic acid sequence inserted into the genome form an RNA strand.

"Nontoxic substance X" generally means substances which, compared to their reaction product Y, under otherwise identical conditions, have a reduced, preferably an essentially lacking biological activity, preferably toxicity. In this context, the toxicity of substance Y is at least twice as high as that of substance X, preferably at least five times as high, particularly preferably at least ten times as high, very particularly preferably at least twenty times as high, most preferably at least one hundred times as high. "Identical conditions" here means that all conditions are kept the same, apart from the different substances X and Y. Accordingly, identical molar concentrations of X and Y are used, with the medium, temperature, type of organism and density of organism, etc. being the same. The substance X may be converted to the substance Y in various ways, for example by hydrolysis, deamination, hydrolysis, dephosphorylation, phosphorylation, oxidation or any other type of activation, metabolization or conversion. The substance X may be, by way of example but not by limitation, the inactive precursor or derivative of a plant growth regulator or herbicide.

"Toxicity" or "toxic effect" means a measurable, negative influence on the physiology of the plant or of the plant cell and may comprise here symptoms such as, for example, but not limited thereto, a reduced or disrupted growth, a reduced or disrupted rate of photosynthesis, a reduced or disrupted cell division, a reduced or disrupted regeneration of a complete plant from cell culture or callus, etc.

The plant cells successfully transformed by means of the process of the invention may, to put it differently, have a growth advantage or selection advantage over the nontransformed cells of the same starting population under the influence of the substance "X". Growth or selection advantage is to be understood here broadly and means, for example, the fact that said transformed plant cells are capable of forming shoots and/or can be regenerated to give complete plants, whereas the nontransformed cells can do this only with a marked delay, if at all.

The term of "marker protein" is to be understood broadly and generally means all of those proteins which are capable of
i) exerting per se a toxic effect on the plant or plant cell, or
ii) converting directly or indirectly a nontoxic substance X into a substance Y which is toxic for the plant or plant cell.

In this context, the marker protein may be a plant-intrinsic, endogenous gene or else a transgene from a different organism. Preferably, the marker protein itself has no essential function for the organism including the marker protein. If the marker protein per se exerts a toxic effect, then it will preferably be expressed, for example, under an inducible promoter rather than constitutively.

Preferably, however, the marker protein converts directly or indirectly a nontoxic substance X into a substance Y which is toxic for the plant or plant cell. Particularly preferred marker proteins are the "negative selection markers" as are used, for example, in the course of targeted deletions from the genome.

Examples of marker proteins which may be mentioned but which are not limiting are:
(a) cytosine deaminases (CodA or CDase), with preference being given to using as the nontoxic substance X substances such as 5-fluorocytosine (5-FC). Cytosine deaminases catalyze the deamination of cytosine to give uracil (Kilstrup M et al. (1989) J Bacteriol 171:2124-2127; Anderson L et al. (1989) Arch Microbiol 152:115-118). Bacteria and fungi which have CDase activity convert 5-FC to the toxic metabolite ("Y") 5-fluorouracil (5-FU) (Polak A & Scholer H J (1975) Chemotherapy (Basel) 21:113-130). 5-FC itself has low toxicity (Bennett J E, in Goodman and Gilman: the Pharmacological Basis of Therapeutics. 8th ed., eds. Gilman A G et al. (Pergamon Press, New York) pp. 1165-1181). However, 5-FU has a highly cytotoxic effect, since it is subsequently metabolized to fluoro-UTP (FUTP) and fluoro-dUMP (FdUMP) and thus inhibits RNA and DNA synthesis (Calabrisi P & Chabner B A in Goodman and Gilman: the Pharmacological Basis of Therapeutics. 8th ed., eds. Gilman A G et al. (Pergamon Press, New York) pp. 1209-1263); Damon L E et al. (1989) Pharmac Ther 43:155-189).

Cells of higher plants and mammalian cells have no significant CDase activity and cannot deaminase 5-FC (Polak A et al. (1976) Chemotherapy 22:137-153; Koechlin B A et al. (1966) Biochemical Pharmacology 15:434-446). In this respect, the CDase is introduced as a transgene (e.g. in the form of a transgenic expression cassette) into plant organisms in the course of the process of the invention. Corresponding transgenic plant cells or organisms are then used as masterplants as starting material. Appropriate CDase sequences, transgenic plant organisms and the process of carrying out negative selection processes using, for example, 5-FC as nontoxic substance X, are known to the skilled worker (WO 93/01281; U.S. Pat. No. 5,358,866; Gleave A P et al. (1999) Plant Mol Biol 40(2):223-35; Perera R J et al. (1993) Plant Mol Biol 23(4):793-799; Stougaard J (1993) Plant J 3:755-761); EP-A1 595 837; Mullen C A et al. (1992) Proc Natl Acad Sci USA 89(1): 33-37; Kobayashi T et al. (1995) Jpn J Genet 70(3):409-422; Schlaman H R M & Hooykaas P F F (1997) Plant J 11:1377-1385; Xiaohui Wang H et al. (2001) Gene 272(1-2): 249-255; Koprek T et al. (1999) Plant J 19(6):719-726; Gleave A P et al. (1999) Plant Mol Biol 40(2):223-235; Gallego M E (1999) Plant Mol Biol 39(1):83-93; Salomon S & Puchta H (1998) EMBO J 17(20):6086-6095; Thykjaer T et al. (1997) Plant Mol Biol 35(4):523-530; Serino G (1997) Plant J 12(3):697-701; Risseeuw E (1997) Plant J 11(4):717-728; Blanc V et al. (1996) Biochimie 78(6):511-517; Corneille S et al. (2001) Plant J 27:171-178). Cytosine deaminases and the genes coding therefor may be obtained from a multiplicity of organisms, preferably microorganisms such as, for example, the fungi *Cryptococcus neoformans, Candida albicans, Torulopsis glabrata, Sporothrix schenckii, Aspergillus, Cladosporium* and *Phialophora* (J E Bennett, Chapter 50: Antifungal Agents, in Goodman and Gilman's the Pharmacological Basis of Therapeutics 8th ed., A. G. Gilman, ed., Pergamon Press, New York, 1990) and the bacteria *E. coli* and *Salmonella typhimurium* (Andersen L et al. (1989) Arch Microbiol 152:115-118). The sequences, materials and processes disclosed in the context of said publications are hereby explicitly referred to.

Particular preference is given to sequences according to GenBank Acc. No: S56903, and to the modified codA sequences described in EP-A1 595 873, which make expression in eukaryotes possible. Preference is given here to nucleic acid sequences coding for polypeptides according to SEQ ID NO: 2 or, preferably, 4, in particular the sequences according to SEQ ID NO: 1 or, preferably, 3.

(b) cytochrome P-450 enzymes, in particular the bacterial cytochrome P-450 SU1 gene product (CYP105A1) from *Streptomyces griseolus* (strain ATCC 11796), with preference being given to using as nontoxic substance X substances such as the pro sulfonylurea herbicide R7402 (2-methylethyl-2-3-dihydro-N-[(4,6-dimethoxypyrimidin-2-yl)aminocarbonyl]-1,2-benzoisothiazole-7-sulfonamide 1,1-dioxide). Corresponding sequences and the process of carrying out negative selection processes using, for example, R7402 as nontoxic substance X are known to the skilled worker (O'Keefe D P et al. (1994) Plant Physiol 105:473-482; Tissier A F et al. (1999) Plant Cell 11:1841-1852; Koprek T et al. (1999) Plant J 19(6):719-726; O'Keefe D P (1991) Biochemistry 30(2):447-55). The sequences, materials and processes disclosed in the context of said publications are hereby explicitly referred to.

Particular preference is given to sequences according to GenBank Acc. No: M32238. Preference is further given to nucleic acid sequences coding for the polypeptide according to SEQ ID NO: 6, in particular the sequence according to SEQ ID NO: 5.

(c) indoleacetic acid hydrolases such as, for example, *Agrobacterium tumefaciens*, tms2 gene product, with preference being given to using as nontoxic substance X substances such as auxin amide compounds or naphthaleneacetamide (NAM) (with NAM being converted to naphthaleneacetic acid, a phytotoxic substance). Corresponding sequences and the process of carrying out negative selection processes using, for example, NAM as nontoxic substance X are known to the skilled worker (Fedoroff N V & Smith D L (1993) Plant J 3:273-289; Upadhyaya N M et al. (2000) Plant Mol Biol Rep 18:227-223; Depicker A G et al. (1988) Plant Cell rep 104:1067-1071; Karlin-Neumannn G A et al. (1991) Plant Cell 3:573-582; Sundaresan V et al. (1995) Gene Develop 9:1797-1810; Cecchini E et al. (1998) Mutat Res 401(1-2):199-206; Zubko E et al. (2000) Nat Biotechnol 18:442-445). The sequences, materials and processes disclosed in the context of said publications are hereby explicitly referred to.

Particular preference is given to sequences according to GenBank Acc. No: NC_003308 (Protein_id="NP_536128.1), AE009419, AB016260 (Protein_id="BAA87807.1) and NC002147. Preference is further given to nucleic acid sequences coding for polypeptides according to SEQ ID NO: 8 or 10, in particular the sequences according to SEQ ID NO: 7 or 9.

(d) haloalkane dehalogenases (dhlA gene product), for example from *Xanthobacter autotropicus* GJ10. The dehalogenase hydrolyzes dihaloalkanes such as 1,2-dichloroethane (DCE) to give halogenated alcohols and inorganic halides (Naested H et al. (1999) Plant J 18(5)571-576; Janssen D B. et al. (1994) Annu Rev Microbiol 48: 163-191; Janssen D B (1989) J Bacteriol 171(12):6791-9). The sequences, materials and processes disclosed in the context of said publications are hereby explicitly referred to.

Particular preference is given to sequences according to GenBank Acc. No: M26950. Preference is further given to nucleic acid sequences coding for the polypeptide according to SEQ ID NO: 12, in particular the sequence according to SEQ ID NO: 11.

(e) thymidine kinases (TK), in particular viral TKs from viruses such as Herpes simplex virus, SV40, cytomegalovirus, Varicella zoster virus, in particular the TK of Herpes simplex virus type 1 (TK HSV-1), with preference being given to using as nontoxic substance X substances such as Acyclovir, Ganciclovir or 1,2-deoxy-2-fluoro-β-D- arabinofuranosil-5-iodouracil (FIAU). Corresponding sequences and the process of carrying out negative selection processes using, for example, Acyclovir, Ganciclovir or FIAU as nontoxic substance X are known to the skilled worker (Czako M & Marton L (1994) Plant Physiol 104: 1067-1071; Wigler M et al. (1977) Cell 11(1):223-232; McKnight S L et al. (1980) Nucl Acids Res 8(24):5949-5964; McKnight S L et al. (1980) Nucl Acids Res 8(24): 5931-5948; Preston et al. (1981) J Virol 38(2):593-605; Wagner et al. (1981) Proc Natl Acad Sci USA 78(3):1441-1445; St. Clair et al. (1987) Antimicrob Agents Chemother 31(6):844-849). The sequences, materials and processes disclosed in the context of said publications are hereby explicitly referred to.

Particular preference is given to sequences according to GenBank Acc. No: J02224, V00470 and V00467. Preference is also given to nucleic acid sequences coding for polypeptides according to SEQ ID NO: 14 or 16, in particular the sequences according to SEQ ID NO: 13 or 15.

(f) guanine phosphoribosyl transferases, hypoxanthine phosphoribosyl transferases or xanthine guanine phosphoribosyl transferases, with preference being given to using as nontoxic substance X substances such as 6-thioxanthine or allopurinol. Preference is given to guanine phosphoribosyl transferases (gpt), for example from *E. Coli* (Besnard et al. (1987) Mol Cell Biol 7:4139; Mzoz and Moolten (1993) Human Gene Therapy 4:589-595; Ono et al. (1997) Hum Gene Ther 8(17):2043-55), hypoxanthine phosphoribosyl transferases (HPRT; Jolly et al. (1983) Proc Natl Acad Sci USA 80:477; Fonwick "The HGPRT Systern", pp. 333-373, M. Gottesman (ed.), Molecular Cell Genetics, John Wiley and Sons, New York, 1985), xanthine guanine phosphoribosyl transferases, for example from *Toxoplasma gondii* (Knoll L J et al. (1998) Mol Cell Biol 18(2):807-814; Donald R G et al. (1996) J Biol Chem 271(24):14010-14019). The sequences, materials and processes disclosed in the context of said publications are hereby explicitly referred to.

Particular preference is given to sequences according to GenBank Acc. No: U10247 (*Toxoplasma gondii* HXG-PRT), M13422 (*E. coli* gpt) and X00221 (*E. coli* gpt). Preference is also given to nucleic acid sequences coding for polypeptides according to SEQ ID NO: 18, 20 or 22, in particular the sequences according to SEQ ID NO: 17, 19 or 21.

(g) purine nucleoside phosphorylases (PNP; DeoD gene product), for example from *E. coli*, with preference being given to using as nontoxic substance X substances such as 6-methylpurine deoxyribonucleoside. Corresponding sequences and the process of carrying out negative selection processes using, for example, 6-methylpurine deoxyribonucleoside as nontoxic substance X are known to the skilled worker (Sorscher E J et al. (1994) Gene Therapy 1:233-238). The sequences, materials and processes disclosed in the context of said publications are hereby explicitly referred to.

Particular preference is given to sequences according to GenBank Acc. No: M60917. Preference is also given to nucleic acid sequences coding for the polypeptide according to SEQ ID NO: 24, in particular the sequence according to SEQ ID NO: 23.

h) phosphonate monoester hydrolases which convert inactive ester derivatives of the herbicide glyphosate (e.g. glycerylglyphosate) into the active form of the herbicide. Corresponding sequences and the process of carrying out negative selection processes using, for example, glycerylglyphosate are known to the skilled worker (U.S. Pat. No. 5,254,801; Dotson S B et al. (1996) Plant J 10(2): 383-392; Dotson S B et al. (1996) J Biol Chem 271(42): 25754-25761). The sequences, materials and processes disclosed in the context of said publications are hereby explicitly referred to.

Particular preference is given to sequences according to GenBank Acc. No: U44852. Preference is also given to nucleic acid sequences coding for the polypeptide according to SEQ ID NO: 26, in particular the sequence according to SEQ ID NO: 25.

(i) aux-1 and, preferably, aux-2 gene products, for example of the Ti plasmids of *Agrobacterium* strains such as *A. rhizogenes* or *A. tumefaciens* (Beclin C et al. (1993) Transgenics Res 2:4855); Gaudin V, Jouanin L. (1995) Plant Mol. Biol. 28(1):123-36.

The activity of the two enzymes causes the plant cell to produce indoleacetamide (IAA). Aux-1 encodes an indoleacetamide synthase (IAMS) and converts tryptophan into indoleacetamide (VanOnckelen et al. (1986) FEBS Lett. 198: 357-360). Aux-2 encodes the enzyme indoleacetamide hydrolase (IAMH) and converts indoleacetamide, a substance without phytohormone activity, into the active auxin indoleacetic acid (Inze D et al. (1984) Mol Gen Genet 194:265-274; Tomashow et al. (1984) Proc Natl Acad Sci USA 81:5071-5075; Schroder et al. (1984) Eur J Biochem 138:387-391). The enzyme IAMH may also hydrolyze a number of indoleamide substrates such as, for example, naphthaleneacetamide, the latter being converted into the plant growth regulator naphthaleneacetic acid (NAA). The use of the IAMH gene as a negative selection marker is described, for example, in U.S. Pat. No. 5,180,873. Corresponding enzymes have also been described in *A. rhizogenes, A. vitis* (Canaday J et al. (1992) Mol Gen Genet 235:292-303) and *Pseudomonas savastanoi* (Yamada et al. (1985) Proc Natl Acad Sci USA 82:6522-6526). The use as a negative selection marker for destroying particular cell tissues (e.g. pollen; U.S. Pat. No. 5,426,041) or transgenic plants (U.S. Pat. No. 5,180,873) has been described. Corresponding sequences and the process of carrying out negative selection processes using, for example, naphthaleneacetamide are known to the skilled worker (see above). The sequences, materials and processes disclosed in the context of said publications are hereby explicitly referred to.

Particular preference is given to sequences according to the GenBank Acc. No: M61151, AF039169 and AB025110. Preference is also given to nucleic acid sequences coding for polypeptides according to SEQ ID NO: 28, 30, 32, 34 or 36, in particular the sequences according to SEQ ID NO: 27, 29, 31, 33 or 35.

(j) adenine phosphoribosyl transferases (APRT), with preference being given to using as nontoxic substance X substances such as 4-aminopyrazolopyrimidine. Corresponding sequences and the process of carrying out negative selection processes with use are known to the skilled worker (Wigler M et al. (1979) Proc Natl Acad Sci USA 76(3):1373-6; Taylor et al. "The APRT Systern", pp., 311-332, M. Gottesman (ed.), Molecular Cell Genetics, John Wiley and Sons, New York, 1985).

k) methoxinine dehydrogenases, with preference being given to using as nontoxic substance X substances such as 2-amino-4-methoxybutanoic acid (methoxinine) which is converted into the toxic methoxyvinyl glycine (Margraff R et al. (1980) Experimentia 36: 846).

l) rhizobitoxin synthases, with preference being given to using as nontoxic substance X substances such as 2-amino-4-methoxybutanoic acid (methoxinine) which is converted into the toxic 2-amino-4-[2-amino-3-hydroxypropyl]-trans-3-butanoic acid (rhizobitoxin) (Owens L D et al. (1973) Weed Science 21:63-66), m) 5-methylthioribose (MTR) kinases, with preference being given to using as nontoxic substance X substances such as 5-(trifluoromethyl)thioribose (MTR analog, "subversive substrate") which is converted, via an unstable intermediate, into the toxic substance (Y) carbothionyl difluoride. The MTR kinase is a key enzyme of the methionine salvage pathway. Corresponding enzyme activities have been described in plants, bacteria and protozoa but not in mammals. MTR kinases of various species have been identified owing to defined sequence motifs (Sekowska A et al. (2001) BMC Microbiol 1:15. Corresponding sequences and the process of carrying out negative selection processes using, for example, 5-(trifluoromethyl)thioribose are known to the skilled worker and readily obtainable from the appropriate sequence database (e.g. GenBank) (Sekowska A et al. (2001) BMC Microbiol 1:15; Cornell K A et al. (1996) 317:285-290). The sequences, materials and processes disclosed in the context of said publications we hereby explicitly referred to.

However, a plant MTR kinase has not yet been identified unambiguously and is provided within the scope of the process of the invention (SEQ ID NO: 39 and, respectively, 40). In addition, homologs from other plant species are provided, namely from corn (SEQ ID NO: 59 and, respectively, 60), oilseed rape (SEQ ID NO: 61, 63 and, respectively, 62, 64), rice (SEQ ID NO: 65 and, respectively, 66) and soybean (SEQ ID NO: 67 and, respectively, 68).

Accordingly, the invention further relates to amino acid sequences encoding a plant 5-methylthioribose kinase, wherein said amino acid sequence contains at least one sequence selected from the group consisting of SEQ ID NO: 60, 62, 64, 66 or 68.

Accordingly, the invention further relates to nucleic acid sequences encoding a plant 5-methylthioribose kinase, wherein said nucleic acid sequence contains at least one sequence selected from the group consisting of SEQ ID NO: 59, 61, 63, 65 or 67. Even if said sequences are in parts only fragments of complete cDNAs, their length is nevertheless more than sufficient in order to ensure a use and functionality as antisense RNA or double-stranded RNA.

Preference is given to using as marker protein a plant endogenous MTR kinase. Further endogenous plant MTR kinases may readily be identified by means of screening databases or gene libraries using conserved, MTK kinase-typical motifs. Said motifs may be derived from FIG. 9*a-b*, for example. Such motifs may comprise, by way of example but not by limitation, the following sequences:

E(V/I)GDGN(L/I)N(L/Y/F)V(F/Y)(SEQ ID NO: 72), preferably EVGDGNLN(Y/F)V(F/Y)(SEQ ID NO: 73)

KQALPY(V/I)RC(SEQ ID NO: 74)

SWPMT(R/K)ERAYF(SEQ ID NO: 75)

PEVYHFDRT(SEQ ID NO: 76)

GMRY(I/L)EPPHI(SEQ ID NO: 77)

CRLTEQVVFSDPY(SEQ ID NO: 78)

HGDLH(S/T)GS(SEQ ID NO: 79)

Further suitable motifs may be derived from FIG. 9*a-b* without difficulty.

Particular preference is given to sequences according to GenBank Acc. No: AF212863 or AC079674 (Protein_ID=AAG51775.1). Preference is also given to nucleic acid sequences coding for polypeptides according to SEQ ID NO: 38 or 40, in particular the sequences according to SEQ ID NO: 37 or 39.)

(n) alcohol dehydrogenases (Adh), in particular plant Adh-1 gene products, with preference being given to using as nontoxic substance X substances such as allyl alcohol which is converted in this manner into the toxic substance (Y) acrolein. Corresponding sequences and the process of carrying out negative selection processes using, for example, allyl alcohol are known to the skilled worker and readily obtainable from the appropriate sequence database (e.g. GenBank) (Wisman E et al. (1991) Mol Gen Genet 226(1-2):120-8; Jacobs M et al. (1988) Biochem Genet 26(1-2):105-22; Schwartz D. (1981) Environ Health Perspect 37:75-7). The sequences, materials and processes disclosed in the context of said publications are hereby explicitly referred to.

Particular preference is given to sequences according to GenBank Acc. No: X77943, M12196, AF172282, X04049 or AF253472. Preference is also given to nucleic acid sequences coding for polypeptides according to SEQ ID NO: 42, 44, 46 or 48, in particular the sequences according to SEQ ID NO: 41, 43, 45 or 47.

(o) Further suitable negative selection markers are those sequences which exert per se a toxic action on plant cells, such as, for example, diphtheria toxin A, ribonucleases such as barnase and also ribosome-inhibiting proteins such as ricin. In this context, these proteins are preferably expressed in the plant cells inducibly rather than constitutively. The induction is preferably carried out chemically, it being possible, for example, to use the chemically inducible promoters mentioned below in order to ensure said chemically induced expression.

"Reduction" or "to reduce" is to be interpreted broadly in connection with a marker protein or with its amount, expression, activity and/or function and comprises the partial or essentially complete stopping or blocking, based on different cell-biological mechanisms, of the functionality of a marker protein in a plant cell, plant or a part, tissue, organ, cells or seeds derived therefrom.

A reduction for the purpose of the invention also comprises a reduction of the amount of a marker protein down to an essentially complete lack of said marker protein (i.e. a lack of detectability of marker protein activity or marker protein function or a lack of immunological detectability of said marker protein). In this context, expression of a particular marker protein (or of its amount, expression, activity and/or function) in a cell or an organism is reduced preferably by more than 50%, particularly preferably by more than 80%, very particularly preferably by more than 90%, most preferably by more than 98%. Reduction means in particular also the complete lack of the marker protein (or of its amount, expression, activity and/or function). In this context, activity and/or function mean preferably the property of the marker protein of exerting a toxic effect on the plant cell or the plant organism and, respectively, the ability to convert the substance X into the substance Y. The toxic effect caused by the marker protein is reduced preferably by more than 50%, particularly preferably by more than 80%, very particularly preferably by more than 90%, most preferably by more than 98%. "Reduction" includes of course within the scope of the present invention also a complete, 100% reduction or removal of the marker protein (or of its amount, expression, activity and/or function) (for example by deleting the marker protein gene from the genome).

The invention comprises various strategies for reducing the expression, amount, activity and/or function of the marker protein. The skilled worker appreciates the fact that a number of various methods are available in order to influence the expression, amount, activity and/or function of a marker protein in the desired way. Examples which may be mentioned but which are not limiting are:

a) introducing at least one marker protein double-stranded ribonucleic acid sequence (MP-dsRNA) or an expression cassette or expression cassettes ensuring expression thereof. Included are those processes in which the MP-dsRNA is directed against a marker protein gene (i.e. genomic DNA sequences such as promoter sequences) or a marker protein gene transcript (i.e. mRNA sequences).

b) introducing at least one marker protein antisense ribonucleic acid sequence (MP-antisenseRNA) or an expression cassette ensuring expression thereof. Included are those processes in which the MP-antisenseRNA is directed against a marker protein gene (i.e. genomic DNA sequences) or a marker protein gene transcript (i.e. RNA sequences). α-anomeric nucleic acid sequences are also included.

c) introducing at least one MP-antisenseRNA combined with a ribozyme or an expression cassette ensuring expression thereof d) introducing at least one marker protein sense ribonucleic acid sequence (MP-senseRNA) for inducing a cosuppression or an expression cassette ensuring expression thereof e) introducing at least one DNA- or protein-binding factor against a marker protein gene, marker protein RNA or marker protein or an expression cassette ensuring expression thereof f) introducing at least one viral nucleic acid sequence causing degradation of the marker protein RNA or an expression cassette ensuring expression thereof g) introducing at least one construct for generating a functional loss (e.g. generation of stop codons, shifts in the reading frame etc.) on a marker protein gene, for example by generating an insertion, deletion, inversion or mutation in a marker protein gene. Preferably, knockout mutants may be generated by means of targeted insertion into said marker protein gene via homologous recombination or by introducing sequence-specific nucleases against marker protein gene sequences.

It is known to the skilled worker that it is also possible to use other processes within the scope of the present invention in order to reduce a marker protein or its activity or function. For example, it may also be advantageous, depending on the type of the marker protein used, to introduce a dominant-negative variant of a marker protein or an expression cassette ensuring expression thereof. In this context, any single one of these processes may cause a reduction in the expression, amount, activity and/or function of a marker protein. A combined application is also conceivable. Further methods are known to the skilled worker and may comprise hindering or stopping the processing of the marker protein, the transport of the marker protein or of its mRNA, the inhibition of ribosome attachment, the inhibition of RNA splicing, the induction of an enzyme degrading marker protein RNA and/or the inhibition of translational elongation or termination.

The embodiments below will describe by way of example the individual preferred processes:

a) Introducing a double-stranded ribonucleic acid sequence of a marker protein (MP-dsRNA)

The process of gene regulation by means of double-stranded RNA ("double-stranded RNA interference"; dsRNAi) has been described many times for animal and plant organisms (e.g. Matzke M A et al. (2000) Plant Mol Biol 43:401-415; Fire A. et al (1998) Nature 391:806-811; WO 99/32619; WO 99/53050; WO 00/68374; WO 00/44914; WO 00/44895; WO 00/49035; WO 00/63364). The processes and methods described in the references indicated are hereby explicitly referred to. dsRNAi processes are based on the phenomenon that simultaneously introducing the complementary strand and contour strand of a gene transcript suppresses expression of the corresponding gene in a highly efficient manner. Preferably, the phenotype caused is very similar to that of a corresponding knockout mutant (Waterhouse P M et al. (1998) Proc Natl Acad Sci USA 95:13959-64). The dsRNAi process has proved to be particularly efficient and advantageous in reducing marker protein expression.

Double-stranded RNA molecule means within the scope of the invention preferably one or more ribonucleic acid sequences which, owing to complementary sequences, are theoretically (e.g. according to the base pair rules by Watson and Crick) and/or actually (e.g. owing to hybridization experiments in vitro and/or in vivo) capable of forming double-stranded RNA structures. The skilled worker is aware of the fact that the formation of double-stranded RNA structures represents a state of equilibrium. Preferably, the ratio of double-stranded molecules to corresponding dissociated forms is at least 1 to 10, preferably 1:1, particularly preferably 5:1, most preferably 10:1.

The invention therefore further relates to double-stranded RNA molecules (dsRNA-molecule) which, when introduced into a plant organism (or into a cell, tissue, organ or propagation material derived therefrom) cause the reduction of at least one marker protein. The double-stranded RNA molecule for reducing expression of a marker protein (MP-dsRNA) here preferably comprises a) a "sense" RNA strand comprising at least one ribonucleotide sequence which is essentially identical to at least a part of the "sense" RNA transcript of a nucleic acid sequence coding for a marker protein, and b) an "antisense" RNA strand which is essentially, preferably fully, complementary to the RNA sense strand under a).

With respect to the dsRNA molecules, marker protein nucleic acid sequence preferably means a sequence according to SEQ ID NO: 1, 3, 5, 7, 9, 11, 13, 15, 17, 19, 21, 23, 25, 27, 29, 31, 33, 35, 37, 39, 41, 43, 45 or 47 or a functional equivalent thereof.

"Essentially identical" means that the dsRNA sequence may also have insertions, deletions and also individual point mutations in comparison with the marker protein target sequence and nevertheless causes an efficient reduction in expression. The homology (as defined hereinbelow) between the "sense" strand of an inhibitory dsRNA and at least one part of the "sense" RNA transcript of a nucleic acid sequence coding for a market protein (or between the "antisense" strand of the complementary strand of a nucleic acid sequence coding for a marker protein) is preferably at least 75%, preferably at least 80%, very particularly preferably at least 90%, most preferably 100%.

A 100% sequence identity between dsRNA and a marker protein gene transcript is not absolutely necessary in order to cause an efficient reduction in marker protein expression. Consequently, the process is advantageously tolerant toward sequence deviations as may be present due to genetic mutations, polymorphisms or evolutionary divergences. Thus it is possible, for example, using the dsRNA which has been generated starting from the marker protein sequence of the first organism, to suppress marker protein expression in a second organism. This is particularly advantageous when the marker protein used is a plant-intrinsic, endogenous marker protein (for example a 5-methylthioribose kinase or alcohol dehydrogenase). For this purpose, the dsRNA preferably includes sequence regions of marker protein gene transcripts which correspond to conserved regions. Said conserved regions may be readily derived from sequence comparisons.

The length of the subsection is at least 10 bases, preferably at least 25 bases, particularly preferably at least 50 bases, very particularly preferably at least 100 bases, most preferably at least 200 bases or at least 300 bases.

Alternatively, an "essentially identical" dsRNA may also be defined as a nucleic acid sequence capable of hybridizing with part of a marker protein gene transcript (e.g. in 400 mM NaCl, 40 mM PIPES pH 6.4, 1 mM EDTA at 50° C. or 70° C. for 12 to 16 h).

"Essentially complementary" means that the "antisense" RNA strand may also have insertions, deletions and also individual point mutations in comparison with the complement of this "sense" RNA strand. The homology between the "antisense" RNA strand and the complement of the "sense" RNA strand is preferably at least 80%, preferably at least 90%, very particularly preferably at least 95%, most preferably 100%.

"Part of the "sense" RNA transcript" of a nucleic acid sequence coding for a marker protein means fragments of an RNA or mRNA transcribed or transcribable from a nucleic acid sequence coding for a marker protein, preferably from a marker protein gene. In this context, the fragments have a sequence length of preferably at least 20 bases, preferably at least 50 bases, particularly preferably at least 100 bases, very particularly preferably at least 200 bases, most preferably at least 500 bases. The complete transcribable RNA or mRNA is also included. Included are also sequences such as those which may be transcribed under artificial conditions from regions of a marker protein gene which are otherwise, under natural conditions, not transcribed, such as promoter regions, for example.

The dsRNA may consist of one or more strands of polyribonucleotides. Naturally, in order to achieve the same purpose, it is also possible to introduce a plurality of individual dsRNA molecules which comprise in each case one of the above-defined ribonucleotide sequence sections into the cell or the organism. The double-stranded dsRNA structure may be formed starting from two complementary, separate RNA strands or, preferably, starting from a single, self-complementary RNA strand. In this case, the "sense" RNA strand and the "antisense" RNA strand are preferably connected covalently to one another in the form of an inverted "repeat".

As described in WO 99/53050, for example, the dsRNA may also comprise a hairpin structure by connecting the "sense" and the "antisense" strands by a connecting sequence ("linker"; for example an intron). Preference is given to the self-complementary dsRNA structures, since they require only the expression of an RNA sequence and always comprise the complementary RNA strands in an equimolar ratio. The connecting sequence may is preferably an intron (e.g. an intron of the potato ST-LS1 gene; Vancanneyt G F et al. (1990) Mol Gen Genet 220(2):245-250).

The nucleic acid sequence coding for a dsRNA may include further elements such as, for example, transcription termination signals or polyadenylation signals.

Bringing together, if intended, the two strands of the dsRNA in a cell or plant may be achieved by way of example in the following way:

a) transformation of the cell or plant with a vector comprising both expression cassettes,
b) cotransformation of the cell or plant with two vectors, one of which comprises the expression cassettes containing the "sense" strand and the other one of which comprises the expression cassettes containing the "antisense" strand.

The formation of the RNA duplex may be initiated either outside or inside the cell.

The dsRNA may be synthesized either in vivo or in vitro. For this purpose, a DNA sequence coding for a dsRNA may be inserted into an expression cassette under the control of at least one genetic control element (such as a promoter, for example). A polyadenylation is not necessary and neither need any elements for initiating a translation be present. Preference is given to the expression cassette for the MP-dsRNA being present on the transformation construct or the transformation vector. For this purpose, the expression cassettes coding for the "antisense" strand and/or the "sense" strand of an MP-dsRNA or for the self-complementary strand of the dsRNA are preferably inserted into a transformation vector and introduced into the plant cell by using the processes described below. A stable insertion into the genome may be advantageous for the process of the invention but is not absolutely necessary. Since a dsRNA causes a long-term effect, transient expression is also sufficient in many cases. The dsRNA may also be part of the RNA to be expressed by the nucleic acid sequence to be inserted by fusing it, for example, to the 3'-untranslated part of said RNA.

The dsRNA may be introduced in an amount which makes possible at least one copy per cell. Higher amounts (e.g. at least 5, 10, 100, 500 or 1000 copies per cell) may, if appropriate, cause a more efficient reduction.

b) Introducing an antisense ribonucleic acid sequence of a marker protein (MP-antisenseRNA)

Processes for reducing a particular protein by means of the "antisense" technique have been described multiple times, also in plants (Sheehy et al. (1988) Proc Natl Acad Sci USA 85: 8805-8809; U.S. Pat. No. 4,801,340; Mol J N et al. (1990) FEBS Lett 268(2):427-430). The antisense nucleic acid molecule hybridizes or binds to the cellular mRNA and/or genomic DNA coding for the marker protein to be reduced, thereby suppressing transcription and/or translation of said marker protein. The hybridization may be produced in a conventional manner via the formation of a stable duplex or, in the case of genomic DNA, by binding of the antisense nucleic acid molecule to the duplex of the genomic DNA via specific interaction in the large groove of the DNA helix.

An MP-antisenseRNA may be derived using the nucleic acid sequence coding for this marker protein, for example the nucleic acid sequence according to SEQ ID NO: 1, 3, 5, 7, 9, 11, 13, 15, 17, 19, 21, 23, 25, 27, 29, 31, 33, 35, 37, 39, 41, 43, 45 or 47 according to the base pair rules by Watson and Crick. The MP-antisenseRNA may be complementary to the entire transcribed mRNA of the marker protein, may be limited to the coding region or may consist only of an oligonucleotide which is complementary to a part of the coding or noncoding sequence of the mRNA. Thus, for example, the oligonucleotide may be complementary to the region comprising the translation start site for the marker protein. The MP-antisenseRNA may be, for example, 5, 10, 15, 20, 25, 30, 35, 40, 45 or 50 nucleotides in length, but may also be longer and comprise at least 100, 200, 500, 1000, 2000 or 5000 nucleotides. MP-antisenseRNA are preferably expressed recombinantly in the target cell in the course of the process of the invention.

The MP-antisenseRNA may also be part of an RNA to be expressed by the nucleic acid sequence to be inserted by being fused, for example, to the 3'-untranslated part of said RNA.

The invention further relates to transgenic expression cassettes containing a nucleic acid sequence coding for at least part of a marker protein, with said nucleic acid sequence being functionally linked in antisense orientation to a promoter functional in plant organisms. Said expression cassettes may be part of a transformation construct or transformation vector or else may be introduced in the course of a cotransformation.

In a further preferred embodiment, expression of a marker protein may be inhibited by nucleotide sequences which are complementary to the regulatory region of a marker protein gene (e.g. a marker protein promoter and/or enhancer) and which form with the DNA double helix there triple-helical structures, thereby reducing transcription of the marker protein gene. Corresponding processes have been described (Helene C (1991) Anticancer Drug Res 6(6):569-84; Helene C et al. (1992) Ann NY Acad Sci 660:27-36; Maher L J (1992) Bioassays 14(12):807-815).

In a further embodiment, the MP-antisenseRNA may be an α-anomeric nucleic acid. Such α-anomeric nucleic acid molecules form with complementary RNA specific double-stranded hybrids in which, in contrast to the conventional β-nucleic acids, the two strands are oriented parallel to one another (Gautier C et al. (1987) Nucleic Acids Res 15:6625-6641).

c) Introducing an MP-antisenseRNA Combined with a Ribozyme

Advantageously, the above-described antisense strategy may be coupled to a ribozyme process. Catalytic RNA molecules or ribozymes may be adapted to any target RNA and cleave the phosphodiester backbone in specific positions, thereby functionally deactivating said target RNA (Tanner N K (1999) FEMS Microbiol Rev 23(3):257-275). In the process, the ribozyme is not modified itself but is capable of cleaving in an analogous manner further target RNA molecules, thereby acquiring the properties of an enzyme. The incorporation of ribozyme sequences into "antisense" RNAs imparts specifically to these "antisense" RNAs this enzyme-like, RNA-cleaving property and thus increases their efficiency in inactivating the target RNA. The preparation and use of appropriate ribozyme "antisense" RNA molecules have been described (inter alia in Haseloff et al. (1988) Nature 334: 585-591; Haseloff and Gerlach (1988) Nature 334: 585-591; Steinecke P et al. (1992) EMBO J 11(4):1525-1530; de Feyter R et al. (1996) Mol Gen Genet. 250(3):329-338).

In this way, it is possible to use ribozymes (e.g. hammerhead ribozymes; Haselhoff and Gerlach (1988) Nature 334: 585-591) in order to catalytically cleave the mRNA of a marker protein to be reduced and thus prevent translation. The ribozyme technique may increase the efficiency of an antisense strategy. Processes for expressing ribozymes in order to reduce particular proteins have been described in (EP 0 291 533, EP 0 321 201, EP 0 360 257). Ribozyme expression has likewise been described in plant cells (Steinecke P et al. (1992) EMBO J 11(4):1525-1530; de Feyter R et al. (1996) Mol Gen Genet. 250(3):329-338). Suitable target sequences and ribozymes may be determined, for example, as described in "Steinecke P, Ribozymes, Methods in Cell Biology 50, Galbraith et al. eds, Academic Press, Inc. (1995), pp. 449-460", by calculating the secondary structures of ribozyme RNA and target RNA and by the interaction thereof (Bayley C C et al. (1992) Plant Mol. Biol. 18(2):353-361; Lloyd A M and Davis R W et al. (1994) Mol Gen Genet. 242(6):653-657). It is possible, for example, to construct derivatives of the *Tetrahymena* L-19 IVS RNA which have regions complementary to the mRNA of the marker protein to be suppressed (see also U.S. Pat. No. 4,987,071 and U.S. Pat. No. 5,116,742). Alternatively, such ribozymes may also be identified via a selection process from a library of various ribozymes (Bartel D and Szostak J W (1993) Science 261:1411-1418).

d) Introducing a Sense Ribonucleic Acid Sequence of a Marker Protein (MP-senseRNA) for Inducing a Cosuppression Expression of a marker protein ribonucleic acid sequence (or a part thereof) in sense orientation may result in a cosuppression of the corresponding marker protein gene. Expression of sense RNA with homology to an endogenous marker protein gene may reduce or switch off expression of the latter, as has been described similarly for antisense approaches (Jorgensen et al. (1996) Plant Mol Biol 31(5):957-973; Goring et al. (1991) Proc Natl Acad Sci USA 88:1770-1774; Smith et al. (1990) Mol Gen Genet 224:447-481; Napoli et al. (1990) Plant Cell 2:279-289; Van der Krol et al. (1990) Plant Cell 2:291-99). In this context, the introduced construct may represent completely or only partially the homologous gene to be reduced. The possibility of translation is not required. The application of this technique to plants has been described (e.g. Napoli et al. (1990) Plant Cell 2:279-289; in U.S. Pat. No. 5,034,323.

The cosuppression is preferably carried out using a sequence which is essentially identical to at least part of the nucleic acid sequence coding for a marker protein, for example the nucleic acid sequence according to SEQ ID NO: 1, 3, 5, 7, 9, 11, 13, 15, 17, 19, 21, 23, 25, 27, 29, 31, 33, 35, 37, 39, 41, 43, 45 or 47.

The MP-senseRNA is preferably chosen in such a way that a translation of the marker protein or a part thereof cannot occur. For this purpose, for example, the 5'-untranslated or 3'-untranslated region may be chosen or else the ATG start codon may be deleted or mutated.

e) Introducing DNA- or Protein-Binding Factors Against Marker Protein Genes, Marker Protein RNAs or Proteins Marker protein expression may also be reduced using specific DNA-binding factors, for example factors of the zinc finger transcription factor type. These factors attach to the genomic sequence of the endogenous target gene, preferably in the regulatory regions, and cause a reduction in expression. Appropriate processes for preparing corresponding factors have been described (Dreier B et al. (2001) J Biol Chem 276(31):29466-78; Dreier B et al. (2000) J Mol Biol 303(4): 489-502; Beerli R R et al. (2000) Proc Natl Acad Sci USA 97 (4):1495-1500; Beerli R R et al. (2000) J Biol Chem 275(42): 32617-32627; Segal D J and Barbas C F 3rd. (2000) Curr Opin Chem Biol 4(1):34-39; Kang J S and Kim J S (2000) J Biol Chem 275(12):8742-8748; Beerli R R et al. (1998) Proc Natl Acad Sci USA 95(25):14628-14633; Kim J S et al. (1997) Proc Natl Acad Sci USA 94(8):3616-3620; Klug A (1999) J Mol Biol 293(2):215-218; Tsai S Y et al. (1998) Adv Drug Deliv Rev 30(1-3):23-31; Mapp A K et al. (2000) Proc Natl Acad Sci USA 97(8):3930-3935; Sharrocks A D et al. (1997) Int J Biochem Cell Biol 29(12):1371-1387; Zhang L et al. (2000) J Biol Chem 275(43):33850-33860).

These factors may be selected using any segment of a marker protein gene. This section is preferably in the region of the promoter region. However, for gene suppression, it may also be in the region of the coding exons or introns.

It is also possible to introduce factors which inhibit the marker protein itself into a cell. These protein-binding factors may be, for example, aptamers (Famulok M and Mayer G (1999) Curr Top Microbiol Immunol 243:123-36) or antibodies or antibody fragments or single-chain antibodies. Obtaining these factors has been described (Owen M et al. (1992) Biotechnology (N Y) 10(7):790-794; Franken E et al. (1997) Curr Opin Biotechnol 8(4):411-416; Whitelam (1996) Trend Plant Sci 1:286-272).

f) Introducing Viral Nucleic Acid Sequences and Expression Constructs Causing the Degradation of Marker Protein RNA Marker protein expression may also be effectively implemented by inducing the specific degradation of marker protein RNA by the plant with the aid of a viral expression system (Amplikon; Angell S M et al. (1999) Plant J 20(3):357-362). These systems, also referred to as "VIGS" (viral induced gene silencing), introduce nucleic acid sequences with homology to the transcript of a marker protein to be reduced into the plant by means of viral vectors. Transcription is then switched off, presumably mediated by plant defence mechanisms against viruses. Appropriate techniques and processes have been described (Ratcliff F et al. (2001) Plant J 25(2):237-45; Fagard M und Vaucheret H (2000) Plant Mol Biol 43(2-3): 285-93; Anandalakshmi R et al. (1998) Proc Natl Acad Sci USA 95(22):13079-84; Ruiz M T (1998) Plant Cell 10(6): 937-46). VIGS-mediated reduction is preferably implemented using a sequence which is essentially identical to at least part of the nucleic acid sequence coding for a marker protein, for example the nucleic acid sequence according to SEQ ID NO: 1, 3, 5, 7, 9, 11, 13, 15, 17, 19, 21, 23, 25, 27, 29, 31, 33, 35, 37, 39, 41, 43, 45 or 47.

g) Introducing Constructs for Generating a Functional Loss or a Functional Reduction of Marker Protein Genes The skilled worker knows numerous possible processes of how to modify genomic sequences in a targeted manner. These include, in particular, processes such as the generation of knockout mutants by means of targeted homologous recombination, for example by generating stop codons, shifts in the reading frame etc. (Hohn B and Puchta H (1999) Proc Natl Acad Sci USA 96:8321-8323) or the targeted deletion or inversion of sequences by means of, for example, sequence-specific recombinases or nucleases (see below).

In a preferred embodiment, the marker protein gene is inactivated by introducing a sequence-specific recombinase. Thus it is possible, for example, for the marker protein gene to include recognition sequences for sequence-specific recombinases or to be flanked by such sequences, and introducing the recombinase then deletes or inverts particular sequences of the marker protein gene, thus leading to inactivation of the marker protein gene. A corresponding procedure is depicted diagrammatically in FIG. 1.

Appropriate processes for deletion/inversion of sequences by means of sequence-specific recombinase systems are known to the skilled worker. Examples which may be mentioned are the Cre/lox system of bacteriophage P1 (Dale E C and Ow D W (1991) Proc Natl Acad Sci USA 88:10558-10562; Russell S H et al. (1992) Mol Gen Genet 234:49-59; Osborne B I et al. (1995) Plant J 7:687-701), the yeast FLP/FRT system (Kilby N J et al. (1995) Plant J 8:637-652; Lyznik L A et al. (1996) Nucl Acids Res 24:3784-3789), the Gin recombinase of the Mu phage, the *E. coli* Pin recombinase and the R/RS system of the pSR1 plasmids (Onouchi H et al. (1995) Mol Gen Genet 247:653-660; Sugita K et al. (2000) Plant J. 22:461-469). In these systems, the recombinase (for example Cre or FLP) interacts specifically with its particular recombination sequences (34 bp lox-Sequenz and, respectively, 47 bp FRT sequence). Preference is given to the bacteriophage P1 Cre/10× and the yeast FLP/FRT systems. The FLP/FRT and cre/lox recombinase systems have already been applied in plant systems (Odell et al. (1990) Mol Gen Genet 223:369-378). Preference is given to introducing the recombinase by means of recombinant expression starting from an expression cassette included on a DNA construct.

The activity or amount of the marker protein may also be reduced by a targeted deletion in the marker protein gene, for example by sequence-specific induction of DNA double-strand breaks at a recognition sequence for specific induction of DNA double-strand breaks in or close to the nucleic acid sequence coding for a marker protein. In its simplest embodiment (cf. FIG. 2, A and B) an enzyme is to this end introduced with the transformation construct, which generates at least one double-strand break in such a way that the resulting illegitimate recombination or deletion causes a reduction in the activity or amount of marker protein, for example by inducing a shift in the reading frame or deletion of essential sequences.

The efficiency of this approach may be increased by the sequence coding for the marker protein being flanked by sequences (A and, respectively, A') which have a sufficient length and homology to one another in order to recombine with one another as a consequence of the induced double-strand break and thus to cause, due to an intramolecular homologous recombination, a deletion of the sequence coding for the marker protein. FIG. 3 depicts diagrammatically a corresponding procedure in an exemplary embodiment of this variant.

The amount, function and/or activity of the marker protein may also be reduced by a targeted insertion of nucleic acid sequences (for example of the nucleic acid sequence to be inserted within the scope of the process of the invention) into the sequence coding for a marker protein (e.g. by means of intermolecular homologous recombination). This embodiment of the process of the invention is particularly advantageous and preferred, since, in addition to the general advantages of the process of the invention, it makes it moreover also possible to insert the nucleic acid sequence to be inserted into the plant genome in a reproducible, predictable, location-specific manner. This avoids the positional effects which otherwise occur in the course of a random, location-unspecific insertion (and which may manifest themselves, for example, in the form of different levels of expression of the transgene or in unintended inactivation of endogenous genes). Preference is given to using as an "anti-marker protein" compound in the course of this embodiment a DNA construct which comprises at least part of the sequence of a marker protein gene or neighbouring sequences and which can thus specifically recombine with said sequences in the target cell so that a deletion, addition or substitution of at least one nucleotide alters the marker protein gene in such a way that the functionality of said marker protein gene is reduced or completely removed. The alteration may also affect the regulatory elents (e.g. the promoter) of the marker protein gene so that the coding sequence remains unaltered, but expression (transcription and/or translation) does not occur and is reduced. In conventional homologous recombination, the sequence to be inserted is flanked at its 5' and/or 3' end by further nucleic acid sequences (A' and, respectively, B') which have a sufficient length and homology to corresponding sequences of the marker protein gene (A and, respectively, B) for making homologous recombination possible. The length is usually in a range from several hundred bases to several kilobases (Thomas K R and Capecchi M R (1987) Cell 51:503; Strepp et al. (1998) Proc Natl Acad Sci USA 95(8):4368-4373). The homologous recombination is carried out by transforming the plant cell containing the recombination construct by using the process described below and selecting successfully recombined clones based on the subsequently inactivated marker protein. Although homologous recombination is a relatively rare event in plant organisms, a selection pressure may be avoided by recombination into the marker protein gene, allowing a selection of the recombined cells and sufficient efficiency of the process. FIG. 4 diagrammatically depicts a corresponding procedure in an exemplary embodiment of this variant.

In an advantageous embodiment of the invention, however, insertion into the marker protein gene is facilitated by means of further functional elements. The term is to be understood as being comprehensive and means the use of sequences or of transcripts or polypeptides derived therefrom which are capable of increasing the efficiency of the specific integration into a marker protein gene. Various processes are available to the skilled worker for this purpose. However, preference is given to implementing the insertion by inducing a sequence-specific double-strand break in or close to the marker protein gene.

In a preferred embodiment of the invention, the marker protein is inactivated (i.e. the amount, expression, activity or function is reduced) by integrating a DNA sequence into a marker protein gene, with the process preferably comprising the following steps:
i) introducing an insertion construct and at least one enzyme suitable for inducing DNA double-strand breaks at a recognition sequence for targeted induction of DNA double-strand breaks in or close to the marker protein gene, and
ii) inducing DNA double-strand breaks at the recognition sequences for targeted induction of DNA double-strand breaks in or close to the marker protein gene, and
iii) inserting the insertion construct into the marker protein gene, with the functionality of the marker protein gene and, preferably, the functionality of the recognition sequence for targeted induction of DNA double-strand breaks is inactivated so that the enzyme suitable for induction of DNA double-strand breaks can no longer cut said recognition sequence, and
iv) selecting plants or plant cells in which the insertion construct has been inserted into the marker protein gene.

The insertion construct, preferably, comprises the nucleic acid sequence to be inserted into the genome but may also be used separately therefrom.

"Enzyme suitable for inducing DNA double-strand breaks at the recognition sequence for targeted induction of DNA double-strand breaks" ("DSBI enzyme" for "double-strand-break inducing enzyme" hereinbelow) means generally all those enzymes which are capable of generating sequence-specifically double-strand breaks in double-stranded DNA. Examples which may be mentioned but which are not limiting are:
1. Restriction endonucleases, preferably type II restriction endonucleases, particularly preferably Homing endonucleases as described in detail hereinbelow.
2. Artificial nucleases as described in detail hereinbelow, such as, for example, chimeric nucleases, mutated restriction or Homing endonucleases or RNA protein particles derived from group II mobile introns.

Both natural and artificially prepared DSBI enzymes are suitable. Preference is given to all of those DSBI enzymes whose recognition sequence is known and which can either be obtained in the form of their proteins (for example by purification) or be expressed using their nucleic acid sequence.

Preference is given to selecting the DSBI enzyme, with the knowledge of its specific recognition sequence, in such a way that it possesses, apart from the target recognition sequence, no further functional recognition regions in the genome of the target plant. Very particular preference is therefore given to Homing endonucleases (overview: Belfort M and Roberts R J (1997) Nucleic Acids Res 25:3379-3388; Jasin M (1996) Trends Genet 12:224-228; Internet: REBASE—The Restriction Enzyme Database; Roberts R J and Macelis D (2001) Nucl Acids Res 29: 268-269). The latter fulfill said requirement, owing to their long recognition sequences. The sequences coding for Homing endonucleases of this kind may be isolated, for example, from the *Chlamydomonas* chromoplast genome (Turmel M et al. (1993) J Mol Biol 232:446-467). Suitable Homing endonucleases are listed under the abovementioned internet address. Examples of Homing endonucleases which may be mentioned are those like F-SceI, F-SceII, F-SuvI, F-TevI, F-TevII, I-AmaI, I-AniI, I-CeuI, I-CeuAIIP, I-ChuI, I-CmoeI, I-CpaI, I-CpaII, I-CreI, I-CrepsbIP, I-CrepsbIIP, I-CrepsbIIIP, I-CrepsbIVP, I-CsmI, I-CvuI, I-CvuAIP, I-DdiII, I-DirI, I-DmoI, I-HspNIP, I-LlaI, I-MsoI, I-NaaI, I-NanI, I-NclIP, I-NgrIP, I-NitI, I-NjaI, I-Nsp236IP, I-PakI, I-PboIP, I-PcuIP, I-PcuAI, I-PcuVI, I-PgrIP, I-PobIP, I-PorI, I-PorIIP, I-PpbIP, I-PpoI, I-SPBetaIP, I-ScaI, I-SceI, I-SceII, I-SceIII, I-SceIV, I-SceV, I-SceVI, I-SceVII, I-SexIP, I-SneIP, I-SpomCP, I-SpomIP, I-SpomIIP, I-SquIP, I-Ssp6803I, I-SthPhiJP, I-SthPhiST3P, I-SthPhiS3bP, I-TdeIP, I-TevI, I-TevII, I-TevIII, I-UarAP, I-UarHGPA1P, I-UarHGPA13P, I-VinIP, I-ZbiIP, PI-MtuI, PI-MtuHIP, PI-MtuHIIP, PI-PfuI, PI-PfuII, PI-PkoI, PI-PkoII, PI-PspI, PI-Rma438121P, PI-SPBetaIP, PI-SceI, PI-TfuI, PI-TfuII, PI-ThyI, PI-TliI, PI-TliII. Preference is given here to those Homing endonucleases whose gene sequences are already known, such as, for example, F-SceI, I-CeuI, I-ChuI, I-DmoI, I-CpaI, I-CpaII, I-CreI, I-CsmI, F-TevI, F-TevII, I-TevI, I-TevII, I-AniI, I-CvuI, I-LlaI, I-NanI, I-MsoI, I-NitI, I-NjaI, I-PakI, I-PorI, I-PpoI, I-ScaI, I-Ssp6803I, PI-PkoI, PI-PkoII, PI-PspI, PI-TfuI, PI-TliI.

Very particular preference is given to
I-CeuI (Cote M J and Turmel M (1995) Curr Genet 27:177-183.; Gauthier A et al. (1991) Curr Genet 19:43-47; Marshall (1991) Gene 104:241-245; GenBank Acc. No.: Z17234 nucleotides 5102 to 5758),
I-ChuI (Cote V et al. (1993) Gene 129:69-76; GenBank Acc. No.: L06107, nucleotides 419 to 1075),
I-CmoeI (Drouin M et al. (2000) Nucl Acids Res 28:4566-4572),
I-CpaI from *Chlamydomonas pallidostigmatica* (GenBank Acc. No.: L36830, nucleotides 357 to 815; Turmel M et al. (1995) Nucleic Acids Res 23:2519-2525; Turmel, M et al. (1995) Mol Biol Evol 12:533-545)
I-CpaII (Turmel M et al. (1995) Mol Biol Evol 12:533-545; GenBank Acc. No.: L39865, nucleotides 719 to 1423),
I-CreI (Wang J et al. (1997) Nucleic Acids Res 25: 3767-3776; Durrenberger, F and Rochaix J D (1991) EMBO J 10:3495-3501; GenBank Acc. No.: X01977, nucleotides 571 to 1062),
I-CsmI (Ma D P et al. (1992) Plant Mol Biol 18:1001-1004)
I-NanI (Elde M et al. (1999) Eur J Biochem. 259:281-288; GenBank Acc. No.: X78280, nucleotides 418 to 1155),
I-NitI (GenBank Acc. No.: X78277, nucleotides 426 to 1163),
I-NjaI (GenBank Acc. No.: X78279, nucleotides 416 to 1153),
I-PpoI (Muscarella D E and Vogt V M (1989) Cell 56:443-454; Lin J and Vogt V M (1998) Mol Cell Biol 18:5809-5817; GenBank Acc. No.: M38131, nucleotides 86 to 577),
I-PspI (GenBank Acc. No.: U00707, nucleotides 1839 to 3449),
I-ScaI (Monteilhet C et al. (2000) Nucleic Acids Res 28: 1245-1251; GenBank Acc. No.: X95974, nucleotides 55 to 465)
I-SceI (WO 96/14408; U.S. Pat. No. 5,962,327, therein Seq ID NO: 1), Endo SceI (Kawasaki et al. (1991) J Biol Chem 266:5342-5347, identical to F-SceI; GenBank Acc. No.: M63839, nucleotides 159 to 1589), I-SceII (Sarguiel B et al. (1990) Nucleic Acids Res 18:5659-5665), I-SceIII (Sarguiel B et al. (1991) Mol Gen Genet. 255:340-341), I-Ssp6803I (GenBank Acc. No.: D64003, nucleotides 35372 to 35824), I-TevI (Chu et al. (1990) Proc Natl Acad Sci USA 87:3574-3578; Bell-Pedersen et al. (1990) Nucleic Acids Res 18:3763-3770; GenBank Acc. No.: AF158101, nucleotides 144431 to 143694), I-TevII (Bell-Pedersen et al. (1990) Nucleic Acids Res 18:3763-3770; GenBank Acc. No.: AF158101, nucleotides 45612 to 44836), I-TevIII (Eddy et al. (1991) Genes Dev. 5:1032-1041).

Very particular preference is given to commercially available Homing endonucleases such as I-CeuI, I-SceI, I-PpoI, PI-PspI or PI-SceI. Most preference is given to I-SceI and I-PpoI. While the gene coding for I-PpoI may be utilized in its natural form, the gene coding for I-SceI possesses an editing site. Since, in contrast to yeast mitochondria, the appropriate editing is not carried out in higher plants, an artificial sequence encoding the I-SceI protein must be used for heterologous expression of this enzyme (U.S. Pat. No. 5,866,361).

The enzymes may be purified from their source organisms in the manner familiar to the skilled worker and/or the nucleic acid sequence encoding said enzymes may be cloned. The sequences of various enzymes have been deposited with GenBank (see above).

Artificial DSBI enzymes which may be mentioned by way of example are chimeric nucleases which are composed of an unspecific nuclease domain and a sequence-specific DNA-binding domain (e.g. consisting of zinc fingers) (Smith J et al. (2000) Nucl Acids Res 28(17):3361-3369; Bibikova M et al. (2001) Mol Cell Biol. 21:289-297). Thus, for example, the catalytic domain of the restriction endonuclease FokI has been fused to zinc finger-binding domains, thereby defining the specificity of the endonuclease (Chandrasegaran S & Smith J (1999) Biol Chem 380:841-848; Kim Y G & Chandrasegaran S (1994) Proc Natl Acad Sci USA 91:883-887; Kim Y G et al. (1996) Proc Natl Acad Sci USA 93:1156-1160). The described technique has also been used previously for imparting a predefined specificity to the catalytic domain of the yeast Ho endonuclease by fusing said domain to the zinc finger domain of transcription factors (Nahon E & Raveh D (1998) Nucl Acids Res 26:1233-1239). It is possible, using suitable mutation and selection processes, to adapt existing Homing endonucleases to any desired recognition sequence.

As mentioned, zinc finger proteins are particularly suitable as DNA-binding domains within chimeric nucleases. These DNA-binding zinc finger domains may be adapted to any DNA sequence. Appropriate processes for preparing corresponding zinc finger domains have been described and are known to the skilled worker (Beerli R R et al. (2000) Proc Natl Acad Sci 97(4):1495-1500; Beerli R R et al. (2000) J Biol Chem 275(42):32617-32627; Segal D J and Barbas C F 3rd. (2000) Curr Opin Chem Biol 4(1):34-39; Kang J S and Kim J S (2000) J Biol Chem 275(12):8742-8748; Beerli R R et al. (1998) Proc Natl Acad Sci USA 95(25):14628-14633; Kim J S et al. (1997) Proc Natl Acad Sci USA 94(8):3616-3620; Klug A (1999) J Mol Biol 293(2):215-218; Tsai S Y et al. (1998) Adv Drug Deliv Rev 30(1-3):23-31; Mapp A K et al. (2000) Proc Natl Acad Sci USA 97(8):3930-3935; Sharrocks A D et al. (1997) Int J Biochem Cell Biol 29(12):1371-1387; Zhang L et al. (2000) J Biol Chem 275(43):33850-33860). Processes for preparing and selecting zinc finger DNA-binding domains with high sequence specificity have been described (WO 96/06166, WO 98/53059, WO 98/53057). Fusing a DNA-binding domain obtained in this way to the catalytic domain of an endonuclease (such as, for example, the FokI or Ho endonuclease) enables chimeric nucleases to be prepared which have any desired specificity and which may be used as DSBI enzymes advantageously within the scope of the present invention.

Artificial DSBI enzymes with altered sequence specificity may also be generated by mutating already known restriction endonucleases or Homing endonucleases, using methods familiar to the skilled worker. Besides the mutagenesis of Homing endonucleases, the mutagenesis of maturases is of particular interest for the purpose of obtaining an altered substrate specificity. Maturases frequently share many features with Homing endonucleases and, if appropriate, can be converted into nucleases by carrying out few mutations. This has been shown, for example, for the maturase in the bakers' yeast bi2 intron. Only two mutations in the maturase-encoding open reading frame (ORF) sufficed to impart to this enzyme a Homing-endonuclease activity (Szczepanek & Lazowska (1996) EMBO J 15:3758-3767).

Further artificial nucleases may be generated with the aid of mobile group II introns and the proteins encoded by them, or parts of these proteins. Mobile group II introns, together with the proteins encoded by them, form RNA-protein particles which are capable of recognizing and cutting DNA in a sequence-specific manner. In this context, the sequence specificity can be adapted to the requirements by mutating particular regions of the intron (see below) (WO 97/10362).

Preference is given to expressing the DSBI enzyme as a fusion protein with a nuclear localization sequence (NLS). This NLS sequence enables facilitated transport into the nucleus and increases the efficiency of the recombination system. Various NLS sequences are known to the skilled worker and described, inter alia, in Jicks G R and Raikhel N V (1995) Annu. Rev. Cell Biol. 11:155-188. For example, the NLS sequence of the SV40 large antigen is preferred for plant organisms. Very particular preference is given to the following NLS sequences:

```
NLS1:   N-Pro-Lys-Thr-Lys-Arg-Lys-Val-C
        (SEQ ID NO: 80)

NLS2:   N-Pro-Lys-Lys-Lys-Arg-Lys-Val-C
        (SEQ ID NO: 81)
```

Owing to the small size of many DSBI enzymes (such as, for example, the Homing endonucleases), an NLS sequence is not absolutely necessary, however. These enzymes are able to pass through the nuclear pores also without this assistance.

"Recognition sequence for targeted induction of DNA double-strand breaks" means in general those sequences which allow recognition and cleavage by the DSBI enzyme under the conditions in the eukaryotic cell or organism used in this case. In this context, mention is made, by way of example but not by limitation, in table 1 below of the recognition sequences for the particular DSBI enzymes listed.

TABLE 1

Recognition sequences and source organisms of DSBI enzymes ("^" indicates the cleavage site of the DSBI enzyme within a recognition sequence)

| DSBI enzyme | Source organism | Recognition sequence | SEQ ID NO: |
|---|---|---|---|
| CRE | Bacteriophage P1 | 5'-AACTCTCATCGCTTCGGATAACTTCCTGTTATCCGAAACAT ATCACTCACTTTGGTGATTTCACCGTAACTGTCTATGATTAATG-3' | 82 |
| FLP | Saccharomyces cerevisiae | 5'-GAAGTTCCTATTCCGAAGTTCCTATTCTCTAGAAAGTA-TAGGAACTTC-3' | 83 |
| R | pSR1 plasmids | 5'-CGAGATCATATCACTGTGGACGTTGATGAAAGAATACGTTA TTCTTTCATCAAATCGT | 84 |
| P-element transposase | Drosophila | 5'-CTAGATGAAATAACATAAGGTGG | 85 |
| I-AniI | Aspergillus nidulans | 5'-TTGAGGAGGTT^TCTCTGTAAATAANNNNNNNNNNNNNNN 3'-AACTCCTCCAAAGAGACATTTATTNNNNNNNNNNNNNNN^ | 86 87 |
| I-DdiI | Dictyostelium discoideumAx3 | 5'-TTTTTTGGTCATCCAGAAGTATAT 3'-AAAAAACCAG^TAGGTCTTCATATA | 88 89 |
| I-CvuI | Chlorella vulgaris | 5'-CTGGGTTCAAAACGTCGTGA^GACAGTTTGG 3'-GACCCAAGTTTTGCAG^CACTCTGTCAAACC | 90 91 |
| I-CsmI | Chlamydomonas smithii | 5'-GTACTAGCATGGGGTCAAATGTCTTTCTGG | 92 |
| I-CmoeI | Chlamydomonas moewusii | 5'-TCGTAGCAGCT^CACGGTT 3'-AGCATCG^TCGAGTGCCAA | 93 94 |
| I-CreI | Chlamydomonas reinhardtii | 5'-CTGGGTTCAAAACGTCGTGA^GACAGTTTGG 3'-GACCCAAGTTTTGCAG^CACTCTGTCAAACC | 95 96 |
| I-ChuI | Chlamydomonas humicola | 5'-GAAGGTTTGGCACCTCG^ATGTCGGCTCATC 3'-CTTCCAAACCGTG^GAGCTACAGCCGAGTAG | 97 98 |
| I-CpaI | Chlamydomonas pallidostig-matica | 5'-CGATCCTAAGGTAGCGAA^ATTCA 3'-GCTAGGATTCCATC^GCTTTAAGT | 99 100 |
| I-CpaII | Chlamydomonas pallidostig-matica | 5'-CCCGGCTAACTC^TGTGCCAG 3'-GGGCCGAT^TGAGACACGGTC | 101 102 |
| I-CeuI | Chlamydomonas eugametos | 5'-CGTAACTATAACGGTCCTAA^GGTAGCGAA 3'-GCATTGATATTGCCAG^GATTCCATCGCTT | 103 104 |
| I-DmoI | Desulfurococ-cus mobilis | 5'-ATGCCTTGCCGGGTAA^GTTCCGGCGCGCAT 3'-TACGGAACGGCC^CATTCAAGGCCGCGCGTA | 105 106 |
| I-SceI | S. cerevisiae | 5'-AGTTACGCTAGGGATAA^CAGGGTAATATAG 3'-TCAATGCGATCCC^TATTGTCCCATTATATC 5'-TAGGGATAA-CAGGGTAAT 3'-ATCCC^TATTGTCCCATTA ("Core" sequence) | 107 108 109 110 |
| I-SceII | S. cerevisiae | 5'-TTTTGATTCTTTGGTCACCC^TGAAGTATA 3'-AAAACTAAGAAACCAG^TGGGACTTCATAT | 111 112 |
| I-SceIII | S. cerevisiae | 5'-ATTGGAGGTTTTGGTAAC^TATTTATTACC 3'-TAACCTCCAAAACC^ATTGATAAATAATGG | 113 114 |
| I-SceIV | S. cerevisiae | 5'-TCTTTTCTCTTGATTA^GCCCTAATCTACG 3'-AGAAAAGAGAAC^TAATCGGGATTAGATGC | 115 116 |
| I-SceV | S. cerevisiae | 5'-AATAATTTTCT^TCTTAGTAATGCC 3'-TTATTAAAAGAAGAATCATTA^CGG | 117 118 |
| I-SceVI | S. cerevisiae | 5'-GTTATTTAATG^TTTTAGTAGTTGG 3'-CAATAAATTACAAAATCATCA^ACC | 119 120 |
| I-SceVII | S. cerevisiae | 5'-TGTCACATTGAGGTGCACTAGTTATTAC | 121 |

TABLE 1-continued

Recognition sequences and source organisms of DSBI enzymes ("^" indicates the cleavage site of the DSBI enzyme within a recognition sequence)

| DSBI enzyme | Source organism | Recognition sequence | SEQ ID NO: |
|---|---|---|---|
| PI-SceI | S. cerevisiae | 5'-ATCTATGTCGGGTGC^GGAGAAAGAGGTAAT<br>3'-TAGATACAGCC^CACGCCTCTTTCTCCATTA | 122<br>123 |
| F-SceI | S. cerevisiae | 5'-GATGCTGTAGGC^ATAGGCTTGGTT<br>3'-CTACGACA^TCCGTATCCGAACCAA | 124<br>125 |
| F-SceII | S. cerevisiae | 5'-CTTTCCGCAACA^GTAAAATT<br>3'-GAAAGGCG^TTGTCATTTTAA | 126<br>127 |
| I-HmuI | Bacillus subtilis bacteriophage SPO1 | 5'-AGTAATGAGCCTAACGCTCAGCAA<br>3'-TCATTACTCGGATTGC^GAGTCGTT | 128<br>129 |
| I-HmuII | Bacillus subtilis bacteriophage SP82 | 5'-AGTAATGAGCCTAACGCTCAACAANNNNNNNNNNNNNNNNNN<br>NNNNNNNNNNNNNNNNNNNNNN | 130 |
| I-LlaI | Lactococcus lactis | 5'-CACATCCATAAC^CATATCATTTTT<br>3'-GTGTAGGTATTGGTATAGTAA^AAA | 131<br>132 |
| I-MsoI | Monomastix species | 5'-CTGGGTTCAAAACGTCGTGA^GACAGTTTGG<br>3'-GACCCAAGTTTTGCAG^CACTCTGTCAAACC | 133<br>134 |
| I-NanI | Naegleria andersoni | 5'-AAGTCTGGTGCCA^GCACCCGC<br>3'-TTCAGACC^ACGGTCGTGGGCG | 135<br>136 |
| I-NitI | Naegleria italica | 5'-AAGTCTGGTGCCA^GCACCCGC<br>3'-TTCAGACC^ACGGTCGTGGGCG | 137<br>138 |
| I-NjaI | Naegleria jamiesoni | 5'-AAGTCTGGTGCCA^GCACCCGC<br>3'-TTCAGACC^ACGGTCGTGGGCG | 139<br>140 |
| I-PakI | Pseudendoclonium akinetum | 5'-CTGGGTTCAAAACGTCGTGA^GACAGTTTGG<br>3'-GACCCAAGTTTTGCAG^CACTCTGTCAAACC | 141<br>142 |
| I-PorI | Pyrobaculum organotrophum | 5'-GCGAGCCCGTAAGGGT^GTGTACGGG<br>3'-CGCTCGGGCATT^CCCACACATGCCC | 143<br>144 |
| I-PpoI | Physarum polycephalum | 5'-TAACTATGACTCTCTTAA^GGTAGCCAAAT<br>3'-ATTGATACTGAGAG^AATTCCATCGGTTTA | 145<br>146 |
| I-ScaI | Saccharomyces capensis | 5'-TGTCACATTGAGGTGCACT^AGTTATTAC<br>3'-ACAGTGTAACTCCAC^GTGATCAATAATG | 147<br>148 |
| I-Ssp6803I | Synechocystis species | 5'-GTCGGGCT^CATAACCCGAA<br>3'-CAGCCCGAGTA^TTGGGCTT | 149<br>150 |
| pI-PfuI | Pyrococcus furiosus Vc1 | 5'-GAAGATGGGAGGAGGG^ACCGGACTCAACTT<br>3'-CTTCTACCCTCC^TCCCTGGCCTGAGTTGAA | 151<br>152 |
| PI-PfuII | Pyrococcus furiosus Vc1 | 5'-ACGAATCCATGTGGAGA^AGAGCCTCTATA<br>3'-TGCTTAGGTACAC^CTCTTCTCGGAGATAT | 153<br>154 |
| PI-PkoI | Pyrococcus kodakaraensis KOD1 | 5'-GATTTTAGAT^CCCTGTACC<br>3'-CTAAAA^TCTAGGGACATGG | 155<br>156 |
| PI-PkoII | Pyrococcus kodakaraensis KOD1 | 5'-CAGTACTACG^GTTAC<br>3'-GTCATG^ATGCCAATG | 157<br>158 |
| PI-PspI | Pyrococcus sp. | 5'-AAAATCCTGGCAAACAGCTATTAT^GGGTAT<br>3'-TTTTAGGACCGTTTGTCGAT^AATACCCATA | 159<br>160 |
| PI-TfuI | Thermococcus fumicolans ST557 | 5'-TAGATTTTAGGT^CGCTATATCCTTCC<br>3'-ATCTAAAA^TCCAGCGATATAGGAAGG | 161<br>162 |

TABLE 1-continued

Recognition sequences and source organisms of DSBI enzymes ("^" indicates the cleavage site of the DSBI enzyme within a recognition sequence)

| DSBI enzyme | Source organism | Recognition sequence | SEQ ID NO: |
|---|---|---|---|
| PI-TfuII | Thermococcus fumicolans ST557 | 5'-TAYGCNGAYACN^GACGGYTTYT<br>3'-ATRCGNCT^RTGNCTGCCRAARA | 163<br>164 |
| PI-ThyI | Thermococcus hydrothermalis | 5'-TAYGCNGAYACN^GACGGYTTYT<br>3'-ATRCGNCT^RTGNCTGCCRAARA | 165<br>166 |
| PI-TliI | Thermococcus litoralis | 5'-TAYGCNGAYACNGACGG^YTTYT<br>3'-ATRCGNCTRTGNC^TGCCRAARA | 167<br>168 |
| PI-TliII | Thermococcus litoralis | 5'-AAATTGCTTGCAAACAGCTATTACGGCTAT | 169 |
| I-TevI | Bacteriophage T4 | 5'-AGTGGTATCAAC^GCTCAGTAGATG<br>3'-TCACCATAGT^TGCGAGTCATCTAC | 170<br>171 |
| I-TevII | Bacteriophage T4 | 5'-GCTTATGAGTATGAAGTGAACACGT^TATTC<br>3'-CGAATACTCATACTTCACTTGTG^CAATAAG | 172<br>173 |
| F-TevI | Bacteriophage T4 | 5'-GAAACACAAGA^AATGTTTAGTAAANNNNNNNNNNNNNN<br>3'-CTTTGTGTTCTTTACAAATCATTTNNNNNNNNNNNNNN^ | 174<br>175 |
| F-TevII | Bacteriophage T4 | 5'-TTTAATCCTCGCTTC^AGATATGGCAACTG<br>3'-AAATTAGGAGCGA^AGTCTATACCGTTGAC | 176<br>177 |

Relatively small deviations (degenerations) of the recognition sequence which nevertheless make possible recognition and cleavage by the particular DSBI enzyme are also included here. Such deviations, also in connection with different basic conditions such as, for example, calcium or magnesium concentration, have been described (Argast G M et al. (1998) J Mol Biol 280:345-353). Core sequences of these recognition sequences are also included. It is known that the inner portions of the recognition sequences also suffice for an induced double-strand break and that the outer portions are not necessarily relevant but may contribute to determining the cleavage efficiency. Thus, for example, an 18 bp core sequence can be defined for I-SceI.

Said DSBI recognition sequences may be localized in various positions in or close to a marker protein gene and, for example when the marker protein used is a transgene, may already be incorporated when constructing the marker protein expression cassette. Various possible localizations are illustrated by way of example in FIGS. 2-A, 2-B, 3 and 5 and in the descriptions thereof.

In a further advantageous embodiment, the insertion sequence comprises at least one homology sequence A which has a sufficient length and a sufficient homology to a sequence A' in the marker protein gene in order to ensure homologous recombination between A and A'. The insertion sequence is preferably flanked by two sequences A and B which have a sufficient length and a sufficient homology to a sequence A' and, respectively, B' in the marker protein gene in order to ensure homologous recombination between A and A' and, respectively, B and B'.

"Sufficient length" means, with respect to the homology sequences A, A' and B, B', preferably sequences with a length of at least 100 base pairs, preferably at least 250 base pairs, particularly preferably at least 500 base pairs, very particularly preferably at least 1000 base pairs, most preferably of at least 2500 base pairs.

"Sufficient homology" means, with respect to the homology sequences, preferably sequences whose homology to one another is at least 70%, preferably 80%, preferentially at least 90%, particularly preferably at least 95%, very particularly preferably at least 99%, most preferably 100%, over a length of at least 20 base pairs, preferably at least 50 base pairs, particularly preferably at least 100 base pairs, very particularly preferably at least 250 base pairs, most preferably at least 500 base pairs.

Homology between two nucleic acids means the identity of the nucleic acid sequence over in each case the entire sequence length, which identity is calculated by way of comparison with the aid of the GAP program algorithm (Wisconsin Package Version 10.0, University of Wisconsin, Genetics Computer Group (GCG), Madison, USA), setting the following parameters:

| | |
|---|---|
| Gap Weight: 12 | Length Weight: 4 |
| Average Match: 2,912 | Average Mismatch: −2,003 |

In a further preferred embodiment, the recombination efficiency is increased by a combination with processes which promote homologous recombination. Such systems have been described and comprise, by way of example, expression of proteins such as RecA or treatment with PARP inhibitors. It has been demonstrated that the intrachromosomal homologous recombination in tobacco plants can be increased by using PARP inhibitors (Puchta H et al. (1995) Plant J 7:203-210). The use of these inhibitors can further increase the rate of homologous recombination in the recombinant constructs, after inducing the sequence-specific DNA double-strand break, and thus the efficiency of the deletion of the transgene sequences. Various PARP inhibitors may be used here. Preference is given to including inhibitors such as 3-amino benzamide, 8-hydroxy-2-methylquinazolin-4-one (NU1025), 1,11b-dihydro-[2H]benzopyrano[4,3,2-de]isoquinolin-3-one (GPI 6150), 5-aminoisoquinolinone, 3,4-dihydro-5-[4-(1-piperidinyl)butoxy]-1(2H)-isoquinolinone or the substances described in WO 00/26192, WO 00/29384, WO 00/32579, WO 00/64878, WO 00/68206, WO 00/67734, WO 01/23386 and WO 01/23390.

Further suitable methods are the introduction of nonsense mutations into endogenous marker protein genes, for example by means of introducing RNA/DNA oligonucleotides into the plant (Zhu et al. (2000) Nat Biotechnol 18(5): 555-558). Point mutations may also be generated by means of DNA-RNA hybrids which are also known as "chimeraplasty" (Cole-Strauss et al. (1999) Nucl Acids Res 27(5):1323-1330; Kmiec (1999) Gene therapy American Scientist 87(3):240-247).

The methods of dsRNAi, cosuppression by means of sense RNA and VIGS (virus induced gene silencing) are also referred to as post-transcriptional gene silencing (PTGS). PTGS processes are particularly advantageous because the demands on the homology between the marker protein gene to be reduced and the transgenically expressed sense or dsRNA nucleic acid sequence are lower than, for example, in the case of a traditional antisense approach. Thus it is possible, using the marker protein nucleic acid sequences from one species, to effectively reduce also expression of homologous marker protein proteins in other species, without it being absolutely necessary to isolate and to elucidate the structure of the marker protein homologues occurring there. Considerably less labor is therefore required.

"Introduction" comprises within the scope of the invention any processes which are suitable for introducing an "anti-marker protein" compound, directly or indirectly, into a plant or a cell, compartment, tissue, organ or seeds of said plant or generating said compound there. The introduction may result in a transient presence of an "anti-marker protein" compound (for example a dsRNA or a recombinase) or else in a permanent (stable) presence.

According to the different nature of the approaches described above, the "anti-marker protein" compound may exert its function directly (for example by way of insertion into an endogenous marker protein gene). However, said function may also be exerted indirectly after transcription into an RNA (for example in antisense approaches) or after transcription and translation into a protein (for example in the case of recombinases or DSBI enzymes). The invention comprises both directly and indirectly acting "anti-marker protein" compounds.

Introducing comprises, for example, processes such as transfection, transduction or transformation.

"Anti-marker protein" compounds thus comprises, for example, also expression cassettes capable of implementing expression (i.e. transcription and, if appropriate, translation) of, for example, an MP-dsRNA, an MP-antisenseRNA, a sequence-specific recombinase or a DSBI enzyme in a plant cell.

"Expression cassette" means within the scope of the present invention generally those constructions in which a nucleic acid sequence to be expressed is functionally linked to at least one genetic control sequence, preferably a promoter sequence. Expression cassettes preferably consist of double-stranded DNA and may have a linear or circular structure.

A functional linkage means, for example, the sequential arrangement of a promoter with a nucleic acid sequence to be transcribed (for example coding for an MP-dsRNA or a DSBI enzyme) and, if appropriate, further regulatory elements such as, for example, a terminator and/or polyadenylation signals in such a way that each of the regulatory elements can fulfill its function during transcription of the nucleic acid sequence, depending on the arrangement of the nucleic acid sequences. In this context, function can mean, for example, the control of expression, i.e. transcription and/or translation, of the nucleic acid sequence (e.g. coding for an MP-dsRNA or a DSBI enzyme). In this context, control comprises, for example, initiating, increasing, controlling or suppressing the expression, i.e. transcription and, if appropriate, translation. This does not necessarily require a direct linkage in the chemical sense. Genetic control sequences such as, for example, enhancer sequences, may exert their function on the target sequence also from positions further afar or even from different DNA molecules. Preference is given to arrangements in which the nucleic acid sequence to be transcribed is positioned downstream of the sequence acting as promoter so that both sequences are covalently connected to one another. The distance between the promoter sequence and the nucleic acid sequence to be expressed transgenically is here preferably less than 200 base pairs, particularly preferably less than 100 base pairs, very particularly preferably less than 50 base pairs.

The skilled worker knows various ways of obtaining any of the expression cassettes of the invention. An expression cassette of the invention is prepared, for example, preferably by direct fusion of a nucleic acid sequence acting as promoter to a nucleotide sequence to be expressed (e.g. coding for an MP-dsRNA or a DSBI enzyme). A functional linkage may be produced by means of common recombination and cloning techniques, as are described, for example, in Maniatis T, Fritsch E F and Sambrook J (1989) Molecular Cloning: A Laboratory Manual, Cold Spring Harbor Laboratory, Cold Spring Harbor, N.Y. and in Silhavy T J et al. (1984) Experiments with Gene Fusions, Cold Spring Harbor Laboratory, Cold Spring Harbor, N.Y. and in Ausubel F M et al. (1987) Current Protocols in Molecular Biology, Greene Publishing Assoc. and Wiley Interscience.

The expression cassettes of the invention preferably comprise a promoter 5' upstream of the particular nucleic acid sequence to be expressed transgenically and a terminator sequence as an additional genetic control sequence 3' downstream and also, if appropriate, further customary regulatory elements, in each case functionally linked to the nucleic acid sequence to be expressed transgenically.

The term "genetic control sequences" is to be understood broadly and means all those sequences which have an influence on the making or function of the expression cassette of the invention. For example, genetic control sequences ensure transcription and, if appropriate, translation in prokaryotic or eukaryotic organisms. Genetic control sequences are described, for example, in "Goeddel; Gene Expression Technology: Methods in Enzymology 185, Academic Press, San Diego, Calif. (1990)" or "Gruber and Crosby, in: Methods in Plant Molecular Biology and Biotechnolgy, CRC Press, Boca Raton, Fla., eds.:Glick and Thompson, Chapter 7, 89-108" and in the references quoted there.

Genetic control sequences comprise, in particular in plants, functional promoters. Preferred promoters suitable for the expression cassettes are in principle any promoters capable of controlling expression of genes, in particular foreign genes, in plants.

Plant-specific promoters or promoters functional in plants or in a plant cell means in principle any promoter capable of controlling expression of genes, in particular foreign genes, in at least one plant or one part, cell, tissue, culture of a plant. In this context, expression may be, for example, constitutive, inducible or development-dependent. Preference is given to:

a) Constitutive promoters

"Constitutive" promoters means those promoters which ensure expression in numerous, preferably all, tissues over a relatively large period of plant development, preferably at all points in time of plant development (Benfey et al. (1989) EMBO J 8:2195-2202). Preference is given in particular to using a plant promoter or a promoter which is derived from a plant virus. Particular preference is given to the promoter of the 35S transcript of the CaMV cauliflower mosaic virus (Franck et al. (1980) Cell 21:285-294; Odell et al. (1985) Nature 313:810-812; Shewmaker et al. (1985) Virology 140:281-288; Gardner et al. (1986) Plant Mol Biol 6:221-228) or the 19S CaMV promoter (U.S. Pat. No. 5,352,605; WO 84/02913; Benfey et al. (1989) EMBO J 8:2195-2202) and also to the promoter of the *Arabidopsis thaliana* nitrilase-1 gene (GenBank Acc. No.: Y07648, nucleotides 2456 (alternatively 2861) to 4308 or alternatively 4340 or 4344. (e.g. bp 2456 to 4340).

Another suitable constitutive promoter is the rubisco small subunit (SSU) promoter (U.S. Pat. No. 4,962,028), the leguminB promoter (GenBank Acc. No.: X03677), the promoter of the *Agrobacterium* nopaline synthase, the TR dual promoter, the *Agrobacterium* OCS (octopine synthase) promoter, the ubiquitin promoter (Holtorf S et al. (1995) Plant Mol Biol 29:637-649), the ubiquitin 1 promoter (Christensen et al. (1992) Plant Mol Biol 18:675-689; Bruce et al. (1989) Proc Natl Acad Sci USA 86:9692-9696), the Smas promoter, the cinnamyl alcohol dehydrogenase promoter (U.S. Pat. No. 5,683,439), the promoters of the vacuolar ATPase subunits or the promoter of a proline-rich protein from wheat (WO 91/13991), and further promoters of genes whose constitutive expression in plants is known to the skilled worker.

b) Tissue-specific promoters

Preference is given to promoters with specificities for the anthers, ovaries, flowers, leaves, stems, roots or seeds.

Seed-specific promoters comprise, for example, the promoter of phaseolin (U.S. Pat. No. 5,504,200; Bustos M M et al. (1989) Plant Cell 1(9):839-53), of the 2S albumin (Joseffson L G et al. (1987) J Biol Chem 262:12196-12201), of legumin (Shirsat A et al. (1989) Mol Gen Genet 215(2): 326-331), of USP (unknown seed protein; Bäumlein H et al. (1991) Mol Gen Genet 225(3):459-67), of napin (U.S. Pat. No. 5,608,152; Stalberg K et al. (1996) L Planta 199:515-519), of the sucrose-binding protein (WO 00/26388), of legumin B4 (LeB4; Bäumlein H et al. (1991) Mol Gen Genet 225: 121-128; Baeumlein et al. (1992) Plant Journal 2(2):233-9; Fiedler U et al. (1995) Biotechnology (NY) 13(10):1090f), of oleosin (WO 98/45461) or of Bce4 (WO 91/13980). Further suitable seed-specific promoters are those of the genes coding for the high molecular weight glutenin (HMWG), gliadin, branching enzyme, ADP glucose pyrophosphatase (AGPase) or starch synthase. Preference is further given to promoters which allow seed-specific expression in monocotyledones such as corn, barley, wheat, rye, rice, etc. promoters which may be employed advantageously are the promoter of the lpt2 or lpt1 gene (WO 95/15389, WO 95/23230) and the promoters described in WO 99/16890 (hordein, glutelin, oryzin, prolamin, gliadin, zein, kasirin or secalin promoters). Further seed-specific promoters are described in WO 89/03887.

Tuber-, storage-root- or root-specific promoters comprise, for example, the class I patatin promoter (B33) or the promoter of the potato cathepsin D inhibitor.

Leaf-specific promoters comprise, for example, the promoter of the potato cytosolic FBPase (WO 97/05900), the SSU promoter (small subunit) of rubisco (ribulose-1,5-bisphosphate carboxylase) or the potato ST-LSI promoter (Stockhaus et al. (1989) EMBO J 8:2445-2451).

Flower-specific promoters comprise, for example, the phytoene synthase promoter (WO 92/16635) or the promoter of the P-rr gene (WO 98/22593).

Anther-specific promoters comprise, for example, the 5126 promoter (U.S. Pat. No. 5,689,049, U.S. Pat. No. 5,689,051), the glob-1 promoter and the γ-zein promoter.

c) Chemically inducible promoters

Chemically inducible promoters allow expression control as a function of an exogenous stimulus (review article: Gatz et al. (1997) Ann Rev Plant Physiol Plant Mol Biol 48:89-108). Examples which may be mentioned are: the PRP1 promoter (Ward et al. (1993) Plant Mol Biol 22:361-366), a salicylic acid-inducible promoter (WO 95/19443), a benzenesulfonamide-inducible promoter (EP-A 0 388 186), a tetracycline-inducible promoter (Gatz et al. (1992) Plant J 2:397-404), an abscisic acid-inducible promoter (EP 0 335 528) and an ethanol- or cyclohexanone-inducible promoter (WO 93/21334). Also suitable is the promoter of the glutathione S-transferase isoform II gene (GST-II-27), which may be activated by exogenously applied safeners such as, for example, N,N-diallyl-2,2-dichloroacetamide (WO 93/01294) and which is functional in numerous tissues of both monocotyledones and dicotyledones.

Particular preference is given to constitutive or inducible promoters.

Preference is further given to plastid-specific promoters for targeted expression in the plastids. Suitable promoters are described, for example, in WO 98/55595 or WO 97/06250. promoters which may be mentioned here are the rpo B promoter element, the atoB promoter element, the clpP promoter element (see also WO 99/46394) and the 16SrDNA promoter element. Viral promoters are also suitable (WO 95/16783).

Targeted expression in plastids may also be achieved by using, for example, a bacterial or bacteriophage promoter, introducing the resulting expression cassette into the plastid DNA and then expressing expression by means of a fusion protein of a bacterial or bacteriophage polymerase and a plastid transit peptide. U.S. Pat. No. 5,925,806 describes an appropriate process.

Genetic control sequences further comprise also the 5'-untranslated regions, introns or noncoding 3' region of genes, such as, for example, the actin-1 intron, or the Adh1-S introns 1, 2 and 6 (general overview: The Maize Handbook, Chapter 116, Freeling and Walbot, Eds., Springer, New York (1994)). These sequences have been shown to be able to play a significant functions in the regulation of gene expression. Thus it has been demonstrated that 5'-untranslated sequences may increase transient expression of heterologous genes. They may further promote tissue specificity (Rouster J et al. (1998) Plant J. 15:435-440). As an example of translation enhancers, mention may be made of the 5' leader sequence of the tobacco mosaic virus (Gallie et al. (1987) Nucl Acids Res 15:8693-8711).

Polyadenylation signals suitable as control sequences are in particular polyadenylation signals of plant genes and also *Agrobacterium tumefaciens* T-DNA polyadenylation signals. Examples of particularly suitable terminator sequences are the OCS (octopine synthase) terminator and the NOS (nopaline synthase) terminator (Depicker A et al (1982) J Mol Appl Genet 1:561-573) and also the terminators of soybean actin, RUBISCO or alpha-amylase from wheat (Baulcombe D C et al (1987) Mol Gen Genet 209:33-40).

Advantageously, the expression cassette may contain one or more "enhancer sequences" functionally linked to the promoter, which make increased transgenic expression of the nucleic acid sequence possible.

Genetic control sequences further means sequences coding for fusion proteins consisting of a signal peptide sequence. The expression of a target gene is possible in any desired cell compartment, such as, for example, the endomembrane system, the vacuole and the chloroplasts. Desired glycosylation reactions, in particular foldings, and the like are possible by utilizing the secretory pathway. Secretion of the target protein to the cell surface or secretion into the culture medium, for example when using suspension-cultured cells or protoplasts, is also possible. The target sequences required for this may both be taken into account in individual vector variations and be introduced into the vector together with the target gene to be cloned by using a suitable cloning strategy. Target sequences which may be used are both endogenous, if present, and heterologous sequences. Additional heterologous sequences which are preferred for functional linkage but not limited thereto are further targeting sequences for ensuring subcellular localization in the apoplast, in the vacuole, in plastids, in the mitochrondrion, in the endoplasmic reticulum (ER), in the nucleus, in elaioplasts or other compartments; and also translation enhancers such as the 5' leader sequence from tobacco mosaic virus (Gallie et al. (1987) Nucl Acids Res 15: 8693-8711) and the like. The process of transporting proteins which are per se not located in the plastids specifically into said plastids has been described (Klosgen R B and Weil J H (1991) Mol Gen Genet 225(2):297-304; Van Breusegem F et al. (1998) Plant Mol Biol 38(3):491-496).

Control sequences are furthermore understood to be those which make possible a homologous recombination or insertion into the genome of a host organism or allow the removal from the genome. Methods such as the cre/lox technique allow the expression cassette to be removed tissue-specifically, possibly inducibly from the genome of the host organism (Sauer B. Methods. 1998; 14(4):381-92). Here, particular flanking sequences are attached to the target gene (lox sequences), which make subsequent removal by means of the cre recombinase possible.

Preferably, the expression cassette, consisting of a linkage of the promoter to the nucleic acid sequence to be transcribed, may have been integrated into a vector and may be transferred into the plant cell or organism, for example, by transformation, according to any of the processes described below.

"Transgenic" means preferably, for example with respect to a transgenic expression cassette, a transgenic expression vector, a transgenic organism or to processes for transgenic expression of nucleic acids, all constructions brought about by genetic engineering methods or processes using said constructions, in which either a) the nucleic acid sequence to be expressed, or
b) the promoter functionally linked to the nucleic acid sequence to be expressed according to a), or
c) (a) and (b)

are not located in their natural, genetic environment (i.e. at their natural chromosomal locus) or have been modified by genetic engineering methods, the modification possibly being, for example, a substitution, addition, deletion, inversion or insertion of one or more nucleotide residues. Natural genetic environment means the natural chromosomal locus in the source organism or the presence in a genomic library.

"Transgenic" means, with respect to expression ("transgenic expression"), preferably all expressions achieved using a transgenic expression cassette, transgenic expression vector or transgenic organism, according to the definitions indicated above.

The DNA constructs employed within the scope of the process of the invention and the vectors derived therefrom may contain further functional elements. The term functional element is to be understood broadly and means all of those elements which influence the preparation, propagation or function of the DNA constructs or of vectors or organisms derived therefrom. Examples which may be mentioned without being limited thereto are:

1. Selection Markers

Selection markers comprise, for example, those nucleic acid or protein sequences whose expression gives to a cell, tissue or organism an advantage (positive selection marker) or disadvantage (negative selection marker) over cells which do not express said nucleic acid or protein. Positive selection markers act, for example, by detoxifying a substance acting on the cell in an inhibitory manner (e.g. resistance to antibiotics/herbicides) or by forming a substance which enables the plant to regenerate better or grow more under the chosen conditions (for example nutritive markers, hormone-producing markers such as ipt; see below). Another type of positive selection mareker comprises mutated proteins or RNAs which are not sensitive to a selective agent (e.g. 16S rRNA mutants which are insensitive to spectinomycin). Negative selection markers act, for example, by catalyzing the formation of a toxic substance in the transformed cells (e.g. the codA gene).

1.1 Positive Selection Markers:

In order to further increase the efficiency, the DNA constructs may comprise additional positive selection markers. In a preferred embodiment, the process of the invention may thus be carried out in the form of a dual selection in which a sequence coding for a resistance to at least one toxin, antibiotic or herbicide is introduced together with the nucleic acid sequence to be inserted and selection is carried out additionally by using the toxin, antibiotic or herbicide.

Appropriate proteins and sequences of positive selection markers and also selection processes are familiar to the skilled worker. The selection marker imparts to the successfully transformed cells a resistance to a biocide (e.g. a herbicide such as phosphinothricin, glyphosate or bromoxynil), a metabolism inhibitor such as 2-deoxyglucose 6-phosphate (WO 98/45456) or an antibiotic such as, for example, tetracycline, ampicillin, kanamycin, G 418, neomycin, bleomycin or hygromycin. Selection markers which may be mentioned by way of example are:

phosphinothricin acetyltransferases (PAT) which acetylate the free amino group of the glutamine synthase inhibitor phosphinothricin (PPT) and thus detoxify PPT (de Block et al. (1987) EMBO J 6:2513-2518) (also referred to as Bialophos® resistance gene (bar)). Corresponding sequences are known to the skilled worker (from *Streptomyces hygroscopicus* GenBank Acc. No.: X17220 and X05822, from *Streptomyces viridochromogenes* GenBank Acc. No.: M 22827 and X65195; U.S. Pat. No. 5,489,520). Furthermore, synthetic genes have been described for expression in plastids. A synthetic PAT gene is described in Becker et al. (1994) Plant J 5:299-307. The genes impart a resistance to the herbicide Bialaphos or glufosinate and are frequently used markers in transgenic plants (Vickers J E et al. (1996) Plant Mol Miol Reporter 14:363-368; Thompson C J et al. (1987) EMBO J 6:2519-2523).

5-enolpyruvylshikimate 3-phosphate synthases (EPSPS) which impart a resistance to glyphosate (N-(phosphonomethyl) glycine). The molecular target of the unselective herbicide glyphosate is 5-enolpyruvyl-3-phosphoshikimate synthase (EPSPS). This enzyme has a key function in the biosynthesis of aromatic amino acids in microbes and plants but not in mammals (Steinrucken H C et al. (1980) Biochem Biophys Res Commun 94:1207-1212; Levin J G and. Sprinson D B (1964) J Biol Chem 239:1142-1150; Cole D J (1985) Mode of action of glyphosate a literature analysis, p. 48-74. In: Grossbard E and Atkinson D (eds.). The herbicide glyphosate. Buttersworths, Boston.). Preference is given to using glyphosate-tolerant EPSPS variants as selection markers (Padgette S R et al. (1996). New weed control opportunities: development of soybeans with a Roundup Ready™ gene. In: Herbicide Resistant Crops (Duke, S. O., ed.), pp. 53-84. CRC Press, Boca Raton, Fla.; Saroha M K and Malik V S (1998) J Plant Biochemistry and Biotechnology 7:65-72). The EPSPS gene of *Agrobacterium* sp. strain CP4 has a natural tolerance for glyphosate, which can be transferred to appropriate transgenic plants. The CP4 EPSPS gene was cloned from *Agrobacterium* sp. strain CP4 (Padgette S R et al. (1995) Crop Science 35(5):1451-1461). Sequences of EPSPS enzymes which are glyphosate-tolerant have been described (inter alia in U.S. Pat. No. 5,510,471; U.S. Pat. No. 5,776,760; U.S. Pat. No. 5,864,425; U.S. Pat. No. 5,633,435; U.S. Pat. No. 5,627;061; U.S. Pat. No. 5,463, 175; EP 0 218 571). Further sequences are described under GenBank Acc. No: X63374 or M10947.

Glyphosat®-degrading enzymes (gox gene; glyphosate oxidoreductase). GOX (for example *Achromobacter* sp. glyphosate oxidoreductase) catalyzes the cleavage of a C—N bond in glyphosate which is thus converted to aminomethylphosphonic acid (AMPA) and glyoxylate. GOX can thereby impart a resistance to glyphosate (Padgette S R et al. (1996) J Nutr 126(3):702-16; Shah D et al. (1986) Science 233:478-481).

The deh gene encodes a dehalogenase which inactivates Dalapon® (GenBank Acc. No.: AX022822, AX022820 and WO 99/27116)

The bxn genes encode bromoxynil-degrading nitrilase enzymes (Genbank Acc. No: E01313 and J03196).

Neomycin phosphotransferases impart a resistance to antibiotics (aminoglycosides) such as neomycin, G418, hygromycin, paromomycin or kanamycin by reducing the inhibiting action of said antibiotics by means of a phosphorylation reaction. Particular preference is given to the nptII gene. Sequences can be obtained from GenBank (AF080390; AF080389). Moreover, the gene is already part of numerous expression vectors and can be isolated therefrom using processes familiar to the skilled worker (AF234316; AF234315; AF234314). The NPTII gene encodes an aminoglycoside 3'-O-phosphotransferase from *E. coli*, Tn5 (GenBank Acc. No: U00004 position 1401-2300; Beck et al. (1982) Gene 19 327-336).

The DOG$^R$1 gene was isolated from the yeast *Saccharomyces* cerevisiae (EP-A 0 807 836) and encodes a 2-deoxyglucose 6-phosphate phosphatase which imparts a resistance to 2-DOG (Randez-Gil et al. (1995) Yeast 11:1233-1240; Sanz et al. (1994) Yeast 10:1195-1202, GenBank Acc. No.: NC001140; position 194799-194056).

Acetolactate synthases which impart a resistance to imidazolinone/sulfonylurea herbicides (GenBank Acc. No.: X51514; Sathasivan K et al. (1990) Nucleic Acids Res. 18(8):2188); AB049823; AF094326; X07645; X07644; A19547; A19546; A19545; I05376; I05373; AL133315)

Hygromycin phosphotransferases (e.g. GenBank Acc. No.: X74325) which impart a resistance to the antibiotic hygromycin. The gene is part of numerous expression vectors and may be isolated therefrom using processes familiar to the skilled worker (such as, for example, polymerase chain reaction) (GenBank Acc. No.: AF294981; AF234301; AF234300; AF234299; AF234298; AF354046; AF354045).

Genes of resistance to
a) Chloramphenicol (chloramphenicol acetyltransferase),
b) tetracycline (inter alia GenBank Acc. No.: X65876; X51366). Moreover, the gene is already part of numerous expression vectors and may be isolated therefrom using processes familiar to the skilled worker (such as, for example, polymerase chain reaction)
c) Streptomycin (inter alia GenBank Acc. No.: AJ278607).
d) Zeocin, the corresponding resistance gene is part of numerous cloning vectors (e.g. GenBank Acc. No.: L36849) and may be isolated therefrom using processes familiar to the skilled worker (such as, for example, polymerase chain reaction).
e) Ampicillin (β-lactamase gene; Datta N, Richmond M H (1966) Biochem J 98(1):204-9; Heffron F et al (1975) J. Bacteriol 122: 250-256; Bolivar F et al. (1977) Gene 2:95-114). The sequence is part of numerous cloning vectors and may be isolated therefrom using processes familiar to the skilled worker (such as, for example, polymerase chain reaction).

Genes such as isopentenyl transferase from *Agrobacterium tumefaciens* (strain:PO22) (Genbank Acc. No.: AB025109) may also be used as selection markers. The ipt gene is a key enzyme of cytokinin biosynthesis. Its overexpression facilitates the regeneration of plants (e.g. selection on cytokinin-free medium). The process for utilizing the ipt gene has been described (Ebinuma H et al. (2000) Proc Natl Acad Sci USA 94:2117-2121; Ebinuma H et al. (2000) Selection of Marker-free transgenic plants using the oncogenes (ipt, rol A, B, C) of *Agrobacterium* as selectable markers, In Molecular Biology of woody Plants. Kluwer Academic Publishers).

Various other positive selection markers which impart to the transformed plants a growth advantage over untransformed plants and also processes for their use are described, inter alia, in EP-A 0 601 092. Examples which may be mentioned are β-glucuronidase (in connection with cytokinin glucuronide, for example), mannose 6-phosphate isomerase (in connection with mannose), UDP-galactose 4-epimerase (in connection with galactose, for example).

For a selection marker functional in plastids, particular preference is given to those which impart a resistance to spectinomycin, streptomycin, kanamycin, lincomycin, gentamycin, hygromycin, methotrexat, bleomycin, phleomycin, blasticidin, sulfonamide, phosphinothricin, chlorsulfuron, bromoxymil, glyphosate, 2,4-datrazine, 4-methyltryptophan, nitrate, S-aminoethyl-L-cysteine, lysine/threonine, aminoethyl-cysteine or betainealdehyde. Particular preference is given to the genes aadA, nptII, BADH, FLARE-S (a fusion of aadA and GFP, described in Khan M S & Maliga P (1999) Nature Biotech 17:910-915). Especially suitable is the aadA gene (Svab Z and Maliga P (1993) Proc Natl Acad Sci USA 90:913-917). Modified 16S rDNA and also betainealdehyde dehydrogenase (BADH) from spinach have also been described (Daniell H et al. (2001) Trends Plant Science 6:237-239; Daniell H et al. (2001) Curr Genet 39:109-116; WO 01/64023; WO 01/64024; WO 01/64850). Lethal agents such as, for example, glyphosate may also be utilized in connection with correspondingly detoxifying or resistance enzymes (WO 01/81605).

The concentrations of the antibiotics, herbicides, biocides or toxins, which are used in each case for selection, must be adapted to the particular test conditions or organisms. Examples which may be mentioned for plants are kanamycin (Km) 50 mg/L, hygromycin B 40 mg/L, phosphinothricin (Ppt) 6 mg/L, spectinomycin (Spec) 500 mg/L.

2. Reporter Genes

Reporter genes code for readily quantifiable proteins and thus ensure, via intrinsic color or enzyme activity, an evaluation of the transformation efficiency and of the location or time of expression. In this context, very particular preference is given to genes coding for reporter proteins (see also Schenborn E, Groskreutz D (1999) Mol Biotechnol 13(1):29-44) such as

- green fluorescence protein (GFP) (Chui W L et al. (1996) Curr Biol 6:325-330; Leffel S M et al. (1997) Biotechniques 23(5):912-8; Sheen et al. (1995) Plant J 8(5):777-784; Haseloff et al. (1997) Proc Natl Acad Sci USA 94(6): 2122-2127; Reichel et al. (1996) Proc Natl Acad Sci USA 93(12):5888-5893; Tian et al. (1997) Plant Cell Rep 16:267-271; WO 97/41228)
- chloramphenicol transferase
- luciferase (Millar et al. (1992) Plant Mol Biol Rep 10: 324-414; Ow et al. (1986) Science 234:856-859); allows bioluminescence detection
- β-galactosidase (encodes an enzyme for which various chromogenic substrates are available)
- β-glucuronidase (GUS) (Jefferson et al. (1987) EMBO J 6: 3901-3907) or the uidA gene (encode enzymes for which various chromogenic substrates are available)
- R-locus gene product which regulates production of anthocyanin pigments (red color) in plant tissue and thus makes possible a direct analysis of the promoter activity without addition of additional auxiliary substances or chromogenic substrates (Dellaporta et al. (1988) In: Chromosome Structure and Function: Impact of New Concepts, 18$^{th}$ Stadler Genetics Symposium, 11:263-282)
- tyrosinase (Katz et al. (1983) J Gen Microbiol 129:2703-2714), enzyme which oxidizes tyrosine to give DOPA and dopaquinone which consequently form the readily detectable melanine.
- aequorin (Prasher et al. (1985) Biochem Biophys Res Commun 126(3):1259-1268), may be used in calcium-sensitive bioluminescence detection.

3. Origins of replication which ensure propagation of the expression cassettes or vectors of the invention, for example in E. coli. Examples which may be mentioned are ORI (origin of DNA replication), the pBR322 ori or the P15A ori (Sambrook et al.: Molecular Cloning. A Laboratory Manual, 2$^{nd}$ ed. Cold Spring Harbor Laboratory Press, Cold Spring Harbor, N.Y., 1989).

4. Elements, for example border sequences, which enable agrobacteria-mediated transfer into plant cells for transfer and integration into the plant genome, such as, for example, the right or left border of T-DNA or the vir region.

5. Multiple cloning regions (MCS) allow and facilitate the insertion of one or more nucleic acid sequences.

Nucleic acid sequences (e.g. expression cassettes) may be introduced into a plant organism or cells, tissues, organs, parts or seeds thereof by advantageously using vectors which contain said sequences. Vectors may be, by way of example, plasmids, cosmids, phages, viruses or else *agrobacteria*. The sequences may be inserted into the vector (preferably a plasmid vector) via suitable restriction cleavage sites. The resulting vector may first be introduced into *E. coli* and amplified. Correctly transformed *E. coli* are selected, grown and the recombinant vector is obtained using methods familiar to the skilled worker. Restriction analysis and sequencing may serve to check the cloning step. Preference is given to those vectors which make possible a stable integration into the host genome.

The preparation of a transformed organism (or a transformed cell or tissue) requires that the corresponding DNA (e.g. the transformation vector) or RNA is introduced into the corresponding host cell. For this process which is referred to as transformation (or transduction or transfection), a multiplicity of methods and vectors are available (Keown et al. (1990) Methods in Enzymology 185:527-537; Plant Molecular Biology and Biotechnology (CRC Press, Boca Raton, Fla.), Chapter 6/7, pp. 71-119 (1993); White F F (1993) Vectors for Gene Transfer in Higher Plants; in: Transgenic Plants, Vol. 1, Engineering and Utilization, Editors: Kung and Wu R, Academic Press, 15-38; Jenes B et al. (1993) Techniques for Gene Transfer, in: Transgenic Plants, Vol. 1, Engineering and Utilization, editors: Kung and R. Wu, Academic Press, pp. 128-143; Potrykus (1991) Annu Rev Plant Physiol Plant Molec Biol 42:205-225; Halford N G, Shewry P R (2000) Br Med Bull 56(1):62-73).

For example, the DNA or RNA may be introduced directly by microinjection (WO 92/09696, WO 94/00583, EP-A 0 331 083, EP-A 0 175 966) or by bombardment with DNA or RNA-coded microparticles (biolistic processes using the gene gun "particle bombardment"; U.S. Pat. No. 5,100,792; EP-A 0 444 882; EP-A 0 434 616; Fromm M E et al. (1990) Bio/Technology 8(9):833-9; Gordon-Kamm et al. (1990) Plant Cell 2:603). The cell may also be permeabilized chemically, for example with polyethylene glycol, so as to enable the DNA to reach the cell by means of diffusion. The DNA may also take place by means of protoplast fusion to other DNA-containing units such as minicells, cells, lysosomes or liposomes (Freeman et al. (1984) Plant Cell Physiol. 29:1353ff; U.S. Pat. No. 4,536,475). Electroporation is another suitable method for introducing DNA, in which the cells are permeabilized reversibly by an electric impulse (EP-A 290 395, WO 87/06614). Further processes comprise the calcium-phosphate-mediated transformation, DEAE-dextran-mediated transformation, the incubation of dry embryos in DNA-containing solution or other methods of direct introduction of DNA (DE 4 005 152, WO 90/12096, U.S. Pat. No. 4,684,611). Appropriate processes have been described (e.g. in Bilang et al. (1991) Gene 100:247-250; Scheid et al. (1991) Mol Gen Genet 228:104-112; Guerche et al. (1987) Plant Science 52:111-116; Neuhause et al. (1987) Theor Appl Genet 75:30-36; Klein et al. (1987) Nature 327: 70-73; Howell et al. (1980) Science 208:1265; Horsch et al. (1985) Science 227:1229-1231; DeBlock et al. (1989) Plant Physiology 91:694-701; Methods for Plant Molecular Biology (Weissbach and Weissbach, eds.) Academic Press Inc. (1988); and Methods in Plant Molecular Biology (Schuler and Zielinski, eds.) Academic Press Inc. (1989)). Physical methods of introducing DNA into plant cells have been reviewed by Oard (1991) Biotech Adv 9:1-11.

In the case of these "direct" transformation methods, no particular requirements are made on the plasmid used. It is possible to use simple plasmids such as those of the pUC series, pBR322, M13mp series, pACYC184 etc.

Besides these "direct" transformation techniques, transformation may also be carried out by bacterial infection by means of *Agrobacterium* (e.g. EP 0 116 718), viral infection by means of viral vectors (EP 0 067 553; U.S. Pat. No. 4,407,956; WO 95/34668; WO 93/03161) or by means of pollen (EP 0 270 356; WO 85/01856; U.S. Pat. No. 4,684, 611).

Transformation is preferably carried out by means of *agrobacteria* which contain disarmed Ti-plasmid vectors, using the latters' natural ability to transfer genes to plants (EP-A 0 270 355; EP-A 0 116 718). *Agrobacterium* transformation is widespread for transforming dicotyledones, but is also increasingly applied to monocotyledones (Toriyama et al. (1988) Bio/Technology 6: 1072-1074; Zhang et al. (1988) Plant Cell Rep 7:379-384; Zhang et al. (1988) Theor Appl Genet 76:835-840; Shimamoto et al. (1989) Nature 338:274-276; Datta et al. (1990) Bio/Technology 8: 736-740; Christou et al. (1991) Bio/Technology 9:957-962; Peng et al. (1991) International Rice Research Institute, Manila, Philippines 563-574; Cao et al. (1992) Plant Cell Rep 11:585-591; Li et al. (1993) Plant Cell Rep 12:250-255; Rathore et al. (1993) Plant Mol Biol 21:871-884; Fromm et al. (1990) Bio/Technology 8:833-839; Gordon-Kamm et al. (1990) Plant Cell 2:603-618; D'Halluin et al. (1992) Plant Cell 4:1495-1505; Walters et al. (1992) Plant Mol Biol 18:189-200; Koziel et al. (1993) Biotechnology 11:194-200; Vasil I K (1994) Plant Mol Biol 25:925-937; Weeks et al. (1993) Plant Physiol 102: 1077-1084; Somers et al. (1992) Bio/Technology 10:1589-1594; WO 92/14828; Hiei et al. (1994) Plant J 6:271-282).

The strains most often used for agrobacterial transformation, *Agrobacterium tumefaciens* or *Agrobacterium rhizogenes*, contain a plasmid (Ti and Ri plasmids, respectively), which is transferred to the plant after agrobacterial infection. Part of this plasmid, called T-DNA (transferred DNA), is integrated into the genome of the plant cell. Alternatively, *Agrobacterium* may also transfer binary vectors (mini. Ti plasmids) to plants and integrate them into the genome of said plants.

The application of *Agrobacterium tumefaciens* to the transformation of plants, using tissue culture explants, has been described (inter alia, Horsch R B et al. (1985) Science 225: 1229ff; Fraley et al. (1983) Proc Natl Acad Sci USA 80: 4803-4807; Bevans et al. (1983) Nature 304:184-187). Many *Agrobacterium tumefaciens* strains are capable of transferring genetic material, such as, for example, the strains EHA101[pEHA101], EHA105[pEHA105], LBA4404 [pAL4404], C58C1[pMP90] and C58C1[pGV2260] (Hood et al. (1993) Transgenic Res 2:208-218; Hoekema et al. (1983) Nature 303:179-181; Koncz and Schell (1986) Gen Genet 204:383-396; Deblaere et al. (1985) Nucl Acids Res 13: 4777-4788).

When using *agrobacteria*, the expression cassette must be integrated into special plasmids, either a shuttle or intermediate vector or a binary vector. When using a Ti or Ri plasmid for transformation, then at least the right border, but usually the right and left borders of the Ti or Ri plasmid T-DNA are connected as a flanking region to the expression cassette to be introduced. Preference is given to using binary vectors. Binary vectors may replicate both in *E. coli* and in *agrobacteria* and contain the components required for transfer into a plant system. They normally contain a selection marker gene for selection of transformed plants (e.g. the nptII gene which imparts a resistance to kanamycin) and a linker or polylinker flanked by the right and left T-DNA border sequences. They contain moreover, outside the T-DNA border sequence, also a selection marker which enables transformed *E. coli* and/or *agrobacteria* to be selected (e.g. the nptIII gene which imparts a resistance to kanamycin). Corresponding vectors may be transformed directly into Agrobacterium (Holsters et al. (1978) Mol Gen Genet 163:181-187).

Binary vectors are based, for example, on "broad host range" plasmids such as pRK252 (Bevan et al. (1984) Nucl Acid Res 12, 8711-8720) and pTJS75 (Watson et al. (1985) EMBO J 4(2):277-284). A large group of the binary vectors used is derived from pBIN19 (Bevan et al. (1984) Nucl Acid Res 12:8711-8720). Hajdukiewicz et al. developed a binary vector (pPZP) which is smaller and more efficient than the previously customary vectors (Hajdukiewicz et al. (1994) Plant Mol Biol 25:989-994). Improved and particularly preferred binary vector systems for Agrobacterium-mediated transformation are described in WO 02/00900.

The *agrobacteria* transformed with a vector of this kind may then be used in the known manner for transforming plants, in particular crop plants such as, for example, oilseed rape, for example by bathing wounded leaves or leaf sections in an agrobacterial solution and subsequently culturing them in suitable media. The transformation of plants by *agrobacteria* has been described (White F F, Vectors for Gene Transfer in Higher Plants; in Transgenic Plants, Vol. 1, Engineering and Utilization, edited by S. D. Kung and R. Wu, Academic Press, 1993, pp. 15-38; Jenes B et al. (1993) Techniques for Gene Transfer, in: Transgenic Plants, Vol. 1, Engineering and Utilization, edited by S. D. Kung and R. Wu, Academic Press, pp. 128-143; Potrykus (1991) Annu Rev Plant Physiol Plant Molec Biol 42:205-225). Transgenic plants may be regenerated in the known manner from the transformed cells of the wounded leaves or leaf sections.

Different explants, cell plants, tissues, organs, embryos, seeds, microspores or other unicellular or multicellular cellular structures derived from a plant organism may be used for transformation. Transformation processes adjusted to the particular explants, cultures or tissues are known to the skilled worker. Examples which may be mentioned are: shoot internodes (Fry J et al. (1987) Plant Cell Rep. 6:321-325), hypocotyls (Radke S E et al. (1988) Theor Appl Genet 75:685-694; Schröder M et al. (1994) Physiologia Plant 92: 37-46.; Stefanov I et al. (1994) Plant Sci. 95:175-186; Weier et al. (1997) Fett/Lipid 99:160-165), cotyledonous petioles (Meloney M M et al. (1989) Plant Cell Rep 8:238-242; Weier D et al. (1998) Molecular Breeding 4:39-46), microspores and pro-embryos (Pechnan (1989) Plant Cell Rep. 8:387-390) and flower stalks (Boulter M E et al. (1990) Plant Sci 70:91-99; Guerche P et al. (1987) Mol Gen Genet 206:382-386). In the case of a direct gene transfer, mesophyllprotoplasts (Chapel P J & Glimelius K (1990) Plant Cell Rep 9: 105-108; Golz et al. (1990) Plant Mol Biol 15:475-483) or else hypocotyl protoplasts (Bergmann P & Glimelius K (1993) Physiologia Plant 88:604-611) and microspores (Chen J L et al. (1994) Theor Appl Genet 88:187-192; Jonesvilleneuve E et al. (1995) Plant Cell Tissue and Organ Cult 40:97-100) and shoot sections (Seki M et al. (1991) Plant Mol Biol 17:259-263) may be employed successfully.

Stably transformed cells, i.e. those which contain the introduced DNA integrated into the DNA of the host cell, may be selected from untransformed cells by using the selection process of the invention. The plants obtained may be grown and crossed in the usual way. Preferably, two or more generations should be cultured in order to ensure that the genomic integration is stable and can be inherited.

As soon as a transformed plant cell has been prepared, it is possible to obtain a complete plant by using processes known to the skilled worker. This involves, for example, starting from callus cultures, individual cells (e.g. protoplasts) or leaf disks (Vasil et al. (1984) Cell Culture and Somatic Cel Genetics of Plants, Vol I, II and III, Laboratory Procedures and Their Applications, Academic Press; Weissbach and Weissbach (1989) Methods for Plant Molecular Biology, Academic Press). It is possible to induce from these still undifferentiated callus cell masses the formation of shoot and root in the known manner. The seedlings obtained may be planted out and grown. Appropriate processes have been described (Fennell et al. (1992) Plant Cell Rep. 11: 567-570; Stoeger et al. (1995) Plant Cell Rep. 14:273-278; Jahne et al. (1994) Theor Appl Genet 89:525-533).

The efficacy of expressing the transgenically expressed nucleic acids may be determined, for example, in vitro by shoot-meristem propagation using any of the selection methods described above. Moreover, changes in the type and level of expression of a target gene and the effect on the phenotype of the plant may be tested in greenhouse experiments using test plants.

The process of the invention is preferably used within the framework of plant biotechnology for generating plants having advantageous properties. The "nucleic acid sequence to be inserted" into the genome of the plant cell or the plant organism preferably comprises at least one expression cassette, said expression cassette being able to express, under the control of a promoter functional in plant cells or plant organisms, an RNA and/or a protein which do not cause reduction of the expression, amount, activity and/or function of a marker protein but, particularly preferably, impart to the plant genetically altered in this way an advantageous phenotype. Numerous genes and proteins which may be used for achieving an advantageous phenotype, for example for the increase in quality of foodstuff or for producing particular chemicals or pharmaceuticals (Dunwell J M (2000) J Exp Bot 51 Spec No:487-96) are known to the skilled worker.

Thus it is possible to improve the suitability of the plants or the seeds thereof as foodstuff or feedstuff, for exmaple by altering the compositions and/or the content of metabolites, in particular proteins, oils, vitamins and/or starch. It is also possible to increase the growth rate, yield or resistance to biotic or abiotic stress factors. Advantageous effects may be achieved both by transgenic expression of nucleic acids or proteins and by targeted reduction of the expression of endogenous genes, with respect to the phenotype of the transgenic plant. The advantageous effects which may be achieved in the transgenic plant comprise, for example:

increased resistance to pathogens (biotic stress)
increased resistance to environmental factors such as heat, cold, frost, drought, UV light, oxidative stress, wetness, salt, etc. (abiotic stress)
increased yield
improved quality, for example increased nutritional value, increased storability The invention further relates to the use of the transgenic plants prepared according to the process of the invention and of the cells, cell cultures, plants or propagation material such as seeds or fruits derived from said plants, for preparing foodstuff or feedstuff, pharmaceuticals or fine chemicals such as, for example, enzymes, vitamins, amino acids, sugars, fatty acids, natural and synthetic flavorings, aroma substances and colorants. Particular preference is given to the production of triacyl glycerides, lipids, oils, fatty acids, starch, tocopherols and tocotrienols and also carotenoids. Genetically modified plants of the invention, which may be consumed by humans and animals may also be used as foodstuff or feedstuff, for example, directly or after preparation known per se.

As already mentioned above, the process of the invention comprises in a particularly advantageous embodiment, in a process step downstream of the selection, the deletion of the sequence coding for the marker protein (e.g. mediated by recombinase or as described in WO03/004659) or the elimination by crossing and/or segregation of said sequences. (It is obvious to the skilled worker that, for this purpose, the nucleic acid sequence integrated into the genome and the sequence coding for the marker protein should have a separate chromosomal locus in the transformed cells. This, however, is the case in the majority of the resulting plants, merely for reasons of statistics). This procedure is particularly advantageous if the marker protein is a transgene which otherwise does not occur in the plant to be transformed. Although the resulting plant may still possibly contain the compound for reducing the expression, amount, activity and/or function of the marker protein, said compound would have no longer any "counterpart" in the form of said marker protein, and thus would have no effect. This is particularly the case if the marker protein is derived from a non-plant organism and/or is synthetic (for example the codA protein). It is, however, also possible to use plant marker proteins from other plant species, which otherwise do not occur in the cell to be transformed (i.e. if not introduced as transgene). Said marker proteins are referred to as "nonendogenous" marker proteins within the scope of the present invention.

Very particularly advantageously, the compound for reducing the expression, amount, activity and/or function of the marker protein is an RNA. After deletion or elimination by crossing/segregation, the resulting transgenic plant would have no longer any unnecessary (and, if appropriate, undesired) foreign protein. The sole foreign protein would be possibly the protein resulting from the nucleic acid sequence inserted into the genome. For reasons of product approval, this embodiment is particularly advantageous. As described above, said RNA may be an antisense RNA or, particularly preferably, a double-stranded RNA. It may be expressed separately from the RNA coding for the target protein but also, possibly, on the same strand as the latter.

In summary, the particularly advantageous embodiment comprises the following features:

A process for preparing transformed plant cells or organisms, which comprises the following steps:

a) transforming a population of plant cells which comprises at least one non-endogenous (preferably non-plant) marker protein capable of converting directly or indirectly a substance X which is nontoxic for said population of plant cells into a substance Y which is toxic for said population, with at least one nucleic acid sequence to be inserted in combination with at least one nucleic acid sequence coding for a ribonucleic acid sequence capable of reducing the expression, amount, activity and/or function of said marker protein, and b) treating said population of plant cells with the substance X at a concentration which causes a toxic effect for nontransformed cells, due to the conversion by the marker protein, and c) selecting transformed plant cells (and/or populations of plant cells, such as plant tissues or plants) whose genome contains said nucleic acid sequence and which have a growth advantage over nontransformed cells, due to the action of said compound, from said population of plant cells, the selection being carried out under conditions under which the marker protein can exert its toxic effect on the nontransformed cells, and d) regenerating fertile plants, and e) eliminating by crossing the nucleic acid sequence coding for the marker protein and isolating fertile plants whose genome contains said nucleic acid sequence but does not contain any longer the sequence coding for the marker protein.

Sequences

SEQ ID NO: 1 Nucleic acid sequence coding for *E. coli* cytosine deaminase (coda)

SEQ ID NO: 2 amino acid sequence coding for *E. coli* cytosine deaminase (codA)

SEQ ID NO: 3 Nucleic acid sequence coding for *E. coli* cytosine deaminase (codA), with modified start codon (GTG/ATG) for expression in eukaryotes SEQ ID NO: 4 Amino acid sequence coding for *E. coli* cytosine deaminase (codA), with modified start codon (GTG/ATG) for expression in eukaryotes SEQ ID NO: 5 Nucleic acid sequence coding for *Streptomyces griseolus* cytochrome P450-SU1 (suaC)

SEQ ID NO: 6 Amino acid sequence coding for *Streptomyces griseolus* cytochrome P450-SU1 (suaC)

SEQ ID NO: 7 Nucleic acid sequence coding for *Agrobacterium tumefaciens* indoleacetamide hydrolase (tms2)

SEQ ID NO: 8 Amino acid sequence coding for *Agrobacterium tumefaciens* indoleacetamide hydrolase (tms2)

SEQ ID NO: 9 Nucleic acid sequence coding for *Agrobacterium tumefaciens* indoleacetamide hydrolase (tms2)

SEQ ID NO: 10 Amino acid sequence coding for *Agrobacterium tumefaciens* indoleacetamide hydrolase (tms2)

SEQ ID NO: 11 Nucleic acid sequence coding for *Xanthobacter autotrophicus* haloalkane dehalogenase (dhlA)

SEQ ID NO: 12 Amino acid sequence coding for *Xanthobacter autotrophicus* haloalkane dehalogenase (dhlA)

SEQ ID NO: 13 Nucleic acid sequence coding for Herpes simplex Virus 1 thymidine kinase SEQ ID NO: 14 Amino acid sequence coding for Herpes simplex Virus 1 thymidine kinase SEQ ID NO: 15 Nucleic acid sequence coding for Herpes simplex Virus 1 thymidine kinase SEQ ID NO: 16 Amino acid sequence coding for Herpes simplex Virus 1 thymidine kinase SEQ ID NO: 17 Nucleic acid sequence coding for *Toxoplasma gondii* hypoxanthine-xanthine-guanine phosphoribosyl transferase SEQ ID NO: 18 Amino acid sequence coding for *Toxoplasma gondii* hypoxanthine-xanthine-guanine phosphoribosyl transferase SEQ ID NO: 19 Nucleic acid sequence coding for *E. coli* xanthine-guanine phosphoribosyl transferase SEQ ID NO: 20 Amino acid sequence coding for *E. coli* xanthine-guanine phosphoribosyl transferase SEQ ID NO: 21 Nucleic acid sequence coding for *E. coli* xanthine-guanine phosphoribosyl transferase SEQ ID NO: 22 Amino acid sequence coding for *E. coli* xanthine-guanine phosphoribosyl transferase SEQ ID NO: 23 Nucleic acid sequence coding for *E. coli* purine nucleoside phosphorylase (deoD)

SEQ ID NO: 24 Nucleic acid sequence coding for *E. coli* purine nucleoside phosphorylase (deoD)

SEQ ID NO: 25 Nucleic acid sequence coding for *Burkholderia caryophylli* phosphonate monoester hydrolase (pehA)

SEQ ID NO: 26 Amino acid sequence coding for *Burkholderia caryophylli* phosphonate monoester hydrolase (pehA)

SEQ ID NO: 27 Nucleic acid sequence coding for *Agrobacterium rhizogenes* tryptophan oxygenase (aux1)

SEQ ID NO: 28 Amino acid sequence coding for *Agrobacterium rhizogenes* tryptophan oxygenase (aux1)

SEQ ID NO: 29 Nucleic acid seuence coding for *Agrobacterium rhizogenes* indoleacetamide hydrolase (aux2)

SEQ ID NO: 30 Amino acid seuence coding for *Agrobacterium rhizogenes* indoleacetamide hydrolase (aux2)

SEQ ID NO: 31 Nucleic acid sequence coding for *Agrobacterium tumefaciens* tryptophan oxygenase (aux1)

SEQ ID NO: 32 Amino acid sequence coding for *Agrobacterium tumefaciens* tryptophan oxygenase (aux1)

SEQ ID NO: 33 Nucleic acid sequence coding for *Agrobacterium tumefaciens* indoleacetamide hydrolase (aux2)

SEQ ID NO: 34 Amino acid sequence coding for *Agrobacterium tumefaciens* indoleacetamide hydrolase (aux2)

SEQ ID NO: 35 Nucleic acid sequence coding for *Agrobacterium vitis* indoleacetamide hydrolase (aux2)

SEQ ID NO: 36 Amino acid sequence coding for *Agrobacterium vitis* indoleacetamide hydrolase (aux2)

SEQ ID NO: 37 Nucleic acid sequence coding for *Arabidopsis thaliana* 5-methylthioribose kinase (mtrK)

SEQ ID NO: 38 Amino acid sequence coding for *Arabidopsis thaliana* 5-methylthioribose kinase (mtrK)

SEQ ID NO: 39 Nucleic acid sequence coding for *Klebsiella pneumoniae* 5-methylthioribose kinase (mtrK)

SEQ ID NO: 40 Amino acid sequence coding for *Klebsiella pneumoniae* 5-methylthioribose kinase (mtrK)

SEQ ID NO: 41 Nucleic acid sequence coding for *Arabidopsis thaliana* alcohol dehydrogenase (adh)

SEQ ID NO: 42 Amino acid sequence coding for *Arabidopsis thaliana* alcohol dehydrogenase (adh)

SEQ ID NO: 43 Nucleic acid sequence coding for *Hordeum vulgare* (barley) alcohol dehydrogenase (adh)

SEQ ID NO: 44 Amino acid sequence coding for *Hordeum vulgare* (barley) alcohol dehydrogenase (adh)

SEQ ID NO: 45 Nucleic acid sequence coding for *Oryza sativa* (rice) alcohol dehydrogenase (adh)

SEQ ID NO: 46 Amino acid sequence coding for *Oryza sativa* (rice) alcohol dehydrogenase (adh)

SEQ ID NO: 47 Nucleic acid sequence coding for *Zea mays* (corn) alcohol dehydrogenase (adh)

SEQ ID NO: 48 Amino acid sequence coding for *Zea mays* (corn) alcohol dehydrogenase (adh)

SEQ ID NO: 49 Nukleic acid sequence coding for a sense RNA fragment of *E. coli* cytosine deaminase (codARNAi-sense)

```
SEQ ID NO: 50  Oligonucleotide primer codA5'HindIII
               5'-AAGCTTGGCTAACAGTGTCGAATAACG-3'

SEQ ID NO: 51  Oligonucleotide primer codA3'SalI
               5'-GTCGACGACAAAATCCCTTCCTGAGG-3'
```

SEQ ID NO: 52 Nucleic acid sequence coding for an antisense RNA fragment of *E. coli* cytosine deaminase (codARNAi-anti)

```
SEQ ID NO: 53  Oligonucleotide primer codA5'EcoRI
               5'-GAATTCGGCTAACAGTGTCGAATAACG-3'

SEQ ID NO: 54  Oligonucleotide primer codA3'BamHI
               5'-GGATCCGACAAAATCCCTTCCTGAGG-3'
```

SEQ ID NO: 55 Vector construct pBluKS-nitP-STLS1-35S-T

SEQ ID NO: 56 Expression vector pSUN-1 SEQ ID NO: 57 Transgenic expression vector pSUN-1-codA-RNAi SEQ ID NO: 58 Transgenic expression vector pSUN1-codA-RNAi-At.Act.-2-At.Als-R-ocsT SEQ ID NO: 59 Nukleic acid sequence coding for 5-methylthioribose kinase (mtrK) from corn (*Zea mays*); fragment SEQ ID NO: 60 Amino acid sequence coding for 5-methylthioribose kinase (mtrK) from corn (*Zea mays*); fragment SEQ ID NO: 61 Nucleic acid sequence coding for 5-methylthioribose kinase (mtrK) from oilseed rape (*Brassica napus*), fragment SEQ ID NO: 62 Amino acid sequence coding for 5-methylthioribose kinase (mtrK) from oilseed rape (*Brassica napus*), fragment SEQ ID NO: 63 Nucleic acid sequence coding for 5-methylthioribose kinase (mtrK) from oilseed rape (*Brassica napus*), fragment SEQ ID NO: 64 Amino acid sequence coding for 5-methylthioribose kinase (mtrK) from oilseed rape (*Brassica napus*), fragment SEQ ID NO: 65 Nucleic acid sequence coding for 5-methylthioribose kinase (mtrK) from rice (*Oryza sativa*), fragment SEQ ID NO: 66 Amino acid sequence coding for 5-methylthioribose kinase (mtrK) from rice (*Oryza sativa*), fragment SEQ ID NO: 67 Nucleic acid sequence coding for 5-methylthioribose kinase (mtrK) from soybean (*Glycine max*), fragment SEQ ID NO: 68 Amino acid sequence coding for 5-methylthioribose kinase (mtrK) from soybean (*Glycine max*), fragment

```
SEQ ID NO: 69 Oligonucleotide primer codA5'C-term
         5'-CGTGAATACGGCGTGGAGTCG-3'

SEQ ID NO: 70 Oligonucleotide primer codA3'C-term
         5'-CGGCAGGATAATCAGGTTGG-3'

SEQ ID NO: 71 Oligonucleotide primer 35sT 5' primer
         5'-GTCAACGTAACCAACCCTGC-3'
```

In a preferred embodiment, the marker protein gene is inactivated by introducing a sequence-specific recombinase. Preference is given to its expressing the recombinase, as depicted here, starting from an expression cassette.

The marker protein gene is flanked by recognition sequences for sequence-specific recombinases, with sequences of said marker protein gene being deleted by introducing said recombinase and thus said marker protein gene being inactivated.

FIG. 2-A: Inactivation of the marker protein gene by the action of a sequence-specific nuclease
P: promoter
DS: Recognition sequence for targeted induction of DNA double-strand breaks
MP-DS-MP': Sequence coding for a marker protein, comprising a DS
nDS: Inactivated DS
E: Sequence-specific enzyme for targeted induction of DNA double-strand breaks The marker protein gene may be established by a targeted mutation or deletion in the marker protein gene, for example by sequence-specific induction of DNA double-strand breaks at a recognition sequence for targeted induction of DNA double-strand breaks in or close to the marker protein gene (P-MP). The double-strand break may occur in the coding region or else the noncoding (such as, for example, the promoter) region, induces an illegitimate recombination (nonhomologous DNA-end joining) and thus, for example, a shift in the reading frame of said marker protein.

FIG. 2-B: Inactivation of the marker protein gene by the action of a sequence-specific nuclease
P: promoter
DS: Recognition sequence for targeted induction of DNA double-strand breaks
MP: Sequence coding for a marker protein
nDS: Inactivated DS
E: Sequence-specific enzyme for targeted induction of DNA double-strand breaks The marker protein gene may be established by a targeted deletion by sequence-specific induction of more than one sequence-specific DNA double-strand break in or close to said marker protein gene. The double-strand breaks may occur in the coding region or else the noncoding (such as, for example, the promoter) region and induce a deletion in the marker protein gene. The marker protein gene is preferably flanked by DS sequences and is completely deleted by the action of enzyme E.

Figure 1:
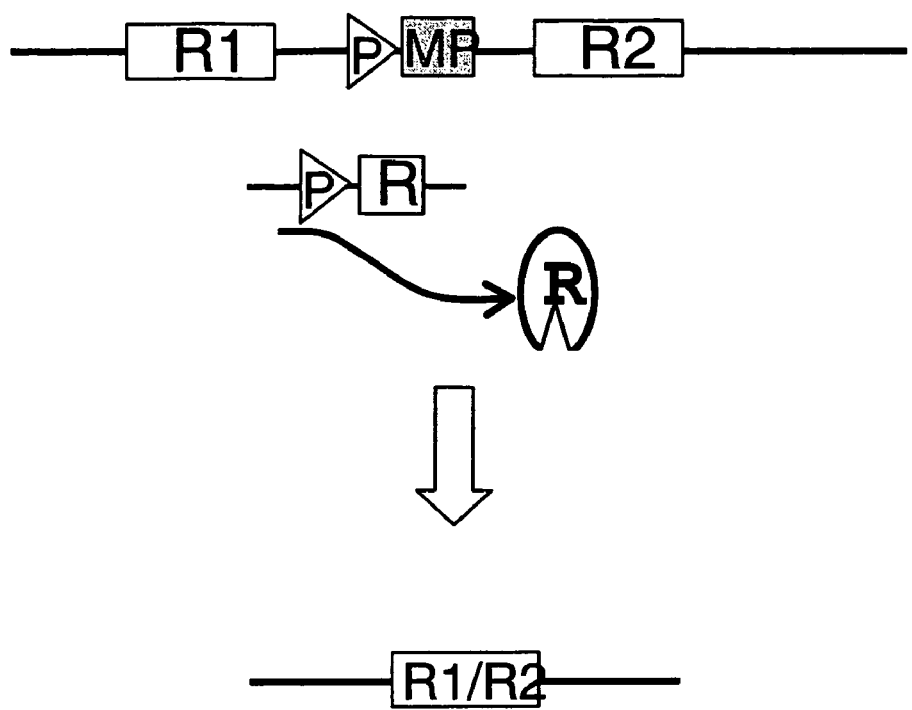
FIG. 1: Inactivation of the marker protein gene by means of introducing a recombinase
P: promoter
MP: Sequence coding for a marker protein
R1/R2: Recombinase recognition sequences
R: Recombinase or sequence coding for recombinase.
Figure 3:
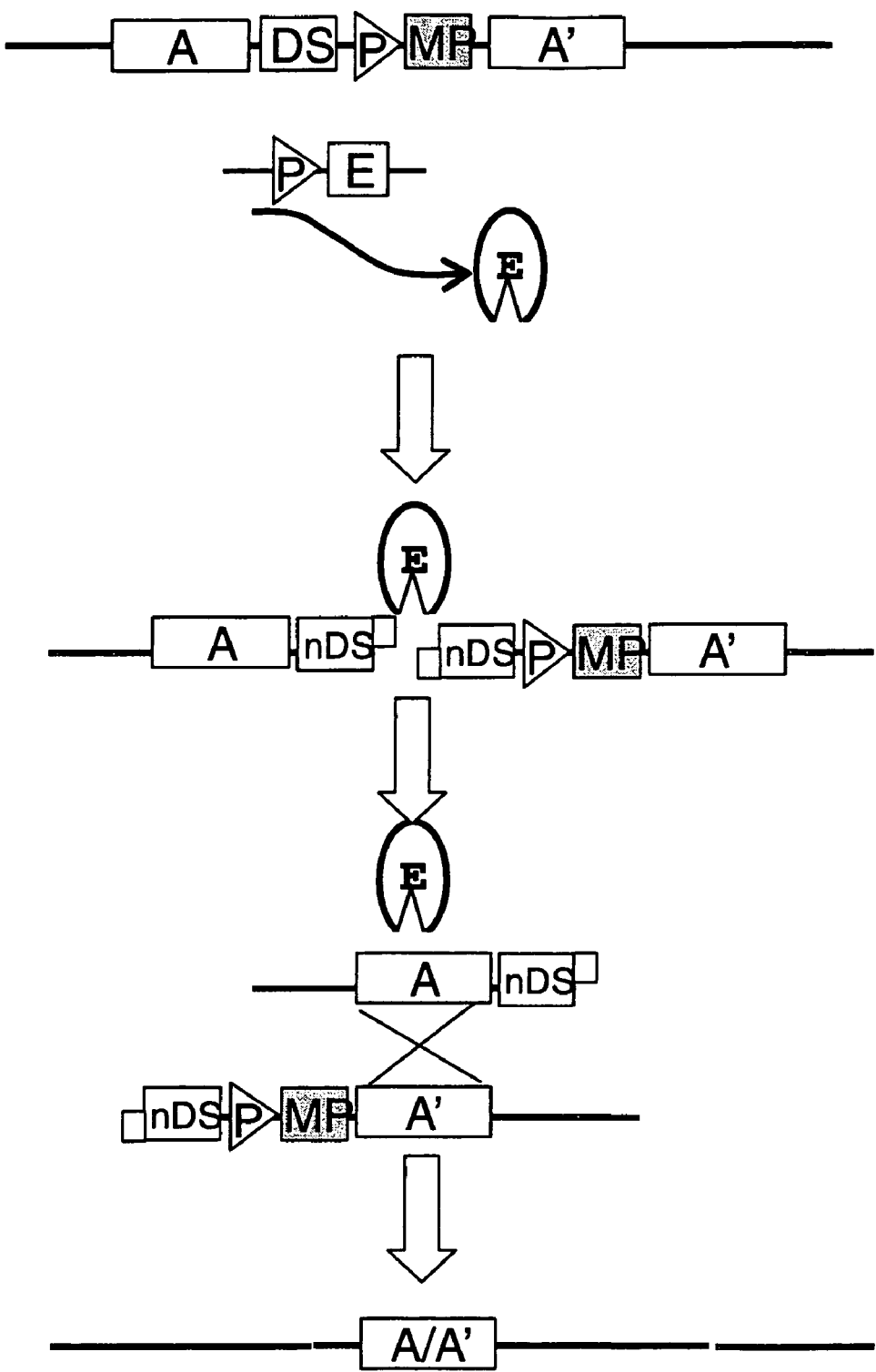

FIG. 3: Inactivation of the marker protein gene by inducing an intramolecular homologous recombination, due to the action of a sequence-specific nuclease
A/A': Sequences with a sufficient length and homology to one another, in order to recombine with one another as a consequence of the induced double-strand break
P: promoter
DS: Recognition sequence for targeted induction of DNA double-strand breaks
MP: Sequence coding for a marker protein
E: Sequence-specific enzyme for targeted induction of DNA double-strand breaks The marker protein gene may be inactivated by a deletion by means of intramolecular homologous recombination. Said homologous recombination may be initiated by sequence-specific induction of DNA double-strand breaks at a recognition sequence for targeted induction of DNA double-strand breaks in or close to the marker protein gene. The homologous recombination occurs between the sequences A and A' which have a sufficient length and homology to one another in order to recombine with one another as a consequence of the induced double-strand break. The recombination causes a deletion of essential sequences of the marker protein gene.

FIG. 4: Inactivation of the marker protein gene by intermolecular homologous recombination
A/A': Sequences with a sufficient length and homology to one another in order to recombine with one another
B/B': Sequences with a sufficient length and homology to one another in order to recombine with one another
P: promoter
I: nucleic acid sequence/gene of interest to be inserted
MP: Sequence coding for a marker protein The marker protein gene (P-MP) may also be inactivated by a targeted insertion into the marker protein gene, for example by means of intermolecular homologous recombination. In this context, the region to be inserted is flanked on its 5' and 3' ends by nucleic acid sequences (A' and B', respectively), which have a sufficient length and homology to corresponding flanking sequences of the marker protein (A and B, respectively) in order to make possible a homologous recombination between A and A' and B and B'. The recombination causes a deletion of essential sequences of the marker protein gene.

Figure 5:
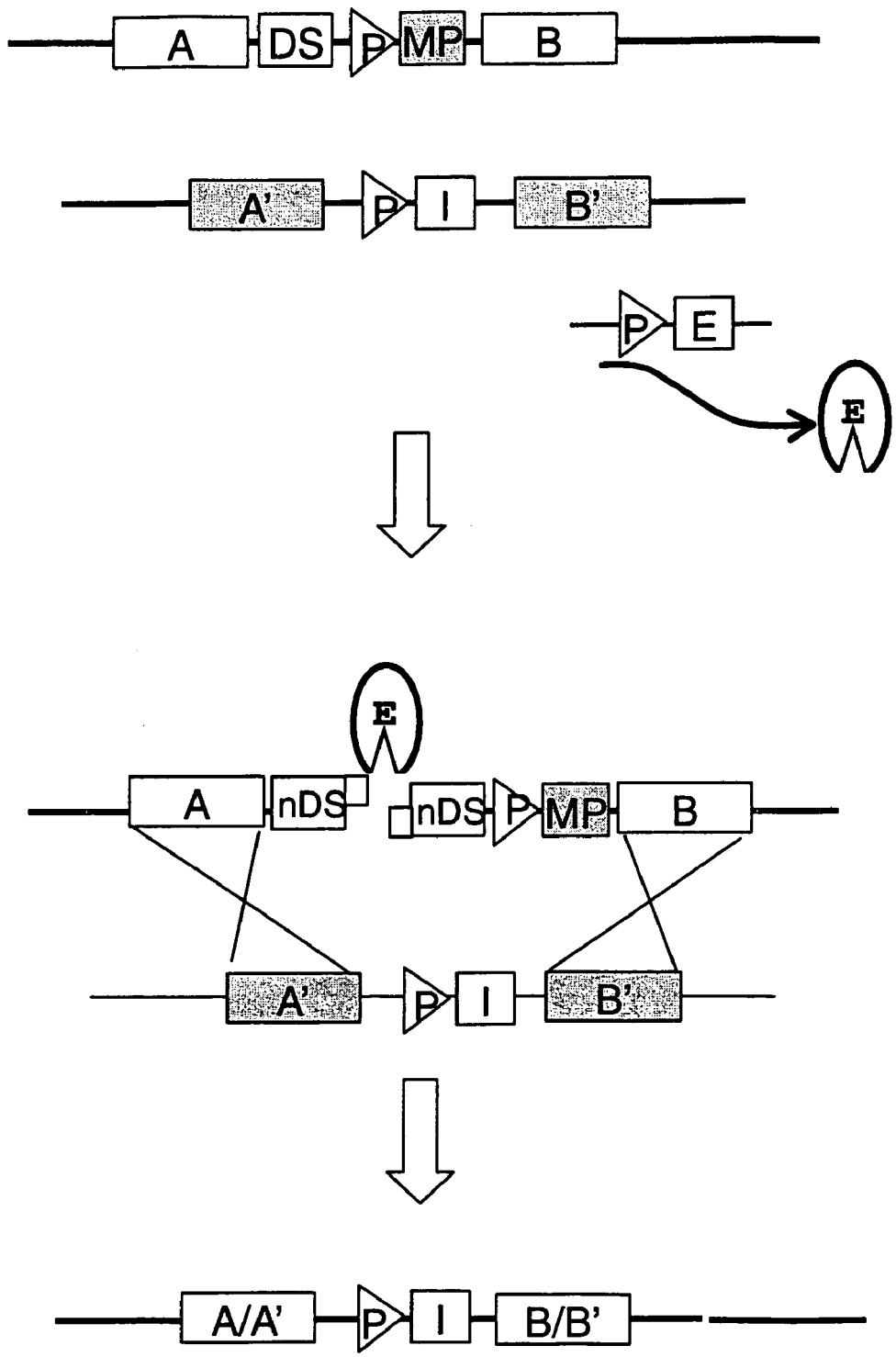

FIG. 5: Inactivation of the marker protein gene by intermolecular homologous recombination due to the action of a sequence-specific nuclease A/A': Sequences with a sufficient length and homology to one another in order to recombine with one another B/B': Sequences with a sufficient length and homology to one another in order to recombine with one another P: promoter I: nucleic acid sequence/gene of interest to be inserted MP: Sequence coding for a marker protein DS: Recognition sequence for targeted induction of DNA double-strand breaks E: Sequence-specific enzyme for targeted induction of DNA double-strand breaks The marker protein gene may also be inactivated by a targeted insertion into the marker protein gene, for example by means of intermolecular homologous recombination. The homologous recombination may be initiated by sequence-specific induction of DNA double-strand breaks at a recognition sequence for targeted induction of DNA double-strand breaks in or close to the marker protein gene. In this context, the region to be inserted is flanked at its 5' and 3' ends by nucleic acid sequences (A' and B', respectively) which have a sufficient length and homology to corresponding flanking sequences of the marker protein gene (A and B, respectively) in order to make possible a homologous recombination between A and A' and B and B'. The recombination causes a deletion of essential sequences of the marker protein gene.

Figure 6:
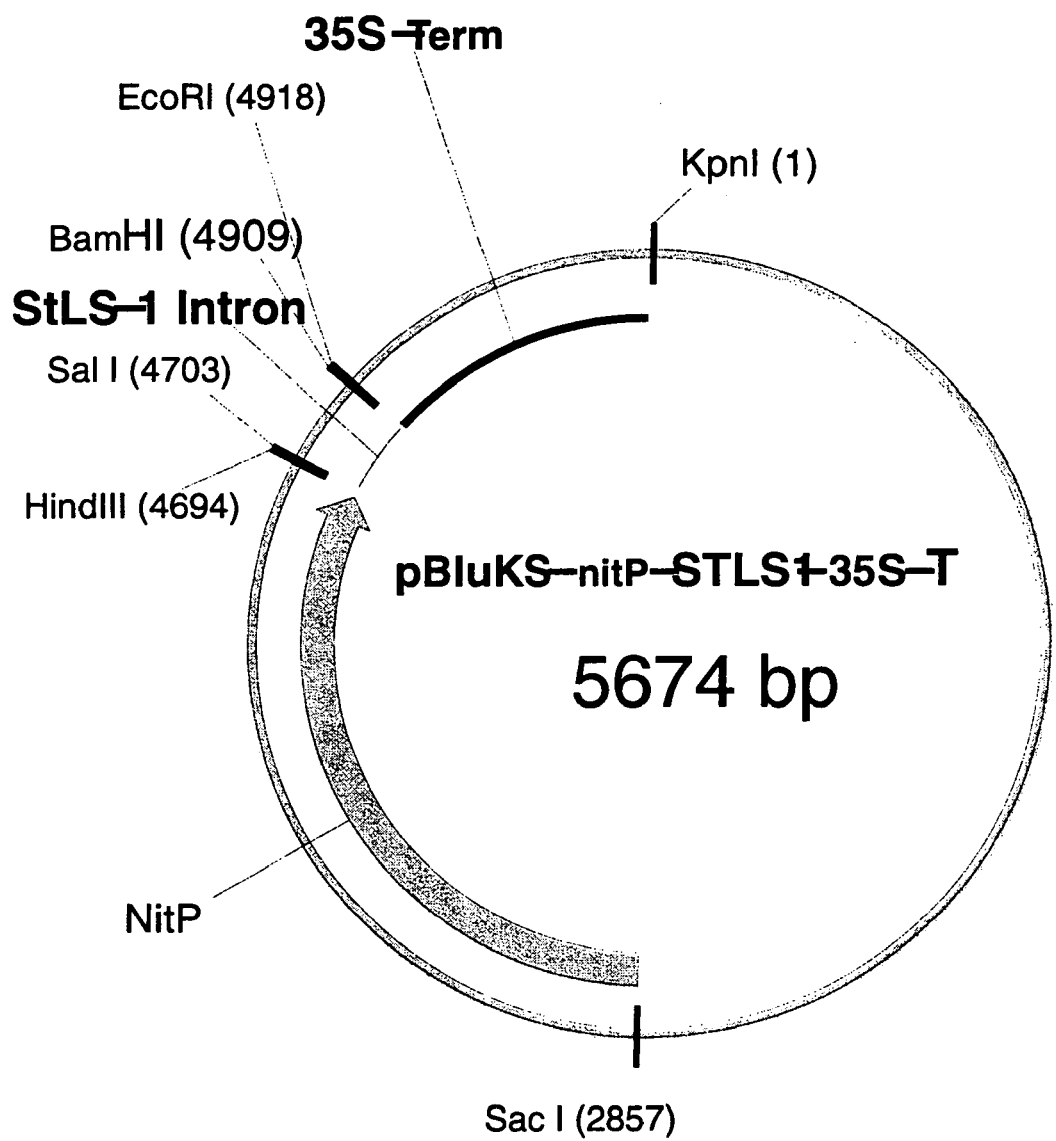

FIG. 6: Vector map for pBluKS-nitP-STLS1-35S-T (SEQ ID NO: 55)

NitP: promoter of the *A. thaliana* nitrilaseI gene (GenBank Acc. No.: Y07648.2, Hillebrand et al. (1996) Gene 170: 197-200)

STLS-1 intron: intron of the potato ST-LS1 gene (Vancanneyt G F et al. (1990) Mol Gen Genet 220(2):245-250).

35S-Term: Terminator of the 35S CaMV gene (cauliflower mosaic virus; Franck et al. (1980) Cell 21:285-294).

Cleavage sites of relevant restriction endonucleases are indicated with their particular cleavage position.

Figure 7:
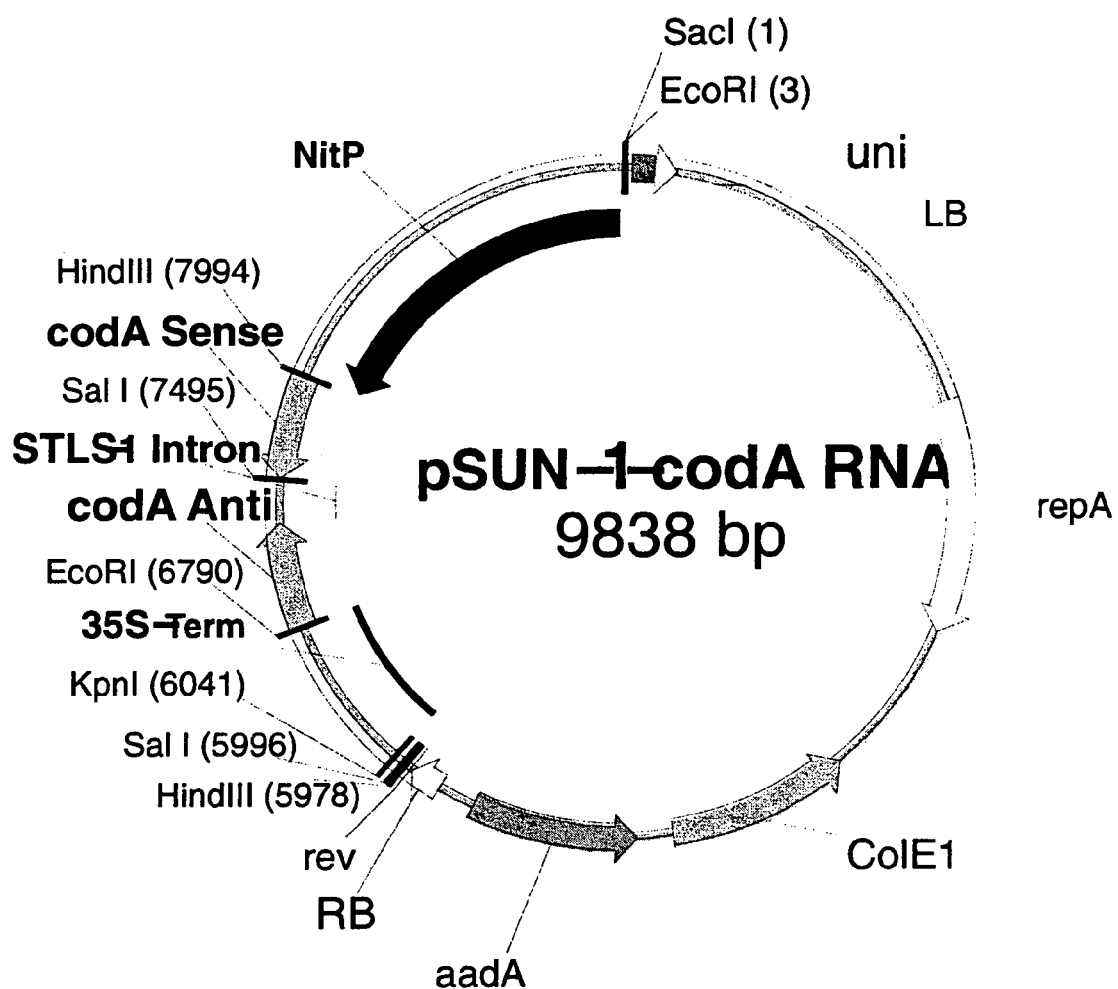

FIG. 7: Vector map for the transgenic expression vector pSUN-1-codA-RNAi (SEQ ID NO: 57)

NitP: promoter of the *A. thaliana* nitrilaseI gene (GenBank Acc. No.: Y07648.2, Hillebrand et al. (1996) Gene 170: 197-200)

STLS-1 intron: intron of the potato ST-LS1 gene (Vancanneyt G F et al. (1990) Mol Gen Genet 220(2):245-250).

35S-Term: Terminator of the 35S CaMV gene (cauliflower mosaic virus; Franck et al. (1980) Cell 21:285-294).

codA-sense: Nucleic acid sequence coding for a sense RNA fragment of *E. coli* cytosine deaminase (codARNAi-sense; SEQ ID NO: 49)

codA-anti: Nucleic acid sequence coding for an antisense RNA fragment of *E. coli* cytosine deaminase (codARNAi-anti; SEQ ID NO: 52)

LB/RB: Left and, respectively, right boundaries of Agrobacterium T-DNA

Cleavage sites of relevant restriction endonucleases are indicated with their particular cleavage position. Further elements represent customary elements of a binary *Agrobacterium* vector (aadA; ColE1; repA)

Figure 8:
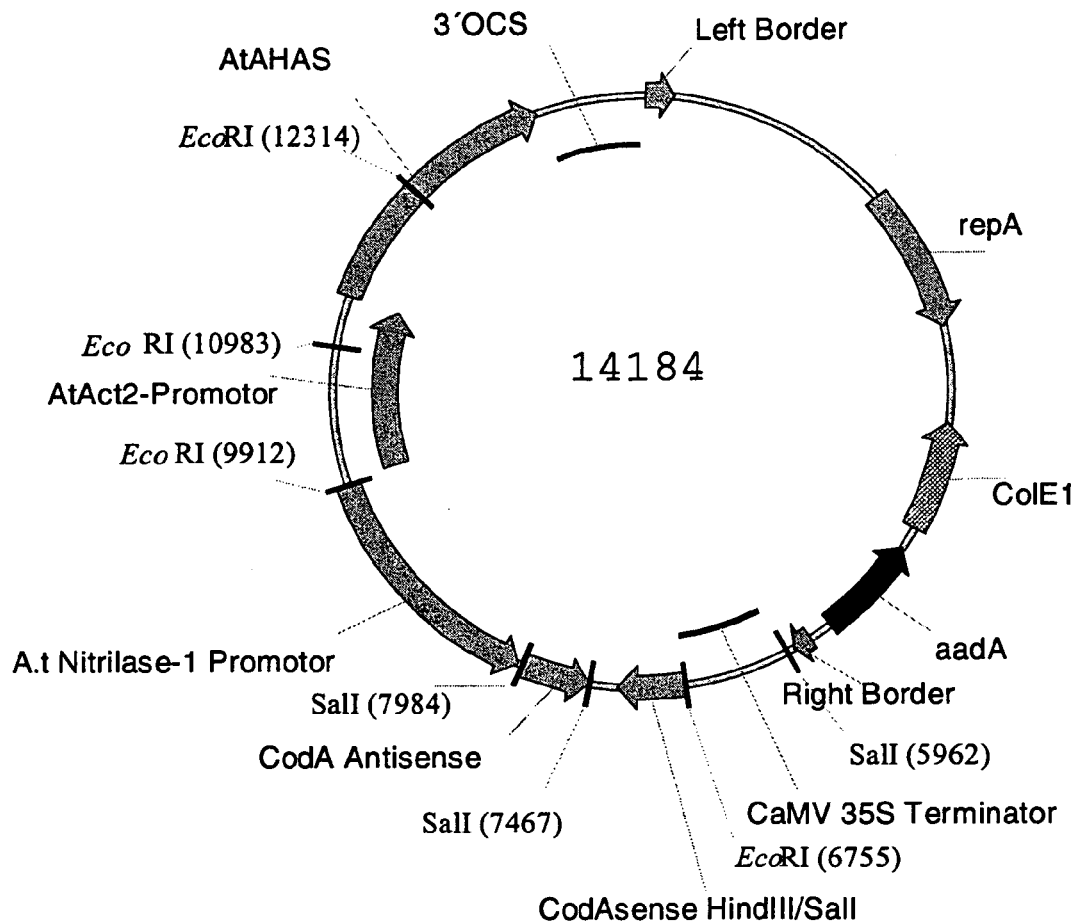

FIG. 8: Vector map for the transgenic expression vector pSUN1-codA-RNAi-At.Act.-2-At.Als-R-ocsT (SEQ ID NO: 58)

NitP: promoter of the *A. thaliana* nitrilaseI gene (GenBank Acc. No.: Y07648.2, Hillebrand et al. (1996) Gene 170: 197-200)

STLS-1 intron: intron of the potato ST-LS1 gene (Vancanneyt G F et al. (1990) Mol Gen Genet 220(2):245-250).

35S-Term: Terminator of the 35S CaMV gene (cauliflower mosaic virus; Franck et al. (1980) Cell 21:285-294).

codA-sense: Nucleic acid sequence coding for a sense RNA fragment of *E. coli* cytosine deaminase (codARNAi-sense; SEQ ID NO: 49)

codA-anti: Nucleic acid sequence coding for an antisense RNA fragment of *E. coli* cytosine deaminase (codARNAi-anti; SEQ ID NO: 52)

Left border/right border: Left and, respectively, right boundaries of *Agrobacterium* T-DNA Cleavage sites of relevant restriction endonucleases are indicated with their particular cleavage position. Further elements represent customary elements of a binary *Agrobacterium* vector (aadA; ColE1; repA)

FIG. 9a-b: Sequence comparison of various 5-methylthioribose (MTR) kinases from various organisms, in particular plant organisms. Sequences from *Klebsiella pneumoniae* (SEQ ID NO: 40), *Clostridium tetani* (SEQ ID NO: 178), *Arabidopsis thaliana* (*A. thaliana*) (SEQ ID NO: 38), oilseed rape (*Brassica napus*) (SEQ ID NO: 64), soybean (Soy-1) (SEQ ID NO: 68), rice (*Oryza* sativa-1) (SEQ ID NO: 66), corn (*Zea mays*) (SEQ ID NO: 60), and also the consensus sequence (Consensus) (SEQ ID NO: 179) are shown. Homologous regions can be readily deduced from the consensus sequence.

DETAILED DESCRIPTION OF EMBODIMENTS OF THE INVENTION

General Methods

The chemical synthesis of oligonucleotides may be carried out, for example, in the known manner by using the phosphoamide method (Voet, Voet, $2^{nd}$ Edition, Wiley Press New York, pages 896-897). The cloning steps carried out within the scope of the present invention, such as, for example, restriction cleavages, agarose gel electrophoresis, purification of DNA fragments, transfer of nucleic acids to nitrocellulose and nylon membranes, linking of DNA fragments, transformation of *E. coli* cells, cultivation of bacteria, propagation of phages and sequence analysis of recombinant DNA, are carried out as described in Sambrook et al. (1989) Cold Spring Harbor Laboratory Press; ISBN 0-87969-309-6. The sequencing of recombinant DNA molecules was carried out using a laser fluorescence DNA sequencer from ABI, according to the method of Sanger (Sanger et al. (1977) Proc Natl Acad Sci USA 74:5463-5467).

EXAMPLE 1

Preparation of codA Fragments

First, a truncated nucleic acid variant of the codA gene, modified by the addition of recognition sequences of the restriction enzymes HindIII and SalI, is prepared using the PCR technique. For this purpose, part of the codA gene (GeneBank Acc. No.: S56903; SEQ ID NO: 1) is amplified from the *E. coli* source organism by means of the polymerase chain reaction (PCR) using a sense-specific primer (codA5'HindIII; SEQ ID NO: 50) and an antisense-specific primer (codA3'SalI; SEQ ID NO: 51).

```
codA5'HindIII:
5'-AAGCTTGGCTAACAGTGTCGAATAACG-3'     (SEQ ID NO: 50)

codA3'SalI:
5'-GTCGACGACAAAATCCCTTCCTGAGG-3'      (SEQ ID NO: 51)
```

The PCR was carried out in 50 µl reaction mixture which contained:
- 2 µl (200 ng) of *E. coli* genomic DNA
- 0.2 mM dATP, dTTP, dGTP, dCTP
- 1.5 mM Mg(OAc)$_2$
- 5 µg of bovine serum albumin
- 40 pmol of "codA5'HindIII" primer
- 40 pmol of "codA3'SalI" primer
- 15 µl of 3.3×rTth DNA Polymerase XLPuffer (PE Applied Biosystems)
- 5U of rTth DNA Polymerase XL (PE Applied Biosystems)

The PCR is carried out under the following cycle conditions:
- Step 1: 5 minutes 94° C. (denaturation)
- Step 2: 3 seconds 94° C.
- Step 3: 1 minute 60° C. (annealing)
- Step 4: 2 minutes 72° C. (elongation)
- 30 repeats of steps 2 to 4
- Step 5: 10 minutes 72° C. (post elongation)
- Step 6: 4° C. (waiting loop)

The amplicon (codARNAi-sense; SEQ ID NO: 49) is cloned using standard methods into the PCR cloning vector pGEM-T (Promega). The identity of the amplicon generated is confirmed by sequencing using the M13F (−40) primer.

Another truncated fragment of the codA gene, modified by the addition of recognition sequences of the restriction enzymes Eco-RI and BamHI, is amplified using a sense-specific primer (codA5'EcoRI; SEQ ID NO: 53) and an anti-sense-specific primer (codA3'BamHI; SEQ ID NO: 54).

```
codA5'EcoRI:
5'-GAATTCGGCTAACAGTGTCGAATAACG-3'     (SEQ ID NO: 53)

codA3'BamHI:
5'-GGATCCGACAAAATCCCTTCCTGAGG-3'      (SEQ ID NO: 54)
```

The PCR was carried out in 50 µl reaction mixture which contained:
- 2 µl (200 ng) of *E. coli* genomic DNA
- 0.2 mM dATP, dTTP, dGTP, dCTP
- 1.5 mM Mg(OAc)$_2$
- 5 µg of bovine serum albumin
- 40 pmol of "codA5'EcoRI" primer
- 40 pmol of "codA3'BamHI" primer
- 15 µl of 3.3×rTth DNA Polymerase XLPuffer (PE Applied Biosystems)
- 5U of rTth DNA Polymerase XL (PE Applied Biosystems)

The PCR is carried out under the following cycle conditions:
- Step 1: 5 minutes 94° C. (denaturation)
- Step 2: 3 seconds 94° C.
- Step 3: 1 minute 60° C. (annealing)
- Step 4: 2 minutes 72° C. (elongation)
- 30 repeats of steps 2 to 4
- Step 5: 10 minutes 72° C. (post elongation)
- Step 6: 4° C. (waiting loop)

The amplicon (codARNAi-anti; SEQ ID NO: 52) is cloned using standard methods into the PCR cloning vector pGEM-T (Promega). The identity of the amplicon generated is confirmed by sequencing using the M13F (−40) primer.

EXAMPLE 2

Preparation of the Transgenic Expression Vector for Expressing a codA Double-Stranded RNA The coda fragments generated in example 1 are used for preparing a DNA construct suitable for expressing a double-stranded codA RNA (pSUN-codA-RNAi). The construct is suitable for reducing the steady-state RNA level of the coda gene in transgenic plants and, as a result therefrom, suppressing codA gene expression by using the double-strand RNA interference (dsRNAi) technique. For this purpose, the codA RNAi cassette is first constructed in the plasmid pBluKS-nitP-STLS1-35S-T and then, in a further cloning step, completely transferred to the pSUN-1 plasmid.

The vector pBluKS-nitP-STLS1-35S-T (SEQ ID NO: 55) is a derivative of pBluescript KS (Stratagene) and contains the promoter of the *A. thaliana* nitrilaseI gene (GenBank Acc. No.: Y07648.2, nucleotides 2456 to 4340, Hillebrand et al. (1996) Gene 170:197-200), the STLS-1 intron (Vancanneyt G F et al. (1990) Mol Gen Genet 220(2):245-250), restriction cleavage sites flanking the intron on its 5' and 3' sides and enabling DNA fragments to be inserted in a directed manner, and the terminator of the 35S CaMV gene (cauliflower mosaic virus; Franck et al. (1980) Cell 21:285-294). Using these restriction cleavage sites (HindIII, SalI, EcoRI, BamHI), the fragments codARNAi-sense (SEQ ID NO: 49) and codARNAi-anti (SEQ ID NO: 52) are inserted into said vector, thereby producing the finished coda RNAi cassette.

For this purpose, the coda sense fragment (codARNAi-sense SEQ ID NO: 49) is first excised from the pGEM-T vector, using the enzymes HindIII and SalI, isolated and ligated into the pBluKS-nitP-STLS1-35S-T vector under standard conditions. This vector had previously been cleaved using the restriction enzymes HindIII and SalI. Correspondingly positive clones are identified by analytical restriction digest and sequencing.

The vector obtained (pBluKS-nitP-codAsense-STLS1-35S-T) is digested using the restriction enzymese BamHI and EcoRI. The codA-anti fragment (codARNAi-anti; SEQ ID NO: 52) is excised from the corresponding pGEM-T vector, using BamHI and EcoRI, isolated and ligated into the cut vector under standard conditions. Correspondingly positive clones which contain the complete codA-RNAi cassette (pBluKS-nitP-codAsense-STLS1-codAanti-35S-T) are identified by analytical restriction digest and sequencing.

The codA-RNAi cassette is transferred into the pSUN-1 vector (SEQ ID NO: 56) by using the SacI and KpnI restriction cleavage sites flanking the cassette. The resulting vector pSUN1-codA-RNAi (see FIG. 7; SEQ ID NO: 57) is used for transforming transgenic *A. thaliana* plants which express an active codA gene (see below). The plant expression vector pSUN-1 is particularly suitable within the scope of the process of the invention, since it does not contain any other positive selection marker.

The resulting vector, pSUN1-codA-RNAi, enables an artificial codA-dsRNA variant consisting of two identical nucleic acid elments which are separated by an intron and inverted to one another to be constitutively expressed. Transcription of this artificial codA-dsRNA variant results in the formation of a double-stranded RNA molecule, owing to the complementarity of the inverted nucleic acid elements. The presence of this molecule induces the suppression of codA gene expression (accummulation of RNA) by means of double-strand RNA interference.

EXAMPLE 4

Preparation of Transgenic *Arabidopis thaliana* Plants

Transgenic *Arabidopsis thaliana* plants which express transgenically the *E. coli* codA gene as a marker protein ("*A. thaliana*-[codA]"), were prepared as described (Kirik et al. (2000) EMBO J 19(20):5562-6).

The *A. thaliana*-[codA] plants are transformed with an *Agrobacterium tumefaciens* strain (GV3101 [pMP90]) on the basis of a modified vacuum infiltration method (Clough S & Bent A (1998) Plant J 16(6):735-43; Bechtold N et al. (1993) CR Acad Sci Paris 1144(2):204-212). The *Agrobacterium tumefaciens* cells used have previously been transformed with the DNA construct described (pSUN1-codA-RNAi). In this way, double transgenic *A. thaliana*-[codA] plants are generated which express an artificial codA double-stranded RNA under the control of the constitutive nitrilaseI promoter. Expression of the codA gene is suppressed as a consequence of the dsRNAi effect induced by the presence of this artificial codA-dsRNA. Said double transgenic plants may be identified owing to their regained ability to grow in the presence of 5-fluorocytosine in the culture medium.

Seeds of primary transformants are selected on the basis of the regained ability to grow in the presence of 5-fluorocytosine. For this purpose, the T1 seeds of the primary transformants are laid out on selection medium containing 200 µg/ml 5-fluorocytosine. These selection plates are incubated under long-day conditions (16 h of light, 21° C./8 h of darkness, 18° C.). Seedlings which develop normally in the presence of 5-fluorocytosine are separated after 7 days and transferred to new selection plates. These plates are incubated for another 14 under unchanged conditions. The resistant seedlings are then transplanted into soil and cultured under short-day conditions (8 h of light, 21° C./16 h of darkness, 18° C.). After 14 days, the young plants are transferred to the greenhouse and cultured under short-day conditions.

EXAMPLE 5

Preparation of a Plant Transformation Vector Containing an Expression Cassette for Expressing a Double-Stranded codA RNA and a Plant Selection Marker A plant selection marker consisting of a mutated variant of the *A. thaliana* Als gene, coding for the acetolactate synthase under the control of the promoter of the *A. thaliana* actin-2 gene (Meagher R B & Williamson R E (1994) The plant cytoskeleton. In The Plant Cytoskeleton (Meyerowitz, E. & Somerville, C., eds), pp. 1049-1084. Cold Spring Harbor Laboratory Press, Cold Spring Harbor, N.Y.), and the octopine synthase terminator (GIELEN J et al. (1984) EMBO J 3:835-846) is inserted into pSUN1-codA-RNAi (see FIG. 7; SEQ ID NO: 57) (At.Act.-2-At.Als-R-ocsT).

For this purpose, the pSUN1-codA-RNAi vector is first linearized using the restriction enzyme Pvu II. Subsequently, a linear DNA fragment with blunt ends, coding for a mutated variant of the acetolactate synthase (Als-R gene), is ligated into said linearized vector under standard conditions. Prior to ligation, this DNA fragment has been digested with the restriction enzyme KpnI and the protruding ends have been converted into blunt ends by treatment with Pwo DNA polymerase (Roche) according to the manufacturer's instructions. This mutated variant of the *A. thaliana* Als gene cannot be inhibited by herbicides of the imidazolinone type. By expressing this mutated A.tAls-R gene, the plants obtain the ability to grow in the presence of the herbicide Pursuit™. Correspondingly positive clones (pSUN1-codA-RNAi-At.Act.-2-At.Als-R-ocsT; SEQ ID NO: 57) are identified by analytical restriction digest and sequencing.

The vector obtained enables an artificial codA RNA variant (consisting of two identical nucleic acid elements which are separated by an intron and inverted to one another) and a mutated variant of the *A. thaliana* Als gene to be expressed constitutively. Transcription of this artificial codA RNA variant results in the formation of a double-stranded RNA molecule, owing to the complementarity of the inverted nucleic acid elements. The presence of this molecule induces the suppression of coda gene expression (accummulation of RNA) by means of double-strand RNA interference. Expression of the Als-R gene imparts to the plants the ability to grow in the presence of herbicides of the imidazolinone type.

EXAMPLE 6

Preparation of Transgenic *Arabidopis thaliana* Plants

Transgenic *Arabidopsis thaliana* plants expressing the *E. coli* codA gene as a marker protein ("*A. thaliana*-[codA]") were prepared as described (Kirik et al. (2000) EMBO J 19(20):5562-6).

The *A. thaliana*-[codA] plants are transformed with an *Agrobacterium tumefaciens* strain (GV3101 [pMP90]) on the basis of a modified vacuum infiltration method (Clough S & Bent A (1998) Plant J 16(6):735-43; Bechtold N et al. (1993) CR Acad Sci Paris 1144(2):204-212). The *Agrobacterium tumefaciens* cells used have previously been transformed with the DNA construct described (pSUN1-codA-RNAi-At.Act.-2-At.Als-R-ocsT; SEQ ID NO: 57). In this way, double transgenic *A. thaliana*-[codA] plants are generated which additionally express an artificial codA double-stranded RNA and a herbicide-insensitive variant of the Als gene (Als-R) under the control of the constitutive nitrilaseI promoter (*A. thaliana*-[codA]-[codA-RNAi-At.Act.-2-At.Als-R-ocsT]). Expression of the codA gene is suppressed as a consequence of the dsRNAi effect induced by the presence of this artificial codA-dsRNA. These double transgenic plants may be identified owing to their regained ability to grow in the presence of 5-fluorocytosine in the culture medium. In addition, positively transformed plants can be selected owing to their ability to grow in the presence of the herbicide Pursuit in the culture medium.

For the purpose of selection, the T1 seeds of primary transformants are therefore laid out on selection medium containing 100 µg/ml 5-fluorocytosine. These selection plates are incubated under long-day conditions (16 h of light, 21° C./8 h of darkness, 18° C.). Seedlings which develop normally in the presence of 5-fluorocytosine are separated after 28 days and transferred to new selection plates. These plates are incubated for another 14 days under unchanged conditions. The resistant seedlings are then transplanted into soil and cultured under short-day conditions (8 h of light, 21° C./16 h of darkness, 18° C.). After a further 14 days, the young plants are transferred to the greenhouse and cultured under short-day conditions.

In addition, seeds of the primary transformants, owing to their ability to grow in the presence of the herbicide Pursuit™, may be selected. It is furthermore possible to carry out dual selection using the herbicide Pursuits and 5-fluorocytosine. For this purpose, the T1 seeds of primary transformants are laid out on selection medium containing the herbicide Pursuits at a concentration of 100 nM (in the case of dual selection, 100 µg/ml 5-fluorocytosine is likewise present). These selection plates are incubated under long-day conditions (16 h of light, 21° C./8 h of darkness, 18° C.).

Seedlings which develop normally in the presence of Pursuit™ (Pursuit™ and 5-fluorocytosine) are separated after 28 days and transferred to new selection plates. These plates are incubated under unchanged conditions for another 14 days. The resistant seedlings are then transplanted into soil and cultured under short-day conditions (8 h of light, 21° C./16 h of darkness, 18° C.). After 14 days, the young plants are transferred to the greenhouse and cultured under short-day conditions.

EXAMPLE 7

Analysis of the Double Transgenic *A. thaliana* Plants Selected Using 5-fluorocytosine and/or Pursuit (*A. thaliana*-[codA]-[codA-RNAi-At.Act.-2-At.Als-R-ocsT])

Integration of the T-DNA region of the vector used for transformation, pSUN1-codA-RNAi-A.tAls-R, into the genomic DNA of the starting plant (*A. thaliana*-[codA]) and the loss of codA-specific mRNA in these transgenic plants (*A. thaliana*-[codA]-[codA-RNAi-At.Act.-2-At.Als-R-ocsT]) can be detected by applying Southern analyses and PCR techniques or Northern analyses.

In order to carry out said analyses, total RNA and DNA are isolated from leaf tissue of the transgenic plants and suitable controls (using the RNeasy Maxi Kit (RNA) and Dneasy Plant Maxi Kit (genomic DNA), respectively, according to the manufacturer's information by Qiagen).

In the PCR analyses, the genomic DNA may be used directly as a basis (template) for the PCR. Total RNA is transcribed to cDNA prior to the PCR. The cDNA synthesis is carried out using the reverse transcriptase Superscript II (Invitrogen) according to the manufacturer's information.

EXAMPLE 8

Detection of the Reduction in the Steady-State Amount of codA RNA in the Positively Selected Double Transgenic Plants (*A. thaliana* [codA]-[codA-RNAi-At.Act.-2-At.Als-R-ocsT]) in Comparison with the Starting Plants (*A. thaliana* [codA]) Used for Transformation, by Means of cDNA Synthesis with Subsequent PCR Amplification PCR Amplification of the codA-Specific cDNA:
The cDNA of the codA gene (ACCESSION S56903) may be amplified using a sense-specific primer (codA5'C-term SEQ ID NO: 69) and an antisense-specific primer (codA3'C-term SEQ ID NO: 70). The PCR conditions to be chosen are as follows:
The PCR was carried out in 50 µl reaction mixture which contained:
2 µl (200 ng) of cDNA from *A. thaliana*-[codA] or *A. thaliana* [codA]-[codA-RNAi-At.Act.-2-At.Als-R-ocsT] plants
0.2 mM dATP, dTTP, dGTP, dCTP
1.5 mM Mg(OAc)$_2$
5 µg of bovine serum albumin
40 pmol of codA5'C-term SEQ ID NO: 69
40 pmol of codA3'C-term SEQ ID NO: 70
15 µl of 3.3×rTth DNA Polymerase XLPuffer (PE Applied Biosystems)
5U of rTth DNA Polymerase XL (PE Applied Biosystems)
The PCR was carried out under the following cycle conditions:
Step 1: 5 minutes 94° C. (denaturation)
Step 2: 3 seconds 94° C.
Step 3: 1 minute 56° C. (annealing)
Step 4: 2 minutes 72° C. (elongation)
30 repeats of steps 2 to 4
Step 5: 10 minutes 72° C. (post elongation)
Step 6: 4° C. (waiting loop)

In the positively selected plants, the steady-state amount of the mRNA of the codA gene and the amount of CODA protein resulting therefrom is reduced so much that a quantitative conversion of 5-fluorocytosine to 5-fluorouracil can no longer occur. Consequently, these plants (in contrast to the untransformed plants) can grow in the presence of 5-fluorocytosine. Thus it is demonstrated that transgenic plants can be identified owing to the applied principle of preventing expression of a negative selection marker.

EXAMPLE 9

Detection of the DNA Coding for codA-RNAi by Using Genomic DNA of the Positively Selected Double Transgenic Plants (*A. thaliana* [codA]-[codA-RNAi-At.Act.-2-At.Als-R-ocsT])

The codA-RNAi transgene may be amplified using a coda-specific primer (e.g. codA5'HindIII SEQ ID NO: 50) and a 35S terminator-specific primer (35 sT 5' Primer SEQ ID NO: 71). Using this primer combination, it is possible to detect specifically only the DNA coding for the codA RNAi construct, since the codA gene which was already present in the starting plants (*A. thaliana* [codA]) used for transformation is flanked by the nos terminator.

The PCR conditions to be chosen are as follows:
The PCR was carried out in a 50 µl reaction mixture which contains:
2 µl (200 ng) of genomic DNA from the *A. thaliana* [codA]-[codA-RNAi-At.Act.-2-At.Als-R-ocsT] plants
0.2 mM dATP, dTTP, dGTP, dCTP
1.5 mM Mg(OAc)$_2$
5 µg of bovine serum albumin
40 pmol of codA-specific sense primer (SEQ ID NO: 50, 53 or 69)
40 pmol of 35 sT 5' primer SEQ ID NO: 71
15 µl of 3.3×rTth DNA Polymerase XLPuffer (PE Applied Biosystems)
5U of rTth DNA Polymerase XL (PE Applied Biosystems)
The PCR was carried out under the following cycle conditions:
Step 1: 5 minutes 94° C. (denaturation)
Step 2: 3 seconds 94° C.
Step 3: 1 minute 56° C. (annealing)
Step 4: 2 minutes 72° C. (elongation)
30 repeats of steps 2 to 4
Step 5: 10 minutes 72° C. (post elongation)
Step 6: 4° C. (waiting loop)

In this way, it is possible to detect in the positively selected plants integration of the codA-RNAi DNA construct into the chromosomal DNA of the starting plants used for transformation. Thus it is demonstrated that transgenic plants can be identified owing to the applied principle of preventing expression of a negative selection marker.

EXAMPLE 10

Detection of the Reduction in the Steady-State Amount of codA RNA in the Positively Selected Double Transgenic Plants (*A. thaliana* [codA]-[codA-RNAi-At.Act.-2-At.Als-R-ocsT]) in Comparison with the Starting Plants (*A. thaliana* [codA]) Used for Transformation, by Northern Analysis Gel-Electrophoretic RNA Fractionation:

For each RNA agarose gel, 3 g of agar are dissolved in 150 ml of $H_2O$ (f.c. 1.5% (w/v)) in a microwave oven and cooled to 60° C. The addition of 20 ml of 10×MEN (0.2 M MOPS, 50 mM sodium acetate, 10 mM EDTA) and 30 ml of formaldehyde (f.c. 2.2 M) causes further cooling so that the well-mixed solution must be poured speedily. Formaldehyde prevents the formation of secondary structures in the RNA, and therefore the rate of migration is approximately proportional to the molecular weight (LEHRBACH H et al. (1977) Biochem J 16: 4743-4751). The RNA samples are denatured, prior to application to the gel, in the following mixture: 20 µl of RNA (1-2 µg/l), 5 µl of 10×MEN buffer, 6 µl of formaldehyde, 20 µl of formamide.

The mixture is mixed and incubated at 65° C. for 10 minutes. 1/10 volume of sample buffer and 1 µl of ethidium bromide (10 mg/ml) are added and the sample is then applied. Gel electrophoresis is carried out in horizontal gels in 1×MEN at 120V for two to three hours. After electrophoresis, the gel is photographed under UV light with the aid of a ruler for subsequent determination of the fragment length. This is followed by blotting the RNA to a nylon membrane according to the information in: SAMBROOK J et al. Molecular cloning: A laboratory manual. Cold Spring Harbor, N.Y., Cold Spring Harbor Laboratory Press, 1989.

Radioactive Labeling of DNA Fragments and Northern Hybridization

The codA cDNA fragment (codARNAi-sense SEQ ID No: 49) can be labeled using, for example, the High Prime kit sold by Roche Diagnostics. The High Prime kit is based on the "random primed" method for DNA labeling originally described by Feinberg and Vogelstein. Labeling is carried out by denaturing approx. 25 ng of DNA in 9-11 µl of $H_2O$ at 95° C. for 10 min. After a short incubation on ice, 4 µl of High Prime solution (contains a random primer mixture, 4 units of Klenow polymerase and 0.125 mM dATP, dTTP and dGTP each in a reaction buffer containing 50% glycerol) and 3-5 µl of [α32P]dCTP (30-50 µCi) are added. The reaction mixture is incubated at 37° C. for at least 10 min and the unincorporated dCTP is then separated from the now radiolabeled DNA by means of gel filtration via a Sephadex G-50 column. The fragment is subsequently denatured at 95° C. for 10 min and kept on ice until used. The following hybridization and pre-incubation buffers are used:

Hypo Hybond
250 mM sodium phosphate buffer pH 7.2
1 mM EDTA
7% SDS (g/v)
250 mM NaCl
10 µg/ml ssDNA
5% polyethylene glycol (PEG) 6000
40% formamide The hybridization temperature when using Hypo Hybond is 42° C. and the duration of hybridization is 16-24 h. The RNA filters are washed using three different solutions: 2×SSC (300 mM NaCl; 30 mM sodium citrate)+0.1% SDS, 1×SSC+0,1% SDS and 0.1×SSC+0.1% SDS. The duration and intensity of washing depend on the strength of the activity bond. After washing, the filters are sealed in plastic foil and an X-ray film (X-OMat, Kodak) is exposed overnight at −70° C. The signal strength on the X-ray films is a measure of the amount of codA mRNA molecules in the total RNA bound on the membranes. Thus it is possible to detect the reduction in codA mRNA in the positively selected plants compared to the starting plants used for transformation.

In the positively selected plants, the steady-state amount of the mRNA of the codA gene and the amount of CODA protein produced resulting therefrom is reduced so much that a quantitative conversion of 5-fluorocytosine to 5-fluorouracil can no longer occur. Consequently, these plants (in contrast to the untransformed plants) can grow in the presence of 5-fluorocytosine. Thus it is demonstrated that transgenic plants can be identified owing to the applied principle of preventing expression of a negative selection marker.

EXAMPLE 11

Summary of the Results of "Negative-Negative" Selection

Transformation of the coda-transgenic *Arabidopsis* plants with the codA-dsRNA construct (pSUN1-codA-RNAi-At.Act.-2-At.Als-R-ocsT; SEQ ID NO: 57) results in a significantly increased number of double transgenic plants into whose genome the RNAi construct has been successfully integrated, in the case of both single selection (with 5-fluorocytosine alone) and dual selection (Pursuit™ and 5-fluorocytosine) (in each case in comparison with untransformed plants). The analysis by means of PCR (see above) confirms the double transgenic state for the majority of the plants generated in this way. This successfully demonstrates the practicability of the present invention, i.e. the usability of repression of a negative marker for positive selection (more or less a "negative-negative" selection).

We claim:

1. A process for preparing transformed plant cells or plant organisms, comprising:
   a) providing a population of plant cells, the cells containing at least one marker protein,
   b) transforming said population of plant cells with at least one nucleic acid sequence which imparts an advantageous phenotype to a plant containing it, and
      i) at least one double-stranded marker protein ribonucleic acid sequence, or
      ii) an expression cassette or expression cassettes for expressing said at least one double-stranded marker protein ribonucleic acid sequence,
   wherein the at least one double-stranded marker protein ribonucleic acid sequence or the expression cassette reduces the expression of the at least one marker protein in the plant cells, and
   wherein the at least one marker protein converts directly or indirectly a substance X which is nontoxic for said population of plant cells into a substance Y which is toxic for said population,
   c) treating the transformed population of plant cells obtained in step b) with the substance X at a concentration which causes a toxic effect for nontransformed cells due to the conversion by the at least one marker protein,
   d) selecting transformed plant cells whose genome contains said at least one nucleic acid sequence and which have a growth advantage over nontransformed cells at said concentration of substance X, and optionally
   e) regenerating a plant organism from the transformed plant cell.

2. The process as claimed in claim 1, wherein the nontoxic substance X is a substance which does not naturally occur in plant cells or plant organisms or occurs naturally therein only at a concentration which can essentially not cause any toxic effect.

3. The process as claimed in claim 1 or 2, wherein the substance X is a 5-fluorocytosine.

4. The process as claimed in claim 1, wherein the at least one marker protein is a cytosine deaminase.

5. The process as claimed in claim 1, wherein the at least one marker protein comprises a polypeptide encoded by the sequence according to SEQ ID NO: 1, or a polypeptide comprising the sequence according to SEQ ID NO: 2.

6. The process as claimed in claim 1, wherein a sequence coding for a polypeptide conferring resistance to at least one toxin, antibiotic or herbicide is introduced together with the at least one nucleic acid sequence and selection is carried out additionally using the toxin, antibiotic or herbicide.

7. The process as claimed in claim 1, wherein the at least one nucleic acid sequence comprises at least one expression cassette capable of expressing, under the control of a promoter functional in plant cells or in plant organisms, an RNA and/or a protein which does not cause the expression, amount, activity and/or function of the at least one marker protein to be reduced.

8. The process as claimed in claim 1, wherein the plant cell is part of a plant organism or of a tissue, part, organ, cell culture or propagation material derived therefrom.

9. The process as claimed in claim 1, wherein the at least one marker protein is a non-endogenous marker protein, and wherein the expression of the at least one marker protein is the expression, amount, activity and/or function of said at least one marker protein, the process further comprising:
   f) regenerating fertile plants, and
   g) eliminating the nucleic acid sequence coding for the marker protein by crossing and isolating fertile plants whose genome contains the inserted at least one nucleic acid sequence but not the sequence coding for the marker protein.

10. The process as claimed in claim 3, wherein the at least one marker protein is a cytosine deaminase.

11. The process as claimed in claim 10, wherein the at least one marker protein comprises a polypeptide encoded by the sequence according to SEQ ID NO: 1, or a polypeptide comprising the sequence according to SEQ ID NO: 2.

12. The process as claimed in claim 9, wherein the at least one marker protein is a cytosine deaminase.

13. The process as claimed in claim 12, wherein the at least one marker protein comprises a polypeptide encoded by the sequence according to SEQ ID NO: 1, or a polypeptide comprising the sequence according to SEQ ID NO: 2.

14. The process as claimed in claim 9 or 2, wherein the at least one nucleic acid sequence comprises at least one expression cassette capable of expressing, under the control of a promoter functional in plant cells or in plant organisms, an RNA and/or a protein which does not cause the expression, amount, activity and/or function of the at least one marker protein to be reduced.

15. The process as claimed in claim 2, wherein the at least one marker protein is a non-endogenous marker protein, and wherein the expression of the at least one marker protein is the expression, amount, activity and/or function of said at least one marker protein, the process further comprising:
   f) regenerating fertile plants, and
   g) eliminating the nucleic acid sequence coding for the marker protein by crossing and isolating fertile plants whose genome contains the inserted at least one nucleic acid sequence but not the sequence coding for the marker protein.

16. The process of claim 1, wherein the at least one marker protein is
   a) a cytosine deaminase which converts directly or indirectly a 5-fluorocytosine;
   b) a cytochrome P-450 enzyme which converts directly or indirectly a proherbicide;
   c) an indoleacetic acid hydrolase which converts directly or indirectly an auxin amide compound or a naphthaleneacetamide;
   d) a haloalkane dehalogenase which converts directly or indirectly a dihaloalkane;
   e) a thymidine kinase which converts directly or indirectly Acyclovir, Ganciclovir, or 1,2-deoxy-2-fluoro-β-D-arabinofuranosil-5-iodouracil;
   f) a guanine phosphoribosyl transferase, a hypoxanthine phosphoribosyl transferase, or a xanthine guanine phosphoribosyl transferase which converts directly or indirectly a 6-thioxanthine or an allopurinol;
   g) a purine nucleoside phosphorylase which converts directly or indirectly a 6-methylpurine deoxyribonucleoside;
   h) a phosphonate monoester hydrolase which converts directly or indirectly a glycerylglyphosate;
   i) an indoleacetamide synthase and an indoleacetamide hydrolase which convert directly or indirectly an indolacetamide;
   j) an indoleacetamide hydrolase which converts directly or indirectly a naphthaleneacetamide;
   k) an adenine phosphoribosyl transferase which converts directly or indirectly a 4-aminopyrazolopyrimidine;
   l) a methoxinine dehydrogenase or a rhizobitoxin synthase which converts directly or indirectly a 2-amino-4-methoxybutanoic acid;
   m) a 5-methylthioribose kinase which converts directly or indirectly a 5-(trifluoromethyl)thioribose; or
   n) an alcohol dehydrogenase which converts directly or indirectly an allyl alcohol.

17. The process of claim 9, wherein the at least one marker protein is
   a) a cytosine deaminase which converts directly or indirectly a 5-fluorocytosine;
   b) a cytochrome P-450 enzyme which converts directly or indirectly a proherbicide;
   c) an indoleacetic acid hydrolase which converts directly or indirectly an auxin amide compound or a naphthaleneacetamide;
   d) a haloalkane dehalogenase which converts directly or indirectly a dihaloalkane;
   e) a thymidine kinase which converts directly or indirectly Acyclovir, Ganciclovir, or 1,2-deoxy-2-fluoro-β-D-arabinofuranosil-5-iodouracil;
   f) a guanine phosphoribosyl transferase, a hypoxanthine phosphoribosyl transferase, or a xanthine guanine phosphoribosyl transferase which converts directly or indirectly a 6-thioxanthine or an allopurinol;
   g) a purine nucleoside phosphorylase which converts directly or indirectly a 6-methylpurine deoxyribonucleoside;
   h) a phosphonate monoester hydrolase which converts directly or indirectly a glycerylglyphosate;
   i) an indoleacetamide synthase and an indoleacetamide hydrolase which convert directly or indirectly an indolacetamide;
   j) an indoleacetamide hydrolase which converts directly or indirectly a naphthaleneacetamide;
   k) an adenine phosphoribosyl transferase which converts directly or indirectly a 4-aminopyrazolopyrimidine;
   l) a methoxinine dehydrogenase or a rhizobitoxin synthase which converts directly or indirectly a 2-amino-4-methoxybutanoic acid;
   m) a 5-methyithioribose kinase which converts directly or indirectly a 5-(trifluoromethyl)thioribose; or
   n) an alcohol dehydrogenase which converts directly or indirectly an allyl alcohol.

18. The process of claim 9, wherein the non-endogenons marker protein is a non-plant marker protein.

* * * * *

SEQUENCE LISTING

```
<160> NUMBER OF SEQ ID NOS: 179

<210> SEQ ID NO 1
<211> LENGTH: 1284
<212> TYPE: DNA
<213> ORGANISM: Escherichia coli
<220> FEATURE:
<221> NAME/KEY: CDS
```

<222> LOCATION: (1)..(1281)
<223> OTHER INFORMATION: coding for cytosine deaminase (codA)

<400> SEQUENCE: 1

| | | | | | | | | | | | | | | | | |
|---|---|---|---|---|---|---|---|---|---|---|---|---|---|---|---|---|
| gtg | tcg | aat | aac | gct | tta | caa | aca | att | att | aac | gcc | cgg | tta | cca | ggc | 48 |
| Val | Ser | Asn | Asn | Ala | Leu | Gln | Thr | Ile | Ile | Asn | Ala | Arg | Leu | Pro | Gly | |
| 1 | | | | 5 | | | | | 10 | | | | | 15 | | |
| gaa | gag | ggg | ctg | tgg | cag | att | cat | ctg | cag | gac | gga | aaa | atc | agc | gcc | 96 |
| Glu | Glu | Gly | Leu | Trp | Gln | Ile | His | Leu | Gln | Asp | Gly | Lys | Ile | Ser | Ala | |
| | | | 20 | | | | | 25 | | | | | 30 | | | |
| att | gat | gcg | caa | tcc | ggc | gtg | atg | ccc | ata | act | gaa | aac | agc | ctg | gat | 144 |
| Ile | Asp | Ala | Gln | Ser | Gly | Val | Met | Pro | Ile | Thr | Glu | Asn | Ser | Leu | Asp | |
| | | 35 | | | | | 40 | | | | | 45 | | | | |
| gcc | gaa | caa | ggt | tta | gtt | ata | ccg | ccg | ttt | gtg | gag | cca | cat | att | cac | 192 |
| Ala | Glu | Gln | Gly | Leu | Val | Ile | Pro | Pro | Phe | Val | Glu | Pro | His | Ile | His | |
| | 50 | | | | | 55 | | | | | 60 | | | | | |
| ctg | gac | acc | acg | caa | acc | gcc | gga | caa | ccg | aac | tgg | aat | cag | tcc | ggc | 240 |
| Leu | Asp | Thr | Thr | Gln | Thr | Ala | Gly | Gln | Pro | Asn | Trp | Asn | Gln | Ser | Gly | |
| 65 | | | | | 70 | | | | | 75 | | | | | 80 | |
| acg | ctg | ttt | gaa | ggc | att | gaa | cgc | tgg | gcc | gag | cgc | aaa | gcg | tta | tta | 288 |
| Thr | Leu | Phe | Glu | Gly | Ile | Glu | Arg | Trp | Ala | Glu | Arg | Lys | Ala | Leu | Leu | |
| | | | | 85 | | | | | 90 | | | | | 95 | | |
| acc | cat | gac | gat | gtg | aaa | caa | cgc | gca | tgg | caa | acg | ctg | aaa | tgg | cag | 336 |
| Thr | His | Asp | Asp | Val | Lys | Gln | Arg | Ala | Trp | Gln | Thr | Leu | Lys | Trp | Gln | |
| | | | 100 | | | | | 105 | | | | | 110 | | | |
| att | gcc | aac | ggc | att | cag | cat | gtg | cgt | acc | cat | gtc | gat | gtt | tcg | gat | 384 |
| Ile | Ala | Asn | Gly | Ile | Gln | His | Val | Arg | Thr | His | Val | Asp | Val | Ser | Asp | |
| | | 115 | | | | | 120 | | | | | 125 | | | | |
| gca | acg | cta | act | gcg | ctg | aaa | gca | atg | ctg | gaa | gtg | aag | cag | gaa | gtc | 432 |
| Ala | Thr | Leu | Thr | Ala | Leu | Lys | Ala | Met | Leu | Glu | Val | Lys | Gln | Glu | Val | |
| | 130 | | | | | 135 | | | | | 140 | | | | | |
| gcg | ccg | tgg | att | gat | ctg | caa | atc | gtc | gcc | ttc | cct | cag | gaa | ggg | att | 480 |
| Ala | Pro | Trp | Ile | Asp | Leu | Gln | Ile | Val | Ala | Phe | Pro | Gln | Glu | Gly | Ile | |
| 145 | | | | | 150 | | | | | 155 | | | | | 160 | |
| ttg | tcg | tat | ccc | aac | ggt | gaa | gcg | ttg | ctg | gaa | gag | gcg | tta | cgc | tta | 528 |
| Leu | Ser | Tyr | Pro | Asn | Gly | Glu | Ala | Leu | Leu | Glu | Glu | Ala | Leu | Arg | Leu | |
| | | | | 165 | | | | | 170 | | | | | 175 | | |
| ggg | gca | gat | gta | gtg | ggg | gcg | att | ccg | cat | ttt | gaa | ttt | acc | cgt | gaa | 576 |
| Gly | Ala | Asp | Val | Val | Gly | Ala | Ile | Pro | His | Phe | Glu | Phe | Thr | Arg | Glu | |
| | | 180 | | | | | 185 | | | | | 190 | | | | |
| tac | ggc | gtg | gag | tcg | ctg | cat | aaa | acc | ttc | gcc | ctg | gcg | caa | aaa | tac | 624 |
| Tyr | Gly | Val | Glu | Ser | Leu | His | Lys | Thr | Phe | Ala | Leu | Ala | Gln | Lys | Tyr | |
| | 195 | | | | | 200 | | | | | 205 | | | | | |
| gac | cgt | ctc | atc | gac | gtt | cac | tgt | gat | gag | atc | gat | gac | gag | cag | tcg | 672 |
| Asp | Arg | Leu | Ile | Asp | Val | His | Cys | Asp | Glu | Ile | Asp | Asp | Glu | Gln | Ser | |
| 210 | | | | | 215 | | | | | 220 | | | | | | |
| cgc | ttt | gtc | gaa | acc | gtt | gct | gcc | ctg | gcg | cac | cat | gaa | ggc | atg | ggc | 720 |
| Arg | Phe | Val | Glu | Thr | Val | Ala | Ala | Leu | Ala | His | His | Glu | Gly | Met | Gly | |
| 225 | | | | | 230 | | | | | 235 | | | | | 240 | |
| gcg | cga | gtc | acc | gcc | agc | cac | acc | acg | gca | atg | cac | tcc | tat | aac | ggg | 768 |
| Ala | Arg | Val | Thr | Ala | Ser | His | Thr | Thr | Ala | Met | His | Ser | Tyr | Asn | Gly | |
| | | | | 245 | | | | | 250 | | | | | 255 | | |
| gcg | tat | acc | tca | cgc | ctg | ttc | cgc | ttg | ctg | aaa | atg | tcc | ggt | att | aac | 816 |
| Ala | Tyr | Thr | Ser | Arg | Leu | Phe | Arg | Leu | Leu | Lys | Met | Ser | Gly | Ile | Asn | |
| | | | 260 | | | | | 265 | | | | | 270 | | | |
| ttt | gtc | gcc | aac | ccg | ctg | gtc | aat | att | cat | ctg | caa | gga | cgt | ttc | gat | 864 |
| Phe | Val | Ala | Asn | Pro | Leu | Val | Asn | Ile | His | Leu | Gln | Gly | Arg | Phe | Asp | |
| | | 275 | | | | | 280 | | | | | 285 | | | | |
| acg | tat | cca | aaa | cgt | cgc | ggc | atc | acg | cgc | gtt | aaa | gag | atg | ctg | gag | 912 |
| Thr | Tyr | Pro | Lys | Arg | Arg | Gly | Ile | Thr | Arg | Val | Lys | Glu | Met | Leu | Glu | |

-continued

```
                 290                 295                 300
tcc ggc att aac gtc tgc ttt ggt cac gat gat gtc ttc gat ccg tgg    960
Ser Gly Ile Asn Val Cys Phe Gly His Asp Asp Val Phe Asp Pro Trp
305                 310                 315                 320 tat ccg ctg gga acg gcg aat atg ctg caa gtg ctg cat atg ggg ctg   1008
Tyr Pro Leu Gly Thr Ala Asn Met Leu Gln Val Leu His Met Gly Leu
                325                 330                 335 cat gtt tgc cag ttg atg ggc tac ggg cag att aac gat ggc ctg aat   1056
His Val Cys Gln Leu Met Gly Tyr Gly Gln Ile Asn Asp Gly Leu Asn
            340                 345                 350 tta atc acc cac cac agc gca agg acg ttg aat ttg cag gat tac ggc   1104
Leu Ile Thr His His Ser Ala Arg Thr Leu Asn Leu Gln Asp Tyr Gly
        355                 360                 365 att gcc gcc gga aac agc gcc aac ctg att atc ctg ccg gct gaa aat   1152
Ile Ala Ala Gly Asn Ser Ala Asn Leu Ile Ile Leu Pro Ala Glu Asn
370                 375                 380 ggg ttt gat gcg ctg cgc cgt cag gtt ccg gta cgt tat tcg gta cgt   1200
Gly Phe Asp Ala Leu Arg Arg Gln Val Pro Val Arg Tyr Ser Val Arg
385                 390                 395                 400 ggc ggc aag gtg att gcc agc aca caa ccg gca caa acc acc gta tat   1248
Gly Gly Lys Val Ile Ala Ser Thr Gln Pro Ala Gln Thr Thr Val Tyr
                405                 410                 415 ctg gag cag cca gaa gcc atc gat tac aaa cgt tga                   1284
Leu Glu Gln Pro Glu Ala Ile Asp Tyr Lys Arg
            420                 425
```

<210> SEQ ID NO 2
<211> LENGTH: 427
<212> TYPE: PRT
<213> ORGANISM: Escherichia coli

<400> SEQUENCE: 2

```
Val Ser Asn Asn Ala Leu Gln Thr Ile Ile Asn Ala Arg Leu Pro Gly
  1               5                  10                  15

Glu Glu Gly Leu Trp Gln Ile His Leu Gln Asp Gly Lys Ile Ser Ala
             20                  25                  30

Ile Asp Ala Gln Ser Gly Val Met Pro Ile Thr Glu Asn Ser Leu Asp
         35                  40                  45

Ala Glu Gln Gly Leu Val Ile Pro Pro Phe Val Glu Pro His Ile His
     50                  55                  60

Leu Asp Thr Thr Gln Thr Ala Gly Gln Pro Asn Trp Asn Gln Ser Gly
 65                  70                  75                  80

Thr Leu Phe Glu Gly Ile Glu Arg Trp Ala Glu Arg Lys Ala Leu Leu
                 85                  90                  95

Thr His Asp Asp Val Lys Gln Arg Ala Trp Gln Thr Leu Lys Trp Gln
            100                 105                 110

Ile Ala Asn Gly Ile Gln His Val Arg Thr His Val Asp Val Ser Asp
        115                 120                 125

Ala Thr Leu Thr Ala Leu Lys Ala Met Leu Glu Val Lys Gln Glu Val
    130                 135                 140

Ala Pro Trp Ile Asp Leu Gln Ile Val Ala Phe Pro Gln Glu Gly Ile
145                 150                 155                 160

Leu Ser Tyr Pro Asn Gly Glu Ala Leu Leu Glu Glu Ala Leu Arg Leu
                165                 170                 175

Gly Ala Asp Val Val Gly Ala Ile Pro His Phe Glu Phe Thr Arg Glu
            180                 185                 190

Tyr Gly Val Glu Ser Leu His Lys Thr Phe Ala Leu Ala Gln Lys Tyr
```

-continued

```
                195                 200                 205
Asp Arg Leu Ile Asp Val His Cys Asp Glu Ile Asp Glu Gln Ser
    210                 215                 220

Arg Phe Val Glu Thr Val Ala Ala Leu Ala His His Glu Gly Met Gly
225                 230                 235                 240

Ala Arg Val Thr Ala Ser His Thr Thr Ala Met His Ser Tyr Asn Gly
                245                 250                 255

Ala Tyr Thr Ser Arg Leu Phe Arg Leu Leu Lys Met Ser Gly Ile Asn
                260                 265                 270

Phe Val Ala Asn Pro Leu Val Asn Ile His Leu Gln Gly Arg Phe Asp
                275                 280                 285

Thr Tyr Pro Lys Arg Arg Gly Ile Thr Arg Val Lys Glu Met Leu Glu
    290                 295                 300

Ser Gly Ile Asn Val Cys Phe Gly His Asp Asp Val Phe Asp Pro Trp
305                 310                 315                 320

Tyr Pro Leu Gly Thr Ala Asn Met Leu Gln Val Leu His Met Gly Leu
                325                 330                 335

His Val Cys Gln Leu Met Gly Tyr Gly Gln Ile Asn Asp Gly Leu Asn
                340                 345                 350

Leu Ile Thr His His Ser Ala Arg Thr Leu Asn Leu Gln Asp Tyr Gly
                355                 360                 365

Ile Ala Ala Gly Asn Ser Ala Asn Leu Ile Ile Leu Pro Ala Glu Asn
    370                 375                 380

Gly Phe Asp Ala Leu Arg Arg Gln Val Pro Val Arg Tyr Ser Val Arg
385                 390                 395                 400

Gly Gly Lys Val Ile Ala Ser Thr Gln Pro Ala Gln Thr Thr Val Tyr
                405                 410                 415

Leu Glu Gln Pro Glu Ala Ile Asp Tyr Lys Arg
                420                 425

<210> SEQ ID NO 3
<211> LENGTH: 1284
<212> TYPE: DNA
<213> ORGANISM: Artificial sequence
<220> FEATURE:
<223> OTHER INFORMATION: Description of the artificial sequence: coding
      for cytosine deaminase (codA)
<220> FEATURE:
<221> NAME/KEY: misc_feature
<222> LOCATION: (1)..(3)
<223> OTHER INFORMATION: mutation of GTG to ATG start codon for
      expression in eukaryotic hosts
<220> FEATURE:
<221> NAME/KEY: CDS
<222> LOCATION: (1)..(1281)
<223> OTHER INFORMATION: coding for cytosine deaminase (codA)

<400> SEQUENCE: 3 atg tcg aat aac gct tta caa aca att att aac gcc cgg tta cca ggc      48
Met Ser Asn Asn Ala Leu Gln Thr Ile Ile Asn Ala Arg Leu Pro Gly
 1               5                  10                  15 gaa gag ggg ctg tgg cag att cat ctg cag gac gga aaa atc agc gcc      96
Glu Glu Gly Leu Trp Gln Ile His Leu Gln Asp Gly Lys Ile Ser Ala
                20                  25                  30 att gat gcg caa tcc ggc gtg atg ccc ata act gaa aac agc ctg gat     144
Ile Asp Ala Gln Ser Gly Val Met Pro Ile Thr Glu Asn Ser Leu Asp
            35                  40                  45 gcc gaa caa ggt tta gtt ata ccg ccg ttt gtg gag cca cat att cac     192
Ala Glu Gln Gly Leu Val Ile Pro Pro Phe Val Glu Pro His Ile His
        50                  55                  60
```

```
ctg gac acc acg caa acc gcc gga caa ccg aac tgg aat cag tcc ggc      240
Leu Asp Thr Thr Gln Thr Ala Gly Gln Pro Asn Trp Asn Gln Ser Gly
 65                  70                  75                  80 acg ctg ttt gaa ggc att gaa cgc tgg gcc gag cgc aaa gcg tta tta      288
Thr Leu Phe Glu Gly Ile Glu Arg Trp Ala Glu Arg Lys Ala Leu Leu
                 85                  90                  95 acc cat gac gat gtg aaa caa cgc gca tgg caa acg ctg aaa tgg cag      336
Thr His Asp Asp Val Lys Gln Arg Ala Trp Gln Thr Leu Lys Trp Gln
            100                 105                 110 att gcc aac ggc att cag cat gtg cgt acc cat gtc gat gtt tcg gat      384
Ile Ala Asn Gly Ile Gln His Val Arg Thr His Val Asp Val Ser Asp
        115                 120                 125 gca acg cta act gcg ctg aaa gca atg ctg gaa gtg aag cag gaa gtc      432
Ala Thr Leu Thr Ala Leu Lys Ala Met Leu Glu Val Lys Gln Glu Val
130                 135                 140 gcg ccg tgg att gat ctg caa atc gtc gcc ttc cct cag gaa ggg att      480
Ala Pro Trp Ile Asp Leu Gln Ile Val Ala Phe Pro Gln Glu Gly Ile
145                 150                 155                 160 ttg tcg tat ccc aac ggt gaa gcg ttg ctg gaa gag gcg tta cgc tta      528
Leu Ser Tyr Pro Asn Gly Glu Ala Leu Leu Glu Glu Ala Leu Arg Leu
                165                 170                 175 ggg gca gat gta gtg ggg gcg att ccg cat ttt gaa ttt acc cgt gaa      576
Gly Ala Asp Val Val Gly Ala Ile Pro His Phe Glu Phe Thr Arg Glu
            180                 185                 190 tac ggc gtg gag tcg ctg cat aaa acc ttc gcc ctg gcg caa aaa tac      624
Tyr Gly Val Glu Ser Leu His Lys Thr Phe Ala Leu Ala Gln Lys Tyr
        195                 200                 205 gac cgt ctc atc gac gtt cac tgt gat gag atc gat gac gag cag tcg      672
Asp Arg Leu Ile Asp Val His Cys Asp Glu Ile Asp Asp Glu Gln Ser
210                 215                 220 cgc ttt gtc gaa acc gtt gct gcc ctg gcg cac cat gaa ggc atg ggc      720
Arg Phe Val Glu Thr Val Ala Ala Leu Ala His His Glu Gly Met Gly
225                 230                 235                 240 gcg cga gtc acc gcc agc cac acc acg gca atg cac tcc tat aac ggg      768
Ala Arg Val Thr Ala Ser His Thr Thr Ala Met His Ser Tyr Asn Gly
                245                 250                 255 gcg tat acc tca cgc ctg ttc cgc ttg ctg aaa atg tcc ggt att aac      816
Ala Tyr Thr Ser Arg Leu Phe Arg Leu Leu Lys Met Ser Gly Ile Asn
            260                 265                 270 ttt gtc gcc aac ccg ctg gtc aat att cat ctg caa gga cgt ttc gat      864
Phe Val Ala Asn Pro Leu Val Asn Ile His Leu Gln Gly Arg Phe Asp
        275                 280                 285 acg tat cca aaa cgt cgc ggc atc acg cgc gtt aaa gag atg ctg gag      912
Thr Tyr Pro Lys Arg Arg Gly Ile Thr Arg Val Lys Glu Met Leu Glu
290                 295                 300 tcc ggc att aac gtc tgc ttt ggt cac gat gat gtc ttc gat ccg tgg      960
Ser Gly Ile Asn Val Cys Phe Gly His Asp Asp Val Phe Asp Pro Trp
305                 310                 315                 320 tat ccg ctg gga acg gcg aat atg ctg caa gtg ctg cat atg ggg ctg     1008
Tyr Pro Leu Gly Thr Ala Asn Met Leu Gln Val Leu His Met Gly Leu
                325                 330                 335 cat gtt tgc cag ttg atg ggc tac ggg cag att aac gat ggc ctg aat     1056
His Val Cys Gln Leu Met Gly Tyr Gly Gln Ile Asn Asp Gly Leu Asn
            340                 345                 350 tta atc acc cac cac agc gca agg acg ttg aat ttg cag gat tac ggc     1104
Leu Ile Thr His His Ser Ala Arg Thr Leu Asn Leu Gln Asp Tyr Gly
        355                 360                 365 att gcc gcc gga aac agc gcc aac ctg att atc ctg ccg gct gaa aat     1152
Ile Ala Ala Gly Asn Ser Ala Asn Leu Ile Ile Leu Pro Ala Glu Asn
```

-continued

```
                                370                 375                 380
ggg ttt gat gcg ctg cgc cgt cag gtt ccg gta cgt tat tcg gta cgt        1200
Gly Phe Asp Ala Leu Arg Arg Gln Val Pro Val Arg Tyr Ser Val Arg
385                 390                 395                 400 ggc ggc aag gtg att gcc agc aca caa ccg gca caa acc acc gta tat        1248
Gly Gly Lys Val Ile Ala Ser Thr Gln Pro Ala Gln Thr Thr Val Tyr
                405                 410                 415 ctg gag cag cca gaa gcc atc gat tac aaa cgt tga                        1284
Leu Glu Gln Pro Glu Ala Ile Asp Tyr Lys Arg
                420                 425

<210> SEQ ID NO 4
<211> LENGTH: 427
<212> TYPE: PRT
<213> ORGANISM: Artificial sequence
<220> FEATURE:
<223> OTHER INFORMATION: Description of the artificial sequence: coding
      for cytosine deaminase (codA)

<400> SEQUENCE: 4

Met Ser Asn Asn Ala Leu Gln Thr Ile Ile Asn Ala Arg Leu Pro Gly
1               5                   10                  15

Glu Glu Gly Leu Trp Gln Ile His Leu Gln Asp Gly Lys Ile Ser Ala
            20                  25                  30

Ile Asp Ala Gln Ser Gly Val Met Pro Ile Thr Glu Asn Ser Leu Asp
        35                  40                  45

Ala Glu Gln Gly Leu Val Ile Pro Pro Phe Val Glu Pro His Ile His
    50                  55                  60

Leu Asp Thr Thr Gln Thr Ala Gly Gln Pro Asn Trp Asn Gln Ser Gly
65                  70                  75                  80

Thr Leu Phe Glu Gly Ile Glu Arg Trp Ala Glu Arg Lys Ala Leu Leu
                85                  90                  95

Thr His Asp Asp Val Lys Gln Arg Ala Trp Gln Thr Leu Lys Trp Gln
            100                 105                 110

Ile Ala Asn Gly Ile Gln His Val Arg Thr His Val Asp Val Ser Asp
        115                 120                 125

Ala Thr Leu Thr Ala Leu Lys Ala Met Leu Glu Val Lys Gln Glu Val
    130                 135                 140

Ala Pro Trp Ile Asp Leu Gln Ile Val Ala Phe Pro Gln Glu Gly Ile
145                 150                 155                 160

Leu Ser Tyr Pro Asn Gly Glu Ala Leu Leu Glu Glu Ala Leu Arg Leu
                165                 170                 175

Gly Ala Asp Val Val Gly Ala Ile Pro His Phe Glu Phe Thr Arg Glu
            180                 185                 190

Tyr Gly Val Glu Ser Leu His Lys Thr Phe Ala Leu Ala Gln Lys Tyr
        195                 200                 205

Asp Arg Leu Ile Asp Val His Cys Asp Glu Ile Asp Asp Glu Gln Ser
    210                 215                 220

Arg Phe Val Glu Thr Val Ala Ala Leu Ala His His Glu Gly Met Gly
225                 230                 235                 240

Ala Arg Val Thr Ala Ser His Thr Thr Ala Met His Ser Tyr Asn Gly
                245                 250                 255

Ala Tyr Thr Ser Arg Leu Phe Arg Leu Leu Lys Met Ser Gly Ile Asn
            260                 265                 270

Phe Val Ala Asn Pro Leu Val Asn Ile His Leu Gln Gly Arg Phe Asp
        275                 280                 285
```

-continued

```
Thr Tyr Pro Lys Arg Arg Gly Ile Thr Arg Val Lys Glu Met Leu Glu
        290                 295                 300

Ser Gly Ile Asn Val Cys Phe Gly His Asp Asp Val Phe Asp Pro Trp
305                 310                 315                 320

Tyr Pro Leu Gly Thr Ala Asn Met Leu Gln Val Leu His Met Gly Leu
                325                 330                 335

His Val Cys Gln Leu Met Gly Tyr Gly Gln Ile Asn Asp Gly Leu Asn
            340                 345                 350

Leu Ile Thr His His Ser Ala Arg Thr Leu Asn Leu Gln Asp Tyr Gly
        355                 360                 365

Ile Ala Ala Gly Asn Ser Ala Asn Leu Ile Ile Leu Pro Ala Glu Asn
370                 375                 380

Gly Phe Asp Ala Leu Arg Arg Gln Val Pro Val Arg Tyr Ser Val Arg
385                 390                 395                 400

Gly Gly Lys Val Ile Ala Ser Thr Gln Pro Ala Gln Thr Thr Val Tyr
                405                 410                 415

Leu Glu Gln Pro Glu Ala Ile Asp Tyr Lys Arg
            420                 425
```

<210> SEQ ID NO 5
<211> LENGTH: 1221
<212> TYPE: DNA
<213> ORGANISM: Streptomyces griseolus
<220> FEATURE:
<221> NAME/KEY: CDS
<222> LOCATION: (1)..(1218)
<223> OTHER INFORMATION: coding for cytochrome P450-Su1 (suaC)

<400> SEQUENCE: 5

```
atg acc gat acc gcc acg acg ccc cag acc acg gac gca ccc gcc ttc        48
Met Thr Asp Thr Ala Thr Thr Pro Gln Thr Thr Asp Ala Pro Ala Phe
 1               5                   10                  15 ccg agc aac cgg agc tgt ccc tac cag tta ccg gac ggc tac gcc cag        96
Pro Ser Asn Arg Ser Cys Pro Tyr Gln Leu Pro Asp Gly Tyr Ala Gln
             20                  25                  30 ctc cgg gac acc ccc ggc ccc ctg cac cgg gtg acg ctc tac gac ggc       144
Leu Arg Asp Thr Pro Gly Pro Leu His Arg Val Thr Leu Tyr Asp Gly
         35                  40                  45 cgt cag gcg tgg gtg gtg acc aag cac gag gcc gcg cgc aaa ctg ctc       192
Arg Gln Ala Trp Val Val Thr Lys His Glu Ala Ala Arg Lys Leu Leu
     50                  55                  60 ggc gac ccc cgg ctg tcc tcc aac cgg acg gac gac aac ttc ccc gcc       240
Gly Asp Pro Arg Leu Ser Ser Asn Arg Thr Asp Asp Asn Phe Pro Ala
 65                  70                  75                  80 acg tca ccg cgc ttc gag gcc gtc cgg gag agc ccg cag gcg ttc atc       288
Thr Ser Pro Arg Phe Glu Ala Val Arg Glu Ser Pro Gln Ala Phe Ile
                 85                  90                  95 ggc ctg gac ccg ccc gag cac ggc acc cgg cgg cgg atg acg atc agc       336
Gly Leu Asp Pro Pro Glu His Gly Thr Arg Arg Arg Met Thr Ile Ser
            100                 105                 110 gag ttc acc gtc aag cgg atc aag ggc atg cgc ccc gag gtc gag gag       384
Glu Phe Thr Val Lys Arg Ile Lys Gly Met Arg Pro Glu Val Glu Glu
        115                 120                 125 gtg gtg cac ggc ttc ctc gac gag atg ctg gcc gcc ggc ccg acc gcc       432
Val Val His Gly Phe Leu Asp Glu Met Leu Ala Ala Gly Pro Thr Ala
    130                 135                 140 gac ctg gtc agt cag ttc gcg ctg ccg gtg ccc tcc atg gtg atc tgc       480
Asp Leu Val Ser Gln Phe Ala Leu Pro Val Pro Ser Met Val Ile Cys
145                 150                 155                 160
```

```
cga ctc ctc ggc gtg ccc tac gcc gac cac gag ttc ttc cag gac gcg     528
Arg Leu Leu Gly Val Pro Tyr Ala Asp His Glu Phe Phe Gln Asp Ala
            165                 170                 175 agc aag cgg ctg gtg cag tcc acg gac gcg cag agc gcg ctc acc gcg     576
Ser Lys Arg Leu Val Gln Ser Thr Asp Ala Gln Ser Ala Leu Thr Ala
        180                 185                 190 cgg aac gac ctc gcg ggt tac ctg gac ggc ctc atc acc cag ttc cag     624
Arg Asn Asp Leu Ala Gly Tyr Leu Asp Gly Leu Ile Thr Gln Phe Gln
    195                 200                 205 acc gaa ccg ggc gcg ggc ctg gtg ggc gct ctg gtc gcc gac cag ctg     672
Thr Glu Pro Gly Ala Gly Leu Val Gly Ala Leu Val Ala Asp Gln Leu
210                 215                 220 gcc aac ggc gag atc gac cgt gag gaa ctg atc tcc acc gcg atg ctg     720
Ala Asn Gly Glu Ile Asp Arg Glu Glu Leu Ile Ser Thr Ala Met Leu
225                 230                 235                 240 ctc ctc atc gcc ggc cac gag acc acg gcc tcg atg acc tcc ctc agc     768
Leu Leu Ile Ala Gly His Glu Thr Thr Ala Ser Met Thr Ser Leu Ser
            245                 250                 255 gtg atc acc ctg ctg gac cac ccc gag cag tac gcc gcc ctg cgc gcc     816
Val Ile Thr Leu Leu Asp His Pro Glu Gln Tyr Ala Ala Leu Arg Ala
        260                 265                 270 gac cgc agc ctc gtg ccc ggc gcg gtg gag gaa ctc ctc cgc tac ctc     864
Asp Arg Ser Leu Val Pro Gly Ala Val Glu Glu Leu Leu Arg Tyr Leu
    275                 280                 285 gcc atc gcc gac atc gcg ggc ggc cgc gtc gcc acg gcg gac atc gag     912
Ala Ile Ala Asp Ile Ala Gly Gly Arg Val Ala Thr Ala Asp Ile Glu
290                 295                 300 gtc gag ggg cac ctc atc cgg gcc ggc gag ggc gtg atc gtc gtc aac     960
Val Glu Gly His Leu Ile Arg Ala Gly Glu Gly Val Ile Val Val Asn
305                 310                 315                 320 tcg ata gcc aac cgg gac ggc acg gtg tac gag gac ccg gac gcc ctc    1008
Ser Ile Ala Asn Arg Asp Gly Thr Val Tyr Glu Asp Pro Asp Ala Leu
            325                 330                 335 gac atc cac cgc tcc gcg cgc cac cac ctc gcc ttc ggc ttc ggc gtg    1056
Asp Ile His Arg Ser Ala Arg His His Leu Ala Phe Gly Phe Gly Val
        340                 345                 350 cac cag tgc ctg ggc cag aac ctc gcc cgg ctg gag ctg gag gtc atc    1104
His Gln Cys Leu Gly Gln Asn Leu Ala Arg Leu Glu Leu Glu Val Ile
    355                 360                 365 ctc aac gcc ctc atg gac cgc gtc ccg acg ctg cga ctg gcc gtc ccc    1152
Leu Asn Ala Leu Met Asp Arg Val Pro Thr Leu Arg Leu Ala Val Pro
370                 375                 380 gtc gag cag ttg gtg ctg cgg ccg ggt acg acg atc cag ggc gtc aac    1200
Val Glu Gln Leu Val Leu Arg Pro Gly Thr Thr Ile Gln Gly Val Asn
385                 390                 395                 400 gaa ctc ccg gtc acc tgg tga                                        1221
Glu Leu Pro Val Thr Trp
            405

<210> SEQ ID NO 6
<211> LENGTH: 406
<212> TYPE: PRT
<213> ORGANISM: Streptomyces griseolus

<400> SEQUENCE: 6

Met Thr Asp Thr Ala Thr Thr Pro Gln Thr Thr Asp Ala Pro Ala Phe
1               5                   10                  15

Pro Ser Asn Arg Ser Cys Pro Tyr Gln Leu Pro Asp Gly Tyr Ala Gln
            20                  25                  30

Leu Arg Asp Thr Pro Gly Pro Leu His Arg Val Thr Leu Tyr Asp Gly
```

```
                35                  40                  45
Arg Gln Ala Trp Val Val Thr Lys His Glu Ala Ala Arg Lys Leu Leu
 50                  55                  60

Gly Asp Pro Arg Leu Ser Ser Asn Arg Thr Asp Asp Asn Phe Pro Ala
 65                  70                  75                  80

Thr Ser Pro Arg Phe Glu Ala Val Arg Glu Ser Pro Gln Ala Phe Ile
                 85                  90                  95

Gly Leu Asp Pro Pro Glu His Gly Thr Arg Arg Met Thr Ile Ser
            100                 105                 110

Glu Phe Thr Val Lys Arg Ile Lys Gly Met Arg Pro Val Glu Glu
        115                 120                 125

Val Val His Gly Phe Leu Asp Glu Met Leu Ala Ala Gly Pro Thr Ala
130                 135                 140

Asp Leu Val Ser Gln Phe Ala Leu Pro Val Pro Ser Met Val Ile Cys
145                 150                 155                 160

Arg Leu Leu Gly Val Pro Tyr Ala Asp His Glu Phe Phe Gln Asp Ala
                165                 170                 175

Ser Lys Arg Leu Val Gln Ser Thr Asp Ala Gln Ser Ala Leu Thr Ala
            180                 185                 190

Arg Asn Asp Leu Ala Gly Tyr Leu Asp Gly Leu Ile Thr Gln Phe Gln
        195                 200                 205

Thr Glu Pro Gly Ala Gly Leu Val Gly Ala Leu Val Ala Asp Gln Leu
210                 215                 220

Ala Asn Gly Glu Ile Asp Arg Glu Glu Leu Ile Ser Thr Ala Met Leu
225                 230                 235                 240

Leu Leu Ile Ala Gly His Glu Thr Thr Ala Ser Met Thr Ser Leu Ser
                245                 250                 255

Val Ile Thr Leu Leu Asp His Pro Glu Gln Tyr Ala Ala Leu Arg Ala
            260                 265                 270

Asp Arg Ser Leu Val Pro Gly Ala Val Glu Glu Leu Leu Arg Tyr Leu
        275                 280                 285

Ala Ile Ala Asp Ile Ala Gly Gly Arg Val Ala Thr Ala Asp Ile Glu
290                 295                 300

Val Glu Gly His Leu Ile Arg Ala Gly Glu Gly Val Ile Val Asn
305                 310                 315                 320

Ser Ile Ala Asn Arg Asp Gly Thr Val Tyr Glu Asp Pro Asp Ala Leu
                325                 330                 335

Asp Ile His Arg Ser Ala Arg His His Leu Ala Phe Gly Phe Gly Val
            340                 345                 350

His Gln Cys Leu Gly Gln Asn Leu Ala Arg Leu Glu Leu Glu Val Ile
        355                 360                 365

Leu Asn Ala Leu Met Asp Arg Val Pro Thr Leu Arg Leu Ala Val Pro
370                 375                 380

Val Glu Gln Leu Val Leu Arg Pro Gly Thr Thr Ile Gln Gly Val Asn
385                 390                 395                 400

Glu Leu Pro Val Thr Trp
                405

<210> SEQ ID NO 7
<211> LENGTH: 1404
<212> TYPE: DNA
<213> ORGANISM: Agrobacterium tumefaciens
<220> FEATURE:
<221> NAME/KEY: CDS
<222> LOCATION: (1)..(1401)
```

<223> OTHER INFORMATION: coding for indoleacetamide hydrolase (tms2)

<400> SEQUENCE: 7

```
atg gtg ccc att acc tcg tta gca caa acc cta gaa cgc ctg aga cgg      48
Met Val Pro Ile Thr Ser Leu Ala Gln Thr Leu Glu Arg Leu Arg Arg
 1               5                  10                  15 aaa gac tac tcc tgc tta gaa cta gta gaa act ctg ata gcg cgt tgc      96
Lys Asp Tyr Ser Cys Leu Glu Leu Val Glu Thr Leu Ile Ala Arg Cys
             20                  25                  30 caa gct gca aaa cca tta aat gcc ctt ctg gct aca gac tgg gat ggc     144
Gln Ala Ala Lys Pro Leu Asn Ala Leu Leu Ala Thr Asp Trp Asp Gly
         35                  40                  45 ttg cgg cga agc gcc aaa aaa att gat cgt cat gga aac gcc gga tta     192
Leu Arg Arg Ser Ala Lys Lys Ile Asp Arg His Gly Asn Ala Gly Leu
     50                  55                  60 ggt ctt tgc ggc att cca ctc tgt ttt aag gcg aac atc gcg acc ggc     240
Gly Leu Cys Gly Ile Pro Leu Cys Phe Lys Ala Asn Ile Ala Thr Gly
 65                  70                  75                  80 ata ttt cct aca agc gct gct act ccg gcg ctg ata aac cac ttg cca     288
Ile Phe Pro Thr Ser Ala Ala Thr Pro Ala Leu Ile Asn His Leu Pro
                 85                  90                  95 aag ata cca tcc cgc gtc gca gaa aga ctt ttt tca gct gga gca ctg     336
Lys Ile Pro Ser Arg Val Ala Glu Arg Leu Phe Ser Ala Gly Ala Leu
            100                 105                 110 ccg ggt gcc tcg gga aac atg cat gag tta tcg ttt gga att acg agc     384
Pro Gly Ala Ser Gly Asn Met His Glu Leu Ser Phe Gly Ile Thr Ser
        115                 120                 125 aac aac tat gcc acc ggt gcg gtg cgg aac ccg tgg aat cca agt ctg     432
Asn Asn Tyr Ala Thr Gly Ala Val Arg Asn Pro Trp Asn Pro Ser Leu
    130                 135                 140 ata cca gga ggc tca agc ggt ggt gtg gct gct gcg gtg gca agc cga     480
Ile Pro Gly Gly Ser Ser Gly Gly Val Ala Ala Ala Val Ala Ser Arg
145                 150                 155                 160 ttg atg tta ggc ggc ata ggc acc gat acc ggt gca tct gtt cgc cta     528
Leu Met Leu Gly Gly Ile Gly Thr Asp Thr Gly Ala Ser Val Arg Leu
                165                 170                 175 ccc gca gcc ctg tgt ggc gta gta gga ttt cga ccg acg ctt gct cga     576
Pro Ala Ala Leu Cys Gly Val Val Gly Phe Arg Pro Thr Leu Ala Arg
            180                 185                 190 tat cca aga gat cgg ata ata ccg gtc agc ccc acc cgg gac acc gcc     624
Tyr Pro Arg Asp Arg Ile Ile Pro Val Ser Pro Thr Arg Asp Thr Ala
        195                 200                 205 gga atc ata gcg cag tgc gta gcc gat gtt ata atc ctc gac cag gtg     672
Gly Ile Ile Ala Gln Cys Val Ala Asp Val Ile Ile Leu Asp Gln Val
    210                 215                 220 att tcc gga cgg tcg gcg aaa att tca ccc atg ccg ctg aag ggg ctt     720
Ile Ser Gly Arg Ser Ala Lys Ile Ser Pro Met Pro Leu Lys Gly Leu
225                 230                 235                 240 cgg atc ggc ctc ccc act acc tac ttt tac gat gac ctt gat gct gat     768
Arg Ile Gly Leu Pro Thr Thr Tyr Phe Tyr Asp Asp Leu Asp Ala Asp
                245                 250                 255 gtg gcc ttc gca gct gaa acg acg att cgc ttg cta gcc aac aga ggc     816
Val Ala Phe Ala Ala Glu Thr Thr Ile Arg Leu Leu Ala Asn Arg Gly
            260                 265                 270 gta acc ttt gtt gaa gcc gac atc ccc cac cta gag gaa ctg aat agt     864
Val Thr Phe Val Glu Ala Asp Ile Pro His Leu Glu Glu Leu Asn Ser
        275                 280                 285 ggg gca agt ttg cca att gcg ctt tac gaa ttt cca cac gct cta aaa     912
Gly Ala Ser Leu Pro Ile Ala Leu Tyr Glu Phe Pro His Ala Leu Lys
    290                 295                 300
```

```
aag tat ctc gac gat ttt gtg gga aca gtt tct ttt tct gac gtt atc      960
Lys Tyr Leu Asp Asp Phe Val Gly Thr Val Ser Phe Ser Asp Val Ile
305                 310                 315                 320 aaa gga att cgt agc ccc gat gta gcg aac att gtc agt gcg caa att     1008
Lys Gly Ile Arg Ser Pro Asp Val Ala Asn Ile Val Ser Ala Gln Ile
            325                 330                 335 gat ggg cat caa att tcc aac gat gaa tat gaa ctg gcg cgt caa tcc     1056
Asp Gly His Gln Ile Ser Asn Asp Glu Tyr Glu Leu Ala Arg Gln Ser
        340                 345                 350 ttc agg cca agg ctc cag gcc act tat cgg aat tac ttc aga ctc tat     1104
Phe Arg Pro Arg Leu Gln Ala Thr Tyr Arg Asn Tyr Phe Arg Leu Tyr
    355                 360                 365 cag tta gat gca atc ctt ttc cca act gca ccc tta gcg gcc aaa gcc     1152
Gln Leu Asp Ala Ile Leu Phe Pro Thr Ala Pro Leu Ala Ala Lys Ala
370                 375                 380 ata ggt cag gag tcg tca gtc atc cac aat ggc tca atg atg aac act     1200
Ile Gly Gln Glu Ser Ser Val Ile His Asn Gly Ser Met Met Asn Thr
385                 390                 395                 400 ttc aag atc tac gtg cga aat gtg gac cca agc agc aac gca ggc cta     1248
Phe Lys Ile Tyr Val Arg Asn Val Asp Pro Ser Ser Asn Ala Gly Leu
            405                 410                 415 cct ggg ttg agc ctt cct gcc tgc ctt aca cct gat cgc ttg cct gtt     1296
Pro Gly Leu Ser Leu Pro Ala Cys Leu Thr Pro Asp Arg Leu Pro Val
        420                 425                 430 gga atg gaa att gat gga tta gcg ggg tca gac cac cgt ctg tta gca     1344
Gly Met Glu Ile Asp Gly Leu Ala Gly Ser Asp His Arg Leu Leu Ala
    435                 440                 445 atc ggg gca gca tta gaa aaa gcc ata aat ttt cct tcc ttt ccc gat     1392
Ile Gly Ala Ala Leu Glu Lys Ala Ile Asn Phe Pro Ser Phe Pro Asp
450                 455                 460 gct ttt aat tag                                                     1404
Ala Phe Asn
465

<210> SEQ ID NO 8
<211> LENGTH: 467
<212> TYPE: PRT
<213> ORGANISM: Agrobacterium tumefaciens

<400> SEQUENCE: 8

Met Val Pro Ile Thr Ser Leu Ala Gln Thr Leu Glu Arg Leu Arg Arg
  1               5                  10                  15

Lys Asp Tyr Ser Cys Leu Glu Leu Val Glu Thr Leu Ile Ala Arg Cys
             20                  25                  30

Gln Ala Ala Lys Pro Leu Asn Ala Leu Leu Ala Thr Asp Trp Asp Gly
         35                  40                  45

Leu Arg Arg Ser Ala Lys Lys Ile Asp Arg His Gly Asn Ala Gly Leu
     50                  55                  60

Gly Leu Cys Gly Ile Pro Leu Cys Phe Lys Ala Asn Ile Ala Thr Gly
 65                  70                  75                  80

Ile Phe Pro Thr Ser Ala Ala Thr Pro Ala Leu Ile Asn His Leu Pro
                 85                  90                  95

Lys Ile Pro Ser Arg Val Ala Glu Arg Leu Phe Ser Ala Gly Ala Leu
            100                 105                 110

Pro Gly Ala Ser Gly Asn Met His Glu Leu Ser Phe Gly Ile Thr Ser
        115                 120                 125

Asn Asn Tyr Ala Thr Gly Ala Val Arg Asn Pro Trp Asn Pro Ser Leu
    130                 135                 140
```

```
Ile Pro Gly Gly Ser Ser Gly Val Ala Ala Val Ala Ser Arg
145                 150                 155                 160

Leu Met Leu Gly Gly Ile Gly Thr Asp Thr Gly Ala Ser Val Arg Leu
                165                 170                 175

Pro Ala Ala Leu Cys Gly Val Val Gly Phe Arg Pro Thr Leu Ala Arg
            180                 185                 190

Tyr Pro Arg Asp Arg Ile Ile Pro Val Ser Pro Thr Arg Asp Thr Ala
        195                 200                 205

Gly Ile Ile Ala Gln Cys Val Ala Asp Val Ile Ile Leu Asp Gln Val
210                 215                 220

Ile Ser Gly Arg Ser Ala Lys Ile Ser Pro Met Pro Leu Lys Gly Leu
225                 230                 235                 240

Arg Ile Gly Leu Pro Thr Thr Tyr Phe Tyr Asp Asp Leu Asp Ala Asp
                245                 250                 255

Val Ala Phe Ala Ala Glu Thr Thr Ile Arg Leu Leu Ala Asn Arg Gly
            260                 265                 270

Val Thr Phe Val Glu Ala Asp Ile Pro His Leu Glu Glu Leu Asn Ser
        275                 280                 285

Gly Ala Ser Leu Pro Ile Ala Leu Tyr Glu Phe Pro His Ala Leu Lys
290                 295                 300

Lys Tyr Leu Asp Asp Phe Val Gly Thr Val Ser Phe Ser Asp Val Ile
305                 310                 315                 320

Lys Gly Ile Arg Ser Pro Asp Val Ala Asn Ile Val Ser Ala Gln Ile
                325                 330                 335

Asp Gly His Gln Ile Ser Asn Asp Glu Tyr Glu Leu Ala Arg Gln Ser
            340                 345                 350

Phe Arg Pro Arg Leu Gln Ala Thr Tyr Arg Asn Tyr Phe Arg Leu Tyr
        355                 360                 365

Gln Leu Asp Ala Ile Leu Phe Pro Thr Ala Pro Leu Ala Ala Lys Ala
370                 375                 380

Ile Gly Gln Glu Ser Ser Val Ile His Asn Gly Ser Met Met Asn Thr
385                 390                 395                 400

Phe Lys Ile Tyr Val Arg Asn Val Asp Pro Ser Ser Asn Ala Gly Leu
                405                 410                 415

Pro Gly Leu Ser Leu Pro Ala Cys Leu Thr Pro Asp Arg Leu Pro Val
            420                 425                 430

Gly Met Glu Ile Asp Gly Leu Ala Gly Ser Asp His Arg Leu Leu Ala
        435                 440                 445

Ile Gly Ala Ala Leu Glu Lys Ala Ile Asn Phe Pro Ser Phe Pro Asp
450                 455                 460

Ala Phe Asn
465

<210> SEQ ID NO 9
<211> LENGTH: 1404
<212> TYPE: DNA
<213> ORGANISM: Agrobacterium tumefaciens
<220> FEATURE:
<221> NAME/KEY: CDS
<222> LOCATION: (1)..(1401)
<223> OTHER INFORMATION: coding for indoleacetamide hydrolase (tms2)

<400> SEQUENCE: 9 atg gtg ccc att acc tcg tta gca caa acc cta gaa cgc ctg aga cgg     48
Met Val Pro Ile Thr Ser Leu Ala Gln Thr Leu Glu Arg Leu Arg Arg
 1               5                  10                  15
```

```
aaa gac tac tcc tgc tta gaa cta gta gaa act ctg ata gcg cgt tgc        96
Lys Asp Tyr Ser Cys Leu Glu Leu Val Glu Thr Leu Ile Ala Arg Cys
             20                  25                  30 caa gct gca aaa cca tta aat gcc ctt ctg gct aca gac tgg gat ggc       144
Gln Ala Ala Lys Pro Leu Asn Ala Leu Leu Ala Thr Asp Trp Asp Gly
         35                  40                  45 ttg cgg cga agc gcc aaa aaa att gat cgt cat gga aac gcc gga tta       192
Leu Arg Arg Ser Ala Lys Lys Ile Asp Arg His Gly Asn Ala Gly Leu
     50                  55                  60 ggt ctt tgc ggc att cca ctc tgt ttt aag gcg aac atc gcg acc ggc       240
Gly Leu Cys Gly Ile Pro Leu Cys Phe Lys Ala Asn Ile Ala Thr Gly
 65                  70                  75                  80 ata ttt cct aca agc gct gct act ccg gcg ctg ata aac cac ttg cca       288
Ile Phe Pro Thr Ser Ala Ala Thr Pro Ala Leu Ile Asn His Leu Pro
                 85                  90                  95 aag ata cca tcc cgc gtc gca gaa aga ctt ttt tca gct gga gca ctg       336
Lys Ile Pro Ser Arg Val Ala Glu Arg Leu Phe Ser Ala Gly Ala Leu
             100                 105                 110 ccg ggt gcc tcg gga aac atg cat gag tta tcg ttt gga att acg agc       384
Pro Gly Ala Ser Gly Asn Met His Glu Leu Ser Phe Gly Ile Thr Ser
         115                 120                 125 aac aac tat gcc acc ggt gcg gtg cgg aac ccg tgg aat cca agt ctg       432
Asn Asn Tyr Ala Thr Gly Ala Val Arg Asn Pro Trp Asn Pro Ser Leu
     130                 135                 140 ata cca gga ggc tca agc ggt ggt gtg gct gct gcg gtg gca agc cga       480
Ile Pro Gly Gly Ser Ser Gly Gly Val Ala Ala Ala Val Ala Ser Arg
145                 150                 155                 160 ttg atg tta ggc ggc ata ggc acc gat acc ggt gca tct gtt cgc cta       528
Leu Met Leu Gly Gly Ile Gly Thr Asp Thr Gly Ala Ser Val Arg Leu
                 165                 170                 175 ccc gca gcc ctg tgt ggc gta gta gga ttt cga ccg acg ctt gct cga       576
Pro Ala Ala Leu Cys Gly Val Val Gly Phe Arg Pro Thr Leu Ala Arg
             180                 185                 190 tat cca aga gat cgg ata ata ccg gtc agc ccc acc cgg gac acc gcc       624
Tyr Pro Arg Asp Arg Ile Ile Pro Val Ser Pro Thr Arg Asp Thr Ala
         195                 200                 205 gga atc ata gcg cag tgc gta gcc gat gtt ata atc ctc gat cag gtg       672
Gly Ile Ile Ala Gln Cys Val Ala Asp Val Ile Ile Leu Asp Gln Val
     210                 215                 220 att tcc gga cgg tcg gcg aaa att tca ccc atg ccg ctg aag ggg ctt       720
Ile Ser Gly Arg Ser Ala Lys Ile Ser Pro Met Pro Leu Lys Gly Leu
225                 230                 235                 240 cgg atc ggc ctc ccc act acc tac ttt tac gat gac ctt gat gct gat       768
Arg Ile Gly Leu Pro Thr Thr Tyr Phe Tyr Asp Asp Leu Asp Ala Asp
                 245                 250                 255 gtg gcc ttc gca gct gaa acg acg att cgc ttg cta gcc aac aga ggc       816
Val Ala Phe Ala Ala Glu Thr Thr Ile Arg Leu Leu Ala Asn Arg Gly
             260                 265                 270 gta acc ttt gtt gaa gcc gac atc ccc cac cta gag gaa ctg aat agt       864
Val Thr Phe Val Glu Ala Asp Ile Pro His Leu Glu Glu Leu Asn Ser
         275                 280                 285 ggg gca agt ttg cca att gcg ctt tac gaa ttt cca cac gct cta aaa       912
Gly Ala Ser Leu Pro Ile Ala Leu Tyr Glu Phe Pro His Ala Leu Lys
     290                 295                 300 aag tat ctc gac gat ttt gtg gga aca gtt tct ttt tct gac gtt atc       960
Lys Tyr Leu Asp Asp Phe Val Gly Thr Val Ser Phe Ser Asp Val Ile
305                 310                 315                 320 aaa gga att cgt agc ccc gat gta gcg aac att gtc agt gcg caa att      1008
Lys Gly Ile Arg Ser Pro Asp Val Ala Asn Ile Val Ser Ala Gln Ile
```

325                 330                 335
gat ggg cat caa att tcc aac gat gaa tat gaa ctg gcg cgt caa tcc      1056
Asp Gly His Gln Ile Ser Asn Asp Glu Tyr Glu Leu Ala Arg Gln Ser
                340                 345                 350 ttc agg cca agg ctc cag gcc act tat cgg aat tac ttc aga ctc tat      1104
Phe Arg Pro Arg Leu Gln Ala Thr Tyr Arg Asn Tyr Phe Arg Leu Tyr
            355                 360                 365 cag tta gat gca atc ctt ttc cca act gca ccc tta gcg gcc aaa gcc      1152
Gln Leu Asp Ala Ile Leu Phe Pro Thr Ala Pro Leu Ala Ala Lys Ala
        370                 375                 380 ata ggt cag gag tcg tca gtc atc cac aat ggc tca atg ata aac act      1200
Ile Gly Gln Glu Ser Ser Val Ile His Asn Gly Ser Met Ile Asn Thr
385                 390                 395                 400 ttc aag atc tac gtg cga aat gtg gac cca agc agc aac gca ggc cta      1248
Phe Lys Ile Tyr Val Arg Asn Val Asp Pro Ser Ser Asn Ala Gly Leu
                405                 410                 415 cct ggg ttg agc ctt cct gcc tgc ctt aca cct gat cgc ttg cct gtt      1296
Pro Gly Leu Ser Leu Pro Ala Cys Leu Thr Pro Asp Arg Leu Pro Val
            420                 425                 430 gga atg gaa att gac gga tta gcg ggg tca gac cac cgt ctg tta gca      1344
Gly Met Glu Ile Asp Gly Leu Ala Gly Ser Asp His Arg Leu Leu Ala
        435                 440                 445 atc ggg gca gca tta gaa aaa gcc ata aat ttt cct tcc ttt ccc gat      1392
Ile Gly Ala Ala Leu Glu Lys Ala Ile Asn Phe Pro Ser Phe Pro Asp
    450                 455                 460 gct ttt aat tag                                                     1404
Ala Phe Asn
465

<210> SEQ ID NO 10
<211> LENGTH: 467
<212> TYPE: PRT
<213> ORGANISM: Agrobacterium tumefaciens

<400> SEQUENCE: 10

Met Val Pro Ile Thr Ser Leu Ala Gln Thr Leu Glu Arg Leu Arg Arg
 1               5                  10                  15

Lys Asp Tyr Ser Cys Leu Glu Leu Val Glu Thr Leu Ile Ala Arg Cys
            20                  25                  30

Gln Ala Ala Lys Pro Leu Asn Ala Leu Leu Ala Thr Asp Trp Asp Gly
        35                  40                  45

Leu Arg Arg Ser Ala Lys Lys Ile Asp Arg His Gly Asn Ala Gly Leu
    50                  55                  60

Gly Leu Cys Gly Ile Pro Leu Cys Phe Lys Ala Asn Ile Ala Thr Gly
65                  70                  75                  80

Ile Phe Pro Thr Ser Ala Ala Thr Pro Ala Leu Ile Asn His Leu Pro
                85                  90                  95

Lys Ile Pro Ser Arg Val Ala Glu Arg Leu Phe Ser Ala Gly Ala Leu
            100                 105                 110

Pro Gly Ala Ser Gly Asn Met His Glu Leu Ser Phe Gly Ile Thr Ser
        115                 120                 125

Asn Asn Tyr Ala Thr Gly Ala Val Arg Asn Pro Trp Asn Pro Ser Leu
    130                 135                 140

Ile Pro Gly Gly Ser Ser Gly Gly Val Ala Ala Val Ala Ser Arg
145                 150                 155                 160

Leu Met Leu Gly Gly Ile Gly Thr Asp Thr Gly Ala Ser Val Arg Leu
                165                 170                 175

```
Pro Ala Ala Leu Cys Gly Val Gly Phe Arg Pro Thr Leu Ala Arg
            180                 185                 190

Tyr Pro Arg Asp Arg Ile Ile Pro Val Ser Pro Thr Arg Asp Thr Ala
        195                 200                 205

Gly Ile Ile Ala Gln Cys Val Ala Asp Val Ile Ile Leu Asp Gln Val
    210                 215                 220

Ile Ser Gly Arg Ser Ala Lys Ile Ser Pro Met Pro Leu Lys Gly Leu
225                 230                 235                 240

Arg Ile Gly Leu Pro Thr Thr Tyr Phe Tyr Asp Leu Asp Ala Asp
                245                 250                 255

Val Ala Phe Ala Ala Glu Thr Thr Ile Arg Leu Leu Ala Asn Arg Gly
            260                 265                 270

Val Thr Phe Val Glu Ala Asp Ile Pro His Leu Glu Glu Leu Asn Ser
        275                 280                 285

Gly Ala Ser Leu Pro Ile Ala Leu Tyr Glu Phe Pro His Ala Leu Lys
    290                 295                 300

Lys Tyr Leu Asp Asp Phe Val Gly Thr Val Ser Phe Ser Asp Val Ile
305                 310                 315                 320

Lys Gly Ile Arg Ser Pro Asp Val Ala Asn Ile Val Ser Ala Gln Ile
                325                 330                 335

Asp Gly His Gln Ile Ser Asn Asp Glu Tyr Glu Leu Ala Arg Gln Ser
            340                 345                 350

Phe Arg Pro Arg Leu Gln Ala Thr Tyr Arg Asn Tyr Phe Arg Leu Tyr
        355                 360                 365

Gln Leu Asp Ala Ile Leu Phe Pro Thr Ala Pro Leu Ala Ala Lys Ala
    370                 375                 380

Ile Gly Gln Glu Ser Ser Val Ile His Asn Gly Ser Met Ile Asn Thr
385                 390                 395                 400

Phe Lys Ile Tyr Val Arg Asn Val Asp Pro Ser Ser Asn Ala Gly Leu
                405                 410                 415

Pro Gly Leu Ser Leu Pro Ala Cys Leu Thr Pro Asp Arg Leu Pro Val
            420                 425                 430

Gly Met Glu Ile Asp Gly Leu Ala Gly Ser Asp His Arg Leu Leu Ala
        435                 440                 445

Ile Gly Ala Ala Leu Glu Lys Ala Ile Asn Phe Pro Ser Phe Pro Asp
    450                 455                 460

Ala Phe Asn
465

<210> SEQ ID NO 11
<211> LENGTH: 609
<212> TYPE: DNA
<213> ORGANISM: Xanthobacter autotrophicus
<220> FEATURE:
<221> NAME/KEY: CDS
<222> LOCATION: (1)..(603)
<223> OTHER INFORMATION: coding for haloalkane dehalogenase

<400> SEQUENCE: 11 atg tca acg ttt ttt gaa ccg gag aac gga atg aaa caa aac gcc aaa      48
Met Ser Thr Phe Phe Glu Pro Glu Asn Gly Met Lys Gln Asn Ala Lys
  1               5                  10                  15 acc gaa cga atc ctg gat gtc gcg ctc gaa ttg ctt gag aca gag ggt      96
Thr Glu Arg Ile Leu Asp Val Ala Leu Glu Leu Leu Glu Thr Glu Gly
             20                  25                  30 gag ttt ggt ttg acg atg agg cag gtg gca acg caa gcg gac atg tcc     144
Glu Phe Gly Leu Thr Met Arg Gln Val Ala Thr Gln Ala Asp Met Ser
         35                  40                  45
```

```
                35                  40                  45
ctg agc aac gtt cag tac tat ttc aag tcc gag gac ctg ctc ctc gtg     192
Leu Ser Asn Val Gln Tyr Tyr Phe Lys Ser Glu Asp Leu Leu Leu Val
    50                  55                  60 gcc atg gca gac cgt tac ttt caa cgg tgc ctg aca acc atg gct gag     240
Ala Met Ala Asp Arg Tyr Phe Gln Arg Cys Leu Thr Thr Met Ala Glu
65                  70                  75                  80 cat ccg ccc tta tcg gca ggg cgt gat caa cac gcc cag tta aga gcg     288
His Pro Pro Leu Ser Ala Gly Arg Asp Gln His Ala Gln Leu Arg Ala
                85                  90                  95 ttg tta cga gaa ctg ctc ggt cat ggt ctt gag att tcc gag atg tgt     336
Leu Leu Arg Glu Leu Leu Gly His Gly Leu Glu Ile Ser Glu Met Cys
            100                 105                 110 cga ata ttc agg gag tac tgg gca atc gcc acc cgt aat gaa act gtt     384
Arg Ile Phe Arg Glu Tyr Trp Ala Ile Ala Thr Arg Asn Glu Thr Val
        115                 120                 125 cac ggc tat ctc aag tcg tac tat cgg gat ctc gcc gaa gtg atg gct     432
His Gly Tyr Leu Lys Ser Tyr Tyr Arg Asp Leu Ala Glu Val Met Ala
    130                 135                 140 gag aag ctt gcg cca ctg gcc agc agc gaa aag gcg ctg gcc gtg gcc     480
Glu Lys Leu Ala Pro Leu Ala Ser Ser Glu Lys Ala Leu Ala Val Ala
145                 150                 155                 160 gta tct ttg gtt att cct tat gtt gag ggg tat tcg gta acg gcc att     528
Val Ser Leu Val Ile Pro Tyr Val Glu Gly Tyr Ser Val Thr Ala Ile
                165                 170                 175 gca atg ccc gaa tcc att gat acg att tcc gag acg ctg acc aat gtg     576
Ala Met Pro Glu Ser Ile Asp Thr Ile Ser Glu Thr Leu Thr Asn Val
            180                 185                 190 gtg ttg gag cag ctt cgc atc agc aat tcatga                         609
Val Leu Glu Gln Leu Arg Ile Ser Asn
        195                 200

<210> SEQ ID NO 12
<211> LENGTH: 201
<212> TYPE: PRT
<213> ORGANISM: Xanthobacter autotrophicus

<400> SEQUENCE: 12

Met Ser Thr Phe Phe Glu Pro Glu Asn Gly Met Lys Gln Asn Ala Lys
1               5                   10                  15

Thr Glu Arg Ile Leu Asp Val Ala Leu Glu Leu Leu Glu Thr Glu Gly
            20                  25                  30

Glu Phe Gly Leu Thr Met Arg Gln Val Ala Thr Gln Ala Asp Met Ser
        35                  40                  45

Leu Ser Asn Val Gln Tyr Tyr Phe Lys Ser Glu Asp Leu Leu Leu Val
    50                  55                  60

Ala Met Ala Asp Arg Tyr Phe Gln Arg Cys Leu Thr Thr Met Ala Glu
65                  70                  75                  80

His Pro Pro Leu Ser Ala Gly Arg Asp Gln His Ala Gln Leu Arg Ala
                85                  90                  95

Leu Leu Arg Glu Leu Leu Gly His Gly Leu Glu Ile Ser Glu Met Cys
            100                 105                 110

Arg Ile Phe Arg Glu Tyr Trp Ala Ile Ala Thr Arg Asn Glu Thr Val
        115                 120                 125

His Gly Tyr Leu Lys Ser Tyr Tyr Arg Asp Leu Ala Glu Val Met Ala
    130                 135                 140

Glu Lys Leu Ala Pro Leu Ala Ser Ser Glu Lys Ala Leu Ala Val Ala
145                 150                 155                 160
```

-continued

```
Val Ser Leu Val Ile Pro Tyr Val Glu Gly Tyr Ser Val Thr Ala Ile
            165                 170                 175

Ala Met Pro Glu Ser Ile Asp Thr Ile Ser Glu Thr Leu Thr Asn Val
        180                 185                 190

Val Leu Glu Gln Leu Arg Ile Ser Asn
    195                 200

<210> SEQ ID NO 13
<211> LENGTH: 1131
<212> TYPE: DNA
<213> ORGANISM: Herpes simplex virus 1
<220> FEATURE:
<221> NAME/KEY: CDS
<222> LOCATION: (1)..(1128)
<223> OTHER INFORMATION: coding for thymidine kinase (TK)

<400> SEQUENCE: 13 atg gct tcg tac ccc tgc cat caa cac gcg tct gcg ttc gac cag gct      48
Met Ala Ser Tyr Pro Cys His Gln His Ala Ser Ala Phe Asp Gln Ala
 1               5                  10                  15 gcg cgt tct cgc ggc cat agc aac cga cgt acg gcg ttg cgc cct cgc      96
Ala Arg Ser Arg Gly His Ser Asn Arg Arg Thr Ala Leu Arg Pro Arg
             20                  25                  30 cgg cag caa gaa gcc acg gaa gtc cgc ctg gag cag aaa atg ccc acg     144
Arg Gln Gln Glu Ala Thr Glu Val Arg Leu Glu Gln Lys Met Pro Thr
         35                  40                  45 cta ctg cgg gtt tat ata gac ggt cct cac ggg atg ggg aaa acc acc     192
Leu Leu Arg Val Tyr Ile Asp Gly Pro His Gly Met Gly Lys Thr Thr
     50                  55                  60 acc acg caa ctg ctg gtg gcc ctg ggt tcg cgc gac gat atc gtc tac     240
Thr Thr Gln Leu Leu Val Ala Leu Gly Ser Arg Asp Asp Ile Val Tyr
 65                  70                  75                  80 gta ccc gag ccg atg act tac tgg cag gtg ctg ggg gct tcc gag aca     288
Val Pro Glu Pro Met Thr Tyr Trp Gln Val Leu Gly Ala Ser Glu Thr
                 85                  90                  95 atc gcg aac atc tac acc aca caa cac cgc ctc gac cag ggt gag ata     336
Ile Ala Asn Ile Tyr Thr Thr Gln His Arg Leu Asp Gln Gly Glu Ile
            100                 105                 110 tcg gcc ggg gac gcg gcg gtg gta atg aca agc gcc cag ata aca atg     384
Ser Ala Gly Asp Ala Ala Val Val Met Thr Ser Ala Gln Ile Thr Met
        115                 120                 125 ggc atg cct tat gcc gtg acc gac gcc gtt ctg gct cct cat gtc ggg     432
Gly Met Pro Tyr Ala Val Thr Asp Ala Val Leu Ala Pro His Val Gly
    130                 135                 140 ggg gag gct ggg agt tca cat gcc ccg ccc ccg gcc ctc acc ctc atc     480
Gly Glu Ala Gly Ser Ser His Ala Pro Pro Pro Ala Leu Thr Leu Ile
145                 150                 155                 160 ttc gac cgc cat ccc atc gcc gcc ctc ctg tgc tac ccg gcc gcg cga     528
Phe Asp Arg His Pro Ile Ala Ala Leu Leu Cys Tyr Pro Ala Ala Arg
                165                 170                 175 tac ctt atg ggc agc atg acc ccc cag gcc gtg ctg gcg ttc gtg gcc     576
Tyr Leu Met Gly Ser Met Thr Pro Gln Ala Val Leu Ala Phe Val Ala
            180                 185                 190 ctc atc ccg ccg acc ttg ccc ggc aca aac atc gtg ttg ggg gcc ctt     624
Leu Ile Pro Pro Thr Leu Pro Gly Thr Asn Ile Val Leu Gly Ala Leu
        195                 200                 205 ccg gag gac aga cac atc gac cgc ctg gcc aaa cgc cag cgc ccc ggc     672
Pro Glu Asp Arg His Ile Asp Arg Leu Ala Lys Arg Gln Arg Pro Gly
    210                 215                 220 gag cgg ctt gac ctg gct atg ctg gcc gcg att cgc cgc gtt tac ggg     720
```

-continued

```
Glu Arg Leu Asp Leu Ala Met Leu Ala Ala Ile Arg Arg Val Tyr Gly
225                 230                 235                 240 ctg ctt gcc aat acg gtg cgg tat ctg cag ggc ggc ggg tcg tgg tgg        768
Leu Leu Ala Asn Thr Val Arg Tyr Leu Gln Gly Gly Gly Ser Trp Trp
                    245                 250                 255 gag gat tgg gga cag ctt tcg ggg acg gcc gtg ccg ccc cag ggt gcc        816
Glu Asp Trp Gly Gln Leu Ser Gly Thr Ala Val Pro Pro Gln Gly Ala
                260                 265                 270 gag ccc cag agc aac gcg ggc cca cga ccc cat atc ggg gac acg tta        864
Glu Pro Gln Ser Asn Ala Gly Pro Arg Pro His Ile Gly Asp Thr Leu
            275                 280                 285 ttt acc ctg ttt cgg gcc ccc gag ttg ctg gcc ccc aac ggc gac ctg        912
Phe Thr Leu Phe Arg Ala Pro Glu Leu Leu Ala Pro Asn Gly Asp Leu
        290                 295                 300 tat aac gtg ttt gcc tgg gcc ttg gac gtc ttg gcc aaa cgc ctc cgt        960
Tyr Asn Val Phe Ala Trp Ala Leu Asp Val Leu Ala Lys Arg Leu Arg
    305                 310                 315                 320 ccc atg cac gtc ttt atc ctg gat tac gac caa tcg ccc gcc ggc tgc       1008
Pro Met His Val Phe Ile Leu Asp Tyr Asp Gln Ser Pro Ala Gly Cys
                    325                 330                 335 cgg gac gcc ctg ctg caa ctt acc tcc ggg atg gtc cag acc cac gtc       1056
Arg Asp Ala Leu Leu Gln Leu Thr Ser Gly Met Val Gln Thr His Val
                340                 345                 350 acc acc cca ggc tcc ata ccg acg atc tgc gac ctg gcg cgc acg ttt       1104
Thr Thr Pro Gly Ser Ile Pro Thr Ile Cys Asp Leu Ala Arg Thr Phe
            355                 360                 365 gcc cgg gag atg ggg gag gct aac tga                                    1131
Ala Arg Glu Met Gly Glu Ala Asn
        370                 375

<210> SEQ ID NO 14
<211> LENGTH: 376
<212> TYPE: PRT
<213> ORGANISM: Herpes simplex virus 1

<400> SEQUENCE: 14

Met Ala Ser Tyr Pro Cys His Gln His Ala Ser Ala Phe Asp Gln Ala
1               5                   10                  15

Ala Arg Ser Arg Gly His Ser Asn Arg Arg Thr Ala Leu Arg Pro Arg
            20                  25                  30

Arg Gln Gln Glu Ala Thr Glu Val Arg Leu Glu Gln Lys Met Pro Thr
        35                  40                  45

Leu Leu Arg Val Tyr Ile Asp Gly Pro His Gly Met Gly Lys Thr Thr
    50                  55                  60

Thr Thr Gln Leu Leu Val Ala Leu Gly Ser Arg Asp Asp Ile Val Tyr
65                  70                  75                  80

Val Pro Glu Pro Met Thr Tyr Trp Gln Val Leu Gly Ala Ser Glu Thr
                85                  90                  95

Ile Ala Asn Ile Tyr Thr Thr Gln His Arg Leu Asp Gln Gly Glu Ile
            100                 105                 110

Ser Ala Gly Asp Ala Ala Val Val Met Thr Ser Ala Gln Ile Thr Met
        115                 120                 125

Gly Met Pro Tyr Ala Val Thr Asp Ala Val Leu Ala Pro His Val Gly
    130                 135                 140

Gly Glu Ala Gly Ser Ser His Ala Pro Pro Ala Leu Thr Leu Ile
145                 150                 155                 160

Phe Asp Arg His Pro Ile Ala Ala Leu Leu Cys Tyr Pro Ala Ala Arg
                165                 170                 175
```

```
Tyr Leu Met Gly Ser Met Thr Pro Gln Ala Val Leu Ala Phe Val Ala
            180                 185                 190

Leu Ile Pro Pro Thr Leu Pro Gly Thr Asn Ile Val Leu Gly Ala Leu
        195                 200                 205

Pro Glu Asp Arg His Ile Asp Arg Leu Ala Lys Arg Gln Arg Pro Gly
    210                 215                 220

Glu Arg Leu Asp Leu Ala Met Leu Ala Ala Ile Arg Arg Val Tyr Gly
225                 230                 235                 240

Leu Leu Ala Asn Thr Val Arg Tyr Leu Gln Gly Gly Gly Ser Trp Trp
                245                 250                 255

Glu Asp Trp Gly Gln Leu Ser Gly Thr Ala Val Pro Pro Gln Gly Ala
            260                 265                 270

Glu Pro Gln Ser Asn Ala Gly Pro Arg Pro His Ile Gly Asp Thr Leu
        275                 280                 285

Phe Thr Leu Phe Arg Ala Pro Glu Leu Leu Ala Pro Asn Gly Asp Leu
    290                 295                 300

Tyr Asn Val Phe Ala Trp Ala Leu Asp Val Leu Ala Lys Arg Leu Arg
305                 310                 315                 320

Pro Met His Val Phe Ile Leu Asp Tyr Asp Gln Ser Pro Ala Gly Cys
                325                 330                 335

Arg Asp Ala Leu Leu Gln Leu Thr Ser Gly Met Val Gln Thr His Val
            340                 345                 350

Thr Thr Pro Gly Ser Ile Pro Thr Ile Cys Asp Leu Ala Arg Thr Phe
        355                 360                 365

Ala Arg Glu Met Gly Glu Ala Asn
    370                 375

<210> SEQ ID NO 15
<211> LENGTH: 1131
<212> TYPE: DNA
<213> ORGANISM: Herpes simplex virus 1
<220> FEATURE:
<221> NAME/KEY: CDS
<222> LOCATION: (1)..(1128)
<223> OTHER INFORMATION: coding for thymidine kinase (TK)

<400> SEQUENCE: 15 atg gct tcg tac ccc tgc cat caa cac gcg tct gcg ttc gac cag gct      48
Met Ala Ser Tyr Pro Cys His Gln His Ala Ser Ala Phe Asp Gln Ala
 1               5                  10                  15 gcg cgt tct cgc ggc cat agc aac cga cgt acg gcg ttg cgc cct cgc      96
Ala Arg Ser Arg Gly His Ser Asn Arg Arg Thr Ala Leu Arg Pro Arg
                20                  25                  30 cgg cag caa gaa gcc acg gaa gtc cgc ctg gag cag aaa atg ccc acg     144
Arg Gln Gln Glu Ala Thr Glu Val Arg Leu Glu Gln Lys Met Pro Thr
            35                  40                  45 cta ctg cgg gtt tat ata gac ggt cct cac ggg atg ggg aaa acc acc     192
Leu Leu Arg Val Tyr Ile Asp Gly Pro His Gly Met Gly Lys Thr Thr
        50                  55                  60 acc acg caa ctg ctg gtg gcc ctg ggt tcg cgc gac gat atc gtc tac     240
Thr Thr Gln Leu Leu Val Ala Leu Gly Ser Arg Asp Asp Ile Val Tyr
 65                  70                  75                  80 gta ccc gag ccg atg act tac tgg cag gtg ctg ggg gct tcc gag aca     288
Val Pro Glu Pro Met Thr Tyr Trp Gln Val Leu Gly Ala Ser Glu Thr
                 85                  90                  95 atc gcg aac atc tac acc aca caa cac cgc ctc gac cag ggt gag ata     336
Ile Ala Asn Ile Tyr Thr Thr Gln His Arg Leu Asp Gln Gly Glu Ile
            100                 105                 110
```

-continued

```
tcg gcc ggg gac gcg gcg gtg gta atg aca agc gcc cag ata aca atg      384
Ser Ala Gly Asp Ala Ala Val Val Met Thr Ser Ala Gln Ile Thr Met
            115                 120                 125 ggc atg cct tat gcc gtg acc gac gcc gtt ctg gct cct cat gtc ggg      432
Gly Met Pro Tyr Ala Val Thr Asp Ala Val Leu Ala Pro His Val Gly
130                 135                 140 ggg gag gct ggg agt tca cat gcc ccg ccc gcc ctc acc ctc atc          480
Gly Glu Ala Gly Ser Ser His Ala Pro Pro Ala Leu Thr Leu Ile
145                 150                 155                 160 ttc gac cgc cat ccc atc gcc gcc ctc ctg tgc tac ccg gcc gcg cga      528
Phe Asp Arg His Pro Ile Ala Ala Leu Leu Cys Tyr Pro Ala Ala Arg
                165                 170                 175 tac ctt atg ggc agc atg acc ccc cag gcc gtg ctg gcg ttc gtg gcc      576
Tyr Leu Met Gly Ser Met Thr Pro Gln Ala Val Leu Ala Phe Val Ala
            180                 185                 190 ctc atc ccg ccg acc ttg ccc ggc aca aac atc gtg ttg ggg gcc ctt      624
Leu Ile Pro Pro Thr Leu Pro Gly Thr Asn Ile Val Leu Gly Ala Leu
        195                 200                 205 ccg gag gac aga cac atc gac cgc ctg gcc aaa cgc cag cgc ccc ggc      672
Pro Glu Asp Arg His Ile Asp Arg Leu Ala Lys Arg Gln Arg Pro Gly
210                 215                 220 gag cgg ctt gac ctg gct atg ctg gcc gcg att cgc cgc gtt tac ggg      720
Glu Arg Leu Asp Leu Ala Met Leu Ala Ala Ile Arg Arg Val Tyr Gly
225                 230                 235                 240 ctg ctt gcc aat acg gtg cgg tat ctg cag ggc ggc ggg tcg tgg tgg      768
Leu Leu Ala Asn Thr Val Arg Tyr Leu Gln Gly Gly Gly Ser Trp Trp
                245                 250                 255 gag gat tgg gga cag ctt tcg ggg acg gcc gtg ccg ccc cag ggt gcc      816
Glu Asp Trp Gly Gln Leu Ser Gly Thr Ala Val Pro Pro Gln Gly Ala
            260                 265                 270 gag ccc cag agc aac gcg ggc cca cga ccc cat atc ggg gac acg tta      864
Glu Pro Gln Ser Asn Ala Gly Pro Arg Pro His Ile Gly Asp Thr Leu
        275                 280                 285 ttt acc ctg ttt cgg gcc ccc gag ttg ctg gcc ccc aac ggc gac ctg      912
Phe Thr Leu Phe Arg Ala Pro Glu Leu Leu Ala Pro Asn Gly Asp Leu
290                 295                 300 tat aac gtg ttt gcc tgg gcc ttg gac gtc ttg gcc aaa cgc ctc cgt      960
Tyr Asn Val Phe Ala Trp Ala Leu Asp Val Leu Ala Lys Arg Leu Arg
305                 310                 315                 320 ccc atg cac gtc ttt atc ctg gat tac gac caa tcg ccc gcc ggc tgc     1008
Pro Met His Val Phe Ile Leu Asp Tyr Asp Gln Ser Pro Ala Gly Cys
                325                 330                 335 cgg gac gcc ctg ctg caa ctt acc tcc ggg atg gtc cag acc cac gtc     1056
Arg Asp Ala Leu Leu Gln Leu Thr Ser Gly Met Val Gln Thr His Val
            340                 345                 350 acc acc cca ggc tcc ata ccg acg atc tgc gac ctg gcg cgc acg ttt     1104
Thr Thr Pro Gly Ser Ile Pro Thr Ile Cys Asp Leu Ala Arg Thr Phe
        355                 360                 365 gcc cgg gag atg ggg gag gct aac tga                                  1131
Ala Arg Glu Met Gly Glu Ala Asn
370                 375

<210> SEQ ID NO 16
<211> LENGTH: 376
<212> TYPE: PRT
<213> ORGANISM: Herpes simplex virus 1

<400> SEQUENCE: 16

Met Ala Ser Tyr Pro Cys His Gln His Ala Ser Ala Phe Asp Gln Ala
1               5                   10                  15
```

```
Ala Arg Ser Arg Gly His Ser Asn Arg Thr Ala Leu Arg Pro Arg
             20                  25                  30

Arg Gln Gln Glu Ala Thr Glu Val Arg Leu Glu Gln Lys Met Pro Thr
         35                  40                  45

Leu Leu Arg Val Tyr Ile Asp Gly Pro His Gly Met Gly Lys Thr Thr
     50                  55                  60

Thr Thr Gln Leu Leu Val Ala Leu Gly Ser Arg Asp Asp Ile Val Tyr
 65                  70                  75                  80

Val Pro Glu Pro Met Thr Tyr Trp Gln Val Leu Gly Ala Ser Glu Thr
                 85                  90                  95

Ile Ala Asn Ile Tyr Thr Thr Gln His Arg Leu Asp Gln Gly Glu Ile
                100                 105                 110

Ser Ala Gly Asp Ala Ala Val Val Met Thr Ser Ala Gln Ile Thr Met
            115                 120                 125

Gly Met Pro Tyr Ala Val Thr Asp Ala Val Leu Ala Pro His Val Gly
        130                 135                 140

Gly Glu Ala Gly Ser Ser His Ala Pro Pro Ala Leu Thr Leu Ile
145                 150                 155                 160

Phe Asp Arg His Pro Ile Ala Ala Leu Leu Cys Tyr Pro Ala Ala Arg
                165                 170                 175

Tyr Leu Met Gly Ser Met Thr Pro Gln Ala Val Leu Ala Phe Val Ala
            180                 185                 190

Leu Ile Pro Pro Thr Leu Pro Gly Thr Asn Ile Val Leu Gly Ala Leu
        195                 200                 205

Pro Glu Asp Arg His Ile Asp Arg Leu Ala Lys Arg Gln Arg Pro Gly
    210                 215                 220

Glu Arg Leu Asp Leu Ala Met Leu Ala Ala Ile Arg Arg Val Tyr Gly
225                 230                 235                 240

Leu Leu Ala Asn Thr Val Arg Tyr Leu Gln Gly Gly Ser Trp Trp
                245                 250                 255

Glu Asp Trp Gly Gln Leu Ser Gly Thr Ala Val Pro Pro Gln Gly Ala
            260                 265                 270

Glu Pro Gln Ser Asn Ala Gly Pro Arg Pro His Ile Gly Asp Thr Leu
        275                 280                 285

Phe Thr Leu Phe Arg Ala Pro Glu Leu Leu Ala Pro Asn Gly Asp Leu
    290                 295                 300

Tyr Asn Val Phe Ala Trp Ala Leu Asp Val Leu Ala Lys Arg Leu Arg
305                 310                 315                 320

Pro Met His Val Phe Ile Leu Asp Tyr Asp Gln Ser Pro Ala Gly Cys
                325                 330                 335

Arg Asp Ala Leu Leu Gln Leu Thr Ser Gly Met Val Gln Thr His Val
            340                 345                 350

Thr Thr Pro Gly Ser Ile Pro Thr Ile Cys Asp Leu Ala Arg Thr Phe
        355                 360                 365

Ala Arg Glu Met Gly Glu Ala Asn
    370                 375

<210> SEQ ID NO 17
<211> LENGTH: 840
<212> TYPE: DNA
<213> ORGANISM: Toxoplasma gondii
<220> FEATURE:
<221> NAME/KEY: CDS
<222> LOCATION: (1)..(837)
<223> OTHER INFORMATION: coding for hypoxanthine-xanthine-guanine
``` phosphoribosyl transferase (HXGPRTase)

<400> SEQUENCE: 17

```
atg gcg tcc aaa ccc att gaa gaa tcc cgg tcg caa aaa cgg agt gcc      48
Met Ala Ser Lys Pro Ile Glu Glu Ser Arg Ser Gln Lys Arg Ser Ala
 1               5                  10                  15 ttc tca gac atc ttc tgt tgt tgc act cct aat gaa ggg gct atc gtg      96
Phe Ser Asp Ile Phe Cys Cys Cys Thr Pro Asn Glu Gly Ala Ile Val
             20                  25                  30 ccc agt gac cca atg gtc tcc acc agt gct cca gca cgc acc agt gct     144
Pro Ser Asp Pro Met Val Ser Thr Ser Ala Pro Ala Arg Thr Ser Ala
         35                  40                  45 cca gcg cgc tcc agt gca ctt caa gac tac ggc aag ggc aag ggc cgt     192
Pro Ala Arg Ser Ser Ala Leu Gln Asp Tyr Gly Lys Gly Lys Gly Arg
     50                  55                  60 att gag ccc atg tat atc ccc gac aac acc ttc tac aac gct gat gac     240
Ile Glu Pro Met Tyr Ile Pro Asp Asn Thr Phe Tyr Asn Ala Asp Asp
 65                  70                  75                  80 ttt ctt gtg ccc ccc cac tgc aag ccc tac att gac aaa atc ctc ctc     288
Phe Leu Val Pro Pro His Cys Lys Pro Tyr Ile Asp Lys Ile Leu Leu
                 85                  90                  95 cct ggt gga ttg gtc aag gac aga gtt gag aag ttg gcg tat gac atc     336
Pro Gly Gly Leu Val Lys Asp Arg Val Glu Lys Leu Ala Tyr Asp Ile
            100                 105                 110 cac aga act tac ttc ggc gag gag ttg cac atc att tgc atc ctg aaa     384
His Arg Thr Tyr Phe Gly Glu Glu Leu His Ile Ile Cys Ile Leu Lys
        115                 120                 125 ggc tct cgc ggc ttc ttc aac ctt ctg atc gac tac ctt gcc acc ata     432
Gly Ser Arg Gly Phe Phe Asn Leu Leu Ile Asp Tyr Leu Ala Thr Ile
    130                 135                 140 cag aag tac agt ggt cgt gag tcc agc gtg ccc ccc ttc ttc gag cac     480
Gln Lys Tyr Ser Gly Arg Glu Ser Ser Val Pro Pro Phe Phe Glu His
145                 150                 155                 160 tat gtc cgc ctg aag tcc tac cag aac gac aac agc aca ggc cag ctc     528
Tyr Val Arg Leu Lys Ser Tyr Gln Asn Asp Asn Ser Thr Gly Gln Leu
                165                 170                 175 acc gtc ttg agc gac gac ttg tca atc ttt cgc gac aag cac gtt ctg     576
Thr Val Leu Ser Asp Asp Leu Ser Ile Phe Arg Asp Lys His Val Leu
            180                 185                 190 att gtt gag gac atc gtc gac acc ggt ttc acc ctc acc gag ttc ggt     624
Ile Val Glu Asp Ile Val Asp Thr Gly Phe Thr Leu Thr Glu Phe Gly
        195                 200                 205 gag cgc ctg aaa gcc gtc ggt ccc aag tcg atg aga atc gcc acc ctc     672
Glu Arg Leu Lys Ala Val Gly Pro Lys Ser Met Arg Ile Ala Thr Leu
    210                 215                 220 gtc gag aag cgc aca gat cgc tcc aac agc ttg aag ggc gac ttc gtc     720
Val Glu Lys Arg Thr Asp Arg Ser Asn Ser Leu Lys Gly Asp Phe Val
225                 230                 235                 240 ggc ttc agc att gaa gac gtc tgg atc gtt ggt tgc tgc tac gac ttc     768
Gly Phe Ser Ile Glu Asp Val Trp Ile Val Gly Cys Cys Tyr Asp Phe
                245                 250                 255 aac gag atg ttc cgc gac ttc gac cac gtc gcc gtc ctg agc gac gcc     816
Asn Glu Met Phe Arg Asp Phe Asp His Val Ala Val Leu Ser Asp Ala
            260                 265                 270 gct cgc aaa aag ttc gag aag taa                                     840
Ala Arg Lys Lys Phe Glu Lys
        275
```

<210> SEQ ID NO 18
<211> LENGTH: 279

```
<212> TYPE: PRT
<213> ORGANISM: Toxoplasma gondii

<400> SEQUENCE: 18

Met Ala Ser Lys Pro Ile Glu Glu Ser Arg Ser Gln Lys Arg Ser Ala
1               5                   10                  15

Phe Ser Asp Ile Phe Cys Cys Thr Pro Asn Glu Gly Ala Ile Val
            20                  25                  30

Pro Ser Asp Pro Met Val Ser Thr Ser Ala Pro Ala Arg Thr Ser Ala
            35                  40                  45

Pro Ala Arg Ser Ser Ala Leu Gln Asp Tyr Gly Lys Gly Lys Gly Arg
    50                  55                  60

Ile Glu Pro Met Tyr Ile Pro Asp Asn Thr Phe Tyr Asn Ala Asp Asp
65                  70                  75                  80

Phe Leu Val Pro Pro His Cys Lys Pro Tyr Ile Asp Lys Ile Leu Leu
                85                  90                  95

Pro Gly Gly Leu Val Lys Asp Arg Val Glu Lys Leu Ala Tyr Asp Ile
            100                 105                 110

His Arg Thr Tyr Phe Gly Glu Glu Leu His Ile Ile Cys Ile Leu Lys
        115                 120                 125

Gly Ser Arg Gly Phe Phe Asn Leu Leu Ile Asp Tyr Leu Ala Thr Ile
130                 135                 140

Gln Lys Tyr Ser Gly Arg Glu Ser Ser Val Pro Pro Phe Phe Glu His
145                 150                 155                 160

Tyr Val Arg Leu Lys Ser Tyr Gln Asn Asp Asn Ser Thr Gly Gln Leu
                165                 170                 175

Thr Val Leu Ser Asp Asp Leu Ser Ile Phe Arg Asp Lys His Val Leu
            180                 185                 190

Ile Val Glu Asp Ile Val Asp Thr Gly Phe Thr Leu Thr Glu Phe Gly
        195                 200                 205

Glu Arg Leu Lys Ala Val Gly Pro Lys Ser Met Arg Ile Ala Thr Leu
210                 215                 220

Val Glu Lys Arg Thr Asp Arg Ser Asn Ser Leu Lys Gly Asp Phe Val
225                 230                 235                 240

Gly Phe Ser Ile Glu Asp Val Trp Ile Val Gly Cys Cys Tyr Asp Phe
                245                 250                 255

Asn Glu Met Phe Arg Asp Phe Asp His Val Ala Val Leu Ser Asp Ala
            260                 265                 270

Ala Arg Lys Lys Phe Glu Lys
        275

<210> SEQ ID NO 19
<211> LENGTH: 459
<212> TYPE: DNA
<213> ORGANISM: Escherichia coli
<220> FEATURE:
<221> NAME/KEY: CDS
<222> LOCATION: (1)..(456)
<223> OTHER INFORMATION: coding for xanthine-guanine phosphoribosyl
      transferase (gpt)

<400> SEQUENCE: 19 atg agc gaa aaa tac atc gtc acc tgg gac atg ttg cag atc cat gca      48
Met Ser Glu Lys Tyr Ile Val Thr Trp Asp Met Leu Gln Ile His Ala
1               5                   10                  15 cgt aaa ctc gca agc cga ctg atg cct tct gaa caa tgg aaa ggc att      96
Arg Lys Leu Ala Ser Arg Leu Met Pro Ser Glu Gln Trp Lys Gly Ile
            20                  25                  30
```

```
att gcc gta agc cgt ggc ggt ctg gta ccg ggt gcg tta ctg gcg cgt      144
Ile Ala Val Ser Arg Gly Gly Leu Val Pro Gly Ala Leu Leu Ala Arg
         35                  40                  45 gaa ctg ggt att cgt cat gtc gat acc gtt tgt att tcc agc tac gat      192
Glu Leu Gly Ile Arg His Val Asp Thr Val Cys Ile Ser Ser Tyr Asp
 50                  55                  60 cac gac aac cag cgc gag ctt aaa gtg ctg aaa cgc gca gaa ggc gat      240
His Asp Asn Gln Arg Glu Leu Lys Val Leu Lys Arg Ala Glu Gly Asp
 65                  70                  75                  80 ggc gaa ggc ttc atc gtt att gat gac ctg gtg gat acc ggt ggt act      288
Gly Glu Gly Phe Ile Val Ile Asp Asp Leu Val Asp Thr Gly Gly Thr
                 85                  90                  95 gcg gtt gcg att cgt gaa atg tat cca aaa gcg cac ttt gtc acc atc      336
Ala Val Ala Ile Arg Glu Met Tyr Pro Lys Ala His Phe Val Thr Ile
            100                 105                 110 ttc gca aaa ccg gct ggt cgt ccg ctg gtt gat gac tat gtt gtt gat      384
Phe Ala Lys Pro Ala Gly Arg Pro Leu Val Asp Asp Tyr Val Val Asp
        115                 120                 125 atc ccg caa gat acc tgg att gaa cag ccg tgg gat atg ggc gtc gta      432
Ile Pro Gln Asp Thr Trp Ile Glu Gln Pro Trp Asp Met Gly Val Val
130                 135                 140 ttc gtc ccg cca atc tcc ggt cgc taa                                  459
Phe Val Pro Pro Ile Ser Gly Arg
145                 150

<210> SEQ ID NO 20
<211> LENGTH: 152
<212> TYPE: PRT
<213> ORGANISM: Escherichia coli

<400> SEQUENCE: 20

Met Ser Glu Lys Tyr Ile Val Thr Trp Asp Met Leu Gln Ile His Ala
  1               5                  10                  15

Arg Lys Leu Ala Ser Arg Leu Met Pro Ser Glu Gln Trp Lys Gly Ile
                 20                  25                  30

Ile Ala Val Ser Arg Gly Gly Leu Val Pro Gly Ala Leu Leu Ala Arg
             35                  40                  45

Glu Leu Gly Ile Arg His Val Asp Thr Val Cys Ile Ser Ser Tyr Asp
 50                  55                  60

His Asp Asn Gln Arg Glu Leu Lys Val Leu Lys Arg Ala Glu Gly Asp
 65                  70                  75                  80

Gly Glu Gly Phe Ile Val Ile Asp Asp Leu Val Asp Thr Gly Gly Thr
                 85                  90                  95

Ala Val Ala Ile Arg Glu Met Tyr Pro Lys Ala His Phe Val Thr Ile
            100                 105                 110

Phe Ala Lys Pro Ala Gly Arg Pro Leu Val Asp Asp Tyr Val Val Asp
        115                 120                 125

Ile Pro Gln Asp Thr Trp Ile Glu Gln Pro Trp Asp Met Gly Val Val
130                 135                 140

Phe Val Pro Pro Ile Ser Gly Arg
145                 150

<210> SEQ ID NO 21
<211> LENGTH: 459
<212> TYPE: DNA
<213> ORGANISM: Escherichia coli
<220> FEATURE:
<221> NAME/KEY: CDS
<222> LOCATION: (1)..(456)
```

<223> OTHER INFORMATION: coding for xanthine-guanine phosphoribosyl transferase (gpt)

<400> SEQUENCE: 21

```
atg agc gaa aaa tac atc gtc acc tgg gac atg ttg cag atc cat gca      48
Met Ser Glu Lys Tyr Ile Val Thr Trp Asp Met Leu Gln Ile His Ala
1               5                   10                  15 cgt aaa ctc gca agc cga ctg atg cct tct gaa caa tgg aaa ggc att      96
Arg Lys Leu Ala Ser Arg Leu Met Pro Ser Glu Gln Trp Lys Gly Ile
                20                  25                  30 att gcc gta agc cgt ggc ggt ctg gta ccg ggt gcg tta ctg gcg cgt     144
Ile Ala Val Ser Arg Gly Gly Leu Val Pro Gly Ala Leu Leu Ala Arg
            35                  40                  45 gaa ctg ggt att cgt cat gtc gat acc gtt tgt att tcc agc tac gat     192
Glu Leu Gly Ile Arg His Val Asp Thr Val Cys Ile Ser Ser Tyr Asp
        50                  55                  60 cac gac aac cag cgc gag ctt aaa gtg ctg aaa cgc gca gaa ggc gat     240
His Asp Asn Gln Arg Glu Leu Lys Val Leu Lys Arg Ala Glu Gly Asp
65                  70                  75                  80 ggc gaa ggc ttc atc gtt att gat gac ctg gtg gat acc ggt ggt act     288
Gly Glu Gly Phe Ile Val Ile Asp Asp Leu Val Asp Thr Gly Gly Thr
                85                  90                  95 gcg gtt gcg att cgt gaa atg tat cca aaa gcg cac ttt gtc acc atc     336
Ala Val Ala Ile Arg Glu Met Tyr Pro Lys Ala His Phe Val Thr Ile
                100                 105                 110 ttc gca aaa ccg gct ggt cgt ccg ctg gtt gat gac tat gtt gtt gat     384
Phe Ala Lys Pro Ala Gly Arg Pro Leu Val Asp Asp Tyr Val Val Asp
            115                 120                 125 atc ccg caa gat acc tgg att gaa cag ccg tgg gat atg ggc gtc gta     432
Ile Pro Gln Asp Thr Trp Ile Glu Gln Pro Trp Asp Met Gly Val Val
        130                 135                 140 ttc gtc ccg cca atc tcc ggt cgc taa                                 459
Phe Val Pro Pro Ile Ser Gly Arg
145                 150
```

<210> SEQ ID NO 22
<211> LENGTH: 152
<212> TYPE: PRT
<213> ORGANISM: Escherichia coli

<400> SEQUENCE: 22

```
Met Ser Glu Lys Tyr Ile Val Thr Trp Asp Met Leu Gln Ile His Ala
1               5                   10                  15

Arg Lys Leu Ala Ser Arg Leu Met Pro Ser Glu Gln Trp Lys Gly Ile
                20                  25                  30

Ile Ala Val Ser Arg Gly Gly Leu Val Pro Gly Ala Leu Leu Ala Arg
            35                  40                  45

Glu Leu Gly Ile Arg His Val Asp Thr Val Cys Ile Ser Ser Tyr Asp
        50                  55                  60

His Asp Asn Gln Arg Glu Leu Lys Val Leu Lys Arg Ala Glu Gly Asp
65                  70                  75                  80

Gly Glu Gly Phe Ile Val Ile Asp Asp Leu Val Asp Thr Gly Gly Thr
                85                  90                  95

Ala Val Ala Ile Arg Glu Met Tyr Pro Lys Ala His Phe Val Thr Ile
                100                 105                 110

Phe Ala Lys Pro Ala Gly Arg Pro Leu Val Asp Asp Tyr Val Val Asp
            115                 120                 125

Ile Pro Gln Asp Thr Trp Ile Glu Gln Pro Trp Asp Met Gly Val Val
        130                 135                 140
```

```
Phe Val Pro Pro Ile Ser Gly Arg
145                 150
```

<210> SEQ ID NO 23
<211> LENGTH: 720
<212> TYPE: DNA
<213> ORGANISM: Escherichia coli
<220> FEATURE:
<221> NAME/KEY: CDS
<222> LOCATION: (1)..(717)
<223> OTHER INFORMATION: coding for purine nucleoside phosphorylase
      (deoD)

<400> SEQUENCE: 23

| | |
|---|---:|
| atg gct acc cca cac att aat gca gaa atg ggc gat ttc gct gac gta<br>Met Ala Thr Pro His Ile Asn Ala Glu Met Gly Asp Phe Ala Asp Val<br>1               5                   10                  15 | 48 |
| gtt ttg atg cca ggc gac ccg ctg cgt gcg aag tat att gct gaa act<br>Val Leu Met Pro Gly Asp Pro Leu Arg Ala Lys Tyr Ile Ala Glu Thr<br>            20                  25                  30 | 96 |
| ttc ctt gaa gat gcc cgt gaa gtg aac aac gtt cgc ggt atg ctg ggc<br>Phe Leu Glu Asp Ala Arg Glu Val Asn Asn Val Arg Gly Met Leu Gly<br>        35                  40                  45 | 144 |
| ttc acc ggt act tac aaa ggc cgc aaa att tcc gta atg ggc cac ggt<br>Phe Thr Gly Thr Tyr Lys Gly Arg Lys Ile Ser Val Met Gly His Gly<br>    50                  55                  60 | 192 |
| atg ggt atc ccg tcc tgc tcc atc tac acc aaa gaa ctg atc acc gat<br>Met Gly Ile Pro Ser Cys Ser Ile Tyr Thr Lys Glu Leu Ile Thr Asp<br>65                  70                  75                  80 | 240 |
| ttc ggc gtg aag aaa att atc cgc gtg ggt tcc tgt ggc gca gtt ctg<br>Phe Gly Val Lys Lys Ile Ile Arg Val Gly Ser Cys Gly Ala Val Leu<br>                85                  90                  95 | 288 |
| ccg cac gta aaa ctg cgc gac gtc gtt atc ggt atg ggt gcc tgc acc<br>Pro His Val Lys Leu Arg Asp Val Val Ile Gly Met Gly Ala Cys Thr<br>            100                 105                 110 | 336 |
| gat tcc aaa gtt aac cgc atc cgt ttt aaa gac cat gac ttt gcc gct<br>Asp Ser Lys Val Asn Arg Ile Arg Phe Lys Asp His Asp Phe Ala Ala<br>        115                 120                 125 | 384 |
| atc gct gac ttc gac atg gtg cgt aac gca gta gat gca gct aaa gca<br>Ile Ala Asp Phe Asp Met Val Arg Asn Ala Val Asp Ala Ala Lys Ala<br>    130                 135                 140 | 432 |
| ctg ggt att gat gct cgc gtg ggt aac ctg ttc tcc gct gac ctg ttc<br>Leu Gly Ile Asp Ala Arg Val Gly Asn Leu Phe Ser Ala Asp Leu Phe<br>145                 150                 155                 160 | 480 |
| tac tct ccg gac ggc gaa atg ttc gac gtg atg gaa aaa tac ggc att<br>Tyr Ser Pro Asp Gly Glu Met Phe Asp Val Met Glu Lys Tyr Gly Ile<br>                165                 170                 175 | 528 |
| ctc ggc gtg gaa atg gaa gcg gct ggt atc tac ggc gtc gct gca gaa<br>Leu Gly Val Glu Met Glu Ala Ala Gly Ile Tyr Gly Val Ala Ala Glu<br>            180                 185                 190 | 576 |
| ttt ggc gcg aaa gcc ctg acc atc tgc acc gta tct gac cac atc cgc<br>Phe Gly Ala Lys Ala Leu Thr Ile Cys Thr Val Ser Asp His Ile Arg<br>        195                 200                 205 | 624 |
| act cac gag cag acc act gcc gct gag cgt cag act acc ttc aac gac<br>Thr His Glu Gln Thr Thr Ala Ala Glu Arg Gln Thr Thr Phe Asn Asp<br>    210                 215                 220 | 672 |
| atg atc aaa atc gca ctg gaa tcc gtt ctg ctg ggc gat aaa gag taa<br>Met Ile Lys Ile Ala Leu Glu Ser Val Leu Leu Gly Asp Lys Glu<br>225                 230                 235 | 720 |

<210> SEQ ID NO 24

<211> LENGTH: 239
<212> TYPE: PRT
<213> ORGANISM: Escherichia coli

<400> SEQUENCE: 24

Met Ala Thr Pro His Ile Asn Ala Glu Met Gly Asp Phe Ala Asp Val
1               5                   10                  15

Val Leu Met Pro Gly Asp Pro Leu Arg Ala Lys Tyr Ile Ala Glu Thr
            20                  25                  30

Phe Leu Glu Asp Ala Arg Glu Val Asn Asn Val Arg Gly Met Leu Gly
        35                  40                  45

Phe Thr Gly Thr Tyr Lys Gly Arg Lys Ile Ser Val Met Gly His Gly
    50                  55                  60

Met Gly Ile Pro Ser Cys Ser Ile Tyr Thr Lys Glu Leu Ile Thr Asp
65                  70                  75                  80

Phe Gly Val Lys Lys Ile Ile Arg Val Gly Ser Cys Gly Ala Val Leu
                85                  90                  95

Pro His Val Lys Leu Arg Asp Val Val Ile Gly Met Gly Ala Cys Thr
            100                 105                 110

Asp Ser Lys Val Asn Arg Ile Arg Phe Lys Asp His Asp Phe Ala Ala
        115                 120                 125

Ile Ala Asp Phe Asp Met Val Arg Asn Ala Val Asp Ala Ala Lys Ala
    130                 135                 140

Leu Gly Ile Asp Ala Arg Val Gly Asn Leu Phe Ser Ala Asp Leu Phe
145                 150                 155                 160

Tyr Ser Pro Asp Gly Glu Met Phe Asp Val Met Glu Lys Tyr Gly Ile
                165                 170                 175

Leu Gly Val Glu Met Glu Ala Ala Gly Ile Tyr Gly Val Ala Ala Glu
            180                 185                 190

Phe Gly Ala Lys Ala Leu Thr Ile Cys Thr Val Ser Asp His Ile Arg
        195                 200                 205

Thr His Glu Gln Thr Thr Ala Ala Glu Arg Gln Thr Thr Phe Asn Asp
    210                 215                 220

Met Ile Lys Ile Ala Leu Glu Ser Val Leu Leu Gly Asp Lys Glu
225                 230                 235

<210> SEQ ID NO 25
<211> LENGTH: 1545
<212> TYPE: DNA
<213> ORGANISM: Burkholderia caryophylli
<220> FEATURE:
<221> NAME/KEY: CDS
<222> LOCATION: (1)..(1542)
<223> OTHER INFORMATION: coding for phosphonate monoester hydrolase
      (pehA)

<400> SEQUENCE: 25

```
atg acc aga aaa aat gtc ctg ctt atc gtc gtt gat caa tgg cga gca    48
Met Thr Arg Lys Asn Val Leu Leu Ile Val Val Asp Gln Trp Arg Ala
1               5                   10                  15 gat ttt atc cct cac ctg atg cgg gcg gag ggg cgc gaa cct ttc ctt    96
Asp Phe Ile Pro His Leu Met Arg Ala Glu Gly Arg Glu Pro Phe Leu
            20                  25                  30 aaa act ccc aat ctt gat cgt ctt tgc cgg gaa ggc ttg acc ttc cgc   144
Lys Thr Pro Asn Leu Asp Arg Leu Cys Arg Glu Gly Leu Thr Phe Arg
        35                  40                  45 aat cat gtc acg acg tgc gtg ccg tgt ggt ccg gca agg gca agc ctg   192
Asn His Val Thr Thr Cys Val Pro Cys Gly Pro Ala Arg Ala Ser Leu
    50                  55                  60
```

| | | |
|---|---|---|
| ctg acg ggc ctc tac ctg atg aac cac cgg gcg gtg cag aac act gtt<br>Leu Thr Gly Leu Tyr Leu Met Asn His Arg Ala Val Gln Asn Thr Val<br>65                         70                     75                   80 | 240 |
| ccg ctt gac cag cgc cat cta aac ctt ggc aag gcc ctg cgc gcc att<br>Pro Leu Asp Gln Arg His Leu Asn Leu Gly Lys Ala Leu Arg Ala Ile<br>                     85                     90                   95 | 288 |
| ggc tac gat ccc gcg ctc att ggt tac acc acc acg cct gat ccg<br>Gly Tyr Asp Pro Ala Leu Ile Gly Tyr Thr Thr Thr Pro Asp Pro<br>            100                  105                  110 | 336 |
| cgc aca acc tct gca agg gat ccg cgt ttc acg gtc ctg ggc gac atc<br>Arg Thr Thr Ser Ala Arg Asp Pro Arg Phe Thr Val Leu Gly Asp Ile<br>            115                  120                  125 | 384 |
| atg gac ggc ttt cgt tcg gtc ggc gca ttc gag ccc aat atg gag ggg<br>Met Asp Gly Phe Arg Ser Val Gly Ala Phe Glu Pro Asn Met Glu Gly<br>130                        135                  140 | 432 |
| tat ttt ggc tgg gtg gcg cag aac ggc ttc gaa ctg cca gag aac cgc<br>Tyr Phe Gly Trp Val Ala Gln Asn Gly Phe Glu Leu Pro Glu Asn Arg<br>145                     150                  155                 160 | 480 |
| gaa gat atc tgg ctg ccg gaa ggt gaa cat tcc gtt ccc ggt gct acc<br>Glu Asp Ile Trp Leu Pro Glu Gly Glu His Ser Val Pro Gly Ala Thr<br>                  165                  170                  175 | 528 |
| gac aaa ccg tcg cgc att ccg aag gaa ttt tcg gat tcg aca ttc ttc<br>Asp Lys Pro Ser Arg Ile Pro Lys Glu Phe Ser Asp Ser Thr Phe Phe<br>            180                  185                  190 | 576 |
| acg gag cgc gcc ctg aca tat ctg aag ggc agg gac ggc aag cct ttc<br>Thr Glu Arg Ala Leu Thr Tyr Leu Lys Gly Arg Asp Gly Lys Pro Phe<br>            195                  200                  205 | 624 |
| ttc ctg cat ctt ggc tat tat cgc ccg cat ccg cct ttc gta gcc tcc<br>Phe Leu His Leu Gly Tyr Tyr Arg Pro His Pro Pro Phe Val Ala Ser<br>            210                  215                  220 | 672 |
| gcg ccc tac cat gcg atg tac aaa gcc gaa gat atg cct gcg cct ata<br>Ala Pro Tyr His Ala Met Tyr Lys Ala Glu Asp Met Pro Ala Pro Ile<br>225                     230                  235                 240 | 720 |
| cgt gcg gag aat ccg gat gcc gaa gcg gca cag cat ccg ctc atg aag<br>Arg Ala Glu Asn Pro Asp Ala Glu Ala Ala Gln His Pro Leu Met Lys<br>                  245                  250                  255 | 768 |
| cac tat atc gac cac atc aga cgc ggc tcg ttc ttc cat ggc gcg gaa<br>His Tyr Ile Asp His Ile Arg Arg Gly Ser Phe Phe His Gly Ala Glu<br>                260                  265                  270 | 816 |
| ggc tcg gga gca acg ctt gat gaa ggc gaa att cgc cag atg cgc gct<br>Gly Ser Gly Ala Thr Leu Asp Glu Gly Glu Ile Arg Gln Met Arg Ala<br>            275                  280                  285 | 864 |
| aca tat tgc gga ctg atc acc gag atc gac gat tgt ctg ggg agg gtc<br>Thr Tyr Cys Gly Leu Ile Thr Glu Ile Asp Asp Cys Leu Gly Arg Val<br>            290                  295                  300 | 912 |
| ttt gcc tat ctc gat gaa acc ggt cag tgg gac gac acg ctg att atc<br>Phe Ala Tyr Leu Asp Glu Thr Gly Gln Trp Asp Asp Thr Leu Ile Ile<br>305                     310                  315                 320 | 960 |
| ttc acg agc gat cat ggc gaa caa ctg ggc gat cat cac ctg ctc ggc<br>Phe Thr Ser Asp His Gly Glu Gln Leu Gly Asp His His Leu Leu Gly<br>                  325                  330                  335 | 1008 |
| aag atc ggt tac aat gcc gaa agc ttc cgt att ccc ttg gtc ata aag<br>Lys Ile Gly Tyr Asn Ala Glu Ser Phe Arg Ile Pro Leu Val Ile Lys<br>                  340                  345                  350 | 1056 |
| gat gcg gga cag aac cgg cac gcc ggc cag atc gaa gaa ggc ttc tcc<br>Asp Ala Gly Gln Asn Arg His Ala Gly Gln Ile Glu Glu Gly Phe Ser<br>            355                  360                  365 | 1104 |
| gaa agc atc gac gtc atg ccg acc atc ctc gaa tgg ctg ggc ggg gaa<br>Glu Ser Ile Asp Val Met Pro Thr Ile Leu Glu Trp Leu Gly Gly Glu | 1152 |

```
                370                 375                 380
acg cct cgc gcc tgc gac ggc cgt tcg ctg ttg ccg ttt ctg gct gag      1200
Thr Pro Arg Ala Cys Asp Gly Arg Ser Leu Leu Pro Phe Leu Ala Glu
385                 390                 395                 400 gga aag ccc tcc gac tgg cgc acg gaa cta cat tac gag ttc gat ttt      1248
Gly Lys Pro Ser Asp Trp Arg Thr Glu Leu His Tyr Glu Phe Asp Phe
                405                 410                 415 cgc gat gtc ttc tac gat cag ccg cag aac tcg gtc cag ctt tcc cag      1296
Arg Asp Val Phe Tyr Asp Gln Pro Gln Asn Ser Val Gln Leu Ser Gln
            420                 425                 430 gat gat tgc agc ctc tgt gtg atc gag gac gaa aac tac aag tac gtg      1344
Asp Asp Cys Ser Leu Cys Val Ile Glu Asp Glu Asn Tyr Lys Tyr Val
        435                 440                 445 cat ttt gcc gcc ctg ccg ccg ctg ttc ttc gat ctg aag gca gac ccg      1392
His Phe Ala Ala Leu Pro Pro Leu Phe Phe Asp Leu Lys Ala Asp Pro
    450                 455                 460 cat gaa ttc agc aat ctg gct ggc gat cct gct tat gcg gcc ctc gtt      1440
His Glu Phe Ser Asn Leu Ala Gly Asp Pro Ala Tyr Ala Ala Leu Val
465                 470                 475                 480 cgt gac tat gcc cag aag gca ttg tcg tgg cga ctg tct cat gcc gac      1488
Arg Asp Tyr Ala Gln Lys Ala Leu Ser Trp Arg Leu Ser His Ala Asp
                485                 490                 495 cgg aca ctc acc cat tac aga tcc agc ccg caa ggg ctg aca acg cgc      1536
Arg Thr Leu Thr His Tyr Arg Ser Ser Pro Gln Gly Leu Thr Thr Arg
            500                 505                 510 aac cat tga                                                          1545
Asn His <210> SEQ ID NO 26
<211> LENGTH: 514
<212> TYPE: PRT
<213> ORGANISM: Burkholderia caryophylli

<400> SEQUENCE: 26

Met Thr Arg Lys Asn Val Leu Leu Ile Val Val Asp Gln Trp Arg Ala
  1               5                  10                  15

Asp Phe Ile Pro His Leu Met Arg Ala Glu Gly Arg Glu Pro Phe Leu
                 20                  25                  30

Lys Thr Pro Asn Leu Asp Arg Leu Cys Arg Glu Gly Leu Thr Phe Arg
             35                  40                  45

Asn His

```
            180                 185                 190
Thr Glu Arg Ala Leu Thr Tyr Leu Lys Gly Arg Asp Gly Lys Pro Phe
            195                 200                 205

Phe Leu His Leu Gly Tyr Tyr Arg Pro His Pro Pro Phe Val Ala Ser
    210                 215                 220

Ala Pro Tyr His Ala Met Tyr Lys Ala Glu Asp Met Pro Ala Pro Ile
225                 230                 235                 240

Arg Ala Glu Asn Pro Asp Ala Glu Ala Gln His Pro Leu Met Lys
            245                 250                 255

His Tyr Ile Asp His Ile Arg Arg Gly Ser Phe Phe His Gly Ala Glu
            260                 265                 270

Gly Ser Gly Ala Thr Leu Asp Glu Gly Glu Ile Arg Gln Met Arg Ala
            275                 280                 285

Thr Tyr Cys Gly Leu Ile Thr Glu Ile Asp Asp Cys Leu Gly Arg Val
            290                 295                 300

Phe Ala Tyr Leu Asp Glu Thr Gly Gln Trp Asp Asp Thr Leu Ile Ile
305                 310                 315                 320

Phe Thr Ser Asp His Gly Glu Gln Leu Gly Asp His His Leu Leu Gly
                    325                 330                 335

Lys Ile Gly Tyr Asn Ala Glu Ser Phe Arg Ile Pro Leu Val Ile Lys
                    340                 345                 350

Asp Ala Gly Gln Asn Arg His Ala Gly Gln Ile Glu Glu Gly Phe Ser
                355                 360                 365

Glu Ser Ile Asp Val Met Pro Thr Ile Leu Glu Trp Leu Gly Gly Glu
    370                 375                 380

Thr Pro Arg Ala Cys Asp Gly Arg Ser Leu Leu Pro Phe Leu Ala Glu
385                 390                 395                 400

Gly Lys Pro Ser Asp Trp Arg Thr Glu Leu His Tyr Glu Phe Asp Phe
                405                 410                 415

Arg Asp Val Phe Tyr Asp Gln Pro Gln Asn Ser Val Gln Leu Ser Gln
                420                 425                 430

Asp Asp Cys Ser Leu Cys Val Ile Glu Asp Glu Asn Tyr Lys Tyr Val
            435                 440                 445

His Phe Ala Ala Leu Pro Pro Leu Phe Phe Asp Leu Lys Ala Asp Pro
450                 455                 460

His Glu Phe Ser Asn Leu Ala Gly Asp Pro Ala Tyr Ala Ala Leu Val
465                 470                 475                 480

Arg Asp Tyr Ala Gln Lys Ala Leu Ser Trp Arg Leu Ser His Ala Asp
                485                 490                 495

Arg Thr Leu Thr His Tyr Arg Ser Ser Pro Gln Gly Leu Thr Thr Arg
                500                 505                 510

Asn His

<210> SEQ ID NO 27
<211> LENGTH: 2250
<212> TYPE: DNA
<213> ORGANISM: Agrobacterium rhizogenes
<220> FEATURE:
<221> NAME/KEY: CDS
<222> LOCATION: (1)..(2247)
<223> OTHER INFORMATION: coding for tryptophan oxygenase (aux1)

<400> SEQUENCE: 27 atg gct gga tcc tcc ttc aca ttg cca tca act ggc tca gcg ccc ctt      48
Met Ala Gly Ser Ser Phe Thr Leu Pro Ser Thr Gly Ser Ala Pro Leu
 1               5                  10                  15
```

```
gat atg atg ctt atc gat gat tca gat ctg ctg caa ttg ggt ctc cag    96
Asp Met Met Leu Ile Asp Asp Ser Asp Leu Leu Gln Leu Gly Leu Gln
         20                  25                  30 cag gta ttc tcg aag cgg tac aca gag aca ccg cag tca cgc tac aaa   144
Gln Val Phe Ser Lys Arg Tyr Thr Glu Thr Pro Gln Ser Arg Tyr Lys
             35                  40                  45 ctg acc agg agg gct tct cca gac gtc tca tct ggc gaa ggc aat gtg   192
Leu Thr Arg Arg Ala Ser Pro Asp Val Ser Ser Gly Glu Gly Asn Val
     50                  55                  60 cat gcc ctt gcg ttc ata tat gtc aac gct gag acg ttg cag atg atc   240
His Ala Leu Ala Phe Ile Tyr Val Asn Ala Glu Thr Leu Gln Met Ile
 65                  70                  75                  80 aaa aac gct cga tcg cta acc gaa gcg aac ggc gtc aaa gat ctt gtc   288
Lys Asn Ala Arg Ser Leu Thr Glu Ala Asn Gly Val Lys Asp Leu Val
                 85                  90                  95 gcc atc gac gtt ccg cca ttt cga aac gac ttc tca aga gcg cta ctc   336
Ala Ile Asp Val Pro Pro Phe Arg Asn Asp Phe Ser Arg Ala Leu Leu
            100                 105                 110 ctt caa gtg atc aac ttg ttg gga aac aac cga aat gcc gat gac gat   384
Leu Gln Val Ile Asn Leu Leu Gly Asn Asn Arg Asn Ala Asp Asp Asp
        115                 120                 125 ctt agt cac ttc ata gca gtt gct ctc cca aac agc gcc cgc tct aag   432
Leu Ser His Phe Ile Ala Val Ala Leu Pro Asn Ser Ala Arg Ser Lys
    130                 135                 140 atc cta acc acg gca ccg ttc gaa gga agc ttg tca gaa aac ttc agg   480
Ile Leu Thr Thr Ala Pro Phe Glu Gly Ser Leu Ser Glu Asn Phe Arg
145                 150                 155                 160 ggg ttc ccg atc act cgt gaa gga aat gtg gca tgt gaa gtg cta gcc   528
Gly Phe Pro Ile Thr Arg Glu Gly Asn Val Ala Cys Glu Val Leu Ala
                165                 170                 175 tat ggg aat aac ttg atg ccc aag gcc tgc tcc gat tcc ttt cca acc   576
Tyr Gly Asn Asn Leu Met Pro Lys Ala Cys Ser Asp Ser Phe Pro Thr
            180                 185                 190 gtg gat ctt ctt tat gac tat ggc aag ttc ttc gag agt tgc gcg gcc   624
Val Asp Leu Leu Tyr Asp Tyr Gly Lys Phe Phe Glu Ser Cys Ala Ala
        195                 200                 205 gat gga cgt atc ggt tat ttt cct gaa ggc gtt acg aaa cct aaa gtg   672
Asp Gly Arg Ile Gly Tyr Phe Pro Glu Gly Val Thr Lys Pro Lys Val
    210                 215                 220 gct ata att ggc gca ggc ttt tcc ggg ctc gtt gca gcg agc gaa cta   720
Ala Ile Ile Gly Ala Gly Phe Ser Gly Leu Val Ala Ala Ser Glu Leu
225                 230                 235                 240 ctt cat gca ggg gta gac gat gtt acg gtg tat gag gcg agt gat cgg   768
Leu His Ala Gly Val Asp Asp Val Thr Val Tyr Glu Ala Ser Asp Arg
                245                 250                 255 ctt gga gga aag cta tgg tca cac gga ttt aag agt gct cca aat gtg   816
Leu Gly Gly Lys Leu Trp Ser His Gly Phe Lys Ser Ala Pro Asn Val
            260                 265                 270 ata gcc gag atg ggg gcc atg cgt ttt ccg cga agt gaa tca tgc ttg   864
Ile Ala Glu Met Gly Ala Met Arg Phe Pro Arg Ser Glu Ser Cys Leu
        275                 280                 285 ttc ttc tat ctc aaa aag cac gga ctg gac tcc gtt ggt ctg ttc ccg   912
Phe Phe Tyr Leu Lys Lys His Gly Leu Asp Ser Val Gly Leu Phe Pro
    290                 295                 300 aat ccg gga agt gtc gat acc gca ttg ttc tac agg ggc cgt caa tat   960
Asn Pro Gly Ser Val Asp Thr Ala Leu Phe Tyr Arg Gly Arg Gln Tyr
305                 310                 315                 320 atc tgg aaa gcg gga gag gag cca ccg gag ctg ttt cgt cgt gtg cac  1008
Ile Trp Lys Ala Gly Glu Glu Pro Pro Glu Leu Phe Arg Arg Val His
```

-continued

```
                    325                    330                    335
cat  gga  tgg  cgc  gca  ttt  ttg  caa  gat  ggc  tat  ctc  cat  gat  gga  gtc    1056
His  Gly  Trp  Arg  Ala  Phe  Leu  Gln  Asp  Gly  Tyr  Leu  His  Asp  Gly  Val
               340                    345                    350 atg  ttg  gcg  tca  ccg  tta  gca  att  gtt  gac  gcc  ttg  aat  tta  ggg  cat    1104
Met  Leu  Ala  Ser  Pro  Leu  Ala  Ile  Val  Asp  Ala  Leu  Asn  Leu  Gly  His
               355                    360                    365 cta  cag  cag  gcg  cat  ggc  ttc  tgg  caa  tct  tgg  ctc  aca  tat  ttt  gag    1152
Leu  Gln  Gln  Ala  His  Gly  Phe  Trp  Gln  Ser  Trp  Leu  Thr  Tyr  Phe  Glu
     370                    375                    380 cga  gag  tct  ttc  tct  tct  ggc  atc  gaa  aaa  atg  ttc  ttg  ggc  aat  cat    1200
Arg  Glu  Ser  Phe  Ser  Ser  Gly  Ile  Glu  Lys  Met  Phe  Leu  Gly  Asn  His
385                    390                    395                    400 cct  ccg  ggg  ggt  gaa  caa  tgg  aat  tcc  cta  gat  gac  ttg  gat  ctt  ttc    1248
Pro  Pro  Gly  Gly  Glu  Gln  Trp  Asn  Ser  Leu  Asp  Asp  Leu  Asp  Leu  Phe
               405                    410                    415 aaa  gcg  ctg  ggt  att  gga  tcc  ggc  gga  ttc  ggc  cct  gta  ttt  gaa  agt    1296
Lys  Ala  Leu  Gly  Ile  Gly  Ser  Gly  Gly  Phe  Gly  Pro  Val  Phe  Glu  Ser
               420                    425                    430 ggg  ttt  atc  gag  atc  ctt  cgc  tta  gtc  gtc  aac  ggg  tat  gag  gat  aac    1344
Gly  Phe  Ile  Glu  Ile  Leu  Arg  Leu  Val  Val  Asn  Gly  Tyr  Glu  Asp  Asn
               435                    440                    445 gtg  cgg  ctg  agt  tac  gaa  gga  att  tct  gag  ctg  cct  cat  agg  atc  gcc    1392
Val  Arg  Leu  Ser  Tyr  Glu  Gly  Ile  Ser  Glu  Leu  Pro  His  Arg  Ile  Ala
     450                    455                    460 tca  cag  gta  att  aac  ggc  aga  tct  att  cgc  gag  cgt  aca  att  cac  gtt    1440
Ser  Gln  Val  Ile  Asn  Gly  Arg  Ser  Ile  Arg  Glu  Arg  Thr  Ile  His  Val
465                    470                    475                    480 caa  gtc  gag  cag  att  gat  aga  gag  gag  gat  aaa  ata  aat  atc  aag  atc    1488
Gln  Val  Glu  Gln  Ile  Asp  Arg  Glu  Glu  Asp  Lys  Ile  Asn  Ile  Lys  Ile
               485                    490                    495 aaa  gga  gga  aag  gtt  gag  gtc  tat  gat  cga  gta  ctg  gtt  aca  tcc  ggg    1536
Lys  Gly  Gly  Lys  Val  Glu  Val  Tyr  Asp  Arg  Val  Leu  Val  Thr  Ser  Gly
               500                    505                    510 ttt  gcg  aac  atc  gaa  atg  cgc  cat  ctc  ctg  aca  tca  agc  aac  gca  ttc    1584
Phe  Ala  Asn  Ile  Glu  Met  Arg  His  Leu  Leu  Thr  Ser  Ser  Asn  Ala  Phe
               515                    520                    525 ttc  cat  gca  gat  gta  agc  cat  gca  ata  ggg  aac  agt  cat  atg  act  ggt    1632
Phe  His  Ala  Asp  Val  Ser  His  Ala  Ile  Gly  Asn  Ser  His  Met  Thr  Gly
     530                    535                    540 gcg  tca  aaa  ctg  ttc  ttg  ctg  act  aac  gaa  aaa  ttc  tgg  cta  caa  cat    1680
Ala  Ser  Lys  Leu  Phe  Leu  Leu  Thr  Asn  Glu  Lys  Phe  Trp  Leu  Gln  His
545                    550                    555                    560 cat  ttg  cca  tcg  tgc  ata  ctc  acc  acc  ggc  gtt  gca  aag  gca  gtt  tat    1728
His  Leu  Pro  Ser  Cys  Ile  Leu  Thr  Thr  Gly  Val  Ala  Lys  Ala  Val  Tyr
               565                    570                    575 tgc  tta  gac  tat  gat  ccg  cga  gat  cca  agc  ggc  aaa  gga  ctg  gtg  ttg    1776
Cys  Leu  Asp  Tyr  Asp  Pro  Arg  Asp  Pro  Ser  Gly  Lys  Gly  Leu  Val  Leu
               580                    585                    590 ata  agc  tat  act  tgg  gag  gat  gac  tca  cat  aag  ctc  cta  gcc  gtc  ccc    1824
Ile  Ser  Tyr  Thr  Trp  Glu  Asp  Asp  Ser  His  Lys  Leu  Leu  Ala  Val  Pro
               595                    600                    605 gac  aaa  aga  gaa  agg  ttc  gca  tcg  ctg  cag  cgc  gat  att  ggg  agg  gca    1872
Asp  Lys  Arg  Glu  Arg  Phe  Ala  Ser  Leu  Gln  Arg  Asp  Ile  Gly  Arg  Ala
     610                    615                    620 ttc  cca  gat  ttt  gcc  aag  cac  cta  act  cct  gca  gac  ggg  aac  tat  gat    1920
Phe  Pro  Asp  Phe  Ala  Lys  His  Leu  Thr  Pro  Ala  Asp  Gly  Asn  Tyr  Asp
625                    630                    635                    640 gat  aat  atc  gtt  caa  cat  gat  tgg  ctg  act  gat  ccc  cac  gct  ggc  gga    1968
```

```
                                                                    -continued Asp Asn Ile Val Gln His Asp Trp Leu Thr Asp Pro His Ala Gly Gly
                645                 650                 655 gcg ttt aaa ctg aac cgc aga ggc aac gac gta tat tca gaa agg ctt      2016
Ala Phe Lys Leu Asn Arg Arg Gly Asn Asp Val Tyr Ser Glu Arg Leu
            660                 665                 670 ttc ttt cag ccc ttt gac gta atg cat ccc gcg gac gat aag gga ctt      2064
Phe Phe Gln Pro Phe Asp Val Met His Pro Ala Asp Asp Lys Gly Leu
        675                 680                 685 tac ttg gcc ggt tgt agc tgt tcc ttc acc gga ggg tgg gtt cat ggt      2112
Tyr Leu Ala Gly Cys Ser Cys Ser Phe Thr Gly Gly Trp Val His Gly
    690                 695                 700 gcc att cag acc gca tgc aac gct acg tgt gcg atc att tat ggt tcc      2160
Ala Ile Gln Thr Ala Cys Asn Ala Thr Cys Ala Ile Ile Tyr Gly Ser
705                 710                 715                 720 gga cac ctg caa gag cta atc cac tgg cga cac ctc aaa gaa ggt aat      2208
Gly His Leu Gln Glu Leu Ile His Trp Arg His Leu Lys Glu Gly Asn
                725                 730                 735 cca ctg gcg cac gct tgg aag cgg tat agg tat caa gcg tga              2250
Pro Leu Ala His Ala Trp Lys Arg Tyr Arg Tyr Gln Ala
            740                 745

<210> SEQ ID NO 28
<211> LENGTH: 749
<212> TYPE: PRT
<213> ORGANISM: Agrobacterium rhizogenes

<400> SEQUENCE: 28

Met Ala Gly Ser Ser Phe Thr Leu Pro Ser Thr Gly Ser Ala Pro Leu
 1               5                  10                  15

Asp Met Met Leu Ile Asp Asp Ser Asp Leu Leu Gln Leu Gly Leu Gln
            20                  25                  30

Gln Val Phe Ser Lys Arg Tyr Thr Glu Thr Pro Gln Ser Arg Tyr Lys
        35                  40                  45

Leu Thr Arg Arg Ala Ser Pro Asp Val Ser Ser Gly Glu Gly Asn Val
    50                  55                  60

His Ala Leu Ala Phe Ile Tyr Val Asn Ala Glu Thr Leu Gln Met Ile
65                  70                  75                  80

Lys Asn Ala Arg Ser Leu Thr Glu Ala Asn Gly Val Lys Asp Leu Val
                85                  90                  95

Ala Ile Asp Val Pro Pro Phe Arg Asn Asp Phe Ser Arg Ala Leu Leu
            100                 105                 110

Leu Gln Val Ile Asn Leu Leu Gly Asn Asn Arg Asn Ala Asp Asp
        115                 120                 125

Leu Ser His Phe Ile Ala Val Ala Leu Pro Asn Ser Ala Arg Ser Lys
    130                 135                 140

Ile Leu Thr Thr Ala Pro Phe Glu Gly Ser Leu Ser Glu Asn Phe Arg
145                 150                 155                 160

Gly Phe Pro Ile Thr Arg Glu Gly Asn Val Ala Cys Glu Val Leu Ala
                165                 170                 175

Tyr Gly Asn Asn Leu Met Pro Lys Ala Cys Ser Asp Ser Phe Pro Thr
            180                 185                 190

Val Asp Leu Leu Tyr Asp Tyr Gly Lys Phe Phe Glu Ser Cys Ala Ala
        195                 200                 205

Asp Gly Arg Ile Gly Tyr Phe Pro Glu Gly Val Thr Lys Pro Lys Val
    210                 215                 220

Ala Ile Ile Gly Ala Gly Phe Ser Gly Leu Val Ala Ala Ser Glu Leu
225                 230                 235                 240
```

-continued

```
Leu His Ala Gly Val Asp Asp Val Thr Val Tyr Glu Ala Ser Asp Arg
            245                 250                 255
Leu Gly Gly Lys Leu Trp Ser His Gly Phe Lys Ser Ala Pro Asn Val
            260                 265                 270
Ile Ala Glu Met Gly Ala Met Arg Phe Pro Arg Ser Glu Ser Cys Leu
            275                 280                 285
Phe Phe Tyr Leu Lys Lys His Gly Leu Asp Ser Val Gly Leu Phe Pro
            290                 295                 300
Asn Pro Gly Ser Val Asp Thr Ala Leu Phe Tyr Arg Gly Arg Gln Tyr
305                 310                 315                 320
Ile Trp Lys Ala Gly Glu Pro Pro Glu Leu Phe Arg Arg Val His
            325                 330                 335
His Gly Trp Arg Ala Phe Leu Gln Asp Gly Tyr Leu His Asp Gly Val
            340                 345                 350
Met Leu Ala Ser Pro Leu Ala Ile Val Asp Ala Leu Asn Leu Gly His
            355                 360                 365
Leu Gln Gln Ala His Gly Phe Trp Gln Ser Trp Leu Thr Tyr Phe Glu
            370                 375                 380
Arg Glu Ser Phe Ser Ser Gly Ile Glu Lys Met Phe Leu Gly Asn His
385                 390                 395                 400
Pro Pro Gly Gly Glu Gln Trp Asn Ser Leu Asp Asp Leu Asp Leu Phe
            405                 410                 415
Lys Ala Leu Gly Ile Gly Ser Gly Gly Phe Gly Pro Val Phe Glu Ser
            420                 425                 430
Gly Phe Ile Glu Ile Leu Arg Leu Val Val Asn Gly Tyr Glu Asp Asn
            435                 440                 445
Val Arg Leu Ser Tyr Glu Gly Ile Ser Glu Leu Pro His Arg Ile Ala
            450                 455                 460
Ser Gln Val Ile Asn Gly Arg Ser Ile Arg Glu Arg Thr Ile His Val
465                 470                 475                 480
Gln Val Glu Gln Ile Asp Arg Glu Glu Asp Lys Ile Asn Ile Lys Ile
            485                 490                 495
Lys Gly Gly Lys Val Glu Val Tyr Asp Arg Val Leu Val Thr Ser Gly
            500                 505                 510
Phe Ala Asn Ile Glu Met Arg His Leu Leu Thr Ser Ser Asn Ala Phe
            515                 520                 525
Phe His Ala Asp Val Ser His Ala Ile Gly Asn Ser His Met Thr Gly
            530                 535                 540
Ala Ser Lys Leu Phe Leu Leu Thr Asn Glu Lys Phe Trp Leu Gln His
545                 550                 555                 560
His Leu Pro Ser Cys Ile Leu Thr Thr Gly Val Ala Lys Ala Val Tyr
            565                 570                 575
Cys Leu Asp Tyr Asp Pro Arg Asp Pro Ser Gly Lys Gly Leu Val Leu
            580                 585                 590
Ile Ser Tyr Thr Trp Glu Asp Asp Ser His Lys Leu Leu Ala Val Pro
            595                 600                 605
Asp Lys Arg Glu Arg Phe Ala Ser Leu Gln Arg Asp Ile Gly Arg Ala
            610                 615                 620
Phe Pro Asp Phe Ala Lys His Leu Thr Pro Ala Asp Gly Asn Tyr Asp
625                 630                 635                 640
Asp Asn Ile Val Gln His Asp Trp Leu Thr Asp Pro His Ala Gly Gly
            645                 650                 655
```

```
                        Ala Phe Lys Leu Asn Arg Arg Gly Asn Asp Val Tyr Ser Glu Arg Leu
                                    660                 665                 670

Phe Phe Gln Pro Phe Asp Val Met His Pro Ala Asp Lys Gly Leu
                                    675                 680                 685

Tyr Leu Ala Gly Cys Ser Cys Ser Phe Thr Gly Trp Val His Gly
                                690                 695                 700

Ala Ile Gln Thr Ala Cys Asn Ala Thr Cys Ala Ile Ile Tyr Gly Ser
                        705                 710                 715                 720

Gly His Leu Gln Glu Leu Ile His Trp Arg His Leu Lys Glu Gly Asn
                                        725                 730                 735

Pro Leu Ala His Ala Trp Lys Arg Tyr Arg Tyr Gln Ala
                                    740                 745

<210> SEQ ID NO 29
<211> LENGTH: 1401
<212> TYPE: DNA
<213> ORGANISM: Agrobacterium rhizogenes
<220> FEATURE:
<221> NAME/KEY: CDS
<222> LOCATION: (1)..(1398)
<223> OTHER INFORMATION: coding for indoleacetamide hydrolase

<400> SEQUENCE: 29
```

| | | | | | | | | | | | | | | | | |
|---|---|---|---|---|---|---|---|---|---|---|---|---|---|---|---|---|
| atg | gtg | acc | ctc | tcc | tcg | atc | acc | gag | acg | ctt | aaa | tgt | ctc | agg | gaa | 48 |
| Met | Val | Thr | Leu | Ser | Ser | Ile | Thr | Glu | Thr | Leu | Lys | Cys | Leu | Arg | Glu | |
| 1 | | | | 5 | | | | | 10 | | | | | 15 | | |
| aga | aaa | tac | tcg | tgc | ttt | gag | tta | atc | gaa | acg | ata | ata | gcc | cgc | tgt | 96 |
| Arg | Lys | Tyr | Ser | Cys | Phe | Glu | Leu | Ile | Glu | Thr | Ile | Ile | Ala | Arg | Cys | |
| | | | 20 | | | | | 25 | | | | | 30 | | | |
| gaa | gca | gca | aga | tcc | tta | aac | gcc | ttt | ctg | gaa | acc | gac | tgg | gcg | cac | 144 |
| Glu | Ala | Ala | Arg | Ser | Leu | Asn | Ala | Phe | Leu | Glu | Thr | Asp | Trp | Ala | His | |
| | | 35 | | | | | 40 | | | | | 45 | | | | |
| cta | cgg | tgg | act | gcc | agc | aaa | atc | gat | caa | cac | gga | ggt | gcc | ggt | gtt | 192 |
| Leu | Arg | Trp | Thr | Ala | Ser | Lys | Ile | Asp | Gln | His | Gly | Gly | Ala | Gly | Val | |
| | 50 | | | | | 55 | | | | | 60 | | | | | |
| ggc | cta | gct | ggc | gtt | ccc | cta | tgc | ttt | aaa | gcg | aat | att | gca | aca | ggc | 240 |
| Gly | Leu | Ala | Gly | Val | Pro | Leu | Cys | Phe | Lys | Ala | Asn | Ile | Ala | Thr | Gly | |
| 65 | | | | | 70 | | | | | 75 | | | | | 80 | |
| agg | ttc | gcc | gcg | acc | gct | ggt | acg | cca | ggc | tta | cag | aac | cac | aaa | ccc | 288 |
| Arg | Phe | Ala | Ala | Thr | Ala | Gly | Thr | Pro | Gly | Leu | Gln | Asn | His | Lys | Pro | |
| | | | | 85 | | | | | 90 | | | | | 95 | | |
| aag | acg | cct | gcc | gga | gtt | gca | cga | caa | ctt | ctc | gcg | gct | ggg | gca | ctg | 336 |
| Lys | Thr | Pro | Ala | Gly | Val | Ala | Arg | Gln | Leu | Leu | Ala | Ala | Gly | Ala | Leu | |
| | | | 100 | | | | | 105 | | | | | 110 | | | |
| cct | ggc | gct | tcg | gga | aac | atg | cac | gaa | ttg | tct | ttt | ggg | atc | acg | agc | 384 |
| Pro | Gly | Ala | Ser | Gly | Asn | Met | His | Glu | Leu | Ser | Phe | Gly | Ile | Thr | Ser | |
| | | 115 | | | | | 120 | | | | | 125 | | | | |
| aac | aac | ttc | gcc | aca | ggc | gcc | gta | cga | aac | ccg | tgg | aac | cct | agt | ctc | 432 |
| Asn | Asn | Phe | Ala | Thr | Gly | Ala | Val | Arg | Asn | Pro | Trp | Asn | Pro | Ser | Leu | |
| | 130 | | | | | 135 | | | | | 140 | | | | | |
| atc | cca | ggg | gga | tca | agt | ggg | ggt | gtg | gcc | gcc | gcg | gtg | gcc | ggc | cga | 480 |
| Ile | Pro | Gly | Gly | Ser | Ser | Gly | Gly | Val | Ala | Ala | Ala | Val | Ala | Gly | Arg | |
| 145 | | | | | 150 | | | | | 155 | | | | | 160 | |
| ttg | atg | ctg | ggc | ggc | gtc | gga | act | gac | acg | gga | gcg | tcg | gtc | cgt | tta | 528 |
| Leu | Met | Leu | Gly | Gly | Val | Gly | Thr | Asp | Thr | Gly | Ala | Ser | Val | Arg | Leu | |
| | | | | 165 | | | | | 170 | | | | | 175 | | |
| ccg | gcc | gcc | ttg | tgc | ggc | gtg | gtg | ggg | ttt | cgt | cct | acc | gtg | ggg | cga | 576 |
| Pro | Ala | Ala | Leu | Cys | Gly | Val | Val | Gly | Phe | Arg | Pro | Thr | Val | Gly | Arg | |
| | | | 180 | | | | | 185 | | | | | 190 | | | |
| tat | cca | acg | gac | gga | ata | gtt | ccg | gta | agc | ccc | acc | cgg | gac | acc | cct | 624 |

| | | | | | | | | | | | | | | | |
|---|---|---|---|---|---|---|---|---|---|---|---|---|---|---|---|
| Tyr | Pro | Thr | Asp | Gly | Ile | Val | Pro | Val | Ser | Pro | Thr | Arg | Asp | Thr | Pro |
| | | 195 | | | | 200 | | | | 205 | | | | | |

```
ggc gtt atc gca cag aat gtt ccg gac gtg att ctt ctt gac ggt atc    672
Gly Val Ile Ala Gln Asn Val Pro Asp Val Ile Leu Leu Asp Gly Ile
210                 215                 220 att tgc ggg aga ccg ccg gtt aat caa acg gtc cgc ctg aag ggg ctg    720
Ile Cys Gly Arg Pro Pro Val Asn Gln Thr Val Arg Leu Lys Gly Leu
225                 230                 235                 240 cgt ata ggc ttg cca acc gct tac ttt tac aac gac ctg gag ccc gat    768
Arg Ile Gly Leu Pro Thr Ala Tyr Phe Tyr Asn Asp Leu Glu Pro Asp
            245                 250                 255 gtc gcc tta gca gcc gag acg att atc aga gtt ctg gca cgc aaa gat    816
Val Ala Leu Ala Ala Glu Thr Ile Ile Arg Val Leu Ala Arg Lys Asp
        260                 265                 270 gtt act ttt gtt gaa gca gat att cct gat tta gcg cat cac aat gaa    864
Val Thr Phe Val Glu Ala Asp Ile Pro Asp Leu Ala His His Asn Glu
    275                 280                 285 ggg gtc agc ttt ccg act gcc atc tac gaa ttt ccg ttg tcc ctt gaa    912
Gly Val Ser Phe Pro Thr Ala Ile Tyr Glu Phe Pro Leu Ser Leu Glu
290                 295                 300 cat tat att cag aac ttc gta gag ggt gtt tcc ttt tct gag gtt gtc    960
His Tyr Ile Gln Asn Phe Val Glu Gly Val Ser Phe Ser Glu Val Val
305                 310                 315                 320 aga gcg att cgc agt ccg gat gtt gca agt att ctc aat gca caa ctc   1008
Arg Ala Ile Arg Ser Pro Asp Val Ala Ser Ile Leu Asn Ala Gln Leu
            325                 330                 335 tcg gat aat ctt att tcc aaa agc gag tat tgt ctg gcg cga cgt ttt   1056
Ser Asp Asn Leu Ile Ser Lys Ser Glu Tyr Cys Leu Ala Arg Arg Phe
        340                 345                 350 ttc aga ccg aga ctc caa gcg gcc tac cac agt tac ttc aag gcg cat   1104
Phe Arg Pro Arg Leu Gln Ala Ala Tyr His Ser Tyr Phe Lys Ala His
    355                 360                 365 cag cta gat gca att ctt ttc cca aca gct ccg ttg aca gcc aag cca   1152
Gln Leu Asp Ala Ile Leu Phe Pro Thr Ala Pro Leu Thr Ala Lys Pro
370                 375                 380 att ggc cat gat cta tcg gtg att cac aat ggc tca atg acc gat acc   1200
Ile Gly His Asp Leu Ser Val Ile His Asn Gly Ser Met Thr Asp Thr
385                 390                 395                 400 ttt aaa atc ttc gtg cgg aat gta gat ccc agc agt aat gcg ggc ctg   1248
Phe Lys Ile Phe Val Arg Asn Val Asp Pro Ser Ser Asn Ala Gly Leu
            405                 410                 415 ccg ggc cta agt ctt ccc gtt tct ctt agt tcc aac ggt ctg cct att   1296
Pro Gly Leu Ser Leu Pro Val Ser Leu Ser Ser Asn Gly Leu Pro Ile
        420                 425                 430 ggc atg gaa atc gat ggc tct gca agc tcg gat gaa cgt ctg tta gca   1344
Gly Met Glu Ile Asp Gly Ser Ala Ser Ser Asp Glu Arg Leu Leu Ala
    435                 440                 445 att gga cta gcg ata gaa gaa gca ata gac ttt agg cat cgt ccg act   1392
Ile Gly Leu Ala Ile Glu Glu Ala Ile Asp Phe Arg His Arg Pro Thr
450                 455                 460 ctg tcg taa                                                        1401
Leu Ser
465
```

<210> SEQ ID NO 30
<211> LENGTH: 466
<212> TYPE: PRT
<213> ORGANISM: Agrobacterium rhizogenes

<400> SEQUENCE: 30

-continued

```
Met Val Thr Leu Ser Ser Ile Thr Glu Thr Leu Lys Cys Leu Arg Glu
 1               5                  10                  15

Arg Lys Tyr Ser Cys Phe Glu Leu Ile Glu Thr Ile Ile Ala Arg Cys
            20                  25                  30

Glu Ala Ala Arg Ser Leu Asn Ala Phe Leu Glu Thr Asp Trp Ala His
        35                  40                  45

Leu Arg Trp Thr Ala Ser Lys Ile Asp Gln His Gly Gly Ala Gly Val
    50                  55                  60

Gly Leu Ala Gly Val Pro Leu Cys Phe Lys Ala Asn Ile Ala Thr Gly
 65                  70                  75                  80

Arg Phe Ala Ala Thr Ala Gly Thr Pro Gly Leu Gln Asn His Lys Pro
                85                  90                  95

Lys Thr Pro Ala Gly Val Ala Arg Gln Leu Leu Ala Ala Gly Ala Leu
            100                 105                 110

Pro Gly Ala Ser Gly Asn Met His Glu Leu Ser Phe Gly Ile Thr Ser
        115                 120                 125

Asn Asn Phe Ala Thr Gly Ala Val Arg Asn Pro Trp Asn Pro Ser Leu
130                 135                 140

Ile Pro Gly Gly Ser Ser Gly Gly Val Ala Ala Val Ala Gly Arg
145                 150                 155                 160

Leu Met Leu Gly Gly Val Gly Thr Asp Thr Gly Ala Ser Val Arg Leu
                165                 170                 175

Pro Ala Ala Leu Cys Gly Val Val Gly Phe Arg Pro Thr Val Gly Arg
            180                 185                 190

Tyr Pro Thr Asp Gly Ile Val Pro Val Ser Pro Thr Arg Asp Thr Pro
        195                 200                 205

Gly Val Ile Ala Gln Asn Val Pro Asp Val Ile Leu Leu Asp Gly Ile
    210                 215                 220

Ile Cys Gly Arg Pro Pro Val Asn Gln Thr Val Arg Leu Lys Gly Leu
225                 230                 235                 240

Arg Ile Gly Leu Pro Thr Ala Tyr Phe Tyr Asn Asp Leu Glu Pro Asp
                245                 250                 255

Val Ala Leu Ala Ala Glu Thr Ile Ile Arg Val Leu Ala Arg Lys Asp
            260                 265                 270

Val Thr Phe Val Glu Ala Asp Ile Pro Asp Leu Ala His His Asn Glu
        275                 280                 285

Gly Val Ser Phe Pro Thr Ala Ile Tyr Glu Phe Pro Leu Ser Leu Glu
    290                 295                 300

His Tyr Ile Gln Asn Phe Val Glu Gly Val Ser Phe Ser Glu Val Val
305                 310                 315                 320

Arg Ala Ile Arg Ser Pro Asp Val Ala Ser Ile Leu Asn Ala Gln Leu
                325                 330                 335

Ser Asp Asn Leu Ile Ser Lys Ser Glu Tyr Cys Leu Ala Arg Arg Phe
            340                 345                 350

Phe Arg Pro Arg Leu Gln Ala Ala Tyr His Ser Tyr Phe Lys Ala His
        355                 360                 365

Gln Leu Asp Ala Ile Leu Phe Pro Thr Ala Pro Leu Thr Ala Lys Pro
    370                 375                 380

Ile Gly His Asp Leu Ser Val Ile His Asn Gly Ser Met Thr Asp Thr
385                 390                 395                 400

Phe Lys Ile Phe Val Arg Asn Val Asp Pro Ser Ser Asn Ala Gly Leu
                405                 410                 415

Pro Gly Leu Ser Leu Pro Val Ser Leu Ser Ser Asn Gly Leu Pro Ile
```

```
                420             425             430
Gly Met Glu Ile Asp Gly Ser Ala Ser Ser Asp Glu Arg Leu Leu Ala
        435                 440                 445

Ile Gly Leu Ala Ile Glu Glu Ala Ile Asp Phe Arg His Arg Pro Thr
    450                 455                 460

Leu Ser
465

<210> SEQ ID NO 31
<211> LENGTH: 2268
<212> TYPE: DNA
<213> ORGANISM: Agrobacterium tumefaciens
<220> FEATURE:
<221> NAME/KEY: CDS
<222> LOCATION: (1)..(2265)
<223> OTHER INFORMATION: coding for tryptophan monooxygenase

<400> SEQUENCE: 31 atg tca gct tca cct ctc ctt gat aac cag tgc gat cat ttc tct acc        48
Met Ser Ala Ser Pro Leu Leu Asp Asn Gln Cys Asp His Phe Ser Thr
  1               5                  10                  15 aaa atg gtg gat ctg ata atg gtc gat aag gct gat gaa ttg gac cgc        96
Lys Met Val Asp Leu Ile Met Val Asp Lys Ala Asp Glu Leu Asp Arg
             20                  25                  30 agg gtt tcc gat gcc ttc tca gaa cgt gaa gct tct agg gga agg agg       144
Arg Val Ser Asp Ala Phe Ser Glu Arg Glu Ala Ser Arg Gly Arg Arg
         35                  40                  45 att act caa atc tcc ggc gag tgc agc gct ggg tta gct tgc aaa agg       192
Ile Thr Gln Ile Ser Gly Glu Cys Ser Ala Gly Leu Ala Cys Lys Arg
     50                  55                  60 ctg gcc gac ggt cgc ttt ccc gag atc tca act ggt gag aag gta gca       240
Leu Ala Asp Gly Arg Phe Pro Glu Ile Ser Thr Gly Glu Lys Val Ala
 65                  70                  75                  80 gcc ctc tcc gct tac atc tat gtt ggc aag gaa att ctg ggg cgg ata       288
Ala Leu Ser Ala Tyr Ile Tyr Val Gly Lys Glu Ile Leu Gly Arg Ile
                 85                  90                  95 ctt gaa tcg gaa cct tgg gcg cga gca aga gtg agt ggt ctc gtt gcc       336
Leu Glu Ser Glu Pro Trp Ala Arg Ala Arg Val Ser Gly Leu Val Ala
            100                 105                 110 atc gac ctt gca cca ttt tgt atg gat ttc tcc gaa gca caa ctt ctc       384
Ile Asp Leu Ala Pro Phe Cys Met Asp Phe Ser Glu Ala Gln Leu Leu
        115                 120                 125 caa acc ctg ttt ttg ctg agc ggt aaa aga tgt gca tcc agc gat ctt       432
Gln Thr Leu Phe Leu Leu Ser Gly Lys Arg Cys Ala Ser Ser Asp Leu
    130                 135                 140 agt cat ttc gtg gcc att tca atc tct aag act gcc cgc tcc cga acc       480
Ser His Phe Val Ala Ile Ser Ile Ser Lys Thr Ala Arg Ser Arg Thr
145                 150                 155                 160 ctg caa atg ccg ccg tac gag aaa ggc acg acg aaa cgc gtt acc ggg       528
Leu Gln Met Pro Pro Tyr Glu Lys Gly Thr Thr Lys Arg Val Thr Gly
                165                 170                 175 ttt acc ctg acc ctt gaa gag gcc gta cca ttt gac atg gta gct tat       576
Phe Thr Leu Thr Leu Glu Glu Ala Val Pro Phe Asp Met Val Ala Tyr
            180                 185                 190 ggt cga aac ctg atg ctg aag gct tcg gca ggt tcc ttt cca aca att       624
Gly Arg Asn Leu Met Leu Lys Ala Ser Ala Gly Ser Phe Pro Thr Ile
        195                 200                 205 gac ttg ctc tat gac tac aga tcg ttt ttt gac caa tgt tcc gat att       672
Asp Leu Leu Tyr Asp Tyr Arg Ser Phe Phe Asp Gln Cys Ser Asp Ile
    210                 215                 220
```

```
gga cgg atc ggc ttc ttt ccg gaa gat gtt cct aag ccg aaa gtg gcg        720
Gly Arg Ile Gly Phe Phe Pro Glu Asp Val Pro Lys Pro Lys Val Ala
225                 230                 235                 240 atc att ggc gct ggc att tcc gga ctc gtg gta gca agc gaa ctg ctt        768
Ile Ile Gly Ala Gly Ile Ser Gly Leu Val Val Ala Ser Glu Leu Leu
                245                 250                 255 cat gct ggt gta gac gat gtt aca ata tat gaa gca agt gat cgg gtt        816
His Ala Gly Val Asp Asp Val Thr Ile Tyr Glu Ala Ser Asp Arg Val
            260                 265                 270 gga ggc aag ctt tgg tca cat gct ttc aag gat gct ccc agc gtg gtg        864
Gly Gly Lys Leu Trp Ser His Ala Phe Lys Asp Ala Pro Ser Val Val
        275                 280                 285 gcc gaa atg ggg gcg atg cga ttt cct cct gct gca tcg tgc ttg ttt        912
Ala Glu Met Gly Ala Met Arg Phe Pro Pro Ala Ala Ser Cys Leu Phe
290                 295                 300 ttc ttc ctc gag cgg tac ggc ctg tct tcg atg agg ccg ttc cca aat        960
Phe Phe Leu Glu Arg Tyr Gly Leu Ser Ser Met Arg Pro Phe Pro Asn
305                 310                 315                 320 ccc ggc aca gtc gac act aac ttg gtc tac caa ggc ctc cga tac gtg       1008
Pro Gly Thr Val Asp Thr Asn Leu Val Tyr Gln Gly Leu Arg Tyr Val
                325                 330                 335 tgg aaa gcc ggg cag cag cca ccg aag ctg ttc cat cgc gtt tac agc       1056
Trp Lys Ala Gly Gln Gln Pro Pro Lys Leu Phe His Arg Val Tyr Ser
            340                 345                 350 ggt tgg cgt gcg ttc ttg agg gac ggt ttc cat gag gga gat att gtg       1104
Gly Trp Arg Ala Phe Leu Arg Asp Gly Phe His Glu Gly Asp Ile Val
        355                 360                 365 ttg gct tcg cct gtt gtt att act caa gcc ttg aaa tca gga gac att       1152
Leu Ala Ser Pro Val Val Ile Thr Gln Ala Leu Lys Ser Gly Asp Ile
370                 375                 380 agg cgg gct cat gac tcc tgg caa act tgg ctg aac cgt ttc ggg agg       1200
Arg Arg Ala His Asp Ser Trp Gln Thr Trp Leu Asn Arg Phe Gly Arg
385                 390                 395                 400 gag tcc ttc tct tca gcg ata gag agg atc ttt ctg ggc acg cat cct       1248
Glu Ser Phe Ser Ser Ala Ile Glu Arg Ile Phe Leu Gly Thr His Pro
                405                 410                 415 cct ggt ggt gaa aca tgg agt ttc cct cat gat tgg gac cta ttc aag       1296
Pro Gly Gly Glu Thr Trp Ser Phe Pro His Asp Trp Asp Leu Phe Lys
            420                 425                 430 cta atg gga ata gga tct ggc ggg ttt ggt cca gtt ttt gaa agc ggg       1344
Leu Met Gly Ile Gly Ser Gly Gly Phe Gly Pro Val Phe Glu Ser Gly
        435                 440                 445 ttt att gag atc ctt cgc ttg gtc ata aac gga tat gaa gaa aat cag       1392
Phe Ile Glu Ile Leu Arg Leu Val Ile Asn Gly Tyr Glu Glu Asn Gln
450                 455                 460 cgg atg tgc tct gaa gga atc tca gaa ctt cca cgt cga ata gcc tct       1440
Arg Met Cys Ser Glu Gly Ile Ser Glu Leu Pro Arg Arg Ile Ala Ser
465                 470                 475                 480 caa gtg gtt aac ggt gtg tct gta agc cag cgt ata cgc cat gtt caa       1488
Gln Val Val Asn Gly Val Ser Val Ser Gln Arg Ile Arg His Val Gln
                485                 490                 495 gtc agg gcg att gag aag gaa aag aca aaa ata aag ata agg ctt aag       1536
Val Arg Ala Ile Glu Lys Glu Lys Thr Lys Ile Lys Ile Arg Leu Lys
            500                 505                 510 agc ggg ata tct gaa ctt tat gat aag gtg gtg gtt aca tct gga ctc       1584
Ser Gly Ile Ser Glu Leu Tyr Asp Lys Val Val Val Thr Ser Gly Leu
        515                 520                 525 gca aat atc caa ctc agg cat tgt ctg aca tgc gat acc acc att ttt       1632
Ala Asn Ile Gln Leu Arg His Cys Leu Thr Cys Asp Thr Thr Ile Phe
530                 535                 540
```

-continued

| | | |
|---|---|---|
| cgt gca cca gtg aac caa gcg gtt gat aac agc cat atg aca ggc tcg<br>Arg Ala Pro Val Asn Gln Ala Val Asp Asn Ser His Met Thr Gly Ser<br>545                    550                    555                    560 | 1680 |
| tca aaa ctc ttt ctg ctg act gaa cga aaa ttt tgg tta gac cat atc<br>Ser Lys Leu Phe Leu Leu Thr Glu Arg Lys Phe Trp Leu Asp His Ile<br>                    565                    570                    575 | 1728 |
| ctc ccg tcc tgt gtc ctc atg gac ggg atc gca aaa gca gtg tac tgc<br>Leu Pro Ser Cys Val Leu Met Asp Gly Ile Ala Lys Ala Val Tyr Cys<br>                  580                    585                    590 | 1776 |
| ttg gac tat gag ccg cag gat ccg aat ggt aaa ggt ctg gtg ccc ccc<br>Leu Asp Tyr Glu Pro Gln Asp Pro Asn Gly Lys Gly Leu Val Pro Pro<br>595                    600                    605 | 1824 |
| act tat aca tgg gag gac gac tcc cac aag ctg ttg gcg gtt ccc gac<br>Thr Tyr Thr Trp Glu Asp Asp Ser His Lys Leu Leu Ala Val Pro Asp<br>610                    615                    620 | 1872 |
| aaa aaa gag cga ttc tgt ctg ctg cgg gac gca att tcg aga tct ttc<br>Lys Lys Glu Arg Phe Cys Leu Leu Arg Asp Ala Ile Ser Arg Ser Phe<br>625                    630                    635                    640 | 1920 |
| ccg gcg ttt gcc cag cat cta gtt cct gcc tgc gct gat tac gac caa<br>Pro Ala Phe Ala Gln His Leu Val Pro Ala Cys Ala Asp Tyr Asp Gln<br>                    645                    650                    655 | 1968 |
| aat gtt gtt caa cat gat tgg ctt aca gac gag aat gcc ggg gga gct<br>Asn Val Val Gln His Asp Trp Leu Thr Asp Glu Asn Ala Gly Gly Ala<br>                    660                    665                    670 | 2016 |
| ttc aaa ctc aac cgg cgt ggc gag gat ttt tat tct gaa gaa ctt ttc<br>Phe Lys Leu Asn Arg Arg Gly Glu Asp Phe Tyr Ser Glu Glu Leu Phe<br>675                    680                    685 | 2064 |
| ttt caa gcg ctg gac atg cct aat gat acc gga gtt tac ttg gcg ggt<br>Phe Gln Ala Leu Asp Met Pro Asn Asp Thr Gly Val Tyr Leu Ala Gly<br>690                    695                    700 | 2112 |
| tgc agt tgt tcc ttc acc ggt gga tgg gtg gag ggc gct att cag acc<br>Cys Ser Cys Ser Phe Thr Gly Gly Trp Val Glu Gly Ala Ile Gln Thr<br>705                    710                    715                    720 | 2160 |
| gcg tgt aac gcc gtc tgt gca att atc cac aat tgt gga ggt att ttg<br>Ala Cys Asn Ala Val Cys Ala Ile Ile His Asn Cys Gly Gly Ile Leu<br>                    725                    730                    735 | 2208 |
| gca aag gac aat cct ctc gaa cac tct tgg aag aga tat aac tac cgc<br>Ala Lys Asp Asn Pro Leu Glu His Ser Trp Lys Arg Tyr Asn Tyr Arg<br>                    740                    745                    750 | 2256 |
| aat aga aat taa<br>Asn Arg Asn<br>                    755 | 2268 |

<210> SEQ ID NO 32
<211> LENGTH: 755
<212> TYPE: PRT
<213> ORGANISM: Agrobacterium tumefaciens

<400> SEQUENCE: 32

Met Ser Ala Ser Pro Leu Leu Asp Asn Gln Cys Asp His Phe Ser Thr
1                 5                    10                  15

Lys Met Val Asp Leu Ile Met Val Asp Lys Ala Asp Glu Leu Asp Arg
                20                    25                    30

Arg Val Ser Asp Ala Phe Ser Glu Arg Glu Ala Ser Arg Gly Arg Arg
            35                    40                    45

Ile Thr Gln Ile Ser Gly Glu Cys Ser Ala Gly Leu Ala Cys Lys Arg
    50                    55                    60

Leu Ala Asp Gly Arg Phe Pro Glu Ile Ser Thr Gly Glu Lys Val Ala
65                    70                    75                    80

-continued

```
Ala Leu Ser Ala Tyr Ile Tyr Val Gly Lys Glu Ile Leu Gly Arg Ile
                85                  90                  95

Leu Glu Ser Glu Pro Trp Ala Arg Ala Arg Val Ser Gly Leu Val Ala
            100                 105                 110

Ile Asp Leu Ala Pro Phe Cys Met Asp Phe Ser Glu Ala Gln Leu Leu
        115                 120                 125

Gln Thr Leu Phe Leu Leu Ser Gly Lys Arg Cys Ala Ser Ser Asp Leu
    130                 135                 140

Ser His Phe Val Ala Ile Ser Ile Ser Lys Thr Ala Arg Ser Arg Thr
145                 150                 155                 160

Leu Gln Met Pro Pro Tyr Glu Lys Gly Thr Thr Lys Arg Val Thr Gly
            165                 170                 175

Phe Thr Leu Thr Leu Glu Glu Ala Val Pro Phe Asp Met Val Ala Tyr
            180                 185                 190

Gly Arg Asn Leu Met Leu Lys Ala Ser Ala Gly Ser Phe Pro Thr Ile
                195                 200                 205

Asp Leu Leu Tyr Asp Tyr Arg Ser Phe Phe Asp Gln Cys Ser Asp Ile
        210                 215                 220

Gly Arg Ile Gly Phe Phe Pro Glu Asp Val Pro Lys Pro Lys Val Ala
225                 230                 235                 240

Ile Ile Gly Ala Gly Ile Ser Gly Leu Val Val Ala Ser Glu Leu Leu
                245                 250                 255

His Ala Gly Val Asp Asp Val Thr Ile Tyr Glu Ala Ser Asp Arg Val
            260                 265                 270

Gly Gly Lys Leu Trp Ser His Ala Phe Lys Asp Ala Pro Ser Val Val
        275                 280                 285

Ala Glu Met Gly Ala Met Arg Phe Pro Pro Ala Ala Ser Cys Leu Phe
    290                 295                 300

Phe Phe Leu Glu Arg Tyr Gly Leu Ser Ser Met Arg Pro Phe Pro Asn
305                 310                 315                 320

Pro Gly Thr Val Asp Thr Asn Leu Val Tyr Gln Gly Leu Arg Tyr Val
            325                 330                 335

Trp Lys Ala Gly Gln Gln Pro Pro Lys Leu Phe His Arg Val Tyr Ser
            340                 345                 350

Gly Trp Arg Ala Phe Leu Arg Asp Gly Phe His Glu Gly Asp Ile Val
        355                 360                 365

Leu Ala Ser Pro Val Val Ile Thr Gln Ala Leu Lys Ser Gly Asp Ile
    370                 375                 380

Arg Arg Ala His Asp Ser Trp Gln Thr Trp Leu Asn Arg Phe Gly Arg
385                 390                 395                 400

Glu Ser Phe Ser Ser Ala Ile Glu Arg Ile Phe Leu Gly Thr His Pro
            405                 410                 415

Pro Gly Gly Glu Thr Trp Ser Phe Pro His Asp Trp Asp Leu Phe Lys
            420                 425                 430

Leu Met Gly Ile Gly Ser Gly Gly Phe Gly Pro Val Phe Glu Ser Gly
        435                 440                 445

Phe Ile Glu Ile Leu Arg Leu Val Ile Asn Gly Tyr Glu Glu Asn Gln
    450                 455                 460

Arg Met Cys Ser Glu Gly Ile Ser Glu Leu Pro Arg Arg Ile Ala Ser
465                 470                 475                 480

Gln Val Val Asn Gly Val Ser Val Ser Gln Arg Ile Arg His Val Gln
            485                 490                 495
```

```
Val Arg Ala Ile Glu Lys Glu Lys Thr Lys Ile Lys Ile Arg Leu Lys
            500                 505                 510

Ser Gly Ile Ser Glu Leu Tyr Asp Lys Val Val Thr Ser Gly Leu
            515                 520                 525

Ala Asn Ile Gln Leu Arg His Cys Leu Thr Cys Asp Thr Thr Ile Phe
            530                 535                 540

Arg Ala Pro Val Asn Gln Ala Val Asp Asn Ser His Met Thr Gly Ser
545                 550                 555                 560

Ser Lys Leu Phe Leu Leu Thr Glu Arg Lys Phe Trp Leu Asp His Ile
                565                 570                 575

Leu Pro Ser Cys Val Leu Met Asp Gly Ile Ala Lys Ala Val Tyr Cys
            580                 585                 590

Leu Asp Tyr Glu Pro Gln Asp Pro Asn Gly Lys Gly Leu Val Pro Pro
            595                 600                 605

Thr Tyr Thr Trp Glu Asp Asp Ser His Lys Leu Leu Ala Val Pro Asp
            610                 615                 620

Lys Lys Glu Arg Phe Cys Leu Leu Arg Asp Ala Ile Ser Arg Ser Phe
625                 630                 635                 640

Pro Ala Phe Ala Gln His Leu Val Pro Ala Cys Ala Asp Tyr Asp Gln
                645                 650                 655

Asn Val Val Gln His Asp Trp Leu Thr Asp Glu Asn Ala Gly Gly Ala
            660                 665                 670

Phe Lys Leu Asn Arg Arg Gly Glu Asp Phe Tyr Ser Glu Glu Leu Phe
                675                 680                 685

Phe Gln Ala Leu Asp Met Pro Asn Asp Thr Gly Val Tyr Leu Ala Gly
            690                 695                 700

Cys Ser Cys Ser Phe Thr Gly Gly Trp Val Glu Gly Ala Ile Gln Thr
705                 710                 715                 720

Ala Cys Asn Ala Val Cys Ala Ile Ile His Asn Cys Gly Gly Ile Leu
                725                 730                 735

Ala Lys Asp Asn Pro Leu Glu His Ser Trp Lys Arg Tyr Asn Tyr Arg
                740                 745                 750

Asn Arg Asn
        755

<210> SEQ ID NO 33
<211> LENGTH: 1404
<212> TYPE: DNA
<213> ORGANISM: Agrobacterium tumefaciens
<220> FEATURE:
<221> NAME/KEY: CDS
<222> LOCATION: (1)..(1401)
<223> OTHER INFORMATION: coding for indoleacetamide hydrolase

<400> SEQUENCE: 33 atg gtg ccc att acc tcg tta gca caa acc cta gaa cgc ctg aga cgg      48
Met Val Pro Ile Thr Ser Leu Ala Gln Thr Leu Glu Arg Leu Arg Arg
  1               5                  10                  15 aaa gac tac tcc tgc tta gaa cta gta gaa act ctg ata gcg cgt tgc      96
Lys Asp Tyr Ser Cys Leu Glu Leu Val Glu Thr Leu Ile Ala Arg Cys
             20                  25                  30 caa gct gca aaa cca tta aat gcc ctt ctg gct aca gac tgg gat ggc     144
Gln Ala Ala Lys Pro Leu Asn Ala Leu Leu Ala Thr Asp Trp Asp Gly
         35                  40                  45 ttg cgg cga agc gcc aaa aaa aat gat cgt cat gga aac gcc gga tta     192
Leu Arg Arg Ser Ala Lys Lys Asn Asp Arg His Gly Asn Ala Gly Leu
     50                  55                  60
```

-continued

| | |
|---|---|
| ggt ctt tgc ggc att cca ctc tgt ttt aag gcg aac atc gcg acc ggc<br>Gly Leu Cys Gly Ile Pro Leu Cys Phe Lys Ala Asn Ile Ala Thr Gly<br>65                     70                    75                  80 | 240 |
| gta ttt cct aca agc gct gct act ccg gcg ctg ata aac cac ttg cca<br>Val Phe Pro Thr Ser Ala Ala Thr Pro Ala Leu Ile Asn His Leu Pro<br>                   85                    90                    95 | 288 |
| aag ata cca tcc cgc gtc gca gaa aga ctt ttt tca gct gga gca ctg<br>Lys Ile Pro Ser Arg Val Ala Glu Arg Leu Phe Ser Ala Gly Ala Leu<br>                  100                   105               110 | 336 |
| ccg ggt gcc tcg gga aac atg cat gag tta tcg ttt gga att acg agc<br>Pro Gly Ala Ser Gly Asn Met His Glu Leu Ser Phe Gly Ile Thr Ser<br>           115                   120                 125 | 384 |
| aac aac tat gcc acc ggt gcg gtg cgg aac ccg tgg aat cca agt ctg<br>Asn Asn Tyr Ala Thr Gly Ala Val Arg Asn Pro Trp Asn Pro Ser Leu<br>130                     135                   140 | 432 |
| ata cca ggg ggt tca agc ggt ggt gtg gct gct gcg gtg gca agc cga<br>Ile Pro Gly Gly Ser Ser Gly Gly Val Ala Ala Ala Val Ala Ser Arg<br>145                     150                   155               160 | 480 |
| ttg atg tta ggc ggc ata ggc acg gat acc ggt gca tct gtt cgc cta<br>Leu Met Leu Gly Gly Ile Gly Thr Asp Thr Gly Ala Ser Val Arg Leu<br>                  165                   170               175 | 528 |
| ccg gca gcc ctg tgt ggc gta gta gga ttt cga ccg acg ctt ggt cga<br>Pro Ala Ala Leu Cys Gly Val Val Gly Phe Arg Pro Thr Leu Gly Arg<br>             180                   185               190 | 576 |
| tat cca aga gat cgg ata ata ccg ttc agc ccc acc cgg gac acc gcc<br>Tyr Pro Arg Asp Arg Ile Ile Pro Phe Ser Pro Thr Arg Asp Thr Ala<br>           195                   200                 205 | 624 |
| gga atc ata gcg cag tgc gta gcc gat gtt ata atc ctc gac cag gtg<br>Gly Ile Ile Ala Gln Cys Val Ala Asp Val Ile Ile Leu Asp Gln Val<br>210                     215                   220 | 672 |
| att tcc gga cgg tcg gcg aaa att tca ccc atg ccg ctg aag ggg ctt<br>Ile Ser Gly Arg Ser Ala Lys Ile Ser Pro Met Pro Leu Lys Gly Leu<br>225                     230                   235               240 | 720 |
| cgg atc ggc ctc ccc act acc tac ttt tac gat gac ctt gat gct gat<br>Arg Ile Gly Leu Pro Thr Thr Tyr Phe Tyr Asp Asp Leu Asp Ala Asp<br>                  245                   250               255 | 768 |
| gtg gcc ttc gca gct gaa acg acg att cgc ttg cta gcc aac aga ggc<br>Val Ala Phe Ala Ala Glu Thr Thr Ile Arg Leu Leu Ala Asn Arg Gly<br>             260                   265               270 | 816 |
| gta acc ttt gtt gaa gcc gac atc ccc cac cta gag gaa ttg aac agt<br>Val Thr Phe Val Glu Ala Asp Ile Pro His Leu Glu Glu Leu Asn Ser<br>           275                   280               285 | 864 |
| ggg gca agt ttg cca att gcg ctt tac gaa ttt cca cac gct cta aaa<br>Gly Ala Ser Leu Pro Ile Ala Leu Tyr Glu Phe Pro His Ala Leu Lys<br>290                     295                   300 | 912 |
| aag tat ctc gac gat ttt gtg gga aca gtt tct ttt tct gac gtt atc<br>Lys Tyr Leu Asp Asp Phe Val Gly Thr Val Ser Phe Ser Asp Val Ile<br>305                     310                   315               320 | 960 |
| aaa gga att cgt agc ccc gat gta gcg aac att gtc agt gcg caa att<br>Lys Gly Ile Arg Ser Pro Asp Val Ala Asn Ile Val Ser Ala Gln Ile<br>                  325                   330               335 | 1008 |
| gat ggg cat caa att tcc aac gat gaa tat gaa ctg gcg cgt caa tcc<br>Asp Gly His Gln Ile Ser Asn Asp Glu Tyr Glu Leu Ala Arg Gln Ser<br>             340                   345               350 | 1056 |
| ttc agg cca agg ctc cag gcc act tat cgg aat tac ttc aga ctc tat<br>Phe Arg Pro Arg Leu Gln Ala Thr Tyr Arg Asn Tyr Phe Arg Leu Tyr<br>           355                   360                 365 | 1104 |
| cag tta gat gca atc ctt ttc cca act gca ccc tta gcg gcc aaa gcc<br>Gln Leu Asp Ala Ile Leu Phe Pro Thr Ala Pro Leu Ala Ala Lys Ala<br>370                     375                   380 | 1152 |

```
ata ggt cag gag tcg tca gtc atc cac aat ggc tca atg atg aac act    1200
Ile Gly Gln Glu Ser Ser Val Ile His Asn Gly Ser Met Met Asn Thr
385                 390                 395                 400 ttc aag atc tac gtg cga aat gtg gac cca agc agc aac gca ggc cta    1248
Phe Lys Ile Tyr Val Arg Asn Val Asp Pro Ser Ser Asn Ala Gly Leu
                405                 410                 415 cct ggg ttg agc ctt cct gcc tgc ctt aca cct gat cgc ttg cct gtt    1296
Pro Gly Leu Ser Leu Pro Ala Cys Leu Thr Pro Asp Arg Leu Pro Val
            420                 425                 430 gga atg gaa att gat gga tta gcg ggg tca gac cac cgt ctg tta gca    1344
Gly Met Glu Ile Asp Gly Leu Ala Gly Ser Asp His Arg Leu Leu Ala
        435                 440                 445 atc ggg gca gca tta gaa aaa gct ata aat ttt tct tcc ttt ccc gat    1392
Ile Gly Ala Ala Leu Glu Lys Ala Ile Asn Phe Ser Ser Phe Pro Asp
    450                 455                 460 gct ttt aat tag                                                    1404
Ala Phe Asn
465
```

<210> SEQ ID NO 34
<211> LENGTH: 467
<212> TYPE: PRT
<213> ORGANISM: Agrobacterium tumefaciens

<400> SEQUENCE: 34

```
Met Val Pro Ile Thr Ser Leu Ala Gln Thr Leu Glu Arg Leu Arg Arg
  1               5                  10                  15

Lys Asp Tyr Ser Cys Leu Glu Leu Val Glu Thr Leu Ile Ala Arg Cys
                 20                  25                  30

Gln Ala Ala Lys Pro Leu Asn Ala Leu Leu Ala Thr Asp Trp Asp Gly
             35                  40                  45

Leu Arg Arg Ser Ala Lys Lys Asn Asp Arg His Gly Asn Ala Gly Leu
         50                  55                  60

Gly Leu Cys Gly Ile Pro Leu Cys Phe Lys Ala Asn Ile Ala Thr Gly
 65                  70                  75                  80

Val Phe Pro Thr Ser Ala Ala Thr Pro Ala Leu Ile Asn His Leu Pro
                 85                  90                  95

Lys Ile Pro Ser Arg Val Ala Glu Arg Leu Phe Ser Ala Gly Ala Leu
            100                 105                 110

Pro Gly Ala Ser Gly Asn Met His Glu Leu Ser Phe Gly Ile Thr Ser
        115                 120                 125

Asn Asn Tyr Ala Thr Gly Ala Val Arg Asn Pro Trp Asn Pro Ser Leu
    130                 135                 140

Ile Pro Gly Gly Ser Ser Gly Gly Val Ala Ala Ala Val Ala Ser Arg
145                 150                 155                 160

Leu Met Leu Gly Gly Ile Gly Thr Asp Thr Gly Ala Ser Val Arg Leu
                165                 170                 175

Pro Ala Ala Leu Cys Gly Val Val Gly Phe Arg Pro Thr Leu Gly Arg
            180                 185                 190

Tyr Pro Arg Asp Arg Ile Ile Pro Phe Ser Pro Thr Arg Asp Thr Ala
        195                 200                 205

Gly Ile Ile Ala Gln Cys Val Ala Asp Val Ile Leu Asp Gln Val
    210                 215                 220

Ile Ser Gly Arg Ser Ala Lys Ile Ser Pro Met Pro Leu Lys Gly Leu
225                 230                 235                 240

Arg Ile Gly Leu Pro Thr Thr Tyr Phe Tyr Asp Asp Leu Asp Ala Asp
```

-continued

```
                245                 250                 255
Val Ala Phe Ala Ala Glu Thr Thr Ile Arg Leu Leu Ala Asn Arg Gly
            260                 265                 270
Val Thr Phe Val Glu Ala Asp Ile Pro His Leu Glu Glu Leu Asn Ser
            275                 280                 285
Gly Ala Ser Leu Pro Ile Ala Leu Tyr Glu Phe Pro His Ala Leu Lys
            290                 295                 300
Lys Tyr Leu Asp Asp Phe Val Gly Thr Val Ser Phe Ser Asp Val Ile
305                 310                 315                 320
Lys Gly Ile Arg Ser Pro Asp Val Ala Asn Ile Val Ser Ala Gln Ile
                325                 330                 335
Asp Gly His Gln Ile Ser Asn Asp Glu Tyr Glu Leu Ala Arg Gln Ser
            340                 345                 350
Phe Arg Pro Arg Leu Gln Ala Thr Tyr Arg Asn Tyr Phe Arg Leu Tyr
            355                 360                 365
Gln Leu Asp Ala Ile Leu Phe Pro Thr Ala Pro Leu Ala Ala Lys Ala
            370                 375                 380
Ile Gly Gln Glu Ser Ser Val Ile His Asn Gly Ser Met Met Asn Thr
385                 390                 395                 400
Phe Lys Ile Tyr Val Arg Asn Val Asp Pro Ser Ser Asn Ala Gly Leu
                405                 410                 415
Pro Gly Leu Ser Leu Pro Ala Cys Leu Thr Pro Asp Arg Leu Pro Val
            420                 425                 430
Gly Met Glu Ile Asp Gly Leu Ala Gly Ser Asp His Arg Leu Leu Ala
            435                 440                 445
Ile Gly Ala Ala Leu Glu Lys Ala Ile Asn Phe Ser Ser Phe Pro Asp
450                 455                 460
Ala Phe Asn
465

<210> SEQ ID NO 35
<211> LENGTH: 1419
<212> TYPE: DNA
<213> ORGANISM: Agrobacterium vitis
<220> FEATURE:
<221> NAME/KEY: CDS
<222> LOCATION: (1)..(1416)
<223> OTHER INFORMATION: coding for indoleacetamide hydrolase

<400> SEQUENCE: 35 atg gtg acc cta ggt tca atc aag gaa acc ctg gaa tgt ctc agg ctg    48
Met Val Thr Leu Gly Ser Ile Lys Glu Thr Leu Glu Cys Leu Arg Leu
  1               5                  10                  15 aaa aaa tac tcc tgt tcc gaa ctg gct gaa acc ata ata gcc cgt tgc    96
Lys Lys Tyr Ser Cys Ser Glu Leu Ala Glu Thr Ile Ile Ala Arg Cys
                 20                  25                  30 gaa gcc gcg aaa tct ctc aat gct ctt ctg gcg act gac tgg gat tac   144
Glu Ala Ala Lys Ser Leu Asn Ala Leu Leu Ala Thr Asp Trp Asp Tyr
             35                  40                  45 ctg cgg cgt aat gcc aag aaa gta gat gaa gat gga agc gcc ggc gag   192
Leu Arg Arg Asn Ala Lys Lys Val Asp Glu Asp Gly Ser Ala Gly Glu
         50                  55                  60 ggt ctt gcc ggc atc ccg ctg tgt tct aaa gcg aac att gca aca ggc   240
Gly Leu Ala Gly Ile Pro Leu Cys Ser Lys Ala Asn Ile Ala Thr Gly
 65                  70                  75                  80 ata ttc cca gca agc gcg gcc acg ccg gcg ctt gat gaa cat tta cct   288
Ile Phe Pro Ala Ser Ala Ala Thr Pro Ala Leu Asp Glu His Leu Pro
                 85                  90                  95
```

```
aca aca cca gcc ggc gtc cgt aaa ccg ctt cta gac gct ggg gca ctg       336
Thr Thr Pro Ala Gly Val Arg Lys Pro Leu Leu Asp Ala Gly Ala Leu
            100                 105                 110 ata ggc gct tcg gga aac atg cat gag tta tcg ttt ggc att acc agt       384
Ile Gly Ala Ser Gly Asn Met His Glu Leu Ser Phe Gly Ile Thr Ser
                115                 120                 125 aac aac cac gcc act ggt gcg gtg aga aac ccc tgg aat ccc agc tta       432
Asn Asn His Ala Thr Gly Ala Val Arg Asn Pro Trp Asn Pro Ser Leu
130                 135                 140 ata cca gga ggc tcg agc ggc ggc gtg gct gct gct gta gca tca cgg       480
Ile Pro Gly Gly Ser Ser Gly Gly Val Ala Ala Ala Val Ala Ser Arg
145                 150                 155                 160 tta atg ctc ggc gga att ggc acc gac acg ggg gct tcg gtc cgc cta       528
Leu Met Leu Gly Gly Ile Gly Thr Asp Thr Gly Ala Ser Val Arg Leu
                165                 170                 175 cct gca tcc cta tgt ggc gta gtg gga ttc cgc ccg acg atc ggc aga       576
Pro Ala Ser Leu Cys Gly Val Val Gly Phe Arg Pro Thr Ile Gly Arg
                180                 185                 190 tat cct gga gac cga att gtg ccg gtt agc ccc acc cgc gat aca gcc       624
Tyr Pro Gly Asp Arg Ile Val Pro Val Ser Pro Thr Arg Asp Thr Ala
            195                 200                 205 gga att atc gca cag agc gtt cct gat gtg ata ctc ctt gac caa atc       672
Gly Ile Ile Ala Gln Ser Val Pro Asp Val Ile Leu Leu Asp Gln Ile
210                 215                 220 att tgc ggg aag ctc acg acc cac caa cct gta ccc ctg gag gga tta       720
Ile Cys Gly Lys Leu Thr Thr His Gln Pro Val Pro Leu Glu Gly Leu
225                 230                 235                 240 cgt atc ggc ttg cca acc act tac ttt tac gat gac ctt gat gct gat       768
Arg Ile Gly Leu Pro Thr Thr Tyr Phe Tyr Asp Asp Leu Asp Ala Asp
                245                 250                 255 gtg gcc ttc gca gct gaa aac ctt atc acg ctg ctg gcc agc aag ggt       816
Val Ala Phe Ala Ala Glu Asn Leu Ile Thr Leu Leu Ala Ser Lys Gly
            260                 265                 270 gta acc ttt gtt aag gcc gag att cca gat ctg cag cgt ctg aac atc       864
Val Thr Phe Val Lys Ala Glu Ile Pro Asp Leu Gln Arg Leu Asn Ile
        275                 280                 285 ggg gtt agc ttt cct att gcc ctg tac gag ttt ccg ttc gcc cta caa       912
Gly Val Ser Phe Pro Ile Ala Leu Tyr Glu Phe Pro Phe Ala Leu Gln
        290                 295                 300 aag tat atc gat gac ttt gtg aag gat gtg tct ttt tct gac gtc atc       960
Lys Tyr Ile Asp Asp Phe Val Lys Asp Val Ser Phe Ser Asp Val Ile
305                 310                 315                 320 aaa gga att cgt agc cct gat gta gcc aac att gcc aat gct caa att      1008
Lys Gly Ile Arg Ser Pro Asp Val Ala Asn Ile Ala Asn Ala Gln Ile
                325                 330                 335 gat gga cat caa att tcc aaa gct tca tat gaa ctg gcg cga caa tct      1056
Asp Gly His Gln Ile Ser Lys Ala Ser Tyr Glu Leu Ala Arg Gln Ser
            340                 345                 350 ttc aga cca aag ctg caa gcc gcc tac cat gat tac ttc aag ctg cac      1104
Phe Arg Pro Lys Leu Gln Ala Ala Tyr His Asp Tyr Phe Lys Leu His
        355                 360                 365 cag cta gac gcg atc ctt ttc ccg aca gct ccc ctg aca gcc aaa ccg      1152
Gln Leu Asp Ala Ile Leu Phe Pro Thr Ala Pro Leu Thr Ala Lys Pro
370                 375                 380 atc ggc caa gat tta tcg gtg atg cac aat ggc gta atg gcc gac acg      1200
Ile Gly Gln Asp Leu Ser Val Met His Asn Gly Val Met Ala Asp Thr
385                 390                 395                 400 ttt aaa atc ttc gtg cga aat gtg gat ccg ggg agc aac gca ggc ctg      1248
Phe Lys Ile Phe Val Arg Asn Val Asp Pro Gly Ser Asn Ala Gly Leu
```

```
                      405                 410                 415
cca gga tta agc ctt ccc gtt tct ctt act tca aag ggt ttg cct att        1296
Pro Gly Leu Ser Leu Pro Val Ser Leu Thr Ser Lys Gly Leu Pro Ile
                420                 425                 430 gga atg gaa atc gat gga tta gcg ggc atg gac gac cgt ttg cta gca        1344
Gly Met Glu Ile Asp Gly Leu Ala Gly Met Asp Asp Arg Leu Leu Ala
                435                 440                 445 atc gga gcg gca cta gag gaa gcg ata gct ttt cat aat tta cct gac        1392
Ile Gly Ala Ala Leu Glu Glu Ala Ile Ala Phe His Asn Leu Pro Asp
    450                 455                 460 ttc ccg aaa gtc gag aca aac tac tga                                    1419
Phe Pro Lys Val Glu Thr Asn Tyr
465                 470

<210> SEQ ID NO 36
<211> LENGTH: 472
<212> TYPE: PRT
<213> ORGANISM: Agrobacterium vitis

<400> SEQUENCE: 36

Met Val Thr Leu Gly Ser Ile Lys Glu Thr Leu Glu Cys Leu Arg Leu
 1               5                  10                  15

Lys Lys Tyr Ser Cys Ser Glu Leu Ala Glu Thr Ile Ile Ala Arg Cys
                20                  25                  30

Glu Ala Ala Lys Ser Leu Asn Ala Leu Leu Ala Thr Asp Trp Asp Tyr
            35                  40                  45

Leu Arg Arg Asn Ala Lys Lys Val Asp Glu Asp Gly Ser Ala Gly Glu
        50                  55                  60

Gly Leu Ala Gly Ile Pro Leu Cys Ser Lys Ala Asn Ile Ala Thr Gly
 65                  70                  75                  80

Ile Phe Pro Ala Ser Ala Ala Thr Pro Ala Leu Asp Glu His Leu Pro
                85                  90                  95

Thr Thr Pro Ala Gly Val Arg Lys Pro Leu Leu Asp Ala Gly Ala Leu
            100                 105                 110

Ile Gly Ala Ser Gly Asn Met His Glu Leu Ser Phe Gly Ile Thr Ser
        115                 120                 125

Asn Asn His Ala Thr Gly Ala Val Arg Asn Pro Trp Asn Pro Ser Leu
    130                 135                 140

Ile Pro Gly Gly Ser Ser Gly Gly Val Ala Ala Val Ala Ser Arg
145                 150                 155                 160

Leu Met Leu Gly Gly Ile Gly Thr Asp Thr Gly Ala Ser Val Arg Leu
                165                 170                 175

Pro Ala Ser Leu Cys Gly Val Val Gly Phe Arg Pro Thr Ile Gly Arg
            180                 185                 190

Tyr Pro Gly Asp Arg Ile Val Pro Val Ser Pro Thr Arg Asp Thr Ala
        195                 200                 205

Gly Ile Ile Ala Gln Ser Val Pro Asp Val Ile Leu Asp Gln Ile
    210                 215                 220

Ile Cys Gly Lys Leu Thr Thr His Gln Pro Val Pro Leu Glu Gly Leu
225                 230                 235                 240

Arg Ile Gly Leu Pro Thr Thr Tyr Phe Tyr Asp Asp Leu Asp Ala Asp
                245                 250                 255

Val Ala Phe Ala Ala Glu Asn Leu Ile Thr Leu Leu Ala Ser Lys Gly
            260                 265                 270

Val Thr Phe Val Lys Ala Glu Ile Pro Asp Leu Gln Arg Leu Asn Ile
        275                 280                 285
```

```
Gly Val Ser Phe Pro Ile Ala Leu Tyr Glu Phe Pro Phe Ala Leu Gln
            290                 295                 300

Lys Tyr Ile Asp Asp Phe Val Lys Asp Val Ser Phe Ser Asp Val Ile
305                 310                 315                 320

Lys Gly Ile Arg Ser Pro Asp Val Ala Asn Ile Ala Asn Ala Gln Ile
                325                 330                 335

Asp Gly His Gln Ile Ser Lys Ala Ser Tyr Glu Leu Ala Arg Gln Ser
            340                 345                 350

Phe Arg Pro Lys Leu Gln Ala Ala Tyr His Asp Tyr Phe Lys Leu His
        355                 360                 365

Gln Leu Asp Ala Ile Leu Phe Pro Thr Ala Pro Leu Thr Ala Lys Pro
370                 375                 380

Ile Gly Gln Asp Leu Ser Val Met His Asn Gly Val Met Ala Asp Thr
385                 390                 395                 400

Phe Lys Ile Phe Val Arg Asn Val Asp Pro Gly Ser Asn Ala Gly Leu
                405                 410                 415

Pro Gly Leu Ser Leu Pro Val Ser Leu Thr Ser Lys Gly Leu Pro Ile
            420                 425                 430

Gly Met Glu Ile Asp Gly Leu Ala Gly Met Asp Asp Arg Leu Leu Ala
        435                 440                 445

Ile Gly Ala Ala Leu Glu Glu Ala Ile Ala Phe His Asn Leu Pro Asp
    450                 455                 460

Phe Pro Lys Val Glu Thr Asn Tyr
465                 470

<210> SEQ ID NO 37
<211> LENGTH: 1263
<212> TYPE: DNA
<213> ORGANISM: Arabidopsis thaliana
<220> FEATURE:
<221> NAME/KEY: CDS
<222> LOCATION: (1)..(1260)
<223> OTHER INFORMATION: coding for 5-methylthioribose kinase

<400> SEQUENCE: 37 atg tct ttt gag gag ttt acg ccg tta aac gag aag tct ctt gta gac      48
Met Ser Phe Glu Glu Phe Thr Pro Leu Asn Glu Lys Ser Leu Val Asp
 1               5                  10                  15 tac atc aag tca aca cct gct ctc tct tcc aag atc gga gcc gac aag      96
Tyr Ile Lys Ser Thr Pro Ala Leu Ser Ser Lys Ile Gly Ala Asp Lys
             20                  25                  30 tcc gat gat gat ttg gtt atc aaa gaa gtt gga gat ggc aat ctc aat     144
Ser Asp Asp Asp Leu Val Ile Lys Glu Val Gly Asp Gly Asn Leu Asn
         35                  40                  45 ttc gtt ttc atc gtt gtt gga tcc tct ggt tct ctt gtc atc aaa cag     192
Phe Val Phe Ile Val Val Gly Ser Ser Gly Ser Leu Val Ile Lys Gln
     50                  55                  60 gct ctt cca tat att cgc tgt atc ggt gaa tca tgg cca atg acg aaa     240
Ala Leu Pro Tyr Ile Arg Cys Ile Gly Glu Ser Trp Pro Met Thr Lys
 65                  70                  75                  80 gaa aga gct tat ttt gaa gca aca act ttg aga aag cat gga aat tta     288
Glu Arg Ala Tyr Phe Glu Ala Thr Thr Leu Arg Lys His Gly Asn Leu
                 85                  90                  95 tca cct gat cat gtt cct gaa gtc tac cat ttt gac aga aca atg gcg     336
Ser Pro Asp His Val Pro Glu Val Tyr His Phe Asp Arg Thr Met Ala
            100                 105                 110 ttg att gga atg aga tac ctt gag cct cct cat atc att ctc cgc aaa     384
Leu Ile Gly Met Arg Tyr Leu Glu Pro Pro His Ile Ile Leu Arg Lys
```

```
                115                 120                 125
gga ctc att gct ggg att gag tat cct ttc ctc gca gac cac atg tct       432
Gly Leu Ile Ala Gly Ile Glu Tyr Pro Phe Leu Ala Asp His Met Ser
    130                 135                 140 gat tac atg gcg aag act ctc ttc ttc act tct ctc ctc tat cac gat       480
Asp Tyr Met Ala Lys Thr Leu Phe Phe Thr Ser Leu Leu Tyr His Asp
145                 150                 155                 160 acc aca gag cac aga aga gca gta acc gaa ttt tgt ggt aat gtg gag       528
Thr Thr Glu His Arg Arg Ala Val Thr Glu Phe Cys Gly Asn Val Glu
                165                 170                 175 tta tgc cga tta acg gag caa gtt gtg ttt tcg gac cca tat aga gtt       576
Leu Cys Arg Leu Thr Glu Gln Val Val Phe Ser Asp Pro Tyr Arg Val
            180                 185                 190 tcc aca ttt aat cgt tgg act tca cct tat ctt gat gat gat gct aag       624
Ser Thr Phe Asn Arg Trp Thr Ser Pro Tyr Leu Asp Asp Asp Ala Lys
        195                 200                 205 gct gtg cgc gaa gac agt gcc ttg aag ctc gaa atc gca gag cta aaa       672
Ala Val Arg Glu Asp Ser Ala Leu Lys Leu Glu Ile Ala Glu Leu Lys
    210                 215                 220 tcg atg ttc tgt gaa aga gct caa gct tta ata cat ggt gat ctt cat       720
Ser Met Phe Cys Glu Arg Ala Gln Ala Leu Ile His Gly Asp Leu His
225                 230                 235                 240 act ggt tct gtc atg gtt act caa gat tca acg caa gtt ata gat cca       768
Thr Gly Ser Val Met Val Thr Gln Asp Ser Thr Gln Val Ile Asp Pro
                245                 250                 255 gag ttt tcg ttc tat gga ccg atg ggt ttc gat att ggc gct tat ctt       816
Glu Phe Ser Phe Tyr Gly Pro Met Gly Phe Asp Ile Gly Ala Tyr Leu
            260                 265                 270 ggt aac ttg ata cta gct ttc ttt gca caa gat gga cac gcc act cag       864
Gly Asn Leu Ile Leu Ala Phe Phe Ala Gln Asp Gly His Ala Thr Gln
        275                 280                 285 gaa aat gat cga aaa gaa tac aag cag tgg atc ttg aga acc att gag       912
Glu Asn Asp Arg Lys Glu Tyr Lys Gln Trp Ile Leu Arg Thr Ile Glu
    290                 295                 300 caa act tgg aat ttg ttt aac aaa agg ttc att gcg cta tgg gat caa       960
Gln Thr Trp Asn Leu Phe Asn Lys Arg Phe Ile Ala Leu Trp Asp Gln
305                 310                 315                 320 aac aaa gat gga cca ggc gaa gca tac ctt gca gat atc tat aac aat      1008
Asn Lys Asp Gly Pro Gly Glu Ala Tyr Leu Ala Asp Ile Tyr Asn Asn
                325                 330                 335 acc gag gtt ttg aag ttt gtt caa gaa aac tac atg agg aat ttg ttg      1056
Thr Glu Val Leu Lys Phe Val Gln Glu Asn Tyr Met Arg Asn Leu Leu
            340                 345                 350 cat gac tca ctc gga ttc ggc gct gca aag atg att agg aga att gtg      1104
His Asp Ser Leu Gly Phe Gly Ala Ala Lys Met Ile Arg Arg Ile Val
        355                 360                 365 gga gtg gca cat gtt gag gac ttt gaa tca atc gaa gaa gat aag cga      1152
Gly Val Ala His Val Glu Asp Phe Glu Ser Ile Glu Glu Asp Lys Arg
    370                 375                 380 aga gct att tgc gag aga agt gca ctc gag ttt gcg aag atg ctt ctc      1200
Arg Ala Ile Cys Glu Arg Ser Ala Leu Glu Phe Ala Lys Met Leu Leu
385                 390                 395                 400 aag gaa agg aga aag ttt aag agt atc ggt gaa gtt gtt tca gca att      1248
Lys Glu Arg Arg Lys Phe Lys Ser Ile Gly Glu Val Val Ser Ala Ile
                405                 410                 415 caa caa caa agc taa                                                  1263
Gln Gln Gln Ser
            420
```

<210> SEQ ID NO 38
<211> LENGTH: 420
<212> TYPE: PRT
<213> ORGANISM: Arabidopsis thaliana

<400> SEQUENCE: 38

```
Met Ser Phe Glu Glu Phe Thr Pro Leu Asn Glu Lys Ser Leu Val Asp
  1               5                  10                  15

Tyr Ile Lys Ser Thr Pro Ala Leu Ser Ser Lys Ile Gly Ala Asp Lys
             20                  25                  30

Ser Asp Asp Asp Leu Val Ile Lys Glu Val Gly Asp Gly Asn Leu Asn
         35                  40                  45

Phe Val Phe Ile Val Val Gly Ser Gly Ser Leu Val Ile Lys Gln
     50                  55                  60

Ala Leu Pro Tyr Ile Arg Cys Ile Gly Glu Ser Trp Pro Met Thr Lys
 65                  70                  75                  80

Glu Arg Ala Tyr Phe Glu Ala Thr Thr Leu Arg Lys His Gly Asn Leu
                 85                  90                  95

Ser Pro Asp His Val Pro Glu Val Tyr His Phe Asp Arg Thr Met Ala
            100                 105                 110

Leu Ile Gly Met Arg Tyr Leu Glu Pro Pro His Ile Ile Leu Arg Lys
        115                 120                 125

Gly Leu Ile Ala Gly Ile Glu Tyr Pro Phe Leu Ala Asp His Met Ser
    130                 135                 140

Asp Tyr Met Ala Lys Thr Leu Phe Phe Thr Ser Leu Leu Tyr His Asp
145                 150                 155                 160

Thr Thr Glu His Arg Arg Ala Val Thr Glu Phe Cys Gly Asn Val Glu
                165                 170                 175

Leu Cys Arg Leu Thr Glu Gln Val Val Phe Ser Asp Pro Tyr Arg Val
            180                 185                 190

Ser Thr Phe Asn Arg Trp Thr Ser Pro Tyr Leu Asp Asp Ala Lys
        195                 200                 205

Ala Val Arg Glu Asp Ser Ala Leu Lys Leu Glu Ile Ala Glu Leu Lys
    210                 215                 220

Ser Met Phe Cys Glu Arg Ala Gln Ala Leu Ile His Gly Asp Leu His
225                 230                 235                 240

Thr Gly Ser Val Met Val Thr Gln Asp Ser Thr Gln Val Ile Asp Pro
                245                 250                 255

Glu Phe Ser Phe Tyr Gly Pro Met Gly Phe Asp Ile Gly Ala Tyr Leu
            260                 265                 270

Gly Asn Leu Ile Leu Ala Phe Phe Ala Gln Asp Gly His Ala Thr Gln
        275                 280                 285

Glu Asn Asp Arg Lys Glu Tyr Lys Gln Trp Ile Leu Arg Thr Ile Glu
    290                 295                 300

Gln Thr Trp Asn Leu Phe Asn Lys Arg Phe Ile Ala Leu Trp Asp Gln
305                 310                 315                 320

Asn Lys Asp Gly Pro Gly Glu Ala Tyr Leu Ala Asp Ile Tyr Asn Asn
                325                 330                 335

Thr Glu Val Leu Lys Phe Val Gln Glu Asn Tyr Met Arg Asn Leu Leu
            340                 345                 350

His Asp Ser Leu Gly Phe Gly Ala Ala Lys Met Ile Arg Arg Ile Val
        355                 360                 365

Gly Val Ala His Val Glu Asp Phe Glu Ser Ile Glu Glu Asp Lys Arg
    370                 375                 380
```

```
Arg Ala Ile Cys Glu Arg Ser Ala Leu Glu Phe Ala Lys Met Leu Leu
385                 390                 395                 400

Lys Glu Arg Arg Lys Phe Lys Ser Ile Gly Glu Val Val Ser Ala Ile
                405                 410                 415

Gln Gln Gln Ser
            420

<210> SEQ ID NO 39
<211> LENGTH: 1200
<212> TYPE: DNA
<213> ORGANISM: Klebsiella pneumoniae
<220> FEATURE:
<221> NAME/KEY: CDS
<222> LOCATION: (1)..(1197)
<223> OTHER INFORMATION: coding for 5-methylthioribose kinase

<400> SEQUENCE: 39 atg tcg caa tac cat acc ttc acc gcc cac gat gcc gtg gct tac gcg      48
Met Ser Gln Tyr His Thr Phe Thr Ala His Asp Ala Val Ala Tyr Ala
1               5                   10                  15 caa cag ttc gcc ggc atc gac aac cca tct gag ctg gtc agc gcg cag      96
Gln Gln Phe Ala Gly Ile Asp Asn Pro Ser Glu Leu Val Ser Ala Gln
            20                  25                  30 gaa gtg ggc gat ggc aac ctc aat ctg gtg ttt aaa gtg ttc gat cgt     144
Glu Val Gly Asp Gly Asn Leu Asn Leu Val Phe Lys Val Phe Asp Arg
        35                  40                  45 cag ggc gtc agc cgg gcg atc gtc aaa cag gcc ctg ccc tac gtg cgc     192
Gln Gly Val Ser Arg Ala Ile Val Lys Gln Ala Leu Pro Tyr Val Arg
    50                  55                  60 tgc gtc ggc gaa tcc tgg ccg ctg acc ctc gac cgc gcc cgt ctc gaa     240
Cys Val Gly Glu Ser Trp Pro Leu Thr Leu Asp Arg Ala Arg Leu Glu
65                  70                  75                  80 gcg cag acc ctg gtc gcc cac tat cag cac agc ccg cag cac acg gta     288
Ala Gln Thr Leu Val Ala His Tyr Gln His Ser Pro Gln His Thr Val
                85                  90                  95 aaa atc cat cac ttt gat ccc gag ctg gcg gtg atg gtg atg gaa gat     336
Lys Ile His His Phe Asp Pro Glu Leu Ala Val Met Val Met Glu Asp
            100                 105                 110 ctt tcc gac cac cgc atc tgg cgc gga gag ctt atc gct aac gtc tac     384
Leu Ser Asp His Arg Ile Trp Arg Gly Glu Leu Ile Ala Asn Val Tyr
        115                 120                 125 tat ccc cag gcg gcc cgc cag ctt ggc gac tat ctg gcg cag gtg ttg     432
Tyr Pro Gln Ala Ala Arg Gln Leu Gly Asp Tyr Leu Ala Gln Val Leu
    130                 135                 140 ttc cac acc agc gat ttc tac ctc cat ccc cac gag aaa aag gcg cag     480
Phe His Thr Ser Asp Phe Tyr Leu His Pro His Glu Lys Lys Ala Gln
145                 150                 155                 160 gtg gcg cag ttt att aac ccg gcg atg tgc gag atc acc gag gat ctg     528
Val Ala Gln Phe Ile Asn Pro Ala Met Cys Glu Ile Thr Glu Asp Leu
                165                 170                 175 ttc ttt aac gac ccg tat cag atc cac gag cgc aat aac tac ccg gcg     576
Phe Phe Asn Asp Pro Tyr Gln Ile His Glu Arg Asn Asn Tyr Pro Ala
            180                 185                 190 gag ctg gag gcc gat gtc gcc gcc ctg cgc gac gac gcc cag ctt aag     624
Glu Leu Glu Ala Asp Val Ala Ala Leu Arg Asp Asp Ala Gln Leu Lys
        195                 200                 205 ctg gcg gtg gcg gcg ctg aag cac cgt ttc ttt gcc cat gcg gaa gcg     672
Leu Ala Val Ala Ala Leu Lys His Arg Phe Phe Ala His Ala Glu Ala
    210                 215                 220 ctg ctg cac ggc gat atc cac agc ggg tcg atc ttc gtt gcc gaa ggt     720
Leu Leu His Gly Asp Ile His Ser Gly Ser Ile Phe Val Ala Glu Gly
```

-continued

```
                    225                 230                 235                 240 agc ctg aag gcc atc gac gcc gag ttc ggc tac ttc ggc ccc atc ggc       768
Ser Leu Lys Ala Ile Asp Ala Glu Phe Gly Tyr Phe Gly Pro Ile Gly
                        245                 250                 255 ttc gat atc ggc acc gcc atc ggc aac ctg ctg ctg aac tac tgc ggc       816
Phe Asp Ile Gly Thr Ala Ile Gly Asn Leu Leu Leu Asn Tyr Cys Gly
                260                 265                 270 ctg ccg ggc cag ctc ggc att cgc gat gcc gcc gcc gcg cgc gag cag       864
Leu Pro Gly Gln Leu Gly Ile Arg Asp Ala Ala Ala Ala Arg Glu Gln
            275                 280                 285 cgg ctg aac gac atc cac cag ctg tgg acc acc ttc gcc gag cgc ttc       912
Arg Leu Asn Asp Ile His Gln Leu Trp Thr Thr Phe Ala Glu Arg Phe
        290                 295                 300 cag gcg ctg gcg gcg gag aaa acc cgc gac gcg gcg ctg gct tac ccc       960
Gln Ala Leu Ala Ala Glu Lys Thr Arg Asp Ala Ala Leu Ala Tyr Pro
305                 310                 315                 320 ggc tac gcc tcc gcc ttt ctg aag aaa gtc tgg gcg gac gcg gtc ggc      1008
Gly Tyr Ala Ser Ala Phe Leu Lys Lys Val Trp Ala Asp Ala Val Gly
                        325                 330                 335 ttc tgc ggc agc gaa ctg atc cgc cgc agc gtc gga ctg tcg cac gtc      1056
Phe Cys Gly Ser Glu Leu Ile Arg Arg Ser Val Gly Leu Ser His Val
                340                 345                 350 gcg gat atc gac act atc cag gac gac gcc atg cgt cat gag tgc ctg      1104
Ala Asp Ile Asp Thr Ile Gln Asp Asp Ala Met Arg His Glu Cys Leu
            355                 360                 365 cgc cac gcc att acc ctg ggc aga gcg ctg atc gtg ctg gcc gag cgt      1152
Arg His Ala Ile Thr Leu Gly Arg Ala Leu Ile Val Leu Ala Glu Arg
        370                 375                 380 atc gac agc gtc gac gag ctg ctg gcg cgg gta cgc cag tac agc tga      1200
Ile Asp Ser Val Asp Glu Leu Leu Ala Arg Val Arg Gln Tyr Ser
385                 390                 395

<210> SEQ ID NO 40
<211> LENGTH: 399
<212> TYPE: PRT
<213> ORGANISM: Klebsiella pneumoniae

<400> SEQUENCE: 40

Met Ser Gln Tyr His Thr Phe Thr Ala His Asp Ala Val Ala Tyr Ala
  1               5                  10                  15

Gln Gln Phe Ala Gly Ile Asp Asn Pro Ser Glu Leu Val Ser Ala Gln
                 20                  25                  30

Glu Val Gly Asp Gly Asn Leu Asn Leu Val Phe Lys Val Phe Asp Arg
             35                  40                  45

Gln Gly Val Ser Arg Ala Ile Val Lys Gln Ala Leu Pro Tyr Val Arg
         50                  55                  60

Cys Val Gly Glu Ser Trp Pro Leu Thr Leu Asp Arg Ala Arg Leu Glu
 65                  70                  75                  80

Ala Gln Thr Leu Val Ala His Tyr Gln His Ser Pro Gln His Thr Val
                 85                  90                  95

Lys Ile His His Phe Asp Pro Glu Leu Ala Val Met Val Met Glu Asp
            100                 105                 110

Leu Ser Asp His Arg Ile Trp Arg Gly Glu Leu Ile Ala Asn Val Tyr
        115                 120                 125

Tyr Pro Gln Ala Ala Arg Gln Leu Gly Asp Tyr Leu Ala Gln Val Leu
    130                 135                 140

Phe His Thr Ser Asp Phe Tyr Leu His Pro His Glu Lys Lys Ala Gln
145                 150                 155                 160
```

```
Val Ala Gln Phe Ile Asn Pro Ala Met Cys Glu Ile Thr Glu Asp Leu
            165                 170                 175

Phe Phe Asn Asp Pro Tyr Gln Ile His Glu Arg Asn Asn Tyr Pro Ala
            180                 185                 190

Glu Leu Glu Ala Asp Val Ala Ala Leu Arg Asp Asp Ala Gln Leu Lys
            195                 200                 205

Leu Ala Val Ala Ala Leu Lys His Arg Phe Phe Ala His Ala Glu Ala
            210                 215                 220

Leu Leu His Gly Asp Ile His Ser Gly Ser Ile Phe Val Ala Glu Gly
225                 230                 235                 240

Ser Leu Lys Ala Ile Asp Ala Glu Phe Gly Tyr Phe Gly Pro Ile Gly
            245                 250                 255

Phe Asp Ile Gly Thr Ala Ile Gly Asn Leu Leu Leu Asn Tyr Cys Gly
            260                 265                 270

Leu Pro Gly Gln Leu Gly Ile Arg Asp Ala Ala Ala Arg Glu Gln
            275                 280                 285

Arg Leu Asn Asp Ile His Gln Leu Trp Thr Thr Phe Ala Glu Arg Phe
290                 295                 300

Gln Ala Leu Ala Ala Glu Lys Thr Arg Asp Ala Ala Leu Ala Tyr Pro
305                 310                 315                 320

Gly Tyr Ala Ser Ala Phe Leu Lys Lys Val Trp Ala Asp Ala Val Gly
            325                 330                 335

Phe Cys Gly Ser Glu Leu Ile Arg Arg Ser Val Gly Leu Ser His Val
            340                 345                 350

Ala Asp Ile Asp Thr Ile Gln Asp Asp Ala Met Arg His Glu Cys Leu
            355                 360                 365

Arg His Ala Ile Thr Leu Gly Arg Ala Leu Ile Val Leu Ala Glu Arg
            370                 375                 380

Ile Asp Ser Val Asp Glu Leu Leu Ala Arg Val Arg Gln Tyr Ser
385                 390                 395

<210> SEQ ID NO 41
<211> LENGTH: 1140
<212> TYPE: DNA
<213> ORGANISM: Arabidopsis thaliana
<220> FEATURE:
<221> NAME/KEY: CDS
<222> LOCATION: (1)..(1137)
<223> OTHER INFORMATION: coding for alcohol dehydrogenase

<400> SEQUENCE: 41 atg tct acc acc gga cag att att cga tgc aaa gct gct gtg gca tgg      48
Met Ser Thr Thr Gly Gln Ile Ile Arg Cys Lys Ala Ala Val Ala Trp
 1               5                  10                  15 gaa gcc gga aag cca ctg gtg atc gag gaa gtg gag gtt gct cca ccg      96
Glu Ala Gly Lys Pro Leu Val Ile Glu Glu Val Glu Val Ala Pro Pro
             20                  25                  30 cag aaa cac gaa gtt cgt atc aag att ctc ttc act tct ctc tgt cac     144
Gln Lys His Glu Val Arg Ile Lys Ile Leu Phe Thr Ser Leu Cys His
         35                  40                  45 acc gat gtt tac ttc tgg gaa gct aag gga caa aca ccg ttg ttt cca     192
Thr Asp Val Tyr Phe Trp Glu Ala Lys Gly Gln Thr Pro Leu Phe Pro
     50                  55                  60 cgt atc ttc ggc cat gaa gct gga ggg att gtt gag agt gtt gga gaa     240
Arg Ile Phe Gly His Glu Ala Gly Gly Ile Val Glu Ser Val Gly Glu
 65                  70                  75                  80 gga gtg act gat ctt cag cca gga gat cat gtg ttg ccg atc ttt acc     288
```

```
              Gly Val Thr Asp Leu Gln Pro Gly Asp His Val Leu Pro Ile Phe Thr
                              85                  90                  95 gga gaa tgt gga gat tgt cgt cat tgc cag tcg gag gaa tca aac atg           336
Gly Glu Cys Gly Asp Cys Arg His Cys Gln Ser Glu Glu Ser Asn Met
                100                 105                 110 tgt gat ctt ctc agg atc aac aca gag cga gga ggt atg att cac gat           384
Cys Asp Leu Leu Arg Ile Asn Thr Glu Arg Gly Gly Met Ile His Asp
            115                 120                 125 ggt gaa tct aga ttc tcc att aat ggc aaa cca atc tac cat ttc ctt           432
Gly Glu Ser Arg Phe Ser Ile Asn Gly Lys Pro Ile Tyr His Phe Leu
        130                 135                 140 ggg acg tcc acg ttc agt gag tac act gtg gtt cac tct ggt cag gtc           480
Gly Thr Ser Thr Phe Ser Glu Tyr Thr Val Val His Ser Gly Gln Val
145                 150                 155                 160 gct aag atc aat ccg gat gct cct ctt gac aag gtc tgt att gtc agt           528
Ala Lys Ile Asn Pro Asp Ala Pro Leu Asp Lys Val Cys Ile Val Ser
                165                 170                 175 tgt ggt ttg tct act ggg tta gga gca act ttg aat gtg gct aaa ccc           576
Cys Gly Leu Ser Thr Gly Leu Gly Ala Thr Leu Asn Val Ala Lys Pro
            180                 185                 190 aag aaa ggt caa agt gtt gcc att ttt ggt ctt ggt gct gtt ggt tta           624
Lys Lys Gly Gln Ser Val Ala Ile Phe Gly Leu Gly Ala Val Gly Leu
        195                 200                 205 ggc gct gca gaa ggt gct aga atc gct ggt gct tct agg atc atc ggt           672
Gly Ala Ala Glu Gly Ala Arg Ile Ala Gly Ala Ser Arg Ile Ile Gly
    210                 215                 220 gtt gat ttt aac tct aaa aga ttc gac caa gct aag gaa ttc ggt gtg           720
Val Asp Phe Asn Ser Lys Arg Phe Asp Gln Ala Lys Glu Phe Gly Val
225                 230                 235                 240 acc gag tgt gtg aac ccg aaa gac cat gac aag cca att caa cag gtg           768
Thr Glu Cys Val Asn Pro Lys Asp His Asp Lys Pro Ile Gln Gln Val
                245                 250                 255 atc gct gag atg acg gat ggt ggg gtg gac agg agt gtg gaa tgc acc           816
Ile Ala Glu Met Thr Asp Gly Gly Val Asp Arg Ser Val Glu Cys Thr
            260                 265                 270 gga agc gtt cag gcc atg att caa gca ttt gaa tgt gtc cac gat ggc           864
Gly Ser Val Gln Ala Met Ile Gln Ala Phe Glu Cys Val His Asp Gly
        275                 280                 285 tgg ggt gtt gca gtg ctg gtg ggt gtg cca agc aaa gac gat gcc ttc           912
Trp Gly Val Ala Val Leu Val Gly Val Pro Ser Lys Asp Asp Ala Phe
    290                 295                 300 aag act cat ccg atg aat ttc ttg aat gag agg act ctt aag ggt act           960
Lys Thr His Pro Met Asn Phe Leu Asn Glu Arg Thr Leu Lys Gly Thr
305                 310                 315                 320 ttc ttc ggg aac tac aaa ccc aaa act gac att ccc ggg gtt gtg gaa          1008
Phe Phe Gly Asn Tyr Lys Pro Lys Thr Asp Ile Pro Gly Val Val Glu
                325                 330                 335 aag tac atg aac aag gag ctg gag ctt gag aaa ttc atc act cac aca          1056
Lys Tyr Met Asn Lys Glu Leu Glu Leu Glu Lys Phe Ile Thr His Thr
            340                 345                 350 gtg cca ttc tcg gaa atc aac aag gcc ttt gat tac atg ctg aag gga          1104
Val Pro Phe Ser Glu Ile Asn Lys Ala Phe Asp Tyr Met Leu Lys Gly
        355                 360                 365 gag agt att cgt tgc atc atc acc atg ggt gct tga                          1140
Glu Ser Ile Arg Cys Ile Ile Thr Met Gly Ala
    370                 375

<210> SEQ ID NO 42
<211> LENGTH: 379
<212> TYPE: PRT
```

<213> ORGANISM: Arabidopsis thaliana

<400> SEQUENCE: 42

```
Met Ser Thr Thr Gly Gln Ile Ile Arg Cys Lys Ala Ala Val Ala Trp
  1               5                  10                  15
Glu Ala Gly Lys Pro Leu Val Ile Glu Val Glu Val Ala Pro Pro
             20                  25                  30
Gln Lys His Glu Val Arg Ile Lys Ile Leu Phe Thr Ser Leu Cys His
         35                  40                  45
Thr Asp Val Tyr Phe Trp Glu Ala Lys Gly Gln Thr Pro Leu Phe Pro
     50                  55                  60
Arg Ile Phe Gly His Glu Ala Gly Gly Ile Val Glu Ser Val Gly Glu
 65                  70                  75                  80
Gly Val Thr Asp Leu Gln Pro Gly Asp His Val Leu Pro Ile Phe Thr
                 85                  90                  95
Gly Glu Cys Gly Asp Cys Arg His Cys Gln Ser Glu Glu Ser Asn Met
            100                 105                 110
Cys Asp Leu Leu Arg Ile Asn Thr Glu Arg Gly Gly Met Ile His Asp
        115                 120                 125
Gly Glu Ser Arg Phe Ser Ile Asn Gly Lys Pro Ile Tyr His Phe Leu
    130                 135                 140
Gly Thr Ser Thr Phe Ser Glu Tyr Thr Val Val His Ser Gly Gln Val
145                 150                 155                 160
Ala Lys Ile Asn Pro Asp Ala Pro Leu Asp Lys Val Cys Ile Val Ser
                165                 170                 175
Cys Gly Leu Ser Thr Gly Leu Gly Ala Thr Leu Asn Val Ala Lys Pro
            180                 185                 190
Lys Lys Gly Gln Ser Val Ala Ile Phe Gly Leu Gly Ala Val Gly Leu
        195                 200                 205
Gly Ala Ala Glu Gly Ala Arg Ile Ala Gly Ala Ser Arg Ile Ile Gly
    210                 215                 220
Val Asp Phe Asn Ser Lys Arg Phe Asp Gln Ala Lys Glu Phe Gly Val
225                 230                 235                 240
Thr Glu Cys Val Asn Pro Lys Asp His Asp Lys Pro Ile Gln Gln Val
                245                 250                 255
Ile Ala Glu Met Thr Asp Gly Gly Val Asp Arg Ser Val Glu Cys Thr
            260                 265                 270
Gly Ser Val Gln Ala Met Ile Gln Ala Phe Glu Cys Val His Asp Gly
        275                 280                 285
Trp Gly Val Ala Val Leu Val Gly Val Pro Ser Lys Asp Asp Ala Phe
    290                 295                 300
Lys Thr His Pro Met Asn Phe Leu Asn Glu Arg Thr Leu Lys Gly Thr
305                 310                 315                 320
Phe Phe Gly Asn Tyr Lys Pro Lys Thr Asp Ile Pro Gly Val Val Glu
                325                 330                 335
Lys Tyr Met Asn Lys Glu Leu Glu Leu Glu Lys Phe Ile Thr His Thr
            340                 345                 350
Val Pro Phe Ser Glu Ile Asn Lys Ala Phe Asp Tyr Met Leu Lys Gly
        355                 360                 365
Glu Ser Ile Arg Cys Ile Ile Thr Met Gly Ala
    370                 375
```

<210> SEQ ID NO 43
<211> LENGTH: 1140

```
<212> TYPE: DNA
<213> ORGANISM: Hordeum vulgare
<220> FEATURE:
<221> NAME/KEY: CDS
<222> LOCATION: (1)..(1137)
<223> OTHER INFORMATION: coding for alcohol dehydrogenase

<400> SEQUENCE: 43 atg gcg acg gcc ggc aag gtg atc aag tgc aaa gcc gcg gtg gcg tgg      48
Met Ala Thr Ala Gly Lys Val Ile Lys Cys Lys Ala Ala Val Ala Trp
 1               5                  10                  15 gag gcc ggg aag ccg ctg acc atg gag gag gtg gag gtg gcg ccg ccg      96
Glu Ala Gly Lys Pro Leu Thr Met Glu Glu Val Glu Val Ala Pro Pro
             20                  25                  30 cag gcc atg gag gtg cgc gtc aag atc ctc ttc acc tcc ctc tgc cac     144
Gln Ala Met Glu Val Arg Val Lys Ile Leu Phe Thr Ser Leu Cys His
         35                  40                  45 acc gac gtc tac ttc tgg gag gcc aag ggg cag acc ccc atg ttc cct     192
Thr Asp Val Tyr Phe Trp Glu Ala Lys Gly Gln Thr Pro Met Phe Pro
     50                  55                  60 cgg atc ttc ggc cat gaa gct gga ggc ata gtg gag agt gtt gga gag     240
Arg Ile Phe Gly His Glu Ala Gly Gly Ile Val Glu Ser Val Gly Glu
 65                  70                  75                  80 ggc gtg act gat gtt gcc cct ggt gac cac gtc ctc cct gtg ttc act     288
Gly Val Thr Asp Val Ala Pro Gly Asp His Val Leu Pro Val Phe Thr
                 85                  90                  95 ggg gag tgt aag gaa tgc cca cat tgc aag tct gcg gag agc aac atg     336
Gly Glu Cys Lys Glu Cys Pro His Cys Lys Ser Ala Glu Ser Asn Met
            100                 105                 110 tgt gat ctg ctc agg atc aac acc gac aga ggt gtg atg atc ggg gat     384
Cys Asp Leu Leu Arg Ile Asn Thr Asp Arg Gly Val Met Ile Gly Asp
        115                 120                 125 ggc aag tcg cgc ttc tct att ggc ggc aag ccg att tac cat ttc gta     432
Gly Lys Ser Arg Phe Ser Ile Gly Gly Lys Pro Ile Tyr His Phe Val
    130                 135                 140 ggg act tcc acc ttc agt gag tac act gtc atg cat gtc ggt tgt gtt     480
Gly Thr Ser Thr Phe Ser Glu Tyr Thr Val Met His Val Gly Cys Val
145                 150                 155                 160 gcc aag atc aac cct gag gct ccc ctt gat aaa gtc tgt gtt ctt agc     528
Ala Lys Ile Asn Pro Glu Ala Pro Leu Asp Lys Val Cys Val Leu Ser
                165                 170                 175 tgt ggt att tgc act ggt ctt ggc gcg tca att aat gtt gca aaa cca     576
Cys Gly Ile Cys Thr Gly Leu Gly Ala Ser Ile Asn Val Ala Lys Pro
            180                 185                 190 cca aag ggt tcc aca gtg gcg ata ttt ggg cta gga gct gtt ggc ctt     624
Pro Lys Gly Ser Thr Val Ala Ile Phe Gly Leu Gly Ala Val Gly Leu
        195                 200                 205 gct gct gca gaa ggt gca agg att gca ggt gca tca agg atc att ggt     672
Ala Ala Ala Glu Gly Ala Arg Ile Ala Gly Ala Ser Arg Ile Ile Gly
    210                 215                 220 gtt gac ctg aac gcc agc aga ttt gaa gag gct agg aag ttt ggc tgc     720
Val Asp Leu Asn Ala Ser Arg Phe Glu Glu Ala Arg Lys Phe Gly Cys
225                 230                 235                 240 acg gaa ttt gtg aac ccg aaa gat cac acc aag cca gtt cag cag gtg     768
Thr Glu Phe Val Asn Pro Lys Asp His Thr Lys Pro Val Gln Gln Val
                245                 250                 255 ctc gct gac atg aca aat ggc gga gtt gac cgc agt gtt gag tgc act     816
Leu Ala Asp Met Thr Asn Gly Gly Val Asp Arg Ser Val Glu Cys Thr
            260                 265                 270 ggc aac gtc aat gct atg ata caa gca ttt gaa tgt gtt cat gat ggc     864
Gly Asn Val Asn Ala Met Ile Gln Ala Phe Glu Cys Val His Asp Gly
```

```
                 275                 280                 285
tgg ggt gta gct gtg ctg gtg ggt gtg cca cac aag gac gct gaa ttc      912
Trp Gly Val Ala Val Leu Val Gly Val Pro His Lys Asp Ala Glu Phe
290                 295                 300 aag acc cac ccg atg aac ttc ctg aat gag agg acc ctg aag ggc acc      960
Lys Thr His Pro Met Asn Phe Leu Asn Glu Arg Thr Leu Lys Gly Thr
305                 310                 315                 320 ttc ttc ggt aac ttc aag ccg cgc act gac ctg ccc aat gtc gtg gag     1008
Phe Phe Gly Asn Phe Lys Pro Arg Thr Asp Leu Pro Asn Val Val Glu
                325                 330                 335 atg tac atg aag aag gag ctg gag gtg gag aag ttc atc aca cac agc     1056
Met Tyr Met Lys Lys Glu Leu Glu Val Glu Lys Phe Ile Thr His Ser
            340                 345                 350 gtg ccg ttc tcg gag ata aac aag gcc ttc gac ctt atg gcg aag ggg     1104
Val Pro Phe Ser Glu Ile Asn Lys Ala Phe Asp Leu Met Ala Lys Gly
        355                 360                 365 gag ggc atc cgt tgc atc atc cgc atg gac aac tag                     1140
Glu Gly Ile Arg Cys Ile Ile Arg Met Asp Asn
    370                 375
```

<210> SEQ ID NO 44
<211> LENGTH: 379
<212> TYPE: PRT
<213> ORGANISM: Hordeum vulgare

<400> SEQUENCE: 44

```
Met Ala Thr Ala Gly Lys Val Ile Lys Cys Lys Ala Val Ala Trp
1               5                   10                  15

Glu Ala Gly Lys Pro Leu Thr Met Glu Glu Val Glu Val Ala Pro Pro
            20                  25                  30

Gln Ala Met Glu Val Arg Val Lys Ile Leu Phe Thr Ser Leu Cys His
        35                  40                  45

Thr Asp Val Tyr Phe Trp Glu Ala Lys Gly Gln Thr Pro Met Phe Pro
    50                  55                  60

Arg Ile Phe Gly His Glu Ala Gly Ile Val Glu Ser Val Gly Glu
65              70                  75                  80

Gly Val Thr Asp Val Ala Pro Gly Asp His Val Leu Pro Val Phe Thr
            85                  90                  95

Gly Glu Cys Lys Glu Cys Pro His Cys Lys Ser Ala Glu Ser Asn Met
        100                 105                 110

Cys Asp Leu Leu Arg Ile Asn Thr Asp Arg Gly Val Met Ile Gly Asp
    115                 120                 125

Gly Lys Ser Arg Phe Ser Ile Gly Gly Lys Pro Ile Tyr His Phe Val
130                 135                 140

Gly Thr Ser Thr Phe Ser Glu Tyr Thr Val Met His Val Gly Cys Val
145                 150                 155                 160

Ala Lys Ile Asn Pro Glu Ala Pro Leu Asp Lys Val Cys Val Leu Ser
            165                 170                 175

Cys Gly Ile Cys Thr Gly Leu Gly Ala Ser Ile Asn Val Ala Lys Pro
        180                 185                 190

Pro Lys Gly Ser Thr Val Ala Ile Phe Gly Leu Gly Ala Val Gly Leu
    195                 200                 205

Ala Ala Ala Glu Gly Ala Arg Ile Ala Gly Ala Ser Arg Ile Ile Gly
210                 215                 220

Val Asp Leu Asn Ala Ser Arg Phe Glu Glu Ala Arg Lys Phe Gly Cys
225                 230                 235                 240
```

```
Thr Glu Phe Val Asn Pro Lys Asp His Thr Lys Pro Val Gln Gln Val
            245                 250                 255

Leu Ala Asp Met Thr Asn Gly Gly Val Asp Arg Ser Val Glu Cys Thr
                260                 265                 270

Gly Asn Val Asn Ala Met Ile Gln Ala Phe Glu Cys Val His Asp Gly
            275                 280                 285

Trp Gly Val Ala Val Leu Val Gly Val Pro His Lys Asp Ala Glu Phe
        290                 295                 300

Lys Thr His Pro Met Asn Phe Leu Asn Glu Arg Thr Leu Lys Gly Thr
305                 310                 315                 320

Phe Phe Gly Asn Phe Lys Pro Arg Thr Asp Leu Pro Asn Val Val Glu
                325                 330                 335

Met Tyr Met Lys Lys Glu Leu Glu Val Glu Lys Phe Ile Thr His Ser
                340                 345                 350

Val Pro Phe Ser Glu Ile Asn Lys Ala Phe Asp Leu Met Ala Lys Gly
            355                 360                 365

Glu Gly Ile Arg Cys Ile Ile Arg Met Asp Asn
            370                 375

<210> SEQ ID NO 45
<211> LENGTH: 1140
<212> TYPE: DNA
<213> ORGANISM: Oryza sativa
<220> FEATURE:
<221> NAME/KEY: CDS
<222> LOCATION: (1)..(1137)
<223> OTHER INFORMATION: coding for alcohol dehydrogenase

<400> SEQUENCE: 45 atg gcg acc gca ggg aag gtg atc aag tgc aaa gcg gcg gtg gca tgg       48
Met Ala Thr Ala Gly Lys Val Ile Lys Cys Lys Ala Ala Val Ala Trp
 1               5                  10                  15 gag gcc gcg aag ccg ctg gtg atc gag gag gtg gag gtg gcg ccg ccg       96
Glu Ala Ala Lys Pro Leu Val Ile Glu Glu Val Glu Val Ala Pro Pro
             20                  25                  30 cag gcc atg gag gtg cgc gtc aag atc ctc ttc acc tcg ctc tgc cac      144
Gln Ala Met Glu Val Arg Val Lys Ile Leu Phe Thr Ser Leu Cys His
         35                  40                  45 acc gac gtc tac ttc tgg gag gcc aag gga cag act ccc gtg ttc cct      192
Thr Asp Val Tyr Phe Trp Glu Ala Lys Gly Gln Thr Pro Val Phe Pro
     50                  55                  60 cgg atc ttc ggc cat gaa gct gga ggt att gtg gag agt gtt gga gag      240
Arg Ile Phe Gly His Glu Ala Gly Gly Ile Val Glu Ser Val Gly Glu
 65                  70                  75                  80 ggt gtg act gat ctt gcc cct ggt gac cat gtt ctc cct gtg ttc act      288
Gly Val Thr Asp Leu Ala Pro Gly Asp His Val Leu Pro Val Phe Thr
                 85                  90                  95 ggg gag tgc aag gag tgt gcc cac tgc aag tca gca gag agc aac atg      336
Gly Glu Cys Lys Glu Cys Ala His Cys Lys Ser Ala Glu Ser Asn Met
            100                 105                 110 tgt gat ctg ctc agg atc aac act gac agg ggt gtg atg att ggt gat      384
Cys Asp Leu Leu Arg Ile Asn Thr Asp Arg Gly Val Met Ile Gly Asp
        115                 120                 125 ggc aaa tca cgc ttt tcc atc aac ggg aag ccc att tac cat ttc gtc      432
Gly Lys Ser Arg Phe Ser Ile Asn Gly Lys Pro Ile Tyr His Phe Val
    130                 135                 140 ggg act tcg acc ttc agc gag tac act gtc atg cat gtt ggt gcg gtt      480
Gly Thr Ser Thr Phe Ser Glu Tyr Thr Val Met His Val Gly Cys Val
145                 150                 155                 160
```

```
gcg aag atc aac ccg gca gct cca ctt gat aaa gtt tgc gtt ctt agc      528
Ala Lys Ile Asn Pro Ala Ala Pro Leu Asp Lys Val Cys Val Leu Ser
            165                 170                 175 tgt ggt att tct act ggt ctt ggt gct aca atc aat gtg gca aag cca      576
Cys Gly Ile Ser Thr Gly Leu Gly Ala Thr Ile Asn Val Ala Lys Pro
        180                 185                 190 cca aag ggt tcg acg gtg gcg ata ttt ggt cta gga gct gta ggc ctt      624
Pro Lys Gly Ser Thr Val Ala Ile Phe Gly Leu Gly Ala Val Gly Leu
    195                 200                 205 gct gcc gca gaa ggt gca agg att gca gga gcg tca agg atc att ggc      672
Ala Ala Ala Glu Gly Ala Arg Ile Ala Gly Ala Ser Arg Ile Ile Gly
210                 215                 220 att gac ctg aac gcc aac aga ttt gaa gaa gct agg aaa ttt ggt tgc      720
Ile Asp Leu Asn Ala Asn Arg Phe Glu Glu Ala Arg Lys Phe Gly Cys
225                 230                 235                 240 act gaa ttt gtg aac cca aag gac cat gac aag cca gtt cag cag gta      768
Thr Glu Phe Val Asn Pro Lys Asp His Asp Lys Pro Val Gln Gln Val
                245                 250                 255 ctt gct gag atg acc aat ggc gga gtt gac cgc agc gtt gaa tgc act      816
Leu Ala Glu Met Thr Asn Gly Gly Val Asp Arg Ser Val Glu Cys Thr
            260                 265                 270 ggc aac atc aac gcc atg atc caa gca ttt gaa tgt gtt cat gat ggc      864
Gly Asn Ile Asn Ala Met Ile Gln Ala Phe Glu Cys Val His Asp Gly
        275                 280                 285 tgg ggt gtt gct gtt ttg gtc ggc gtg cca cac aag gac gcc gag ttc      912
Trp Gly Val Ala Val Leu Val Gly Val Pro His Lys Asp Ala Glu Phe
    290                 295                 300 aag acc cac ccg atg aac ttc ctg aac gag agg act ctc aag gga acc      960
Lys Thr His Pro Met Asn Phe Leu Asn Glu Arg Thr Leu Lys Gly Thr
305                 310                 315                 320 ttc ttc ggc aac tac aag cca cgc acc gat ctg ccc aac gtc gtc gag     1008
Phe Phe Gly Asn Tyr Lys Pro Arg Thr Asp Leu Pro Asn Val Val Glu
                325                 330                 335 ctc tac atg aag aag gag ctg gag gtg gag aag ttc atc aca cac agc     1056
Leu Tyr Met Lys Lys Glu Leu Glu Val Glu Lys Phe Ile Thr His Ser
            340                 345                 350 gtg ccg ttc tcg gag atc aac acg gcg ttc gac ctg atg cac aag ggc     1104
Val Pro Phe Ser Glu Ile Asn Thr Ala Phe Asp Leu Met His Lys Gly
        355                 360                 365 gag ggc atc cgc tgc atc atc cgc atg gag aac tga                     1140
Glu Gly Ile Arg Cys Ile Ile Arg Met Glu Asn
    370                 375

<210> SEQ ID NO 46
<211> LENGTH: 379
<212> TYPE: PRT
<213> ORGANISM: Oryza sativa

<400> SEQUENCE: 46

Met Ala Thr Ala Gly Lys Val Ile Lys Cys Lys Ala Ala Val Ala Trp
1               5                   10                  15

Glu Ala Ala Lys Pro Leu Val Ile Glu Glu Val Glu Val Ala Pro Pro
            20                  25                  30

Gln Ala Met Glu Val Arg Val Lys Ile Leu Phe Thr Ser Leu Cys His
        35                  40                  45

Thr Asp Val Tyr Phe Trp Glu Ala Lys Gly Gln Thr Pro Val Phe Pro
    50                  55                  60

Arg Ile Phe Gly His Glu Ala Gly Gly Ile Val Glu Ser Val Gly Glu
65                  70                  75                  80
```

```
Gly Val Thr Asp Leu Ala Pro Gly Asp His Val Leu Pro Val Phe Thr
             85                  90                  95
Gly Glu Cys Lys Glu Cys Ala His Cys Lys Ser Ala Glu Ser Asn Met
        100                 105                 110
Cys Asp Leu Leu Arg Ile Asn Thr Asp Arg Gly Val Met Ile Gly Asp
            115                 120                 125
Gly Lys Ser Arg Phe Ser Ile Asn Gly Lys Pro Ile Tyr His Phe Val
130                 135                 140
Gly Thr Ser Thr Phe Ser Glu Tyr Thr Val Met His Val Gly Cys Val
145                 150                 155                 160
Ala Lys Ile Asn Pro Ala Ala Pro Leu Asp Lys Val Cys Val Leu Ser
                165                 170                 175
Cys Gly Ile Ser Thr Gly Leu Gly Ala Thr Ile Asn Val Ala Lys Pro
            180                 185                 190
Pro Lys Gly Ser Thr Val Ala Ile Phe Gly Leu Gly Ala Val Gly Leu
        195                 200                 205
Ala Ala Ala Glu Gly Ala Arg Ile Ala Gly Ala Ser Arg Ile Ile Gly
    210                 215                 220
Ile Asp Leu Asn Ala Asn Arg Phe Glu Glu Ala Arg Lys Phe Gly Cys
225                 230                 235                 240
Thr Glu Phe Val Asn Pro Lys Asp His Asp Lys Pro Val Gln Gln Val
                245                 250                 255
Leu Ala Glu Met Thr Asn Gly Gly Val Asp Arg Ser Val Glu Cys Thr
            260                 265                 270
Gly Asn Ile Asn Ala Met Ile Gln Ala Phe Glu Cys Val His Asp Gly
        275                 280                 285
Trp Gly Val Ala Val Leu Val Gly Val Pro His Lys Asp Ala Glu Phe
    290                 295                 300
Lys Thr His Pro Met Asn Phe Leu Asn Glu Arg Thr Leu Lys Gly Thr
305                 310                 315                 320
Phe Phe Gly Asn Tyr Lys Pro Arg Thr Asp Leu Pro Asn Val Val Glu
                325                 330                 335
Leu Tyr Met Lys Lys Glu Leu Glu Val Lys Phe Ile Thr His Ser
            340                 345                 350
Val Pro Phe Ser Glu Ile Asn Thr Ala Phe Asp Leu Met His Lys Gly
        355                 360                 365
Glu Gly Ile Arg Cys Ile Ile Arg Met Glu Asn
    370                 375
```

<210> SEQ ID NO 47
<211> LENGTH: 1140
<212> TYPE: DNA
<213> ORGANISM: Zea mays
<220> FEATURE:
<221> NAME/KEY: CDS
<222> LOCATION: (1)..(1137)
<223> OTHER INFORMATION: coding for alcohol dehydrogenase

<400> SEQUENCE: 47

```
atg gcg acc gcg ggg aag gtg atc aag tgc aaa gct gcg gtg gca tgg      48
Met Ala Thr Ala Gly Lys Val Ile Lys Cys Lys Ala Ala Val Ala Trp
  1               5                  10                  15 gag gcc ggc aag cca ctg tcg atc gag gag gtg gag gta gcg cct ccg      96
Glu Ala Gly Lys Pro Leu Ser Ile Glu Glu Val Glu Val Ala Pro Pro
             20                  25                  30 cag gcc atg gag gtg cgc gtc aag atc ctc ttc acc tcg ctc tgc cac     144
Gln Ala Met Glu Val Arg Val Lys Ile Leu Phe Thr Ser Leu Cys His
```

-continued

```
                35                   40                   45
acc gac gtc tac ttc tgg gag gcc aag ggg cag act ccc gtg ttc cct      192
Thr Asp Val Tyr Phe Trp Glu Ala Lys Gly Gln Thr Pro Val Phe Pro
     50                  55                  60 cgg atc ttt ggc cat gag gct gga ggt atc ata gag agt gtt gga gag      240
Arg Ile Phe Gly His Glu Ala Gly Gly Ile Ile Glu Ser Val Gly Glu
 65                  70                  75                  80 ggt gtg act gac gta gct ccg ggc gac cat gtc ctt cct gtg ttc act      288
Gly Val Thr Asp Val Ala Pro Gly Asp His Val Leu Pro Val Phe Thr
                 85                  90                  95 ggg gag tgc aag gag tgc gcc cac tgc aag tcg gca gag agc aac atg      336
Gly Glu Cys Lys Glu Cys Ala His Cys Lys Ser Ala Glu Ser Asn Met
             100                 105                 110 tgt gat ttg ctc agg atc aac act gac cgc ggt gtg atg att ggc gat      384
Cys Asp Leu Leu Arg Ile Asn Thr Asp Arg Gly Val Met Ile Gly Asp
         115                 120                 125 ggc aag tcg cgg ttt tca atc aat ggg aag cct atc tac cac ttt gtt      432
Gly Lys Ser Arg Phe Ser Ile Asn Gly Lys Pro Ile Tyr His Phe Val
     130                 135                 140 ggg act tcc acc ttc agc gag tac acc gtc atg cat gtc ggt tgt gtt      480
Gly Thr Ser Thr Phe Ser Glu Tyr Thr Val Met His Val Gly Cys Val
145                 150                 155                 160 gca aag atc aac cct cag gct ccc ctt gat aaa gtt tgc gtc ctt agc      528
Ala Lys Ile Asn Pro Gln Ala Pro Leu Asp Lys Val Cys Val Leu Ser
                165                 170                 175 tgt ggt att tct act ggt ctt ggt gca tca att aat gtt gca aaa cct      576
Cys Gly Ile Ser Thr Gly Leu Gly Ala Ser Ile Asn Val Ala Lys Pro
            180                 185                 190 ccg aag ggt tcg aca gtg gct gtt ttc ggt tta gga gcc gtt ggt ctt      624
Pro Lys Gly Ser Thr Val Ala Val Phe Gly Leu Gly Ala Val Gly Leu
        195                 200                 205 gcc gct gca gaa ggt gca agg att gct gga gcg tca agg atc att ggt      672
Ala Ala Ala Glu Gly Ala Arg Ile Ala Gly Ala Ser Arg Ile Ile Gly
    210                 215                 220 gtc gac ctg aac ccc agc aga ttc gaa gaa gct agg aag ttc ggt tgc      720
Val Asp Leu Asn Pro Ser Arg Phe Glu Glu Ala Arg Lys Phe Gly Cys
225                 230                 235                 240 act gaa ttt gtg aac cca aaa gac cac aac aag ccg gtg cag gag gta      768
Thr Glu Phe Val Asn Pro Lys Asp His Asn Lys Pro Val Gln Glu Val
                245                 250                 255 ctt gct gag atg acc aac gga ggg gtc gac cgc agc gtg gaa tgc act      816
Leu Ala Glu Met Thr Asn Gly Gly Val Asp Arg Ser Val Glu Cys Thr
            260                 265                 270 ggc aac atc aat gct atg atc caa gct ttc gaa tgt gtt cat gat ggc      864
Gly Asn Ile Asn Ala Met Ile Gln Ala Phe Glu Cys Val His Asp Gly
        275                 280                 285 tgg ggt gtt gcc gtg ctg gtg ggt gtg ccg cat aag gac gct gag ttc      912
Trp Gly Val Ala Val Leu Val Gly Val Pro His Lys Asp Ala Glu Phe
    290                 295                 300 aag acc cac ccg atg aac ttc ctg aac gaa agg acc ctg aag ggg acc      960
Lys Thr His Pro Met Asn Phe Leu Asn Glu Arg Thr Leu Lys Gly Thr
305                 310                 315                 320 ttc ttt ggc aac tat aag cca cgc act gat ctg cca aat gtg gtg gag     1008
Phe Phe Gly Asn Tyr Lys Pro Arg Thr Asp Leu Pro Asn Val Val Glu
                325                 330                 335 ctg tac atg aaa aag gag ctg gag gtg gag aag ttc atc acg cac agc     1056
Leu Tyr Met Lys Lys Glu Leu Glu Val Glu Lys Phe Ile Thr His Ser
            340                 345                 350 gtc ccg ttc gcg gag atc aac aag gcg ttc aac ctg atg gcc aag ggg     1104
Val Pro Phe Ala Glu Ile Asn Lys Ala Phe Asn Leu Met Ala Lys Gly
```

```
Val Pro Phe Ala Glu Ile Asn Lys Ala Phe Asn Leu Met Ala Lys Gly
        355                 360                 365 gag ggc atc cgc tgc atc atc cgc atg gag aac tag                    1140
Glu Gly Ile Arg Cys Ile Ile Arg Met Glu Asn
370                 375
```

<210> SEQ ID NO 48
<211> LENGTH: 379
<212> TYPE: PRT
<213> ORGANISM: Zea mays

<400> SEQUENCE: 48

```
Met Ala Thr Ala Gly Lys Val Ile Lys Cys Lys Ala Val Ala Trp
1               5                   10                  15

Glu Ala Gly Lys Pro Leu Ser Ile Glu Glu Val Glu Val Ala Pro Pro
                20                  25                  30

Gln Ala Met Glu Val Arg Val Lys Ile Leu Phe Thr Ser Leu Cys His
            35                  40                  45

Thr Asp Val Tyr Phe Trp Glu Ala Lys Gly Gln Thr Pro Val Phe Pro
    50                  55                  60

Arg Ile Phe Gly His Glu Ala Gly Ile Ile Glu Ser Val Gly Glu
65                  70                  75                  80

Gly Val Thr Asp Val Ala Pro Gly Asp His Val Leu Pro Val Phe Thr
                85                  90                  95

Gly Glu Cys Lys Glu Cys Ala His Cys Lys Ser Ala Glu Ser Asn Met
            100                 105                 110

Cys Asp Leu Leu Arg Ile Asn Thr Asp Arg Gly Val Met Ile Gly Asp
        115                 120                 125

Gly Lys Ser Arg Phe Ser Ile Asn Gly Lys Pro Ile Tyr His Phe Val
    130                 135                 140

Gly Thr Ser Thr Phe Ser Glu Tyr Thr Val Met His Val Gly Cys Val
145                 150                 155                 160

Ala Lys Ile Asn Pro Gln Ala Pro Leu Asp Lys Val Cys Val Leu Ser
                165                 170                 175

Cys Gly Ile Ser Thr Gly Leu Gly Ala Ser Ile Asn Val Ala Lys Pro
            180                 185                 190

Pro Lys Gly Ser Thr Val Ala Val Phe Gly Leu Gly Ala Val Gly Leu
        195                 200                 205

Ala Ala Ala Glu Gly Ala Arg Ile Ala Gly Ala Ser Arg Ile Ile Gly
    210                 215                 220

Val Asp Leu Asn Pro Ser Arg Phe Glu Glu Ala Arg Lys Phe Gly Cys
225                 230                 235                 240

Thr Glu Phe Val Asn Pro Lys Asp His Asn Lys Pro Val Gln Glu Val
                245                 250                 255

Leu Ala Glu Met Thr Asn Gly Gly Val Asp Arg Ser Val Glu Cys Thr
            260                 265                 270

Gly Asn Ile Asn Ala Met Ile Gln Ala Phe Glu Cys Val His Asp Gly
        275                 280                 285

Trp Gly Val Ala Val Leu Val Gly Val Pro His Lys Asp Ala Glu Phe
    290                 295                 300

Lys Thr His Pro Met Asn Phe Leu Asn Glu Arg Thr Leu Lys Gly Thr
305                 310                 315                 320

Phe Phe Gly Asn Tyr Lys Pro Arg Thr Asp Leu Pro Asn Val Val Glu
                325                 330                 335

Leu Tyr Met Lys Lys Glu Leu Glu Val Glu Lys Phe Ile Thr His Ser
```

```
            340                 345                 350
Val Pro Phe Ala Glu Ile Asn Lys Ala Phe Asn Leu Met Ala Lys Gly
        355                 360                 365

Glu Gly Ile Arg Cys Ile Ile Arg Met Glu Asn
    370                 375
```

<210> SEQ ID NO 49
<211> LENGTH: 505
<212> TYPE: DNA
<213> ORGANISM: Artificial sequence
<220> FEATURE:
<223> OTHER INFORMATION: Description of the artificial sequence: coding
      for sense RNA-fragment of E.coli codA gene

<400> SEQUENCE: 49

```
aagcttggct aacagtgtcg aataacgctt tacaaacaat tattaacgcc cggttaccag    60
gcgaagaggg gctgtggcag attcatctgc aggacggaaa atcagcgcc  attgatgcgc   120 aatccggcgt gatgcccata actgaaaaca gcctggatgc cgaacaaggt ttagttatac   180
cgccgtttgt ggagccacat attcacctgg acaccacgca aaccgccgga caaccgaact   240
ggaatcagtc cggcacgctg tttgaaggca ttgaacgctg ggccgagcgc aaagcgttat   300
taacccatga cgatgtgaaa caacgcgcat ggcaaacgct gaaatggcag attgccaacg   360
gcattcagca tgtgcgtacc catgtcgatg tttcggatgc aacgctaact gcgctgaaag   420
caatgctgga agtgaagcag gaagtcgcgc cgtggattga tctgcaaatc gtcgccttcc   480
ctcaggaagg gatttttgtcg tcgac                                        505
```

<210> SEQ ID NO 50
<211> LENGTH: 27
<212> TYPE: DNA
<213> ORGANISM: Artificial sequence
<220> FEATURE:
<223> OTHER INFORMATION: Description of the artificial sequence:
      oligonucleotide primer

<400> SEQUENCE: 50

```
aagcttggct aacagtgtcg aataacg                                        27
```

<210> SEQ ID NO 51
<211> LENGTH: 26
<212> TYPE: DNA
<213> ORGANISM: Artificial sequence
<220> FEATURE:
<223> OTHER INFORMATION: Description of the artificial sequence:
      oligonucleotide primer

<400> SEQUENCE: 51

```
gtcgacgaca aaatcccttc ctgagg                                         26
```

<210> SEQ ID NO 52
<211> LENGTH: 505
<212> TYPE: DNA
<213> ORGANISM: Artificial sequence
<220> FEATURE:
<223> OTHER INFORMATION: Description of the artificial sequence: coding
      for antisense RNA-fragment of E.coli codA gene

<400> SEQUENCE: 52

```
gaattcggct aacagtgtcg aataacgctt tacaaacaat tattaacgcc cggttaccag    60
gcgaagaggg gctgtggcag attcatctgc aggacggaaa atcagcgcc  attgatgcgc   120 aatccggcgt gatgcccata actgaaaaca gcctggatgc cgaacaaggt ttagttatac   180
```

```
cgccgtttgt ggagccacat attcacctgg acaccacgca aaccgccgga caaccgaact      240
ggaatcagtc cggcacgctg tttgaaggca ttgaacgctg ggccgagcgc aaagcgttat      300
taacccatga cgatgtgaaa caacgcgcat ggcaaacgct gaaatggcag attgccaacg      360
gcattcagca tgtgcgtacc catgtcgatg tttcggatgc aacgctaact gcgctgaaag      420
caatgctgga agtgaagcag gaagtcgcgc cgtggattga tctgcaaatc gtcgccttcc      480
ctcaggaagg gattttgtcg gatcc                                             505
```

<210> SEQ ID NO 53
<211> LENGTH: 27
<212> TYPE: DNA
<213> ORGANISM: Artificial sequence
<220> FEATURE:
<223> OTHER INFORMATION: Description of the artificial sequence:
      oligonucleotide primer

<400> SEQUENCE: 53

```
gaattcggct aacagtgtcg aataacg                                           27
```

<210> SEQ ID NO 54
<211> LENGTH: 26
<212> TYPE: DNA
<213> ORGANISM: Artificial sequence
<220> FEATURE:
<223> OTHER INFORMATION: Description of the artificial sequence:
      oligonucleotide primer

<400> SEQUENCE: 54

```
ggatccgaca aaatcccttc ctgagg                                            26
```

<210> SEQ ID NO 55
<211> LENGTH: 5674
<212> TYPE: DNA
<213> ORGANISM: Artificial sequence
<220> FEATURE:
<223> OTHER INFORMATION: Description of the artificial sequence: vector
      construct pBluKS-nitP-STLS1-35S-T
<220> FEATURE:
<221> NAME/KEY: misc_feature
<222> LOCATION: (5014)..(5014)
<223> OTHER INFORMATION: n is a, c, g, or t

<400> SEQUENCE: 55

```
ccagcttttg ttcccttag tgagggttaa tttcgagctt ggcgtaatca tggtcatagc       60
tgtttcctgt gtgaaattgt tatccgctca caattccaca caacatacga gccggaagca      120
taaagtgtaa agcctggggt gcctaatgag tgagctaact cacattaatt gcgttgcgct      180
cactgcccgc tttccagtcg ggaaacctgt cgtgccagct gcattaatga atcggccaac      240
gcgcggggag aggcggtttg cgtattgggc gctcttccgc ttcctcgctc actgactcgc      300
tgcgctcggt cgttcggctg cggcgagcgg tatcagctca ctcaaaggcg gtaatacggt      360
tatccacaga atcaggggat aacgcaggaa agaacatgtg agcaaaaggc cagcaaaagg      420
ccaggaaccg taaaaaggcc gcgttgctgg cgttttttcca taggctccgc cccccctgacg     480 agcatcacaa aaatcgacgc tcaagtcaga ggtggcgaaa cccgacagga ctataaagat      540
accaggcgtt tccccctgga agctccctcg tgcgctctcc tgttccgacc ctgccgctta      600
ccggatacct gtccgccttt ctcccttcgg gaagcgtggc gctttctcat agctcacgct      660
gtaggtatct cagttcggtg taggtcgttc gctccaagct gggctgtgtg cacgaacccc      720
ccgttcagcc cgaccgctgc gccttatccg gtaactatcg tcttgagtcc aacccggtaa      780
```

-continued

```
gacacgactt atcgccactg gcagcagcca ctggtaacag gattagcaga gcgaggtatg      840
taggcggtgc tacagagttc ttgaagtggt ggcctaacta cggctacact agaaggacag      900
tatttggtat ctgcgctctg ctgaagccag ttaccttcgg aaaaagagtt ggtagctctt      960
gatccggcaa acaaaccacc gctggtagcg gtggttttt tgtttgcaag cagcagatta     1020
cgcgcagaaa aaaggatct caagaagatc ctttgatctt ttctacgggg tctgacgctc      1080
agtggaacga aaactcacgt taagggattt tggtcatgag attatcaaaa aggatcttca     1140
cctagatcct tttaaattaa aaatgaagtt ttaaatcaat ctaaagtata tatgagtaaa     1200
cttggtctga cagttaccaa tgcttaatca gtgaggcacc tatctcagcg atctgtctat     1260
ttcgttcatc catagttgcc tgactcccg tcgtgtagat aactacgata cgggagggct      1320
taccatctgg ccccagtgct gcaatgatac cgcgagaccc acgctcaccg gctccagatt     1380
tatcagcaat aaaccagcca gccggaaggg ccgagcgcag aagtggtcct gcaactttat     1440
ccgcctccat ccagtctatt aattgttgcc gggaagctag agtaagtagt tcgccagtta     1500
atagtttgcg caacgttgtt gccattgcta caggcatcgt ggtgtcacgc tcgtcgtttg     1560
gtatggcttc attcagctcc ggttcccaac gatcaaggcg agttacatga tcccccatgt     1620
tgtgcaaaaa agcggttagc tccttcggtc ctccgatcgt tgtcagaagt aagttggccg     1680
cagtgttatc actcatggtt atggcagcac tgcataattc tcttactgtc atgccatccg     1740
taagatgctt ttctgtgact ggtgagtact caaccaagtc attctgagaa tagtgtatgc     1800
ggcgaccgag ttgctcttgc ccggcgtcaa tacgggataa taccgcgcca catagcagaa     1860
ctttaaaagt gctcatcatt ggaaaacgtt cttcggggcg aaaactctca aggatcttac     1920
cgctgttgag atccagttcg atgtaaccca ctcgtgcacc caactgatct tcagcatctt     1980
ttactttcac cagcgtttct gggtgagcaa aaacaggaag gcaaaatgcc gcaaaaaagg     2040
gaataagggc gacacggaaa tgttgaatac tcatactctt cctttttcaa tattattgaa     2100
gcatttatca gggttattgt ctcatgagcg gatacatatt tgaatgtatt tagaaaaata     2160
aacaaatagg ggttccgcgc acatttcccc gaaaagtgcc acctgacgcg ccctgtagcg     2220
gcgcattaag cgcggcgggt gtggtggtta cgcgcagcgt gaccgctaca cttgccagcg     2280
ccctagcgcc cgctccttc gctttcttcc cttcctttct cgccacgttc gccggctttc      2340
cccgtcaagc tctaaatcgg gggctccctt tagggttccg atttagtgct ttacggcacc     2400
tcgaccccaa aaaacttgat tagggtgatg gttcacgtag tgggccatcg ccctgataga     2460 cggttttcg ccctttgacg ttggagtcca cgttctttaa tagtggactc ttgttccaaa      2520
ctggaacaac actcaaccct atctcggtct attcttttga tttataaggg attttgccga     2580
tttcggccta ttggttaaaa aatgagctga tttaacaaaa atttaacgcg aattttaaca     2640
aaatattaac gcttacaatt tccattcgcc attcaggctg cgcaactgtt gggaagggcg     2700
atcggtgcgg gcctcttcgc tattacgcca gctggcgaaa gggggatgtg ctgcaaggcg     2760
attaagttgg gtaacgccag ggttttccca gtcacgacgt tgtaaaacga cggccagtga     2820
attgtaatac gactcactat agggcgaatt ggagctcgtc gagaccagat gttttacact     2880
tgaccgtaaa tgagcacccg aagaaaccgg tcacattcat ttcgaaggtg gagaaagcgg     2940
aagatgactc aaacaagtaa tcggttgtga ttcgtcagtt catgtcactc ctatgaagga     3000
gtcaagttca aaatgttatg ttgagtttca aacttttatg ctaaactttt tttcttatt     3060 ttcgttaata atggaagaga accaattctc ttgtatctaa agattatcca tctatcatcc     3120
```

```
aatttgagtg ttcaattctg gatgttgtgt taccctacat tctacaacca tgtagccaat    3180
tattatgaat ctggctttga tttcagttgt gttcttttct ttttttttctt tgcatatttt    3240 catttagaat gtttaataat taagttactg tatttccaca tacattagtt ccaagaatat    3300
acatatatta atttatttt cttaaaaatg ttttggaatg actaatattg acaacgaaaa    3360
tagaagctat gctaaaccat tacgtatatg tgacttcaca tgttgttgtt ttacattccc    3420
tatatatatg gatggctgtc acaatcagaa acgtgatcga aaaaagacaa acagtgtttg    3480
cataaaaaga ctatttcgtt tcattgacaa tttgtgttta tttgtaaaga aaagtggcaa    3540
agtggaattt gagttcctgc aagtaagaaa gatgaaataa aagacttgag tgtgtgtttt    3600
tttcttttat ctgaaagctg caatgaaata ttcctaccaa gcccgtttga ttattaattg    3660
gggtttggtt ttcttgatgc gaactaattg gttatataag aaactataca atccatgtta    3720
attcaaaaat tttgatttct cttgtaggaa tatgatttac tatatgagac tttcttttcg    3780
ccaataatag taaatccaaa gatatttgac cggaccaaaa cacattgatc tatttttag    3840 tttatttaat ccagtttctc tgagataatt cattaaggaa aacttagtat taacccatcc    3900
taagattaaa taggagccaa actcacattt caaatattaa ataacataaa atggatttaa    3960
aaaatctata cgtcaaattt tatttatgac atttcttatt taaatttata tttaatgaaa    4020
tacagctaag acaaaccaaa aaaaaaatac tttctaagtg gtccaaaaca tcaattccgt    4080
tcaatattat taggtagaat cgtacgacca aaaaaaggta ggttaatacg aattagaaac    4140
atatctataa catagtatat attattaccct attatgagga atcaaaatgc atcaaatatg    4200
gatttaagga atccataaaa gaataaattc tacgggaaaa aaaatggaat aaattctttt    4260 aagttttta tttgtttttt atttggtagt tctccatttt gttttatttc gtttggatt    4320 attgtgtcca aatactttgt aaaccaccgt tgtaattctt aaacggggtt ttcacttctt    4380
ttttatattc agacataaag catcggctgg tttaatcaat caatagattt tattttctt    4440 ctcaattatt agtaggtttg atgtgaactt tacaaaaaaa acaaaaacaa atcaatgcag    4500
agaaaagaaa ccacgtgggc tagtcccacc ttgtttcatt tccaccacag gttcgatctt    4560
cgttaccgtc tccaatagga aaataaacgt gaccacaaaa aaaaaacaaa aaaaagtcta    4620
tatattgctt ctctcaagtc tctgagtgtc atgaaccaaa gtaaaaaaca aagactcgac    4680
ctgcaggcat gcaagcttat cgtcgactac gtaagtttct gcttctacct ttgatatata    4740
tataataatt atcattaatt agtagtaata taatatttca aatatttttt tcaaaataaa    4800
agaatgtagt atatagcaat tgcttttctg tagtttataa gtgtgtatat tttaatttat    4860
aactttctca atatatgacc aaaatttgtt gatgtgcagg tatcaccgga tccatcgaat    4920
tcggtacgct gaaatcacca gtctctctct acaaatctat ctctctctat tttctccata    4980
aataatgtgt gagtagtttc ccgataaggg gaanttaggg ttcttatagg gtttcgctca    5040
tgtgttgagc atataagaaa cccttagtat gtatttgtat ttgtaaaata cttctatcaa    5100 taaaattct aattcctaaa accaaaatcc agtactaaaa tccagatctc ctaaagtccc    5160
tatagatctt tgtcgtgaat ataaaccaga cacgagacga ctaaacctgg agcccagacg    5220
ccgttcgaag ctagaagtac cgcttaggca ggaggccgtt agggaaaaga tgctaaggca    5280
gggttggtta cgttgactcc cccgtaggtt tggtttaaat atgatgaagt ggacggaagg    5340
aaggaggaag acaaggaagg ataaggttgc aggccctgtg caaggtaaga agatggaaat    5400
ttgatagagg tacgctacta tacttatact atacgctaag ggaatgcttg tatttatacc    5460
ctataccccc taataacccc ttatcaattt aagaaataat ccgcataagc cccgcttaa    5520
```

-continued

```
aaattggtat cagagccatg aataggtcta tgaccaaaac tcaagaggat aaaacctcac    5580
caaaatacga aagagttctt aactctaaag ataaaagatc tttcaagatc aaaactagtt    5640
ccctcacacc ggtgacgggg atcgcgatgg gtac                                5674

<210> SEQ ID NO 56
<211> LENGTH: 6046
<212> TYPE: DNA
<213> ORGANISM: Artificial sequence
<220> FEATURE:
<223> OTHER INFORMATION: Description of the artificial sequence: binary
      vector pSUN1

<400> SEQUENCE: 56
ttccatggac atacaaatgg acgaacggat aaacctttc acgcccttt aaatatccga       60 ttattctaat aaacgctctt ttctcttagg tttacccgcc aatatatcct gtcaaacact    120
gatagtttaa actgaaggcg ggaaacgaca atcagatcta gtaggaaaca gctatgacca    180
tgattacgcc aagcttgcat gcctgcaggt cgactctaga ctagtggatc cgatatcgcc    240
cgggctcgag gtaccgagct cgaattcact ggccgtcgtt ttacaacgac tcagctgctt    300
ggtaataatt gtcattagat tgtttttatg catagatgca ctcgaaatca gccaatttta    360
gacaagtatc aaacggatgt taattcagta cattaaagac gtccgcaatg tgttattaag    420
ttgtctaagc gtcaatttgt ttacaccaca atatatcctg ccaccagcca gccaacagct    480
ccccgaccgg cagctcggca caaaatcacc acgcgttacc accacgccgg ccggccgcat    540
ggtgttgacc gtgttcgccg gcattgccga gttcgagcgt tccctaatca tcgaccgcac    600
ccggagcggg cgcgaggccg ccaaggcccg aggcgtgaag tttggccccc gccctaccct    660
caccccggca cagatcgcgc acgcccgcga gctgatcgac caggaaggcc gcaccgtgaa    720
agaggcggct gcactgcttg gcgtgcatcg ctcgaccctg taccgcgcac ttgagcgcag    780
cgaggaagtg acgcccaccg aggccaggcg gcgcggtgcc ttccgtgagg acgcattgac    840
cgaggccgac gccctggcgg ccgccgagaa tgaacgccaa gaggaacaag catgaaaccg    900
caccaggacg gccaggacga accgtttttc attaccgaag agatcgaggc ggagatgatc    960
gcggccgggt acgtgttcga gccgcccgcg cacgtctcaa ccgtgcggct gcatgaaatc    1020
ctggccggtt tgtctgatgc caagctggcg gcctggccgg ccagcttggc cgctgaagaa    1080
accgagcgcc gccgtctaaa aggtgatgt gtatttgagt aaaacagctt gcgtcatgcg    1140
gtcgctgcgt atatgatgcg atgagtaaat aaacaaatac gcaaggggaa cgcatgaagg    1200
ttatcgctgt acttaaccag aaaggcgggt caggcaagac gaccatcgca acccatctag    1260
cccgcgccct gcaactcgcc ggggccgatg ttctgttagt cgattccgat ccccagggca    1320
gtgcccgcga ttgggcggcc gtgcgggaag atcaaccgct aaccgttgtc ggcatcgacc    1380
gcccgacgat tgaccgcgac gtgaaggcca tcggccggcg cgacttcgta gtgatcgacg    1440
gagcgcccca gcggcggac ttggctgtgt ccgcgatcaa ggcagccgac ttcgtgctga    1500
ttccggtgca gccaagcct tacgacatat gggccaccgc cgacctggtg gagctggtta    1560
agcagcgcat tgaggtcacg gatggaaggc tacaagcggc ctttgtcgtg tcgcgggcga    1620
tcaaaggcac gcgcatcggc ggtgaggttg ccgaggcgct ggccgggtac gagctgccca    1680
ttcttgagtc ccgtatcacg cagcgcgtga gctacccagg cactgccgcc gccggcacaa    1740
ccgttcttga atcagaaccc gagggcgacg ctgcccgcga ggtccaggcg ctggccgctg    1800
aaattaaatc aaaactcatt tgagttaatg aggtaaagag aaaatgagca aaagcacaaa    1860
```

```
cacgctaagt gccggccgtc cgagcgcacg cagcagcaag gctgcaacgt tggccagcct   1920
ggcagacacg ccagccatga agcgggtcaa ctttcagttg ccggcggagg atcacaccaa   1980
gctgaagatg tacgcggtac gccaaggcaa gaccattacc gagctgctat ctgaatacat   2040
cgcgcagcta ccagagtaaa tgagcaaatg aataaatgag tagatgaatt ttagcggcta   2100
aaggaggcgg catggaaaat caagaacaac caggcaccga cgccgtggaa tgccccatgt   2160
gtggaggaac gggcggttgg ccaggcgtaa gcggctgggt tgtctgccgg ccctgcaatg   2220
gcactggaac ccccaagccc gaggaatcgg cgtgagcggc cgcaaaccat ccggcccggt   2280
acaaatcggc gcggcgctgg gtgatgacct ggtggagaag ttgaaggccg cgcaggccgc   2340
ccagcggcaa cgcatcgagg cagaagcacg ccccggtgaa tcgtggcaag cggccgctga   2400
tcgaatccgc aaagaatccc ggcaaccgcc ggcagccggt gcgccgtcga ttaggaagcc   2460
gcccaagggc gacgagcaac cagatttttt cgttccgatg ctctatgacg tgggcacccg   2520
cgatagtcgc agcatcatgg acgtggccgt tttccgtctg tcgaagcgtg accgacgagc   2580
tggcgaggtg atccgctacg agcttccaga cgggcacgta gaggtttccg cagggccggc   2640
cggcatggcc agtgtgtggg attacgacct ggtactgatg gcggtttccc atctaaccga   2700
atccatgaac cgataccggg aagggaaggg agacaagccc ggccgcgtgt ccgtccaca   2760 cgttgcggac gtactcaagt tctgccggcg agccgatggc ggaaagcaga aagacgacct   2820
ggtagaaacc tgcattcggt taaacaccac gcacgttgcc atgcagcgta cgaagaaggc   2880
caagaacggc cgcctggtga cggtatccga gggtgaagcc ttgattagcc gctacaagat   2940
cgtaaagagc gaaaccgggc ggccggagta catcgagatc gagctagctg attggatgta   3000
ccgcgagatc acagaaggca agaacccgga cgtgctgacg gttcaccccg attactttt   3060 gatcgatccc ggcatcggcc gttttctcta ccgcctggca cgccgcgccg caggcaaggc   3120
agaagccaga tggttgttca agacgatcta cgaacgcagt ggcagcgccg gagagttcaa   3180
gaagttctgt ttcaccgtgc gcaagctgat cgggtcaaat gacctgccgg agtacgattt   3240
gaaggaggag gcggggcagg ctggcccgat cctagtcatg cgctaccgca acctgatcga   3300
gggcgaagca tccgccggtt cctaatgtac ggagcagatg ctagggcaaa ttgccctagc   3360
aggggaaaaa ggtcgaaaag gtctctttcc tgtggatagc acgtacattg gaacccaaa   3420 gccgtacatt gggaaccgga acccgtacat tgggaaccca agccgtaca ttgggaaccg   3480 gtcacacatg taagtgactg atataaaaga gaaaaaggc gattttccg cctaaaactc   3540 tttaaacctt attaaaactc ttaaacccg cctggcctgt gcataactgt ctggccagcg   3600
cacagccgaa gagctgcaaa aagcgcctac ccttcggtcg ctgcgctccc tacgccccgc   3660
cgcttcgcgt cggcctatcg cggccgctgg ccgctcaaaa atggctggcc tacggccagg   3720
caatctacca gggcgcggac aagcgcgcc gtcgccactc gaccgccggc gcccacatca   3780
aggcaccctg cctcgcgcgt ttcggtgatg acggtgaaaa cctctgacac atgcagctcc   3840
cggagacggt cacagcttgt ctgtaagcgg atgccgggag cagacaagcc cgtcagggcg   3900
cgtcagcggg tgttggcggg tgtcggggcg cagccatgac ccagtcacgt agcgatagcg   3960
gagtgtatac tggcttaact atgcggcatc agagcagatt gtactgagag tgcaccatat   4020
gcggtgtgaa ataccgcaca gatgcgtaag gagaaaatac cgcatcaggc gctcttccgc   4080
ttcctcgctc actgactcgc tgcgctcggt cgttcggctg cggcgagcgg tatcagctca   4140
ctcaaaggcg gtaatacggt tatccacaga atcagggat aacgcaggaa agaacatgtg   4200
```

```
agcaaaaggc cagcaaaagg ccaggaaccg taaaaaggcc gcgttgctgg cgttttccca    4260
taggctccgc ccccctgacg agcatcacaa aaatcgacgc tcaagtcaga ggtggcgaaa    4320
cccgacagga ctataaagat accaggcgtt tccccctgga agctccctcg tgcgctctcc    4380
tgttccgacc ctgccgctta ccggatacct gtccgccttt ctcccttcgg gaagcgtggc    4440
gctttctcat agctcacgct gtaggtatct cagttcggtg taggtcgttc gctccaagct    4500
gggctgtgtg cacgaacccc ccgttcagcc cgaccgctgc gccttatccg gtaactatcg    4560
tcttgagtcc aacccggtaa gacacgactt atcgccactg gcagcagcca ctggtaacag    4620
gattagcaga gcgaggtatg taggcggtgc tacagagttc ttgaagtggt ggcctaacta    4680
cggctacact agaaggacag tatttggtat ctgcgctctg ctgaagccag ttaccttcgg    4740
aaaaagagtt ggtagctctt gatccggcaa acaaaccacc gctggtagcg gtggtttttt    4800
tgtttgcaag cagcagatta cgcgcagaaa aaaaggatct caagaagatc ctttgatctt    4860
ttctacgggg tctgacgctc agtggaacga aaactcacgt taagggattt tggtcatgca    4920
tgatatatct cccaatttgt gtagggctta ttatgcacgc ttaaaaataa taaaagcaga    4980
cttgacctga tagtttggct gtgagcaatt atgtgcttag tgcatctaac gcttgagtta    5040
agccgcgccg cgaagcggcg tcggcttgaa cgaatttcta gctagacatt atttgccgac    5100
taccttggtg atctcgcctt tcacgtagtg acaaattct tccaactgat ctgcgcgcga    5160
ggccaagcga tcttcttctt gtccaagata agcctgtcta gcttcaagta tgacgggctg    5220
atactgggcc ggcaggcgct ccattgccca gtcggcagcg acatccttcg gcgcgatttt    5280
gccggttact gcgctgtacc aaatgcggga caacgtaagc actacatttc gctcatcgcc    5340
agcccagtcg ggcggcgagt tccatagcgt taaggtttca tttagcgcct caaatagatc    5400
ctgttcagga accggatcaa agagttcctc cgccgctgga cctaccaagg caacgctatg    5460
ttctcttgct tttgtcagca agatagccag atcaatgtcg atcgtggctg gctcgaagat    5520
acctgcaaga atgtcattgc gctgccattc tccaaattgc agttcgcgct tagctggata    5580
acgccacgga atgatgtcgt cgtgcacaac aatggtgact tctacagcgc ggagaatctc    5640
gctctctcca ggggaagccg aagtttccaa aaggtcgttg atcaaagctc gccgcgttgt    5700
ttcatcaagc cttacggtca ccgtaaccag caaatcaata tcactgtgtg gcttcaggcc    5760
gccatccact gcggagccgt acaaatgtac ggccagcaac gtcggttcga gatggcgctc    5820
gatgacgcca actacctctg atagttgagt cgatacttcg gcgatcaccg cttccccccat    5880 gatgtttaac tttgttttag ggcgactgcc ctgctgcgta acatcgttgc tgctccataa    5940
catcaaacat cgacccacgg cgtaacgcgc ttgctgcttg gatgcccgag gcatagactg    6000
taccccaaaa aaacagtcat aacaagccat gaaaaccgcc actgcg                    6046
```

<210> SEQ ID NO 57
<211> LENGTH: 9838
<212> TYPE: DNA
<213> ORGANISM: Artificial sequence
<220> FEATURE:
<223> OTHER INFORMATION: Description of the artificial sequence:
      Transgenic expression vector for codA dsRNA pSUN1-codA-RNAi
<220> FEATURE:
<221> NAME/KEY: misc_feature
<222> LOCATION: (6697)..(6697)
<223> OTHER INFORMATION: n is a, c, g, or t

<400> SEQUENCE: 57

```
cgaattcact ggccgtcgtt ttacaacgac tcagctgctt ggtaataatt gtcattagat    60
```

```
tgtttttatg catagatgca ctcgaaatca gccaatttta gacaagtatc aaacggatgt    120
taattcagta cattaaagac gtccgcaatg tgttattaag ttgtctaagc gtcaatttgt    180
ttacaccaca atatatcctg ccaccagcca gccaacagct ccccgaccgg cagctcggca    240
caaaatcacc acgcgttacc accacgccgg ccggccgcat ggtgttgacc gtgttcgccg    300
gcattgccga gttcgagcgt tccctaatca tcgaccgcac ccggagcggg cgcgaggccg    360
ccaaggcccg aggcgtgaag tttggccccc gccctaccct caccccggca cagatcgcgc    420
acgcccgcga gctgatcgac caggaaggcc gcaccgtgaa agaggcggct gcactgcttg    480
gcgtgcatcg ctcgaccctg taccgcgcac ttgagcgcag cgaggaagtg acgcccaccg    540
aggccaggcg gcgcggtgcc ttccgtgagg acgcattgac cgaggccgac gccctggcgg    600
ccgccgagaa tgaacgccaa gaggaacaag catgaaaccg caccaggacg ccaggacga    660 accgttttc attaccgaag agatcgaggc ggagatgatc gcggccgggt acgtgttcga    720
gccgcccgcg cacgtctcaa ccgtgcggct gcatgaaatc ctggccggtt tgtctgatgc    780
caagctggcg gcctggccgg ccagcttggc cgctgaagaa accgagcgcc gccgtctaaa    840
aaggtgatgt gtatttgagt aaaacagctt gcgtcatgcg gtcgctgcgt atatgatgcg    900
atgagtaaat aaacaaatac gcaaggggaa cgcatgaagg ttatcgctgt acttaaccag    960
aaaggcgggt caggcaagac gaccatcgca acccatctag cccgcgccct gcaactcgcc   1020
ggggccgatg ttctgttagt cgattccgat ccccagggca gtgcccgcga ttgggcggcc   1080
gtgcgggaag atcaaccgct aaccgttgtc ggcatcgacc gcccgacgat tgaccgcgac   1140
gtgaaggcca tcggccggcg cgacttcgta gtgatcgacg gagcgcccca ggcggcggac   1200
ttggctgtgt ccgcgatcaa gcagccgac ttcgtgctga ttccggtgca gccaagccct   1260
tacgacatat gggccaccgc cgacctggtg gagctggtta agcagcgcat tgaggtcacg   1320
gatggaaggc tacaagcggc cttcgtcgtg tcgcgggcga tcaaaggcac gcgcatcggc   1380
ggtgaggttg ccgaggcgct ggccgggtac gagctgccca ttcttgagtc ccgtatcacg   1440
cagcgcgtga gctacccagg cactgccgcc gccggcacaa ccgttcttga atcagaaccc   1500
gagggcgacg ctgcccgcga ggtccaggcg ctggccgctg aaattaaatc aaaactcatt   1560
tgagttaatg aggtaaagag aaaatgagca aaagcacaaa cacgctaagt gccggccgtc   1620
cgagcgcacg cagcagcaag gctgcaacgt tggccagcct ggcagacacg ccagccatga   1680
agcgggtcaa ctttcagttg ccggcggagg atcacaccaa gctgaagatg tacgcggtac   1740
gccaaggcaa gaccattacc gagctgctat ctgaatacat cgcgcagcta ccagagtaaa   1800
tgagcaaatg aataaatgag tagatgaatt ttagcggcta aaggaggcgg catggaaaat   1860
caagaacaac caggcaccga cgccgtggaa tgccccatgt gtggaggaac gggcggttgg   1920
ccaggcgtaa gcggctgggt tgtctgccgg ccctgcaatg gcactggaac ccccaagccc   1980
gaggaatcgg cgtgagcggt cgcaaaccat ccggcccggt acaaatcggc gcggcgctgg   2040
gtgatgacct ggtggagaag ttgaaggccg cgcaggccgc ccagcggcaa cgcatcgagg   2100
cagaagcacg ccccggtgaa tcgtggcaag cggccgctga tcgaatccgc aaagaatccc   2160
ggcaaccgcc ggcagccggt gcgccgtcga ttaggaagcc gcccaagggc gacgagcaac   2220
cagatttttt cgttccgatg ctctatgacg tgggcacccg cgatagtcgc agcatcatgg   2280
acgtggccgt tttccgtctg tcgaagcgtg accgacgagc tggcgaggtg atccgctacg   2340
agcttccaga cgggcacgta gaggtttccg caggccggc cggcatggcc agtgtgtggg   2400
attacgacct ggtactgatg gcggtttccc atctaaccga atccatgaac cgataccggg   2460
```

```
aagggaaggg agacaagccc ggccgcgtgt tccgtccaca cgttgcggac gtactcaagt    2520
tctgccggcg agccgatggc ggaaagcaga aagacgacct ggtagaaacc tgcattcggt    2580
taaacaccac gcacgttgcc atgcagcgta cgaagaaggc caagaacggc cgcctggtga    2640
cggtatccga gggtgaagcc ttgattagcc gctacaagat cgtaaagagc gaaaccgggc    2700
ggccggagta catcgagatc gagctagctg attggatgta ccgcgagatc acagaaggca    2760
agaacccgga cgtgctgacg gttcaccccg attactttt gatcgatccc ggcatcggcc    2820
gttttctcta ccgcctggca cgccgcgccg caggcaaggc agaagccaga tggttgttca    2880
agacgatcta cgaacgcagt ggcagcgccg gagagttcaa gaagttctgt ttcaccgtgc    2940
gcaagctgat cgggtcaaat gacctgccgg agtacgattt gaaggaggag gcggggcagg    3000
ctggcccgat cctagtcatg cgctaccgca acctgatcga gggcgaagca tccgccggtt    3060
cctaatgtac ggagcagatg ctagggcaaa ttgccctagc aggggaaaaa ggtcgaaaag    3120
gtctctttcc tgtggatagc acgtacattg ggaacccaaa gccgtacatt gggaaccgga    3180
acccgtacat tgggaaccca aagccgtaca ttgggaaccg gtcacacatg taagtgactg    3240
atataaaaga gaaaaaggc gattttccg cctaaaactc tttaaaactt attaaaactc    3300
ttaaaacccg cctggcctgt gcataactgt ctggccagcg cacagccgaa gagctgcaaa    3360
aagcgcctac ccttcggtcg ctgcgctccc tacgcccgc cgcttcgcgt cggcctatcg    3420
cggccgctgg ccgctcaaaa atggctggcc tacggccagg caatctacca gggcgcggac    3480
aagccgcgcc gtcgccactc gaccgccggc gcccacatca aggcaccctg cctcgcgcgt    3540
ttcggtgatg acggtgaaaa cctctgacac atgcagctcc cggagacggt cacagcttgt    3600
ctgtaagcgg atgccgggag cagacaagcc cgtcagggcg cgtcagcggg tgttggcggg    3660
tgtcggggcg cagccatgac ccagtcacgt agcgatagcg gagtgtatac tggcttaact    3720
atgcggcatc agagcagatt gtactgagag tgcaccatat gcggtgtgaa ataccgcaca    3780
gatgcgtaag gagaaaatac cgcatcaggc gctcttccgc ttcctcgctc actgactcgc    3840
tgcgctcggt cgttcggctg cggcgagcgg tatcagctca ctcaaaggcg gtaatacggt    3900
tatccacaga atcaggggat aacgcaggaa agaacatgtg agcaaaaggc cagcaaaagg    3960
ccaggaaccg taaaaaggcc gcgttgctgg cgttttccca taggctccgc cccctgacg    4020 agcatcacaa aaatcgacgc tcaagtcaga ggtggcgaaa cccgacagga ctataaagat    4080
accaggcgtt tccccctgga agctccctcg tgcgctctcc tgttccgacc ctgccgctta    4140
ccggatacct gtccgccttt ctcccttcgg gaagcgtggc gctttctcat agctcacgct    4200
gtaggtatct cagttcggtg taggtcgttc gctccaagct gggctgtgtg cacgaacccc    4260
ccgttcagcc cgaccgctgc gccttatccg gtaactatcg tcttgagtcc aacccggtaa    4320
gacacgactt atcgccactg gcagcagcca ctggtaacag gattagcaga gcgaggtatg    4380
taggcggtgc tacagagttc ttgaagtggt ggcctaacta cggctacact agaaggacag    4440
tatttggtat ctgcgctctg ctgaagccag ttaccttcgg aaaaagagtt ggtagctctt    4500
gatccggcaa acaaaccacc gctggtagcg gtggtttttt tgtttgcaag cagcagatta    4560
cgcgcagaaa aaaaggatct caagaagatc ctttgatctt ttctacgggg tctgacgctc    4620
agtggaacga aaactcacgt taagggattt tggtcatgca tgatatatct cccaatttgt    4680
gtagggctta ttatgcacgc ttaaaaataa taaaagcaga cttgacctga tagtttggct    4740
gtgagcaatt atgtgcttag tgcatctaac gcttgagtta agccgcgccg cgaagcggcg    4800
```

```
tcggcttgaa cgaatttcta gctagacatt atttgccgac taccttggtg atctcgcctt    4860
tcacgtagtg gacaaattct tccaactgat ctgcgcgcga ggccaagcga tcttcttctt    4920
gtccaagata agcctgtcta gcttcaagta tgacgggctg atactgggcc ggcaggcgct    4980
ccattgccca gtcggcagcg acatccttcg gcgcgatttt gccggttact gcgctgtacc    5040
aaatgcggga caacgtaagc actacatttc gctcatcgcc agcccagtcg ggcggcgagt    5100
tccatagcgt taaggtttca tttagcgcct caaatagatc ctgttcagga accggatcaa    5160
agagttcctc cgccgctgga cctaccaagg caacgctatg ttctcttgct tttgtcagca    5220
agatagccag atcaatgtcg atcgtggctg gctcgaagat acctgcaaga atgtcattgc    5280
gctgccattc tccaaattgc agttcgcgct tagctggata acgccacgga atgatgtcgt    5340
cgtgcacaac aatggtgact tctacagcgc ggagaatctc gctctctcca ggggaagccg    5400
aagtttccaa aaggtcgttg atcaaagctc gccgcgttgt tcatcaagc cttacggtca     5460
ccgtaaccag caaatcaata tcactgtgtg gcttcaggcc gccatccact gcggagccgt    5520
acaaatgtac ggccagcaac gtcggttcga gatggcgctc gatgacgcca actacctctg    5580
atagttgagt cgatacttcg gcgatcaccg cttcccccat gatgtttaac tttgttttag    5640
ggcgactgcc ctgctgcgta acatcgttgc tgctccataa catcaaacat cgacccacgg    5700
cgtaacgcgc ttgctgcttg gatgcccgag gcatagactg taccccaaaa aaacagtcat    5760
aacaagccat gaaaaccgcc actgcgttcc atggacatac aaatggacga acggataaac    5820
cttttcacgc ccttttaaat atccgattat tctaataaac gctcttttct cttaggttta    5880
cccgccaata tatcctgtca aacactgata gtttaaactg aaggcgggaa acgacaatca    5940
gatctagtag gaaacagcta tgaccatgat tacgccaagc ttgcatgcct gcaggtcgac    6000
tctagactag tggatccgat atcgcccggg ctcgaggtac ccatcgcgat ccccgtcacc    6060
ggtgtgaggg aactagtttt gatcttgaaa gatcttttat ctttagagtt aagaactctt    6120
tcgtattttg gtgaggtttt atcctcttga gttttggtca tagacctatt catggctctg    6180
ataccaattt ttaagcgggg gcttatgcgg attatttctt aaattgataa ggggttatta    6240
gggggtatag ggtataaata caagcattcc cttagcgtat agtataagta tagtagcgta    6300
cctctatcaa atttccatct tcttaccttg cacagggcct gcaaccttat ccttccttgt    6360
cttcctcctt ccttccgtcc acttcatcat atttaaacca aacctacggg ggagtcaacg    6420
taaccaaccc tgccttagca tctttttccct aacggcctcc tgcctaagcg gtacttctag    6480
cttcgaacgg cgtctgggct ccaggtttag tcgtctcgtg tctggtttat attcacgaca    6540
aagatctata gggactttag gagatctgga ttttagtact ggattttggt tttaggaatt    6600
agaaatttta ttgatagaag tattttacaa atacaaatac atactaaggg tttcttatat    6660
gctcaacaca tgagcgaaac cctataagaa ccctaanttc cccttatcgg gaaactactc    6720
acacattatt tatggagaaa atagagagag atagatttgt agagagagac tggtgatttc    6780
agcgtaccga attcggctaa cagtgtcgaa taacgcttta caaacaatta ttaacgcccg    6840
gttaccaggc gaagagggc tgtggcagat tcatctgcag gacggaaaaa tcagcgccat     6900
tgatgcgcaa tccggcgtga tgcccataac tgaaacagc ctggatgccg aacaaggttt     6960
agttataccg ccgtttgtgg agccacatat tcacctggac accacgcaaa ccgccggaca    7020
accgaactgg aatcagtccg gcacgctgtt tgaaggcatt gaacgctggg ccgagcgcaa    7080
agcgttatta acccatgacg atgtgaaaca acgcgcatgg caaacgctga atgcgcagat    7140
tgccaacggc attcagcatg tgcgtaccca tgtcgatgtt tcggatgcaa cgctaactgc    7200
```

```
gctgaaagca atgctggaag tgaagcagga agtcgcgccg tggattgatc tgcaaatcgt   7260
cgccttccct caggaaggga ttttgtcgga tccggtgata cctgcacatc aacaaatttt   7320
ggtcatatat tagaaaagtt ataaattaaa atatacacac ttataaacta cagaaaagca   7380
attgctatat actacattct tttatttga aaaaaatatt tgaaatatta tattactact    7440
aattaatgat aattattata tatatatcaa aggtagaagc agaaacttac gtagtcgacg   7500
acaaaatccc ttcctgaggg aaggcgacga tttgcagatc aatccacggc gcgacttcct   7560
gcttcacttc cagcattgct ttcagcgcag ttagcgttgc atccgaaaca tcgacatggg   7620
tacgcacatg ctgaatgccg ttggcaatct gccatttcag cgtttgccat gcgcgttgtt   7680
tcacatcgtc atgggttaat aacgctttgc gctcggccca gcgttcaatg ccttcaaaca   7740
gcgtgccgga ctgattccag ttcggttgtc cggcggtttg cgtggtgtcc aggtgaatat   7800
gtggctccac aaacggcggt ataactaaac cttgttcggc atccaggctg ttttcagtta   7860
tgggcatcac gccggattgc gcatcaatgg cgctgatttt tccgtcctgc agatgaatct   7920
gccacagccc ctcttcgcct ggtaaccggg cgttaataat tgtttgtaaa gcgttattcg   7980
acactgttag ccaagcttgc atgcctgcag gtcgagtctt tgttttttac tttggttcat   8040
gacactcaga gacttgagag aagcaatata tagacttttt tttgtttttt tttgtggtc    8100 acgtttattt tcctattgga gacggtaacg aagatcgaac ctgtggtgga aatgaaacaa   8160
ggtgggacta gcccacgtgg tttcttttct ctgcattgat ttgttttgt ttttttgta    8220 aagttcacat caaacctact aataattgag aagaaaata aaatctattg attgattaaa   8280
ccagccgatg ctttatgtct gaatataaaa aagaagtgaa accccgtttt aagaattaca   8340
acggtggttt acaagtatt tggacacaat aaatccaaac gaaataaaac aaaatggaga   8400
actaccaaat aaaaaacaaa taaaaaactt aaagaattt attccatttt ttttcccgta    8460
gaatttattc ttttatggat tcctaaatc catatttgat gcattttgat tcctcataat    8520
aggtaataat atatactatg ttatagatat gtttctaatt cgtattaacc tacctttttt   8580
tggtcgtacg attctaccta ataatattga acggaattga tgttttggac cacttagaaa   8640
gtattttttt tttggtttgt cttagctgta tttcattaaa tataaattta aataagaaat   8700
gtcataaata aaatttgacg tatagatttt ttaaatccat tttatgttat ttaatatttg   8760
aaatgtgagt ttggctccta tttaatctta ggatgggtta atactaagtt ttccttaatg   8820
aattatctca gagaaactgg attaaataaa ctaaaaaata gatcaatgtg ttttggtccg   8880
gtcaaatatc tttggattta ctattattgg cgaaaagaaa gtctcatata gtaaatcata   8940
ttcctacaag agaaatcaaa attttgaat aacatggat tgtatagttt cttatataac    9000
caattagttc gcatcaagaa aaccaaaccc caattaataa tcaaacgggc ttggtaggaa   9060
tatttcattg cagctttcag ataaaagaaa aaaacacaca ctcaagtctt ttatttcatc   9120
tttcttactt gcaggaactc aaattccact ttgccacttt tctttacaaa taaacacaaa   9180
ttgtcaatga acgaaatag tcttttatg caaacactgt ttgtcttttt tcgatcacgt    9240
ttctgattgt gacagccatc catatatata gggaatgtaa acaacaaca tgtgaagtca    9300 catatacgta atggtttagc atagcttcta ttttcgttgt caatattagt cattccaaaa   9360
catttttaag aaaaataaat taatatatgt atattcttgg aactaatgta tgtggaaata   9420
cagtaactta attattaaac attctaaatg caaatatgca agaaaaaaa agaaaagaac    9480 acaactgaaa tcaaagccag attcataata attggctaca tggttgtaga atgtagggta   9540
```

```
acacaacatc cagaattgaa cactcaaatt ggatgataga tggataatct ttagatacaa    9600
gagaattggt tctcttccat tattaacgaa aataaagaaa aaaagtttag cataaaagtt    9660
tgaaactcaa cataacattt tgaacttgac tccttcatag gagtgacatg aactgacgaa    9720
tcacaaccga ttacttgttt gagtcatctt ccgctttctc caccttcgaa atgaatgtga    9780
ccggtttctt cgggtgctca tttacggtca agtgtaaaac atctggtctc gacgagct     9838

<210> SEQ ID NO 58
<211> LENGTH: 14184
<212> TYPE: DNA
<213> ORGANISM: Artificial sequence
<220> FEATURE:
<223> OTHER INFORMATION: Description of the artificial sequence:
      Expression vector pSUN1-codA-RNAi-At.Act.-2-At.Als-R-ocsT

<400> SEQUENCE: 58
ctgcttggta ataattgtca ttagattgtt tttatgcata gatgcactcg aaatcagcca      60
attttagaca agtatcaaac ggatgttaat tcagtacatt aaagacgtcc gcaatgtgtt     120
attaagttgt ctaagcgtca atttgtttac accacaatat atcctgccac cagccagcca     180
acagctcccc gaccggcagc tcggcacaaa atcaccacgc gttaccacca cgccggccgg     240
ccgcatggtg ttgaccgtgt tcgccggcat tgccgagttc gagcgttccc taatcatcga     300
ccgcacccgg agcgggcgcg aggccgccaa ggcccgaggc gtgaagtttg gcccccgccc     360
taccctcacc ccggcacaga tcgcgcacgc ccgcgagctg atcgaccagg aaggccgcac     420
cgtgaaagag gcgcctgcac tgcttggcgt gcatcgctcg accctgtacc gcgcacttga     480
gcgcagcgag gaagtgacgc ccaccgaggc caggcggcgc ggtgccttcc gtgaggacgc     540
attgaccgag gccgacgccc tggcggccgc cgagaatgaa cgccaagagg aacaagcatg     600
aaaccgcacc aggacggcca ggacgaaccg ttttcatta ccgaagagat cgaggcggag     660
atgatcgcgg ccgggtacgt gttcgagccg cccgcgcacg tctcaaccgt gcggctgcat     720
gaaatcctgg ccggtttgtc tgatgccaag ctggcggcct ggccggccag cttggccgct     780
gaagaaaccg agcgccgccg tctaaaaagg tgatgtgtat ttgagtaaaa cagcttgcgt     840
catgcggtcg ctgcgtatat gatgcgatga gtaaataaac aaatacgcaa ggggaacgca     900
tgaaggttat cgctgtactt aaccagaaag gcgggtcagg caagacgacc atcgcaaccc     960
atctagcccg cgccctgcaa ctcgccgggg ccgatgttct gttagtcgat tccgatcccc    1020
agggcagtgc ccgcgattgg gcggccgtgc gggaagatca accgctaacc gttgtcggca    1080
tcgaccgccc gacgattgac cgcgacgtga aggccatcgg ccggcgcgac ttcgtagtga    1140
tcgacggagc gccccaggcg gcggacttgg ctgtgtccgc gatcaaggca gccgacttcg    1200
tgctgattcc ggtgcagcca agcccttacg acatatgggc caccgccgac ctggtggagc    1260
tggttaagca gcgcattgag gtcacggatg aaggctaca agcggccttt gtcgtgtcgc    1320
gggcgatcaa aggcacgcgc atcggcggtg aggttgccga ggcgctggcc gggtacgagc    1380
tgcccattct tgagtcccgt atcacgcagc gcgtgagcta cccaggcact gccgccgccg    1440
gcacaaccgt tcttgaatca gaacccgagg gcgacgctgc ccgcgaggtc caggcgctgg    1500
ccgctgaaat taaatcaaaa ctcatttgag ttaatgaggt aaagagaaaa tgagcaaaag    1560
cacaaacacg ctaagtgccg gccgtccgag cgcacgcagc agcaaggctg caacgttggc    1620
cagcctggca gacacgccag ccatgaagcg ggtcaacttt cagttgccgg cggaggatca    1680
caccaagctg aagatgtacg cggtacgcca aggcaagacc attaccgagc tgctatctga    1740
```

```
atacatcgcg cagctaccag agtaaatgag caaatgaata aatgagtaga tgaattttag   1800
cggctaaagg aggcggcatg gaaaatcaag aacaaccagg caccgacgcc gtggaatgcc   1860
ccatgtgtgg aggaacgggc ggttggccag gcgtaagcgg ctgggttgtc tgccggccct   1920
gcaatggcac tggaaccccc aagcccgagg aatcggcgtg agcggtcgca aaccatccgg   1980
cccggtacaa atcggcgcgg cgctgggtga tgacctggtg gagaagttga aggccgcgca   2040
ggccgcccag cggcaacgca tcgaggcaga agcacgcccc ggtgaatcgt ggcaagcggc   2100
cgctgatcga atccgcaaag aatcccggca accgccggca gccggtgcgc cgtcgattag   2160
gaagccgccc aagggcgacg agcaaccaga ttttttcgtt ccgatgctct atgacgtggg   2220
cacccgcgat agtcgcagca tcatggacgt ggccgttttc cgtctgtcga agcgtgaccg   2280
acgagctggc gaggtgatcc gctacgagct tccagacggg cacgtagagg tttccgcagg   2340
gccggccggc atggccagtg tgtgggatta cgacctggta ctgatggcgg tttcccatct   2400
aaccgaatcc atgaaccgat accgggaagg gaagggagac aagcccggcc gcgtgttccg   2460
tccacacgtt gcggacgtac tcaagttctg ccggcgagcc gatggcggaa agcagaaaga   2520
cgacctggta gaaacctgca ttcggttaaa caccacgcac gttgccatgc agcgtacgaa   2580
gaaggccaag aacggccgcc tggtgacggt atccgagggt gaagccttga ttagccgcta   2640
caagatcgta aagagcgaaa ccgggcggcc ggagtacatc gagatcgagc tagctgattg   2700
gatgtaccgc gagatcacag aaggcaagaa cccggacgtg ctgacggttc accccgatta   2760
cttttttgatc gatcccggca tcggccgttt tctctaccgc ctggcacgcc cgcgccgcagg   2820
caaggcagaa gccagatggt tgttcaagac gatctacgaa cgcagtggca gcgccggaga   2880
gttcaagaag ttctgtttca ccgtgcgcaa gctgatcggg tcaaatgacc tgccggagta   2940
cgatttgaag gaggaggcgg ggcaggctgg cccgatccta gtcatgcgct accgcaacct   3000
gatcgagggc gaagcatccg ccggttccta atgtacggag cagatgctag gcaaattgc    3060
cctagcaggg gaaaaaggtc gaaaaggtct ctttcctgtg gatagcacgt acattgggaa   3120
cccaaagccg tacattggga accggaaccc gtacattggg aacccaaagc cgtacattgg   3180
gaaccggtca cacatgtaag tgactgatat aaaagagaaa aaaggcgatt tttccgccta   3240
aaactctttta aaacttatta aaactcttaa aacccgcctg gcctgtgcat aactgtctgg   3300
ccagcgcaca gccgaagagc tgcaaaaagc gcctacccct cggtcgctgc gctccctacg   3360
ccccgccgct tcgcgtcggc ctatcgcggc cgctggccgc tcaaaaatgg ctggcctacg   3420
gccaggcaat ctaccaggcc gcggacaagc cgcgccgtcg ccactcgacc gccggcgccc   3480
acatcaaggc accctgcctc gcgcgtttcg gtgatgacgg tgaaaacctc tgacacatgc   3540
agctcccgga gacggtcaca gcttgtctgt aagcggatgc cggagcagaa caagcccgtc   3600
agggcgcgtc agcgggtgtt ggcgggtgtc ggggcgcagc catgacccag tcacgtagcg   3660
atagcggagt gtatactggc ttaactatgc ggcatcagag cagattgtac tgagagtgca   3720
ccatatgcgg tgtgaaatac cgcacagatg cgtaaggaga aaataccgca tcaggcgctc   3780
ttccgcttcc tcgctcactg actcgctgcg ctcggtcgtt cggctgcggc gagcggtatc   3840
agctcactca aaggcggtaa tacggttatc cacagaatca ggggataacg caggaaagaa   3900
catgtgagca aaaggccagc aaaaggccag gaaccgtaaa aaggccgcgt tgctggcgtt   3960
tttccatagg ctccgccccc ctgacgagca tcacaaaaat cgacgctcaa gtcagaggtg   4020
gcgaaacccg acaggactat aaagatacca ggcgtttccc cctggaagct ccctcgtgcg   4080
ctctcctgtt ccgaccctgc cgcttaccgg atacctgtcc gcctttctcc cttcgggaag   4140
```

```
cgtggcgctt tctcatagct cacgctgtag gtatctcagt tcggtgtagg tcgttcgctc    4200
caagctgggc tgtgtgcacg aaccccccgt tcagcccgac cgctgcgcct tatccggtaa    4260
ctatcgtctt gagtccaacc cggtaagaca cgacttatcg ccactggcag cagccactgg    4320
taacaggatt agcagagcga ggtatgtagg cggtgctaca gagttcttga agtggtggcc    4380
taactacggc tacactagaa ggacagtatt tggtatctgc gctctgctga agccagttac    4440
cttcggaaaa agagttggta gctcttgatc cggcaaacaa accaccgctg gtagcggtgg    4500
tttttttgtt tgcaagcagc agattacgcg cagaaaaaaa ggatctcaag aagatccttt    4560
gatcttttct acggggtctg acgctcagtg gaacgaaaac tcacgttaag gattttggt    4620 catgcatgat atatctccca atttgtgtag ggcttattat gcacgcttaa aaataataaa    4680
agcagacttg acctgatagt ttggctgtga gcaattatgt gcttagtgca tctaacgctt    4740
gagttaagcc gcgccgcgaa gcggcgtcgg cttgaacgaa tttctagcta gacattattt    4800
gccgactacc ttggtgatct cgcctttcac gtagtggaca aattcttcca actgatctgc    4860
gcgcgaggcc aagcgatctt cttcttgtcc aagataagcc tgtctagctt caagtatgac    4920
gggctgatac tgggccggca ggcgctccat tgcccagtcg gcagcgacat ccttcggcgc    4980
gattttgccg gttactgcgc tgtaccaaat gcgggacaac gtaagcacta catttcgctc    5040
atcgccagcc cagtcgggcg gcgagttcca tagcgttaag gtttcattta gcgcctcaaa    5100
tagatcctgt tcaggaaccg gatcaaagag ttcctccgcc gctggaccta ccaaggcaac    5160
gctatgttct cttgcttttg tcagcaagat agccagatca atgtcgatcg tggctggctc    5220
gaagatacct gcaagaatgt cattgcgctg ccattctcca aattgcagtt cgcgcttagc    5280
tggataacgc cacggaatga tgtcgtcgtg cacaacaatg gtgacttcta cagcgcggag    5340
aatctcgctc tctccagggg aagccgaagt ttccaaaagg tcgttgatca agctcgccg    5400 cgttgtttca tcaagcctta cggtcaccgt aaccagcaaa tcaatatcac tgtgtggctt    5460
caggccgcca tccactgcgg agccgtacaa atgtacggcc agcaacgtcg gttcgagatg    5520
gcgctcgatg acgccaacta cctctgatag ttgagtcgat acttcggcga tcaccgcttc    5580
ccccatgatg tttaactttg ttttagggcg actgccctgc tgcgtaacat cgttgctgct    5640
ccataacatc aaacatcgac ccacggcgta acgcgcttgc tgcttggatg cccgaggcat    5700
agactgtacc ccaaaaaaac agtcataaca agccatgaaa accgccactg cgttccatgg    5760
acatacaaat ggacgaacgg ataaacccttt tcacgcccct ttaaatatcc gattattcta    5820
ataaacgctc ttttctctta ggtttacccg ccaatatatc ctgtcaaaca ctgatagttt    5880
aaactgaagg cgggaaacga caatcagatc tagtaggaaa cagctatgac catgattacg    5940
ccaagcttgc atgcctgcag gtcgactcta gactagtgga tccgatatcg cccgggctcg    6000
aggtacccat cgcgatcccc gtcaccggtg tgagggaact agttttgatc ttgaaagatc    6060
ttttatcttt agagttaaga actctttcgt attttggtga ggttttatcc tcttgagttt    6120
tggtcataga cctattcatg gctctgatac caatttttaa gcggggggctt atgcggatta    6180 tttcttaaat tgataagggg ttattagggg gtataggggta taaatacaag cattccctta    6240
gcgtatagta taagtatagt agcgtacctc tatcaaattt ccatcttctt accttgcaca    6300
gggcctgcaa ccttatcctt ccttgtcttc ctccttcctt ccgtccactt catcatattt    6360
aaaccaaacc tacggggggag tcaacgtaac caacccctgcc ttagcatctt ttccctaacg    6420
gcctcctgcc taagcggtac ttctagcttc gaacggcgtc tgggctccag gtttagtcgt    6480
```

```
ctcgtgtctg gtttatattc acgacaaaga tctataggga ctttaggaga tctggatttt    6540
agtactggat tttggtttta ggaattagaa attttattga tagaagtatt ttacaaatac    6600
aaatacatac taagggtttc ttatatgctc aacacatgag cgaaacccta taagaaccct    6660
aatttcccTT atcgggaaac tactcacaca ttatttatgg agaaaataga gagagataga    6720
tttgtagaga gagactggtg atttcagcgt accgaattcg attttcggct aacagtgtcg    6780
aataacgctt tacaaacaat tattaacgcc cggttaccag cgaagaggg gctgtggcag    6840 attcatctgc aggacggaaa atcagcgcc attgatgcgc aatccggcgt gatgcccata    6900
actgaaaaca gcctggatgc cgaacaaggt ttagttatac cgccgtttgt ggagccacat    6960
attcacctgg acaccacgca aaccgccgga caaccgaact ggaatcagtc cggcacgctg    7020
tttgaaggca ttgaacgctg ggccgagcgc aaagcgttat aacccatga cgatgtgaaa    7080 caacgcgcat ggcaaacgct gaaatggcag attgccaacg gcattcagca tgtgcgtacc    7140
catgtcgatg tttcggatgc aacgctaact gcgctgaaag caatgctgga agtgaagcag    7200
gaagtcgcgc cgtggattga tctgcaaatc gtcgccttcc ctcaggaagg gattttgtcg    7260
gatccggtga tacctgcaca tcaacaaatt ttggtcatat attagaaaag ttataaatta    7320
aaatatacac acttataaac tacagaaaag caattgctat atactacatt cttttatttt    7380 gaaaaaata tttgaaatat tatattacta ctaattaatg ataattatta tatatatatc    7440
aaaggtagaa gcagaaactt acgtagtcga cgacaaaatc ccgtcctgag ggaaggcgac    7500
gatttgcaga tcaatccacg gcgcgacttc ctgcttcact tccagcattg ctttcagcgc    7560
agttagcgtt gcatccgaaa catcgacatg ggtacgcaca tgctgaatgc cgttggcaat    7620
ctgccatttc agcgtttgcc atgcgcgttg tttcacatcg tcatgggtta ataacgcttt    7680
gcgctcggcc cagcgttcaa tgccttcaaa cagcgtgccg gactgattcc agttcggttg    7740
tccggcggtt tgcgtggtgt ccaggtgaat atgtggctcc acaaacggcg gtataactaa    7800
accttgttcg gcatccaggc tgttttcagt tatgggcatc acgccggatt gcgcatcaat    7860
ggcgctgatt tttccgtcct gcagatgaat ctgccacagc ccctcttcgc ctggtaaccg    7920
ggcgttaata attgtttgta aagcgttatt cgacactgtt agccaagctt gcatgcctgc    7980
aggtcgactc tagaggatcc ccgatccact cgagtctttg ttttttactt tggttcatga    8040
cactcagaga cttgagagaa gcaatatata gactttttt tgttttttt ttgtggtcac    8100 gtttattttc ctattggaga cggtaacgaa gatcgaacct gtggtggaaa tgaaacmagg    8160
tgggactagc ccacgtggtt tcttttctct gcattgattt gttttttgttt tttytgtaaa    8220 gttcacatca aacctactaa taattgagaa gaaaaataaa atctattgat tgattaaacc    8280
agccgatgct ttatgtctga atataaaaaa gaagtgaaaa ccccgtttaa gaattacaac    8340
ggtggtttac aaagtatttg gacacaataa atccaaacga aataaaacaa aatggagaac    8400
taccaaataa aaaacaaata aaaaacttaa aagaatttat tccattttttt ttcccgtaga    8460 atttattctt ttatggattc cttaaatcca tatttgatgc attttgattc ctcataatag    8520
gtaataatat atactatgtt atagatatgt ttctaattcg tattaaccta ccttttttttg    8580 gtcgtacgat tctacctaat aatattgaac ggaattgatg ttttggacca cttagaaagt    8640 atttttttt tggtttgtct tagctgtatt tcattaaata taaatttaaa taagaaatgt    8700
cataaataaa atttgacgta tagatttttt aaatccattt tatgttattt aatatttgaa    8760
atgtgagttt ggctccctatt taatcttagg atgggttaat actaagtttt ccttaatgaa    8820
ttatctcaga gaaactggat taaataaact aaaaaataga tcaatgtgtt ttggtccggt    8880
```

```
caaatatctt tggatttact attattggcg aaaagaaagt ctcatatagt aaatcatatt    8940
cctacaagag aaatcaaaat ttttgaatta acatggattg tatagtttct tatataacca    9000
attagttcgc atcaagaaaa ccaaaccccca attaataatc aaacgggctt ggtaggaata    9060
tttcattgca gctttcagat aaaagaaaaa aacacacact caagtctttt atttcatctt    9120
tcttacttgc aggaactcaa attccacttt gccactttc tttacaaata aacacaaatt    9180
gtcaatgaaa cgaaatagtc ttttatgca aacactgttt gtcttttttc gatcacgttt    9240
ctgattgtga cagccatcca tatatatagg gaatgtaaaa caacaacatg tgaagtcaca    9300
tatacgtaat ggtttagcat agcttctatt ttcgttgtca atattagtca ttccaaaaca    9360
tttttaagaa aaataaatta atatatgtat attcttggaa ctaatgtatg tggaaataca    9420
gtaacttaat tattaaacat tctaaatgca aatatgcaaa gaaaaaaaag aaaagaacac    9480
aactgaaatc aaagccagat tcataataat tggctacatg gttgtagaat gtagggtaac    9540
acaacatcca gaattgaaca ctcaaattgg atgatagatg gataatcttt agatacaaga    9600
gaattggttc tcttccatta ttaacgaaaa taaagaaaaa aagtttagca taaaagtttg    9660
aaactcaaca taacatttg aacttgactc cttcatagga gtgacatgaa ctgacgaatc    9720
acaaccgatt acttgtttga gtcatcttcc gctttctcca ccttcgaaat gaatgtgacc    9780
ggtttcttcg ggtgctcatt tacggtcaag tgtaaaacat ctggtctcga gtaatgtcca    9840
accgaatcga agtacaactt agctcttgct acatcaccaa gatcttgatg ggggatcggg    9900
taccgagctc gaattcactg gccgtcgttt tacaacgact cagcacgcgt tggtttcgac    9960
aaaatttaga acgaacttaa ttatgatctc aaatacattg atacatatct catctagatc    10020
taggttatca ttatgtaaga aagttttgac gaatatggca cgacaaaatg gctagactcg    10080
atgtaattgg tatctcaact caacattata cttataccaa acattagtta gacaaaattt    10140
aaacaactat tttttatgta tgcaagagtc agcatatgta taattgattc agaatcgttt    10200
tgacgagttc ggatgtagta gtagccatta tttaatgtac atactaatcg tgaatagtga    10260
atatgatgaa acattgtatc ttattgtata aatatccata aacacatcat gaaagacact    10320
ttctttcacg gtctgaatta attatgatac aattctaata gaaaacgaat taaattacgt    10380
tgaattgtat gaaatctaat tgaacaagcc aaccacgacg acgactaacg ttgcctggat    10440
tgactcggtt taagttaacc actaaaaaaa cggagctgtc atgtaacacg cggatcgagc    10500
aggtcacagt catgaagcca tcaaagcaaa agaactaatc caagggctga gatgattaat    10560
tagtttaaaa attagttaac acgagggaaa aggctgtctg acagccaggt cacgttatct    10620
ttacctgtgg tcgaaatgat tcgtgtctgt cgattttaat tattttttg aaaggccgaa    10680 aataaagttg taagagataa acccgcctat ataaattcat atattttcct ctccgctttg    10740
aattgtctcg ttgtcctcct cactttcatc agccgttttg aatctccggc gacttgacag    10800
agaagaacaa ggaagaagac taagagagaa agtaagagat aatccaggag attcattctc    10860
cgttttgaat cttcctcaat ctcatcttct tccgctcttt cttccaagg taataggaac    10920 tttctggatc tactttatt gctggatctc gatcttgttt tctcaatttc cttgagatct    10980
ggaattcgtt taatttggat ctgtgaacct ccactaaatc ttttggtttt actagaatcg    11040
atctaagttg accgatcagt tagctcgatt atagctacca gaatttggct tgaccttgat    11100
ggagagatcc atgttcatgt tacctgggaa atgatttgta tatgtgaatt gaaatctgaa    11160
ctgttgaagt tagattgaat ctgaacactg tcaatgttag attgaatctg aacactgttt    11220
```

```
aaggttagat gaagtttgtg tatagattct tcgaaacttt aggatttgta gtgtcgtacg    11280
ttgaacagaa agctatttct gattcaatca gggtttattt gactgtattg aactcttttt    11340
gtgtgtttgc agctcataaa aaaaacgcga acctgcaggc atggcggcgg caacaacaac    11400
aacaacaaca tcttcttcga tctccttctc caccaaacca tctccttcct cctcaaatc     11460 accattacca atctccagat tctccctccc attctcccta aacccaaca aatcatcctc     11520 ctcctcccgc cgccgcggta tcaaatccag ctctccctcc tccatctccg ccgtgctcaa    11580
cacaaccacc aatgtcacaa ccactccctc tccaaccaaa cctaccaaac ccgaaacatt    11640
catctcccga ttcgctccag atcaaccccg caaaggcgct gatatcctcg tcgaagcttt    11700
agaacgtcaa ggcgtagaaa ccgtattcgc ttaccctgga ggtgcatcaa tggagattca    11760
ccaagcctta acccgctctt cctcaatccg taacgtcctt cctcgtcacg aacaaggagg    11820
tgtattcgca gcagaaggat acgctcgatc ctcaggtaaa ccaggtatct gtatagccac    11880
ttcaggtccc ggagctacaa atctcgttag cggattagcc gatgcgttgt tagatagtgt    11940
tcctcttgta gcaatcacag gacaagtccc tcgtcgtatg attggtacag atgcgtttca    12000
agagactccg attgttgagg taacgcgttc gattacgaag cataactatc ttgtgatgga    12060
tgttgaagat atccctagga ttattgagga agctttcttt ttagctactt ctggtagacc    12120
tggacctgtt ttggttgatg ttcctaaaga tattcaacaa cagcttgcga ttcctaattg    12180
ggaacaggct atgagattac ctggttatat gtctaggatg cctaaacctc cggaagattc    12240
tcatttggag cagattgtta ggttgatttc tgagtctaag aagcctgtgt tgtatgttgg    12300
tggtggttgt ttgaattcta gcgatgaatt gggtaggttt gttgagctta cggggatccc    12360
tgttgcgagt acgttgatgg ggctgggatc ttatccttgt gatgatgagt tgtcgttaca    12420
tatgcttgga atgcatggga ctgtgtatgc aaattacgct gtggagcata tgatttgtt     12480 gttggcgttt ggggtaaggt ttgatgatcg tgtcacgggt aagcttgagg cttttgctag    12540
tagggctaag attgttcata ttgatattga ctcggctgag attgggaaga ataagactcc    12600
tcatgtgtct gtgtgtggtg atgttaagct ggctttgcaa gggatgaata aggttcttga    12660
gaaccgagcg gaggagctta agcttgattt tggagtttgg aggaatgagt tgaacgtaca    12720
gaaacagaag tttccgttga gctttaagac gtttggggaa gctattcctc acagtatgc     12780 gattaaggtc cttgatgagt tgactgatgg aaaagccata ataagtactg gtgtcgggca    12840
acatcaaatg tgggcggcgc agttctacaa ttacaagaaa ccaaggcagt ggctatcatc    12900
aggaggcctt ggagctatgg gatttggact tcctgctgcg attggagcgt ctgttgctaa    12960
ccctgatgcg atagttgtgg atattgacgg agatggaagc tttataatga atgtgcaaga    13020
gctagccact attcgtgtag agaatcttcc agtgaaggta cttttattaa caaccagca    13080 tcttggcatg ttatgcaat gggaagatcg gttctacaaa gctaaccgag ctcacacatt     13140
tctcggggat ccggctcagg aggacgagat attcccgaac atgttgctgt ttgcagcagc    13200
ttgcgggatt ccagcggcga gggtgacaaa gaaagcagat ctccgagaag ctattcagac    13260
aatgctggat acaccaggac cttacctgtt ggatgtgatt tgtccgcacc aagaacatgt    13320
gttgccgatg atcccgaatg gtggcacttt caacgatgtc ataacggaag gagatggccg    13380
gattaaatac tgagagatga aaccggcctg gccggcccgg agtggggagg cacgatggcc    13440
gctttggtcg atcgacggga tcgatcctgc tttaatgaga tatgcgagac gcctatgatc    13500
gcatgatatt tgctttcaat tctgttgtgc acgttgtaaa aaacctgagc atgtgtagct    13560
cagatcctta ccgccggttt cggttcattc taatgaatat atcacccgtt actatcgtat    13620
```

-continued

```
ttttatgaat aatattctcc gttcaattta ctgattgtac cctactactt atatgtacaa    13680
tattaaaatg aaaacaatat attgtgctga ataggtttat agcgacatct atgatagagc    13740
gccacaataa caaacaattg cgttttatta ttacaaatcc aattttaaaa aaagcggcag    13800
aaccggtcaa acctaaaaga ctgattacat aaatcttatt caaatttcaa aaggccccag    13860
gggctagtat ctacgacaca ccgagcggcg aactaataac gttcactgaa gggaactccg    13920
gttccccgcc ggcgcgcatg ggtgagattc cttgaagttg agtattggcc gtccgctcta    13980
ccgaaagtta cgggcaccat tcaacccggt ccagcacggc ggccgggtaa ccgacttgct    14040
gccccgagaa ttatgcagca ttttttttggt gtatgtgggc cccaaatgaa gtgcaggtca    14100
aaccttgaca gtgacgacaa atcgttgggc gggtccaggg cgaattttgc gacaacatgt    14160
cgaggctcag caggatgggc ccag                                            14184
```

<210> SEQ ID NO 59
<211> LENGTH: 1011
<212> TYPE: DNA
<213> ORGANISM: Zea mays
<220> FEATURE:
<221> NAME/KEY: CDS
<222> LOCATION: (1)..(981)
<223> OTHER INFORMATION: coding for 5-methylthioribose kinase

<400> SEQUENCE: 59

```
gca cga gca ctc ctc tcc tct cct ctc gcc ggc gca tcg ccc gac tgt       48
Ala Arg Ala Leu Leu Ser Ser Pro Leu Ala Gly Ala Ser Pro Asp Cys
  1               5                  10                  15 cag tca gcc tca gcc atg gcc gcg gag gag gag cag ggc ttc cgc ccg       96
Gln Ser Ala Ser Ala Met Ala Ala Glu Glu Glu Gln Gly Phe Arg Pro
             20                  25                  30 ctg gac gag tcg tcc ctg ctc gcc tac atc aag gcc acg ccg gcg ctc      144
Leu Asp Glu Ser Ser Leu Leu Ala Tyr Ile Lys Ala Thr Pro Ala Leu
         35                  40                  45 gcc tcc cgc ctc ggc ggc ggt ggc agt cta gac tcc atc gag atc aag      192
Ala Ser Arg Leu Gly Gly Gly Gly Ser Leu Asp Ser Ile Glu Ile Lys
     50                  55                  60 gag gtc ggc gac ggc aac ctc aac ttc gtc tac atc gtg cag tcc gag      240
Glu Val Gly Asp Gly Asn Leu Asn Phe Val Tyr Ile Val Gln Ser Glu
 65                  70                  75                  80 gcc ggc gcc atc gtc gtc aag cag gcg ctc ccg tac gtg cgc tgc gtg      288
Ala Gly Ala Ile Val Val Lys Gln Ala Leu Pro Tyr Val Arg Cys Val
                 85                  90                  95 ggg gat tcg tgg ccc atg acg cgg gag cgc gcc tac ttc gag gcc tcc      336
Gly Asp Ser Trp Pro Met Thr Arg Glu Arg Ala Tyr Phe Glu Ala Ser
            100                 105                 110 acg ctg cgg gag cac ggc cgc ctg tgc ccg gag cac acc ccc gag gtg      384
Thr Leu Arg Glu His Gly Arg Leu Cys Pro Glu His Thr Pro Glu Val
        115                 120                 125 tac cac ttc gac cgg acc ttg tcg ctg atg ggg atg cgc tac atc gag      432
Tyr His Phe Asp Arg Thr Leu Ser Leu Met Gly Met Arg Tyr Ile Glu
    130                 135                 140 ccc ccg cac atc atc ctc cgc aag ggc ctc gtc gcc ggt gtc gag tac      480
Pro Pro His Ile Ile Leu Arg Lys Gly Leu Val Ala Gly Val Glu Tyr
145                 150                 155                 160 ccg ctg ctc gcc gac cac atg tcc gat tac atg gcc aag acg ctc ttc      528
Pro Leu Leu Ala Asp His Met Ser Asp Tyr Met Ala Lys Thr Leu Phe
                165                 170                 175 ttc acc tcc ctc ctc tat aac aat acc acg gat cat aag aac gga gtt      576
Phe Thr Ser Leu Leu Tyr Asn Asn Thr Thr Asp His Lys Asn Gly Val
```

```
                180                 185                 190
gct aag tac tct gcg aac gtg gag atg tgt agg ctc acg gag caa gtt        624
Ala Lys Tyr Ser Ala Asn Val Glu Met Cys Arg Leu Thr Glu Gln Val
        195                 200                 205 gtg ttc tcg gac cca tac cgt gtt tcc aaa ttt aat cgg tgg acc tcg        672
Val Phe Ser Asp Pro Tyr Arg Val Ser Lys Phe Asn Arg Trp Thr Ser
210                 215                 220 cct tat ctc gac aaa gat gct gag gca gtt cgc gag gat gat gag ctc        720
Pro Tyr Leu Asp Lys Asp Ala Glu Ala Val Arg Glu Asp Asp Glu Leu
225                 230                 235                 240 aag ttg gaa gta gct ggg ctg aaa tcg atg ttt atc gag aga gct caa        768
Lys Leu Glu Val Ala Gly Leu Lys Ser Met Phe Ile Glu Arg Ala Gln
                245                 250                 255 gct ctg att cat gga gat ctc cac act ggt tct atc atg gtg acc gaa        816
Ala Leu Ile His Gly Asp Leu His Thr Gly Ser Ile Met Val Thr Glu
                260                 265                 270 gtt caa ctc aag tca ttg atc cag aat ttg ggt tct atg ggg cca atg        864
Val Gln Leu Lys Ser Leu Ile Gln Asn Leu Gly Ser Met Gly Pro Met
            275                 280                 285 ggg ttt gat att ggg agc ctt cct tgg aaa cct gat ttt ggg cat act        912
Gly Phe Asp Ile Gly Ser Leu Pro Trp Lys Pro Asp Phe Gly His Thr
        290                 295                 300 atg cac aga atg ggc atg ctg atc aag cga atg atc gta agg ctt aca        960
Met His Arg Met Gly Met Leu Ile Lys Arg Met Ile Val Arg Leu Thr
305                 310                 315                 320 aga atg gat ctt gaa gac aat tgaagagtcg tggaatttgt tccacaaaaa         1011
Arg Met Asp Leu Glu Asp Asn
                325

<210> SEQ ID NO 60
<211> LENGTH: 327
<212> TYPE: PRT
<213> ORGANISM: Zea mays

<400> SEQUENCE: 60

Ala Arg Ala Leu Leu Ser Ser Pro Leu Ala Gly Ala Ser Pro Asp Cys
1               5                   10                  15

Gln Ser Ala Ser Ala Met Ala Ala Glu Glu Glu Gln Gly Phe Arg Pro
            20                  25                  30

Leu Asp Glu Ser Ser Leu Leu Ala Tyr Ile Lys Ala Thr Pro Ala Leu
        35                  40                  45

Ala Ser Arg Leu Gly Gly Gly Ser Leu Asp Ser Ile Glu Ile Lys
    50                  55                  60

Glu Val Gly Asp Gly Asn Leu Asn Phe Val Tyr Ile Val Gln Ser Glu
65                  70                  75                  80

Ala Gly Ala Ile Val Val Lys Gln Ala Leu Pro Tyr Val Arg Cys Val
                85                  90                  95

Gly Asp Ser Trp Pro Met Thr Arg Glu Arg Ala Tyr Phe Glu Ala Ser
            100                 105                 110

Thr Leu Arg Glu His Gly Arg Leu Cys Pro Glu His Thr Pro Glu Val
        115                 120                 125

Tyr His Phe Asp Arg Thr Leu Ser Leu Met Gly Met Arg Tyr Ile Glu
    130                 135                 140

Pro Pro His Ile Ile Leu Arg Lys Gly Leu Val Ala Gly Val Glu Tyr
145                 150                 155                 160

Pro Leu Leu Ala Asp His Met Ser Asp Tyr Met Ala Lys Thr Leu Phe
                165                 170                 175
```

```
Phe Thr Ser Leu Leu Tyr Asn Thr Thr Asp His Lys Asn Gly Val
            180                 185                 190

Ala Lys Tyr Ser Ala Asn Val Glu Met Cys Arg Leu Thr Glu Gln Val
        195                 200                 205

Val Phe Ser Asp Pro Tyr Arg Val Ser Lys Phe Asn Arg Trp Thr Ser
    210                 215                 220

Pro Tyr Leu Asp Lys Asp Ala Glu Ala Val Arg Glu Asp Asp Glu Leu
225                 230                 235                 240

Lys Leu Glu Val Ala Gly Leu Lys Ser Met Phe Ile Glu Arg Ala Gln
                245                 250                 255

Ala Leu Ile His Gly Asp Leu His Thr Gly Ser Ile Met Val Thr Glu
            260                 265                 270

Val Gln Leu Lys Ser Leu Ile Gln Asn Leu Gly Ser Met Gly Pro Met
        275                 280                 285

Gly Phe Asp Ile Gly Ser Leu Pro Trp Lys Pro Asp Phe Gly His Thr
    290                 295                 300

Met His Arg Met Gly Met Leu Ile Lys Arg Met Ile Val Arg Leu Thr
305                 310                 315                 320

Arg Met Asp Leu Glu Asp Asn
            325

<210> SEQ ID NO 61
<211> LENGTH: 471
<212> TYPE: DNA
<213> ORGANISM: Brassica napus
<220> FEATURE:
<221> NAME/KEY: CDS
<222> LOCATION: (2)..(469)
<223> OTHER INFORMATION: coding for 5-methylthioribose kinase

<400> SEQUENCE: 61 a ttt ccg ggt cga cga ttt cgt ggc aat ctc aac ttc gtt ttc atc gtc      49
  Phe Pro Gly Arg Arg Phe Arg Gly Asn Leu Asn Phe Val Phe Ile Val
   1               5                   10                  15 atc gga tcc act ggc tca ctc gtc atc aaa cag gcg ctt ccg tat ata        97
Ile Gly Ser Thr Gly Ser Leu Val Ile Lys Gln Ala Leu Pro Tyr Ile
            20                  25                  30 cgt tgt att ggg gag tct tgg cca atg acg aaa gaa aga gct tac ttt       145
Arg Cys Ile Gly Glu Ser Trp Pro Met Thr Lys Glu Arg Ala Tyr Phe
        35                  40                  45 gaa gct aca act ctg aga aag cac gga gct ttg tct cct gat cat gtt       193
Glu Ala Thr Thr Leu Arg Lys His Gly Ala Leu Ser Pro Asp His Val
    50                  55                  60 cct gaa gtc tac cat ttt gac agg acc atg gct ttg att gga atg agg       241
Pro Glu Val Tyr His Phe Asp Arg Thr Met Ala Leu Ile Gly Met Arg
65                  70                  75                  80 tat ctg gag cct cct cac atc atc ctc cgc aaa gga ctc gtt gct gga       289
Tyr Leu Glu Pro Pro His Ile Ile Leu Arg Lys Gly Leu Val Ala Gly
                85                  90                  95 atc cag tac cct ttc ctt gca gaa cac atg gct gat tac atg gcc aaa       337
Ile Gln Tyr Pro Phe Leu Ala Glu His Met Ala Asp Tyr Met Ala Lys
            100                 105                 110 acc ctc ttc ttc act tcg ctc ctc tat cat gat acc aca gag cac aaa       385
Thr Leu Phe Phe Thr Ser Leu Leu Tyr His Asp Thr Thr Glu His Lys
        115                 120                 125 aga gca gta acc gag ttt tgt ggt aat gtg gag tta tgc cgg tta acg       433
Arg Ala Val Thr Glu Phe Cys Gly Asn Val Glu Leu Cys Arg Leu Thr
    130                 135                 140 gag caa gta gtg ttc tct gac ccg tat aga gtt tct ag                    471
Glu Gln Val Val Phe Ser Asp Pro Tyr Arg Val Ser
```

```
Glu Gln Val Val Phe Ser Asp Pro Tyr Arg Val Ser
145                 150                 155
```

<210> SEQ ID NO 62
<211> LENGTH: 156
<212> TYPE: PRT
<213> ORGANISM: Brassica napus

<400> SEQUENCE: 62

```
Phe Pro Gly Arg Arg Phe Arg Gly Asn Leu Asn Phe Val Phe Ile Val
 1               5                  10                  15

Ile Gly Ser Thr Gly Ser Leu Val Ile Lys Gln Ala Leu Pro Tyr Ile
            20                  25                  30

Arg Cys Ile Gly Glu Ser Trp Pro Met Thr Lys Glu Arg Ala Tyr Phe
        35                  40                  45

Glu Ala Thr Thr Leu Arg Lys His Gly Ala Leu Ser Pro Asp His Val
    50                  55                  60

Pro Glu Val Tyr His Phe Asp Arg Thr Met Ala Leu Ile Gly Met Arg
65                  70                  75                  80

Tyr Leu Glu Pro Pro His Ile Ile Leu Arg Lys Gly Leu Val Ala Gly
                85                  90                  95

Ile Gln Tyr Pro Phe Leu Ala Glu His Met Ala Asp Tyr Met Ala Lys
            100                 105                 110

Thr Leu Phe Phe Thr Ser Leu Leu Tyr His Asp Thr Thr Glu His Lys
        115                 120                 125

Arg Ala Val Thr Glu Phe Cys Gly Asn Val Glu Leu Cys Arg Leu Thr
    130                 135                 140

Glu Gln Val Val Phe Ser Asp Pro Tyr Arg Val Ser
145                 150                 155
```

<210> SEQ ID NO 63
<211> LENGTH: 415
<212> TYPE: DNA
<213> ORGANISM: Brassica napus
<220> FEATURE:
<221> NAME/KEY: CDS
<222> LOCATION: (3)..(413)
<223> OTHER INFORMATION: coding for 5-methylthioribose kinase

<400> SEQUENCE: 63

```
gg gtc gac gat ttc gtg ctg aga gca aaa gag atg tcg ttc gat gag       47
   Val Asp Asp Phe Val Leu Arg Ala Lys Glu Met Ser Phe Asp Glu
    1               5                  10                  15 ttc aag ccg ttg aac gag aaa tct cta gta gag tac ata aag gca acg      95
Phe Lys Pro Leu Asn Glu Lys Ser Leu Val Glu Tyr Ile Lys Ala Thr
                20                  25                  30 cct gcc ctc tcc tcc agg ctc gga gac aag tac gat gat ctg gtc atc     143
Pro Ala Leu Ser Ser Arg Leu Gly Asp Lys Tyr Asp Asp Leu Val Ile
            35                  40                  45 aag gaa gtt gga gat ggc aat ctc aac ttc gtt ttc atc gtt gtc gga     191
Lys Glu Val Gly Asp Gly Asn Leu Asn Phe Val Phe Ile Val Val Gly
        50                  55                  60 tcc act ggc tca ctc gtc atc aaa cag gcg ctt ccg tat ata cgt tgt     239
Ser Thr Gly Ser Leu Val Ile Lys Gln Ala Leu Pro Tyr Ile Arg Cys
65                  70                  75 att gga gaa tca tgg cca atg acg aaa gaa aga gct tac ttt gaa gca     287
Ile Gly Glu Ser Trp Pro Met Thr Lys Glu Arg Ala Tyr Phe Glu Ala
80                  85                  90                  95 aca act ctg aga aag cac ggt ggt ttg tct ccg gat cat gtt cct gaa     335
Thr Thr Leu Arg Lys His Gly Gly Leu Ser Pro Asp His Val Pro Glu
```

```
gtc tac cat ttt gac aga acc atg gct ttg att gga atg aga tac ctc    383
Val Tyr His Phe Asp Arg Thr Met Ala Leu Ile Gly Met Arg Tyr Leu
            115                 120                 125 gag cct cct cac atc atc ctc cgc aaa gga ct                         415
Glu Pro Pro His Ile Ile Leu Arg Lys Gly
        130                 135
```

<210> SEQ ID NO 64
<211> LENGTH: 137
<212> TYPE: PRT
<213> ORGANISM: Brassica napus

<400> SEQUENCE: 64

```
Val Asp Asp Phe Val Leu Arg Ala Lys Glu Met Ser Phe Asp Glu Phe
 1               5                  10                  15

Lys Pro Leu Asn Glu Lys Ser Leu Val Glu Tyr Ile Lys Ala Thr Pro
            20                  25                  30

Ala Leu Ser Ser Arg Leu Gly Asp Lys Tyr Asp Asp Leu Val Ile Lys
        35                  40                  45

Glu Val Gly Asp Gly Asn Leu Asn Phe Val Phe Ile Val Val Gly Ser
    50                  55                  60

Thr Gly Ser Leu Val Ile Lys Gln Ala Leu Pro Tyr Ile Arg Cys Ile
65                  70                  75                  80

Gly Glu Ser Trp Pro Met Thr Lys Glu Arg Ala Tyr Phe Glu Ala Thr
                85                  90                  95

Thr Leu Arg Lys His Gly Gly Leu Ser Pro Asp His Val Pro Glu Val
            100                 105                 110

Tyr His Phe Asp Arg Thr Met Ala Leu Ile Gly Met Arg Tyr Leu Glu
        115                 120                 125

Pro Pro His Ile Ile Leu Arg Lys Gly
    130                 135
```

<210> SEQ ID NO 65
<211> LENGTH: 424
<212> TYPE: DNA
<213> ORGANISM: Oryza sativa
<220> FEATURE:
<221> NAME/KEY: CDS
<222> LOCATION: (3)..(422)
<223> OTHER INFORMATION: coding for 5-methylthioribose kinase

<400> SEQUENCE: 65

```
cc ctt ctc tac aac tcc acc act gat cac aag aaa gga gtt gct cag    47
   Leu Leu Tyr Asn Ser Thr Thr Asp His Lys Lys Gly Val Ala Gln
    1               5                  10                  15 tac tgc gat aat gtg gag atg tgt agg ctc aca gag caa gtc gtg ttc    95
Tyr Cys Asp Asn Val Glu Met Cys Arg Leu Thr Glu Gln Val Val Phe
            20                  25                  30 tca gac cca tac atg ctc gcc aaa tac aat cgt tgc aca tca ccc ttc   143
Ser Asp Pro Tyr Met Leu Ala Lys Tyr Asn Arg Cys Thr Ser Pro Phe
        35                  40                  45 cta gat aat gat gct gca gcg gtt cga gag gat gct gag ctt aaa ttg   191
Leu Asp Asn Asp Ala Ala Ala Val Arg Glu Asp Ala Glu Leu Lys Leu
    50                  55                  60 gag att gct gaa ttg aaa tca atg ttt att gag aga gca cag gct ctt   239
Glu Ile Ala Glu Leu Lys Ser Met Phe Ile Glu Arg Ala Gln Ala Leu
65                  70                  75 ctt cat gga gat ctc cac act ggt tcc atc atg gtg aca cca gat tct   287
Leu His Gly Asp Leu His Thr Gly Ser Ile Met Val Thr Pro Asp Ser
```

```
                80                  85                  90                  95
act caa gtg att gat cca gaa ttt gct ttc tat ggc cca atg ggt tac         335
Thr Gln Val Ile Asp Pro Glu Phe Ala Phe Tyr Gly Pro Met Gly Tyr
                100                 105                 110 gac att ggg gcc ttc ctg ggg aac ttg att ttg gca tat ttt tca caa         383
Asp Ile Gly Ala Phe Leu Gly Asn Leu Ile Leu Ala Tyr Phe Ser Gln
            115                 120                 125 gat gga cac gct gat caa gca aat gat cgt aag gct tac aa                  424
Asp Gly His Ala Asp Gln Ala Asn Asp Arg Lys Ala Tyr
            130                 135                 140
```

<210> SEQ ID NO 66
<211> LENGTH: 140
<212> TYPE: PRT
<213> ORGANISM: Oryza sativa

<400> SEQUENCE: 66

```
Leu Leu Tyr Asn Ser Thr Thr Asp His Lys Lys Gly Val Ala Gln Tyr
1               5                   10                  15

Cys Asp Asn Val Glu Met Cys Arg Leu Thr Glu Gln Val Val Phe Ser
            20                  25                  30

Asp Pro Tyr Met Leu Ala Lys Tyr Asn Arg Cys Thr Ser Pro Phe Leu
        35                  40                  45

Asp Asn Asp Ala Ala Val Arg Glu Asp Ala Glu Leu Lys Leu Glu
    50                  55                  60

Ile Ala Glu Leu Lys Ser Met Phe Ile Glu Arg Ala Gln Ala Leu Leu
65                  70                  75                  80

His Gly Asp Leu His Thr Gly Ser Ile Met Val Thr Pro Asp Ser Thr
            85                  90                  95

Gln Val Ile Asp Pro Glu Phe Ala Phe Tyr Gly Pro Met Gly Tyr Asp
        100                 105                 110

Ile Gly Ala Phe Leu Gly Asn Leu Ile Leu Ala Tyr Phe Ser Gln Asp
    115                 120                 125

Gly His Ala Asp Gln Ala Asn Asp Arg Lys Ala Tyr
    130                 135                 140
```

<210> SEQ ID NO 67
<211> LENGTH: 404
<212> TYPE: DNA
<213> ORGANISM: Glycine max
<220> FEATURE:
<221> NAME/KEY: CDS
<222> LOCATION: (3)..(404)
<223> OTHER INFORMATION: coding for 5-methylthioribose kinase

<400> SEQUENCE: 67

```
ta atc ccc gaa cat gtt cct gaa gtg tat cac ttt gac cgt acc atg          47
   Ile Pro Glu His Val Pro Glu Val Tyr His Phe Asp Arg Thr Met
   1               5                   10                  15 tct ttg atc ggt atg cgt tac ttg gag ccc cca cat ata atc ctc ata         95
Ser Leu Ile Gly Met Arg Tyr Leu Glu Pro Pro His Ile Ile Leu Ile
            20                  25                  30 aaa ggg ttg att gct ggg att gag tac cct ttt ttg gct gaa cac atg         143
Lys Gly Leu Ile Ala Gly Ile Glu Tyr Pro Phe Leu Ala Glu His Met
        35                  40                  45 gct gat ttc atg gcg aag aca ctc ttc ttc acg tct ctg ctt ttc cgt         191
Ala Asp Phe Met Ala Lys Thr Leu Phe Phe Thr Ser Leu Leu Phe Arg
    50                  55                  60 tcc act gct gac cac aaa cgg gac gtt gcc gaa ttt tgt ggg aat gtg         239
Ser Thr Ala Asp His Lys Arg Asp Val Ala Glu Phe Cys Gly Asn Val
```

-continued

```
                     65                  70                  75
gag tta tgc agg ctc act gaa cag gtc gtt ttc tct gac cct tat aaa      287
Glu Leu Cys Arg Leu Thr Glu Gln Val Val Phe Ser Asp Pro Tyr Lys
 80                  85                  90                  95 gtt tct caa tat aat cgt tgg act tcc ccc tat ctt gat cgt gat gct      335
Val Ser Gln Tyr Asn Arg Trp Thr Ser Pro Tyr Leu Asp Arg Asp Ala
                100                 105                 110 gag gct gtt cgg gaa gac aat ctg ctg aag ctt gaa gtt gct gag ctg      383
Glu Ala Val Arg Glu Asp Asn Leu Leu Lys Leu Glu Val Ala Glu Leu
                115                 120                 125 aaa tcc aag ttc att gag agc                                          404
Lys Ser Lys Phe Ile Glu Ser
            130

<210> SEQ ID NO 68
<211> LENGTH: 134
<212> TYPE: PRT
<213> ORGANISM: Glycine max

<400> SEQUENCE: 68

Ile Pro Glu His Val Pro Glu Val Tyr His Phe Asp Arg Thr Met Ser
  1               5                  10                  15

Leu Ile Gly Met Arg Tyr Leu Glu Pro Pro His Ile Ile Leu Ile Lys
                 20                  25                  30

Gly Leu Ile Ala Gly Ile Glu Tyr Pro Phe Leu Ala Glu His Met Ala
             35                  40                  45

Asp Phe Met Ala Lys Thr Leu Phe Phe Thr Ser Leu Leu Phe Arg Ser
         50                  55                  60

Thr Ala Asp His Lys Arg Asp Val Ala Glu Phe Cys Gly Asn Val Glu
 65                  70                  75                  80

Leu Cys Arg Leu Thr Glu Gln Val Val Phe Ser Asp Pro Tyr Lys Val
                 85                  90                  95

Ser Gln Tyr Asn Arg Trp Thr Ser Pro Tyr Leu Asp Arg Asp Ala Glu
                100                 105                 110

Ala Val Arg Glu Asp Asn Leu Leu Lys Leu Glu Val Ala Glu Leu Lys
            115                 120                 125

Ser Lys Phe Ile Glu Ser
        130

<210> SEQ ID NO 69
<211> LENGTH: 21
<212> TYPE: DNA
<213> ORGANISM: Artificial sequence
<220> FEATURE:
<223> OTHER INFORMATION: Description of the artificial sequence:
      oligonucleotide primer

<400> SEQUENCE: 69
cgtgaatacg gcgtggagtc g                                              21

<210> SEQ ID NO 70
<211> LENGTH: 20
<212> TYPE: DNA
<213> ORGANISM: Artificial sequence
<220> FEATURE:
<223> OTHER INFORMATION: Description of the artificial sequence:
      oligonucleotide primer

<400> SEQUENCE: 70
cggcaggata atcaggttgg                                                20
```

```
<210> SEQ ID NO 71
<211> LENGTH: 20
<212> TYPE: DNA
<213> ORGANISM: Artificial sequence
<220> FEATURE:
<223> OTHER INFORMATION: Description of the artificial sequence:
      oligonucleotide primer

<400> SEQUENCE: 71
gtcaacgtaa ccaaccctgc                                              20

<210> SEQ ID NO 72
<211> LENGTH: 11
<212> TYPE: PRT
<213> ORGANISM: Artificial sequence
<220> FEATURE:
<223> OTHER INFORMATION: Sequence motif
<220> FEATURE:
<221> NAME/KEY: misc_feature
<222> LOCATION: (2)..(2)
<223> OTHER INFORMATION: Xaa is Val or Ile
<220> FEATURE:
<221> NAME/KEY: misc_feature
<222> LOCATION: (7)..(7)
<223> OTHER INFORMATION: Xaa is Leu or Ile
<220> FEATURE:
<221> NAME/KEY: misc_feature
<222> LOCATION: (9)..(9)
<223> OTHER INFORMATION: Xaa is Leu or Tyr or Phe
<220> FEATURE:
<221> NAME/KEY: misc_feature
<222> LOCATION: (11)..(11)
<223> OTHER INFORMATION: Xaa is Phe or Tyr

<400> SEQUENCE: 72

Glu Xaa Gly Asp Gly Asn Xaa Asn Xaa Val Xaa
1               5                   10

<210> SEQ ID NO 73
<211> LENGTH: 11
<212> TYPE: PRT
<213> ORGANISM: Artificial sequence
<220> FEATURE:
<223> OTHER INFORMATION: Sequence motif
<220> FEATURE:
<221> NAME/KEY: misc_feature
<222> LOCATION: (9)..(9)
<223> OTHER INFORMATION: Xaa is Tyr or Phe
<220> FEATURE:
<221> NAME/KEY: misc_feature
<222> LOCATION: (11)..(11)
<223> OTHER INFORMATION: Xaa is Phe or Tyr

<400> SEQUENCE: 73

Glu Val Gly Asp Gly Asn Leu Asn Xaa Val Xaa
1               5                   10

<210> SEQ ID NO 74
<211> LENGTH: 9
<212> TYPE: PRT
<213> ORGANISM: Artificial sequence
<220> FEATURE:
<223> OTHER INFORMATION: Sequence motif
<220> FEATURE:
<221> NAME/KEY: misc_feature
<222> LOCATION: (7)..(7)
<223> OTHER INFORMATION: Xaa is Val or Ile

<400> SEQUENCE: 74

Lys Gln Ala Leu Pro Tyr Xaa Arg Cys
1               5
```

```
<210> SEQ ID NO 75
<211> LENGTH: 11
<212> TYPE: PRT
<213> ORGANISM: Artificial sequence
<220> FEATURE:
<223> OTHER INFORMATION: Sequence motif
<220> FEATURE:
<221> NAME/KEY: misc_feature
<222> LOCATION: (6)..(6)
<223> OTHER INFORMATION: Xaa is Arg or Lys

<400> SEQUENCE: 75

Ser Trp Pro Met Thr Xaa Glu Arg Ala Tyr Phe
1               5                   10

<210> SEQ ID NO 76
<211> LENGTH: 9
<212> TYPE: PRT
<213> ORGANISM: Artificial sequence
<220> FEATURE:
<223> OTHER INFORMATION: Sequence motif

<400> SEQUENCE: 76

Pro Glu Val Tyr His Phe Asp Arg Thr
1               5

<210> SEQ ID NO 77
<211> LENGTH: 10
<212> TYPE: PRT
<213> ORGANISM: Artificial sequence
<220> FEATURE:
<223> OTHER INFORMATION: Sequence motif
<220> FEATURE:
<221> NAME/KEY: misc_feature
<222> LOCATION: (5)..(5)
<223> OTHER INFORMATION: Xaa is Ile or Leu

<400> SEQUENCE: 77

Gly Met Arg Tyr Xaa Glu Pro Pro His Ile
1               5                   10

<210> SEQ ID NO 78
<211> LENGTH: 13
<212> TYPE: PRT
<213> ORGANISM: Artificial sequence
<220> FEATURE:
<223> OTHER INFORMATION: Sequence motif

<400> SEQUENCE: 78

Cys Arg Leu Thr Glu Gln Val Val Phe Ser Asp Pro Tyr
1               5                   10

<210> SEQ ID NO 79
<211> LENGTH: 8
<212> TYPE: PRT
<213> ORGANISM: Artificial sequence
<220> FEATURE:
<223> OTHER INFORMATION: Sequence motif
<220> FEATURE:
<221> NAME/KEY: misc_feature
<222> LOCATION: (6)..(6)
<223> OTHER INFORMATION: Xaa is Ser or Thr

<400> SEQUENCE: 79

His Gly Asp Leu His Xaa Gly Ser
1               5
```

<210> SEQ ID NO 80
<211> LENGTH: 7
<212> TYPE: PRT
<213> ORGANISM: Artificial sequence
<220> FEATURE:
<223> OTHER INFORMATION: Nuclear localization sequence: NLS1

<400> SEQUENCE: 80

Pro Lys Thr Lys Arg Lys Val
1               5

<210> SEQ ID NO 81
<211> LENGTH: 7
<212> TYPE: PRT
<213> ORGANISM: Artificial sequence
<220> FEATURE:
<223> OTHER INFORMATION: Nuclear localization sequence: NLS2

<400> SEQUENCE: 81

Pro Lys Lys Lys Arg Lys Val
1               5

<210> SEQ ID NO 82
<211> LENGTH: 85
<212> TYPE: DNA
<213> ORGANISM: Artificial sequence
<220> FEATURE:
<223> OTHER INFORMATION: Recognition sequence for DSBI enzyme CRE

<400> SEQUENCE: 82
aactctcatc gcttcggata acttcctgtt atccgaaaca tatcactcac tttggtgatt     60
tcaccgtaac tgtctatgat taatg                                          85

<210> SEQ ID NO 83
<211> LENGTH: 48
<212> TYPE: DNA
<213> ORGANISM: Artificial sequence
<220> FEATURE:
<223> OTHER INFORMATION: Recognition sequence for DSBI enzyme FLP

<400> SEQUENCE: 83
gaagttccta ttccgaagtt cctattctct agaaagtata ggaacttc                 48

<210> SEQ ID NO 84
<211> LENGTH: 58
<212> TYPE: DNA
<213> ORGANISM: Artificial sequence
<220> FEATURE:
<223> OTHER INFORMATION: Recognition sequence for DSBI enzyme R

<400> SEQUENCE: 84
cgagatcata tcactgtgga cgttgatgaa agaatacgtt attctttcat caaatcgt      58

<210> SEQ ID NO 85
<211> LENGTH: 23
<212> TYPE: DNA
<213> ORGANISM: Artificial sequence
<220> FEATURE:
<223> OTHER INFORMATION: Recognition sequence for DSBI enzyme P-element
      transposase

<400> SEQUENCE: 85
ctagatgaaa taacataagg tgg                                            23

<210> SEQ ID NO 86
<211> LENGTH: 39

```
<212> TYPE: DNA
<213> ORGANISM: Artificial sequence
<220> FEATURE:
<223> OTHER INFORMATION: Recognition sequence for DSBI enzyme I-AniI
<220> FEATURE:
<221> NAME/KEY: misc_feature
<222> LOCATION: (25)..(39)
<223> OTHER INFORMATION: n is a, c, g, or t

<400> SEQUENCE: 86
ttgaggaggt ttctctgtaa ataannnnnn nnnnnnnn                              39

<210> SEQ ID NO 87
<211> LENGTH: 39
<212> TYPE: DNA
<213> ORGANISM: Artificial sequence
<220> FEATURE:
<223> OTHER INFORMATION: Recognition sequence for DSBI enzyme I-AniI
<220> FEATURE:
<221> NAME/KEY: misc_feature
<222> LOCATION: (25)..(39)
<223> OTHER INFORMATION: n is a, c, g, or t

<400> SEQUENCE: 87
aactcctcca aagagacatt tattnnnnnn nnnnnnnn                              39

<210> SEQ ID NO 88
<211> LENGTH: 24
<212> TYPE: DNA
<213> ORGANISM: Artificial sequence
<220> FEATURE:
<223> OTHER INFORMATION: Recognition sequence for DSBI enzyme I-DdiI

<400> SEQUENCE: 88 tttttggtc atccagaagt atat                                              24

<210> SEQ ID NO 89
<211> LENGTH: 24
<212> TYPE: DNA
<213> ORGANISM: Artificial sequence
<220> FEATURE:
<223> OTHER INFORMATION: Recognition sequence for DSBI enzyme I-DdiI

<400> SEQUENCE: 89
aaaaaaccag taggtcttca tata                                             24

<210> SEQ ID NO 90
<211> LENGTH: 30
<212> TYPE: DNA
<213> ORGANISM: Artificial sequence
<220> FEATURE:
<223> OTHER INFORMATION: Recognition sequence for DSBI enzyme I-CvuI

<400> SEQUENCE: 90
ctgggttcaa aacgtcgtga gacagtttgg                                       30

<210> SEQ ID NO 91
<211> LENGTH: 30
<212> TYPE: DNA
<213> ORGANISM: Artificial sequence
<220> FEATURE:
<223> OTHER INFORMATION: Recognition sequence for DSBI enzyme I-CvuI

<400> SEQUENCE: 91
gacccaagtt ttgcagcact ctgtcaaacc                                       30

<210> SEQ ID NO 92
```

```
<211> LENGTH: 30
<212> TYPE: DNA
<213> ORGANISM: Artificial sequence
<220> FEATURE:
<223> OTHER INFORMATION: Recognition sequence for DSBI enzyme I-CsmI

<400> SEQUENCE: 92
gtactagcat ggggtcaaat gtctttctgg                                    30

<210> SEQ ID NO 93
<211> LENGTH: 18
<212> TYPE: DNA
<213> ORGANISM: Artificial sequence
<220> FEATURE:
<223> OTHER INFORMATION: Recognition sequence for DSBI enzyme I-CmoeI

<400> SEQUENCE: 93
tcgtagcagc tcacggtt                                                 18

<210> SEQ ID NO 94
<211> LENGTH: 18
<212> TYPE: DNA
<213> ORGANISM: Artificial sequence
<220> FEATURE:
<223> OTHER INFORMATION: Recognition sequence for DSBI enzyme I-CmoeI

<400> SEQUENCE: 94
agcatcgtcg agtgccaa                                                 18

<210> SEQ ID NO 95
<211> LENGTH: 30
<212> TYPE: DNA
<213> ORGANISM: Artificial sequence
<220> FEATURE:
<223> OTHER INFORMATION: Recognition sequence for DSBI enzyme I-CreI

<400> SEQUENCE: 95
ctgggttcaa aacgtcgtga gacagtttgg                                    30

<210> SEQ ID NO 96
<211> LENGTH: 30
<212> TYPE: DNA
<213> ORGANISM: Artificial sequence
<220> FEATURE:
<223> OTHER INFORMATION: Recognition sequence for DSBI enzyme I-CreI

<400> SEQUENCE: 96
gacccaagtt ttgcagcact ctgtcaaacc                                    30

<210> SEQ ID NO 97
<211> LENGTH: 30
<212> TYPE: DNA
<213> ORGANISM: Artificial sequence
<220> FEATURE:
<223> OTHER INFORMATION: Recognition sequence for DSBI enzyme I-ChuI

<400> SEQUENCE: 97
gaaggtttgg cacctcgatg tcggctcatc                                    30

<210> SEQ ID NO 98
<211> LENGTH: 30
<212> TYPE: DNA
<213> ORGANISM: Artificial sequence
<220> FEATURE:
<223> OTHER INFORMATION: Recognition sequence for DSBI enzyme I-ChuI

<400> SEQUENCE: 98
```

```
cttccaaacc gtggagctac agccgagtag                                          30

<210> SEQ ID NO 99
<211> LENGTH: 23
<212> TYPE: DNA
<213> ORGANISM: Artificial sequence
<220> FEATURE:
<223> OTHER INFORMATION: Recognition sequence for DSBI enzyme I-CpaI

<400> SEQUENCE: 99
cgatcctaag gtagcgaaat tca                                                 23

<210> SEQ ID NO 100
<211> LENGTH: 23
<212> TYPE: DNA
<213> ORGANISM: Artificial sequence
<220> FEATURE:
<223> OTHER INFORMATION: Recognition sequence for DSBI enzyme I-CpaI

<400> SEQUENCE: 100
gctaggattc catcgcttta agt                                                 23

<210> SEQ ID NO 101
<211> LENGTH: 20
<212> TYPE: DNA
<213> ORGANISM: Artificial sequence
<220> FEATURE:
<223> OTHER INFORMATION: Recognition sequence for DSBI enzyme I-CpaII

<400> SEQUENCE: 101
cccggctaac tctgtgccag                                                     20

<210> SEQ ID NO 102
<211> LENGTH: 20
<212> TYPE: DNA
<213> ORGANISM: Artificial sequence
<220> FEATURE:
<223> OTHER INFORMATION: Recognition sequence for DSBI enzyme I-CpaII

<400> SEQUENCE: 102
gggccgattg agacacggtc                                                     20

<210> SEQ ID NO 103
<211> LENGTH: 29
<212> TYPE: DNA
<213> ORGANISM: Artificial sequence
<220> FEATURE:
<223> OTHER INFORMATION: Recognition sequence for DSBI enzyme I-CeuI

<400> SEQUENCE: 103
cgtaactata acggtcctaa ggtagcgaa                                           29

<210> SEQ ID NO 104
<211> LENGTH: 29
<212> TYPE: DNA
<213> ORGANISM: Artificial sequence
<220> FEATURE:
<223> OTHER INFORMATION: Recognition sequence for DSBI enzyme I-CeuI

<400> SEQUENCE: 104
gcattgatat tgccaggatt ccatcgctt                                           29

<210> SEQ ID NO 105
<211> LENGTH: 30
<212> TYPE: DNA
```

```
<213> ORGANISM: Artificial sequence
<220> FEATURE:
<223> OTHER INFORMATION: Recognition sequence for DSBI enzyme I-DmoI

<400> SEQUENCE: 105
atgccttgcc gggtaagttc cggcgcgcat                               30

<210> SEQ ID NO 106
<211> LENGTH: 30
<212> TYPE: DNA
<213> ORGANISM: Artificial sequence
<220> FEATURE:
<223> OTHER INFORMATION: Recognition sequence for DSBI enzyme I-DmoI

<400> SEQUENCE: 106
tacggaacgg cccattcaag gccgcgcgta                               30

<210> SEQ ID NO 107
<211> LENGTH: 30
<212> TYPE: DNA
<213> ORGANISM: Artificial sequence
<220> FEATURE:
<223> OTHER INFORMATION: Recognition sequence for DSBI enzyme I-SceI

<400> SEQUENCE: 107
agttacgcta gggataacag ggtaatatag                               30

<210> SEQ ID NO 108
<211> LENGTH: 30
<212> TYPE: DNA
<213> ORGANISM: Artificial sequence
<220> FEATURE:
<223> OTHER INFORMATION: Recognition sequence for DSBI enzyme I-SceI

<400> SEQUENCE: 108
tcaatgcgat ccctattgtc ccattatatc                               30

<210> SEQ ID NO 109
<211> LENGTH: 18
<212> TYPE: DNA
<213> ORGANISM: Artificial sequence
<220> FEATURE:
<223> OTHER INFORMATION: Recognition sequence for DSBI enzyme I-SceI

<400> SEQUENCE: 109
tagggataac agggtaat                                            18

<210> SEQ ID NO 110
<211> LENGTH: 18
<212> TYPE: DNA
<213> ORGANISM: Artificial sequence
<220> FEATURE:
<223> OTHER INFORMATION: Recognition sequence for DSBI enzyme I-SceI

<400> SEQUENCE: 110
atccctattg tcccatta                                            18

<210> SEQ ID NO 111
<211> LENGTH: 29
<212> TYPE: DNA
<213> ORGANISM: Artificial sequence
<220> FEATURE:
<223> OTHER INFORMATION: Recognition sequence for DSBI enzyme I-SceII

<400> SEQUENCE: 111
ttttgattct ttggtcaccc tgaagtata                                29
```

```
<210> SEQ ID NO 112
<211> LENGTH: 29
<212> TYPE: DNA
<213> ORGANISM: Artificial sequence
<220> FEATURE:
<223> OTHER INFORMATION: Recognition sequence for DSBI enzyme I-SceII

<400> SEQUENCE: 112
aaaactaaga aaccagtggg acttcatat                                             29

<210> SEQ ID NO 113
<211> LENGTH: 29
<212> TYPE: DNA
<213> ORGANISM: Artificial sequence
<220> FEATURE:
<223> OTHER INFORMATION: Recognition sequence for DSBI enzyme I-SceIII

<400> SEQUENCE: 113
attggaggtt ttggtaacta tttattacc                                             29

<210> SEQ ID NO 114
<211> LENGTH: 29
<212> TYPE: DNA
<213> ORGANISM: Artificial sequence
<220> FEATURE:
<223> OTHER INFORMATION: Recognition sequence for DSBI enzyme I-SceIII

<400> SEQUENCE: 114
taacctccaa aaccattgat aaataatgg                                             29

<210> SEQ ID NO 115
<211> LENGTH: 29
<212> TYPE: DNA
<213> ORGANISM: Artificial sequence
<220> FEATURE:
<223> OTHER INFORMATION: Recognition sequence for DSBI enzyme I-SceIV

<400> SEQUENCE: 115
tcttttctct tgattagccc taatctacg                                             29

<210> SEQ ID NO 116
<211> LENGTH: 29
<212> TYPE: DNA
<213> ORGANISM: Artificial sequence
<220> FEATURE:
<223> OTHER INFORMATION: Recognition sequence for DSBI enzyme I-SceIV

<400> SEQUENCE: 116
agaaaagaga actaatcggg attagatgc                                             29

<210> SEQ ID NO 117
<211> LENGTH: 24
<212> TYPE: DNA
<213> ORGANISM: Artificial sequence
<220> FEATURE:
<223> OTHER INFORMATION: Recognition sequence for DSBI enzyme I-SceV

<400> SEQUENCE: 117
aataattttc ttcttagtaa tgcc                                                  24

<210> SEQ ID NO 118
<211> LENGTH: 24
<212> TYPE: DNA
<213> ORGANISM: Artificial sequence
<220> FEATURE:
```

```
<223> OTHER INFORMATION: Recognition sequence for DSBI enzyme I-SceV

<400> SEQUENCE: 118
ttattaaaag aagaatcatt acgg                                          24

<210> SEQ ID NO 119
<211> LENGTH: 24
<212> TYPE: DNA
<213> ORGANISM: Artificial sequence
<220> FEATURE:
<223> OTHER INFORMATION: Recognition sequence for DSBI enzyme I-SceVI

<400> SEQUENCE: 119
gttatttaat gttttagtag ttgg                                          24

<210> SEQ ID NO 120
<211> LENGTH: 24
<212> TYPE: DNA
<213> ORGANISM: Artificial sequence
<220> FEATURE:
<223> OTHER INFORMATION: Recognition sequence for DSBI enzyme I-SceVI

<400> SEQUENCE: 120
caataaatta caaaatcatc aacc                                          24

<210> SEQ ID NO 121
<211> LENGTH: 28
<212> TYPE: DNA
<213> ORGANISM: Artificial sequence
<220> FEATURE:
<223> OTHER INFORMATION: Recognition sequence for DSBI enzyme I-SceVII

<400> SEQUENCE: 121
tgtcacattg aggtgcacta gttattac                                      28

<210> SEQ ID NO 122
<211> LENGTH: 30
<212> TYPE: DNA
<213> ORGANISM: Artificial sequence
<220> FEATURE:
<223> OTHER INFORMATION: Recognition sequence for DSBI enzyme PI-SceI

<400> SEQUENCE: 122
atctatgtcg ggtgcggaga aagaggtaat                                    30

<210> SEQ ID NO 123
<211> LENGTH: 30
<212> TYPE: DNA
<213> ORGANISM: Artificial sequence
<220> FEATURE:
<223> OTHER INFORMATION: Recognition sequence for DSBI enzyme PI-SceI

<400> SEQUENCE: 123
tagatacagc ccacgcctct ttctccatta                                    30

<210> SEQ ID NO 124
<211> LENGTH: 24
<212> TYPE: DNA
<213> ORGANISM: Artificial sequence
<220> FEATURE:
<223> OTHER INFORMATION: Recognition sequence for DSBI enzyme F-SceI

<400> SEQUENCE: 124
gatgctgtag gcataggctt ggtt                                          24
```

```
<210> SEQ ID NO 125
<211> LENGTH: 24
<212> TYPE: DNA
<213> ORGANISM: Artificial sequence
<220> FEATURE:
<223> OTHER INFORMATION: Recognition sequence for DSBI enzyme F-SceI

<400> SEQUENCE: 125
ctacgacatc cgtatccgaa ccaa                                             24

<210> SEQ ID NO 126
<211> LENGTH: 20
<212> TYPE: DNA
<213> ORGANISM: Artificial sequence
<220> FEATURE:
<223> OTHER INFORMATION: Recognition sequence for DSBI enzyme F-SceII

<400> SEQUENCE: 126
ctttccgcaa cagtaaaatt                                                  20

<210> SEQ ID NO 127
<211> LENGTH: 20
<212> TYPE: DNA
<213> ORGANISM: Artificial sequence
<220> FEATURE:
<223> OTHER INFORMATION: Recognition sequence for DSBI enzyme F-SceII

<400> SEQUENCE: 127
gaaaggcgtt gtcattttaa                                                  20

<210> SEQ ID NO 128
<211> LENGTH: 24
<212> TYPE: DNA
<213> ORGANISM: Artificial sequence
<220> FEATURE:
<223> OTHER INFORMATION: Recognition sequence for DSBI enzyme I-HmuI

<400> SEQUENCE: 128
agtaatgagc ctaacgctca gcaa                                             24

<210> SEQ ID NO 129
<211> LENGTH: 24
<212> TYPE: DNA
<213> ORGANISM: Artificial sequence
<220> FEATURE:
<223> OTHER INFORMATION: Recognition sequence for DSBI enzyme I-HmuI

<400> SEQUENCE: 129
tcattactcg gattgcgagt cgtt                                             24

<210> SEQ ID NO 130
<211> LENGTH: 63
<212> TYPE: DNA
<213> ORGANISM: Artificial sequence
<220> FEATURE:
<223> OTHER INFORMATION: Recognition sequence for DSBI enzyme I-HmuII
<220> FEATURE:
<221> NAME/KEY: misc_feature
<222> LOCATION: (25)..(63)
<223> OTHER INFORMATION: n is a, c, g, or t

<400> SEQUENCE: 130
agtaatgagc ctaacgctca acaannnnnn nnnnnnnnnn nnnnnnnnnn nnnnnnnnn       60 nnn                                                                    63

<210> SEQ ID NO 131
```

```
<211> LENGTH: 24
<212> TYPE: DNA
<213> ORGANISM: Artificial sequence
<220> FEATURE:
<223> OTHER INFORMATION: Recognition sequence for DSBI enzyme I-LlaI

<400> SEQUENCE: 131
cacatccata accatatcat tttt                                              24

<210> SEQ ID NO 132
<211> LENGTH: 24
<212> TYPE: DNA
<213> ORGANISM: Artificial sequence
<220> FEATURE:
<223> OTHER INFORMATION: Recognition sequence for DSBI enzyme I-LlaI

<400> SEQUENCE: 132
gtgtaggtat tggtatagta aaaa                                              24

<210> SEQ ID NO 133
<211> LENGTH: 30
<212> TYPE: DNA
<213> ORGANISM: Artificial sequence
<220> FEATURE:
<223> OTHER INFORMATION: Recognition sequence for DSBI enzyme I-MsoI

<400> SEQUENCE: 133
ctgggttcaa aacgtcgtga gacagtttgg                                        30

<210> SEQ ID NO 134
<211> LENGTH: 30
<212> TYPE: DNA
<213> ORGANISM: Artificial sequence
<220> FEATURE:
<223> OTHER INFORMATION: Recognition sequence for DSBI enzyme I-MsoI

<400> SEQUENCE: 134
gacccaagtt ttgcagcact ctgtcaaacc                                        30

<210> SEQ ID NO 135
<211> LENGTH: 21
<212> TYPE: DNA
<213> ORGANISM: Artificial sequence
<220> FEATURE:
<223> OTHER INFORMATION: Recognition sequence for DSBI enzyme I-NanI

<400> SEQUENCE: 135
aagtctggtg ccagcacccg c                                                 21

<210> SEQ ID NO 136
<211> LENGTH: 21
<212> TYPE: DNA
<213> ORGANISM: Artificial sequence
<220> FEATURE:
<223> OTHER INFORMATION: Recognition sequence for DSBI enzyme I-NanI

<400> SEQUENCE: 136
ttcagaccac ggtcgtgggc g                                                 21

<210> SEQ ID NO 137
<211> LENGTH: 21
<212> TYPE: DNA
<213> ORGANISM: Artificial sequence
<220> FEATURE:
<223> OTHER INFORMATION: Recognition sequence for DSBI enzyme I-NitI

<400> SEQUENCE: 137
```

```
aagtctggtg ccagcacccg c                                              21

<210> SEQ ID NO 138
<211> LENGTH: 21
<212> TYPE: DNA
<213> ORGANISM: Artificial sequence
<220> FEATURE:
<223> OTHER INFORMATION: Recognition sequence for DSBI enzyme I-NitI

<400> SEQUENCE: 138
ttcagaccac ggtcgtgggc g                                              21

<210> SEQ ID NO 139
<211> LENGTH: 21
<212> TYPE: DNA
<213> ORGANISM: Artificial sequence
<220> FEATURE:
<223> OTHER INFORMATION: Recognition sequence for DSBI enzyme I-NjaI

<400> SEQUENCE: 139
aagtctggtg ccagcacccg c                                              21

<210> SEQ ID NO 140
<211> LENGTH: 21
<212> TYPE: DNA
<213> ORGANISM: Artificial sequence
<220> FEATURE:
<223> OTHER INFORMATION: Recognition sequence for DSBI enzyme I-NjaI

<400> SEQUENCE: 140
ttcagaccac ggtcgtgggc g                                              21

<210> SEQ ID NO 141
<211> LENGTH: 30
<212> TYPE: DNA
<213> ORGANISM: Artificial sequence
<220> FEATURE:
<223> OTHER INFORMATION: Recognition sequence for DSBI enzyme I-PakI

<400> SEQUENCE: 141
ctgggttcaa aacgtcgtga gacagtttgg                                     30

<210> SEQ ID NO 142
<211> LENGTH: 30
<212> TYPE: DNA
<213> ORGANISM: Artificial sequence
<220> FEATURE:
<223> OTHER INFORMATION: Recognition sequence for DSBI enzyme I-PakI

<400> SEQUENCE: 142
gacccaagtt ttgcagcact ctgtcaaacc                                     30

<210> SEQ ID NO 143
<211> LENGTH: 25
<212> TYPE: DNA
<213> ORGANISM: Artificial sequence
<220> FEATURE:
<223> OTHER INFORMATION: Recognition sequence for DSBI enzyme I-PorI

<400> SEQUENCE: 143
gcgagcccgt aagggtgtgt acggg                                          25

<210> SEQ ID NO 144
<211> LENGTH: 25
<212> TYPE: DNA
```

```
<213> ORGANISM: Artificial sequence
<220> FEATURE:
<223> OTHER INFORMATION: Recognition sequence for DSBI enzyme I-PorI

<400> SEQUENCE: 144
cgctcgggca ttcccacaca tgccc                                             25

<210> SEQ ID NO 145
<211> LENGTH: 29
<212> TYPE: DNA
<213> ORGANISM: Artificial sequence
<220> FEATURE:
<223> OTHER INFORMATION: Recognition sequence for DSBI enzyme I-PpoI

<400> SEQUENCE: 145
taactatgac tctcttaagg tagccaaat                                         29

<210> SEQ ID NO 146
<211> LENGTH: 29
<212> TYPE: DNA
<213> ORGANISM: Artificial sequence
<220> FEATURE:
<223> OTHER INFORMATION: Recognition sequence for DSBI enzyme I-PpoI

<400> SEQUENCE: 146
attgatactg agagaattcc atcggttta                                         29

<210> SEQ ID NO 147
<211> LENGTH: 28
<212> TYPE: DNA
<213> ORGANISM: Artificial sequence
<220> FEATURE:
<223> OTHER INFORMATION: Recognition sequence for DSBI enzyme I-ScaI

<400> SEQUENCE: 147
tgtcacattg aggtgcacta gttattac                                          28

<210> SEQ ID NO 148
<211> LENGTH: 28
<212> TYPE: DNA
<213> ORGANISM: Artificial sequence
<220> FEATURE:
<223> OTHER INFORMATION: Recognition sequence for DSBI enzyme I-ScaI

<400> SEQUENCE: 148
acagtgtaac tccacgtgat caataatg                                          28

<210> SEQ ID NO 149
<211> LENGTH: 19
<212> TYPE: DNA
<213> ORGANISM: Artificial sequence
<220> FEATURE:
<223> OTHER INFORMATION: Recognition sequence for DSBI enzyme I-Ssp6803I

<400> SEQUENCE: 149
gtcgggctca tacccgaa                                                     19

<210> SEQ ID NO 150
<211> LENGTH: 19
<212> TYPE: DNA
<213> ORGANISM: Artificial sequence
<220> FEATURE:
<223> OTHER INFORMATION: Recognition sequence for DSBI enzyme I-Ssp6803I

<400> SEQUENCE: 150
cagcccgagt attgggctt                                                    19
```

```
<210> SEQ ID NO 151
<211> LENGTH: 30
<212> TYPE: DNA
<213> ORGANISM: Artificial sequence
<220> FEATURE:
<223> OTHER INFORMATION: Recognition sequence for DSBI enzyme PI-PfuI

<400> SEQUENCE: 151
gaagatggga ggagggaccg gactcaactt                                            30

<210> SEQ ID NO 152
<211> LENGTH: 30
<212> TYPE: DNA
<213> ORGANISM: Artificial sequence
<220> FEATURE:
<223> OTHER INFORMATION: Recognition sequence for DSBI enzyme PI-PfuI

<400> SEQUENCE: 152
cttctaccct cctccctggc ctgagttgaa                                            30

<210> SEQ ID NO 153
<211> LENGTH: 29
<212> TYPE: DNA
<213> ORGANISM: Artificial sequence
<220> FEATURE:
<223> OTHER INFORMATION: Recognition sequence for DSBI enzyme PI-PfuII

<400> SEQUENCE: 153
acgaatccat gtggagaaga gcctctata                                             29

<210> SEQ ID NO 154
<211> LENGTH: 29
<212> TYPE: DNA
<213> ORGANISM: Artificial sequence
<220> FEATURE:
<223> OTHER INFORMATION: Recognition sequence for DSBI enzyme PI-PfuII

<400> SEQUENCE: 154
tgcttaggta cacctcttct cggagatat                                             29

<210> SEQ ID NO 155
<211> LENGTH: 19
<212> TYPE: DNA
<213> ORGANISM: Artificial sequence
<220> FEATURE:
<223> OTHER INFORMATION: Recognition sequence for DSBI enzyme PI-PkoI

<400> SEQUENCE: 155
gattttagat ccctgtacc                                                        19

<210> SEQ ID NO 156
<211> LENGTH: 19
<212> TYPE: DNA
<213> ORGANISM: Artificial sequence
<220> FEATURE:
<223> OTHER INFORMATION: Recognition sequence for DSBI enzyme PI-PkoI

<400> SEQUENCE: 156
ctaaaatcta gggacatgg                                                        19

<210> SEQ ID NO 157
<211> LENGTH: 15
<212> TYPE: DNA
<213> ORGANISM: Artificial sequence
<220> FEATURE:
```

<223> OTHER INFORMATION: Recognition sequence for DSBI enzyme PI-PkoII

<400> SEQUENCE: 157
cagtactacg gttac					15

<210> SEQ ID NO 158
<211> LENGTH: 15
<212> TYPE: DNA
<213> ORGANISM: Artificial sequence
<220> FEATURE:
<223> OTHER INFORMATION: Recognition sequence for DSBI enzyme PI-PkoII

<400> SEQUENCE: 158
gtcatgatgc caatg					15

<210> SEQ ID NO 159
<211> LENGTH: 30
<212> TYPE: DNA
<213> ORGANISM: Artificial sequence
<220> FEATURE:
<223> OTHER INFORMATION: Recognition sequence for DSBI enzyme PI-PspI

<400> SEQUENCE: 159
aaaatcctgg caaacagcta ttatgggtat					30

<210> SEQ ID NO 160
<211> LENGTH: 30
<212> TYPE: DNA
<213> ORGANISM: Artificial sequence
<220> FEATURE:
<223> OTHER INFORMATION: Recognition sequence for DSBI enzyme PI-PspI

<400> SEQUENCE: 160
ttttaggacc gtttgtcgat aatacccata					30

<210> SEQ ID NO 161
<211> LENGTH: 26
<212> TYPE: DNA
<213> ORGANISM: Artificial sequence
<220> FEATURE:
<223> OTHER INFORMATION: Recognition sequence for DSBI enzyme PI-TfuI

<400> SEQUENCE: 161
tagattttag gtcgctatat ccttcc					26

<210> SEQ ID NO 162
<211> LENGTH: 26
<212> TYPE: DNA
<213> ORGANISM: Artificial sequence
<220> FEATURE:
<223> OTHER INFORMATION: Recognition sequence for DSBI enzyme PI-TfuI

<400> SEQUENCE: 162
atctaaaatc cagcgatata ggaagg					26

<210> SEQ ID NO 163
<211> LENGTH: 22
<212> TYPE: DNA
<213> ORGANISM: Artificial sequence
<220> FEATURE:
<223> OTHER INFORMATION: Recognition sequence for DSBI enzyme PI-TfuII
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (12)..(12)
<223> OTHER INFORMATION: n is a, c, g, or t

<400> SEQUENCE: 163
taygcngaya cngacggytt yt                                                    22

<210> SEQ ID NO 164
<211> LENGTH: 22
<212> TYPE: DNA
<213> ORGANISM: Artificial sequence
<220> FEATURE:
<223> OTHER INFORMATION: Recognition sequence for DSBI enzyme PI-TfuII
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (12)..(12)
<223> OTHER INFORMATION: n is a, c, g, or t

<400> SEQUENCE: 164
atrcgnctrt gnctgccraa ra                                                    22

<210> SEQ ID NO 165
<211> LENGTH: 22
<212> TYPE: DNA
<213> ORGANISM: Artificial sequence
<220> FEATURE:
<223> OTHER INFORMATION: Recognition sequence for DSBI enzyme PI-ThyI
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (12)..(12)
<223> OTHER INFORMATION: n is a, c, g, or t

<400> SEQUENCE: 165
taygcngaya cngacggytt yt                                                    22

<210> SEQ ID NO 166
<211> LENGTH: 22
<212> TYPE: DNA
<213> ORGANISM: Artificial sequence
<220> FEATURE:
<223> OTHER INFORMATION: Recognition sequence for DSBI enzyme PI-ThyI
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (12)..(12)
<223> OTHER INFORMATION: n is a, c, g, or t

<400> SEQUENCE: 166
atrcgnctrt gnctgccraa ra                                                    22

<210> SEQ ID NO 167
<211> LENGTH: 22
<212> TYPE: DNA
<213> ORGANISM: Artificial sequence
<220> FEATURE:
<223> OTHER INFORMATION: Recognition sequence for DSBI enzyme PI-TliI
<220> FEATURE:
<221> NAME/KEY: misc_feature
<222> LOCATION: (6)..(6)
<223> OTHER INFORMATION: n is a, c, g, or t
<220> FEATURE:

```
<221> NAME/KEY: misc_feature
<222> LOCATION: (12)..(12)
<223> OTHER INFORMATION: n is a, c, g, or t

<400> SEQUENCE: 167
taygcngaya cngacggytt yt                                              22

<210> SEQ ID NO 168
<211> LENGTH: 22
<212> TYPE: DNA
<213> ORGANISM: Artificial sequence
<220> FEATURE:
<223> OTHER INFORMATION: Recognition sequence for DSBI enzyme PI-TliI
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (12)..(12)
<223> OTHER INFORMATION: n is a, c, g, or t

<400> SEQUENCE: 168
atrcgnctrt gnctgccraa ra                                              22

<210> SEQ ID NO 169
<211> LENGTH: 30
<212> TYPE: DNA
<213> ORGANISM: Artificial sequence
<220> FEATURE:
<223> OTHER INFORMATION: Recognition sequence for DSBI enzyme PI-TliII

<400> SEQUENCE: 169
aaattgcttg caaacagcta ttacggctat                                      30

<210> SEQ ID NO 170
<211> LENGTH: 24
<212> TYPE: DNA
<213> ORGANISM: Artificial sequence
<220> FEATURE:
<223> OTHER INFORMATION: Recognition sequence for DSBI enzyme I-TevI

<400> SEQUENCE: 170
agtggtatca acgctcagta gatg                                            24

<210> SEQ ID NO 171
<211> LENGTH: 24
<212> TYPE: DNA
<213> ORGANISM: Artificial sequence
<220> FEATURE:
<223> OTHER INFORMATION: Recognition sequence for DSBI enzyme I-TevI

<400> SEQUENCE: 171
tcaccatagt tgcgagtcat ctac                                            24

<210> SEQ ID NO 172
<211> LENGTH: 30
<212> TYPE: DNA
<213> ORGANISM: Artificial sequence
<220> FEATURE:
<223> OTHER INFORMATION: Recognition sequence for DSBI enzyme I-TevII

<400> SEQUENCE: 172
gcttatgagt atgaagtgaa cacgttattc                                      30

<210> SEQ ID NO 173
<211> LENGTH: 30
```

```
<212> TYPE: DNA
<213> ORGANISM: Artificial sequence
<220> FEATURE:
<223> OTHER INFORMATION: Recognition sequence for DSBI enzyme I-TevII

<400> SEQUENCE: 173
cgaatactca tacttcactt gtgcaataag                                        30

<210> SEQ ID NO 174
<211> LENGTH: 38
<212> TYPE: DNA
<213> ORGANISM: Artificial sequence
<220> FEATURE:
<223> OTHER INFORMATION: Recognition sequence for DSBI enzyme F-TevI
<220> FEATURE:
<221> NAME/KEY: misc_feature
<222> LOCATION: (25)..(38)
<223> OTHER INFORMATION: n is a, c, g, or t

<400> SEQUENCE: 174
gaaacacaag aaatgtttag taaannnnnn nnnnnnnn                               38

<210> SEQ ID NO 175
<211> LENGTH: 38
<212> TYPE: DNA
<213> ORGANISM: Artificial sequence
<220> FEATURE:
<223> OTHER INFORMATION: Recognition sequence for DSBI enzyme F-TevI
<220> FEATURE:
<221> NAME/KEY: misc_feature
<222> LOCATION: (25)..(38)
<223> OTHER INFORMATION: n is a, c, g, or t

<400> SEQUENCE: 175
ctttgtgttc tttacaaatc atttnnnnnn nnnnnnnn                               38

<210> SEQ ID NO 176
<211> LENGTH: 29
<212> TYPE: DNA
<213> ORGANISM: Artificial sequence
<220> FEATURE:
<223> OTHER INFORMATION: Recognition sequence for DSBI enzyme F-TevII

<400> SEQUENCE: 176
tttaatcctc gcttcagata tggcaactg                                         29

<210> SEQ ID NO 177
<211> LENGTH: 29
<212> TYPE: DNA
<213> ORGANISM: Artificial sequence
<220> FEATURE:
<223> OTHER INFORMATION: Recognition sequence for DSBI enzyme F-TevII

<400> SEQUENCE: 177
aaattaggag cgaagtctat accgttgac                                         29

<210> SEQ ID NO 178
<211> LENGTH: 403
<212> TYPE: PRT
<213> ORGANISM: Clostridium tetani

<400> SEQUENCE: 178

Met Ser Arg Phe Asp Ser His Phe Arg Met Glu Thr Glu Asp Ala Ile
1               5                   10                  15

Leu Tyr Ala Lys Glu Lys Leu Gly Ile Phe Asp Glu His Ala Lys Leu
            20                  25                  30
```

```
Gln Ala Glu Glu Ile Gly Asp Gly Asn Ile Asn Tyr Val Phe Lys Val
            35                  40                  45

Trp Asp Val Asn Thr Lys Lys Ser Val Ile Ile Lys His Ala Asp Ile
 50                  55                  60

Phe Leu Arg Ser Ser Gly Arg Glu Leu Asp Val Asp Arg Asn Arg Ile
 65                  70                  75                  80

Glu Ala Glu Val Leu Met Leu Gln Gly Ile Leu Ala Pro Gly Leu Val
                 85                  90                  95

Pro Lys Val Tyr Lys Tyr Asp Ser Val Met Cys Asn Leu Ser Met Glu
            100                 105                 110

Asp Ile Ser Asp His Arg Asn Leu Arg Lys Glu Leu Leu Lys Arg Asn
            115                 120                 125

Thr Phe Pro Ser Phe Ala Glu His Ile Thr Thr Phe Ile Val Asp Thr
    130                 135                 140

Leu Leu Pro Thr Thr Asp Leu Val Met Asp Ser Gly Glu Lys Lys Asp
145                 150                 155                 160

Asn Val Lys Lys Tyr Ile Asn Lys Asp Leu Cys Lys Ile Ser Glu Asp
                165                 170                 175

Leu Val Phe Thr Glu Pro Phe Ile Asp Tyr Lys Ser Arg Asn Thr Val
            180                 185                 190

Leu Glu Glu Asn Ile Glu Phe Val Lys Arg Gln Leu Tyr Glu Asp Lys
            195                 200                 205

Glu Leu Ile Leu Glu Ala Gly Lys Leu Lys Asn Asn Phe Met Asn Asn
    210                 215                 220

Ser Gln Ala Leu Ile His Gly Asp Leu His Ser Gly Ser Ile Phe Val
225                 230                 235                 240

Asn Glu Glu Ser Thr Lys Ile Leu Asp Pro Glu Phe Ala Phe Tyr Gly
                245                 250                 255

Pro Ile Gly Tyr Asp Leu Gly Asn Val Ile Gly Asn Leu Phe Phe Ala
            260                 265                 270

Trp Ala Asn Ala Tyr Val Thr Glu Asp Gly Lys Glu Val Glu Glu Phe
            275                 280                 285

Thr Ile Trp Ile Glu Lys Thr Ile Glu Asn Ile Leu Glu Leu Phe Lys
    290                 295                 300

Glu Lys Phe Ile Lys Lys Tyr Lys Glu Ile Val Thr Asp Val Met Ala
305                 310                 315                 320

Lys Glu Glu Tyr Tyr Met Asn Trp Tyr Leu His Ser Ile Leu Ser Asp
                325                 330                 335

Thr Ala Gly Gln Val Gly Leu Glu Ile Ile Arg Arg Val Val Gly Asp
            340                 345                 350

Ser Lys Val Leu Asp Ile Thr Ser Ile Thr Asp Ile Asn Lys Arg Val
            355                 360                 365

Lys Ala Glu Arg Ile Leu Ile Leu Ser Ala Lys Thr Phe Ile Lys Asn
    370                 375                 380

Arg His Lys Ile Lys Thr Gly Lys Arg Tyr Val Glu Ile Phe Asn Ser
385                 390                 395                 400

Asn Met Tyr

<210> SEQ ID NO 179
<211> LENGTH: 197
<212> TYPE: PRT
<213> ORGANISM: Unknown
<220> FEATURE:
<223> OTHER INFORMATION: Consensus sequence
```

-continued

```
<400> SEQUENCE: 179

Leu Val Ala Lys Leu Gly Asp Leu Glu Val Gly Asp Gly Asn Leu Asn
1               5                   10                  15

Phe Val Phe Val Gly Leu Val Ile Lys Gln Ala Leu Pro Tyr Ile Arg
            20                  25                  30

Cys Ile Gly Glu Ser Trp Pro Met Thr Glu Arg Ala Glu Ala Thr Leu
        35                  40                  45

His Gly Leu Ser Pro Asp His Val Pro Glu Val Tyr His Phe Asp Arg
    50                  55                  60

Thr Met Ala Leu Ile Gly Met Arg Tyr Leu Glu Pro Pro His Ile Ile
65                  70                  75                  80

Leu Arg Lys Gly Leu Ile Ala Ile Tyr Pro Ala Asp His Met Asp Tyr
                85                  90                  95

Met Ala Thr Leu Phe Thr Ser Leu Leu Tyr Thr Asp His Lys Val Ala
            100                 105                 110

Phe Asn Val Glu Leu Cys Arg Leu Thr Glu Gln Val Val Phe Ser Asp
            115                 120                 125

Pro Tyr Val Ser Phe Asn Arg Thr Ser Pro Tyr Leu Asp Asp Ala Ala
    130                 135                 140

Val Arg Glu Asp Leu Lys Leu Glu Val Ala Leu Lys Ser Phe Ile Glu
145                 150                 155                 160

Ala Gln Ala Leu Ile His Gly Asp Leu His Thr Gly Ser Ile Val Ser
                165                 170                 175

Ile Asp Glu Phe Ala Phe Tyr Gly Pro Met Gly Phe Asp Ile Gly Ile
            180                 185                 190

Gly Asn Leu Ala Tyr
            195
```